(12) United States Patent
Woodson et al.

(10) Patent No.: US 7,934,506 B2
(45) Date of Patent: May 3, 2011

(54) SYSTEM AND METHOD FOR TEMPORARY TONGUE SUSPENSION

(75) Inventors: Beverly Tucker Woodson, Menominee Falls, MN (US); Chad Roue, San Jose, CA (US); Erik van der Burg, Los Gatos, CA (US); Michael Dineen, Portola Valley, CA (US); Mark Hirotsuka, San Jose, CA (US); Jasper Jackson, Newark, CA (US); Andrew Frazier, Sunnyvale, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 258 days.

(21) Appl. No.: 11/765,235

(22) Filed: Jun. 19, 2007

(65) Prior Publication Data

US 2008/0035160 A1      Feb. 14, 2008

Related U.S. Application Data

(60) Provisional application No. 60/815,731, filed on Jun. 21, 2006.

(51) Int. Cl.
| | |
|---|---|
| A61C 5/14 | (2006.01) |
| A61B 19/00 | (2006.01) |
| A61M 5/00 | (2006.01) |
| A61M 29/00 | (2006.01) |

(52) U.S. Cl. ......... 128/860; 128/899; 604/264; 606/199
(58) Field of Classification Search .................. 128/899, 128/848, 859–862; 606/232, 219, 108, 199, 606/1; 600/185, 201, 210, 215, 219, 226, 600/237, 239–240; 604/506, 264, 272, 164.01, 604/523; 601/902
See application file for complete search history.

(56) References Cited

U.S. PATENT DOCUMENTS

| | | | | | |
|---|---|---|---|---|---|
| 5,106,369 | A | * | 4/1992 | Christmas | 604/506 |
| 5,254,097 | A | * | 10/1993 | Schock et al. | 604/167.04 |
| 5,320,602 | A | * | 6/1994 | Karpiel | 604/514 |
| 5,512,037 | A | * | 4/1996 | Russell et al. | 600/206 |
| 5,534,005 | A | * | 7/1996 | Tokish et al. | 606/80 |
| 5,613,968 | A | * | 3/1997 | Lin | 606/320 |
| 5,626,597 | A | * | 5/1997 | Urban et al. | 606/170 |
| 5,797,888 | A | | 8/1998 | Yoon | |
| 5,988,171 | A | * | 11/1999 | Sohn et al. | 128/848 |
| 6,431,174 | B1 | * | 8/2002 | Knudson et al. | 128/898 |
| 6,626,916 | B1 | * | 9/2003 | Yeung et al. | 606/139 |
| 7,226,468 | B2 | * | 6/2007 | Ruff | 606/216 |

OTHER PUBLICATIONS

B.T. Woodson, "A Tongue Suspension Suture for Obstructive Sleep Apnea and Snorers", Otolaryngol Head Neck Surg. Mar. 2001; 124(3):297-303.
F.R. Miller et al., "Role of the Tongue Base Suspension Suture With The Repose System Bone Screw in the Multilevel Surgical Management of Obstructive Sleep Apnea", Otolaryngol Head Neck Surg. 202 Apr.;126(4):392-8.

* cited by examiner

Primary Examiner — Patricia M Bianco
Assistant Examiner — Ophelia Hawthorne

(57) ABSTRACT

Methods and devices are disclosed for manipulating the tongue, and more particularly for temporarily suspending the tongue. One embodiment of the device comprises an elongate member with a retractable distal tissue-engaging tip that is movable within the lumen of tubular member configured for insertion into the tongue, preferably from an inferior surface of the jaw. The device may be used diagnostically assess the effect of performing tongue suspension in a patient prior to permanent implantation of a glossopexy device. The retractable distal tissue-engaging tip may be removed after diagnostic assessment, or left in place and attached to a temporary external securing device.

31 Claims, 91 Drawing Sheets

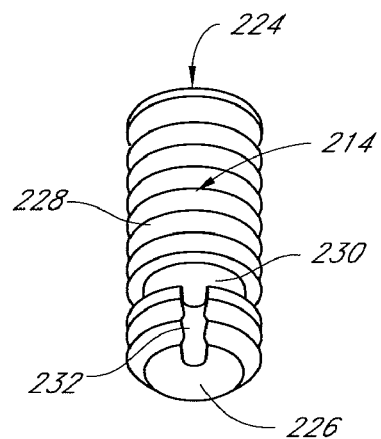
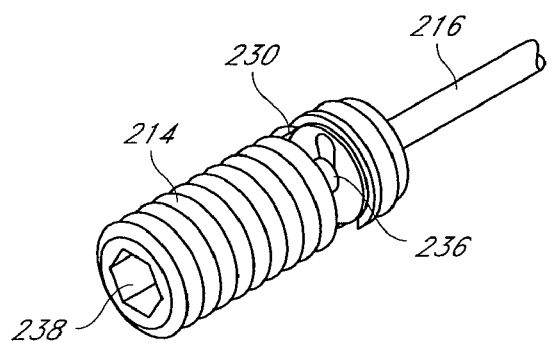
FIG. 42A  FIG. 42B
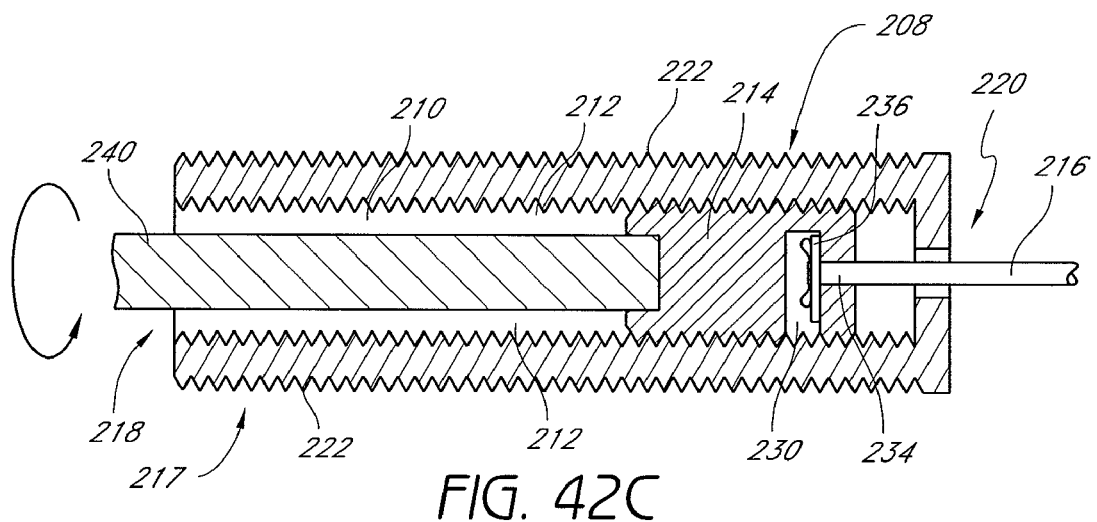
FIG. 42C
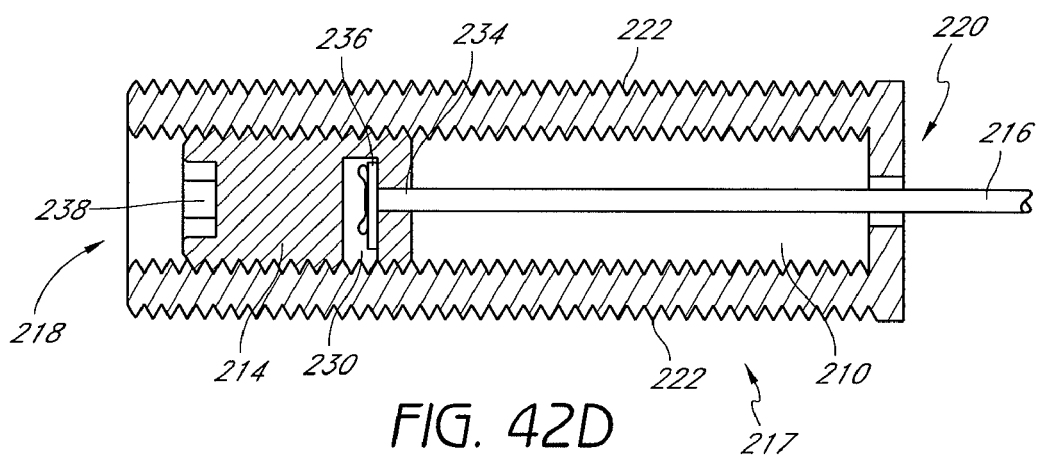
FIG. 42D

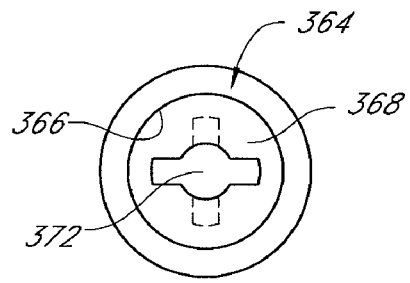 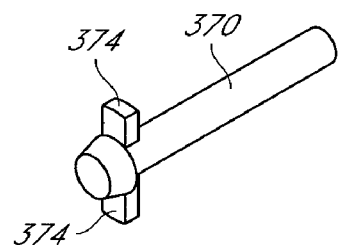
FIG. 50A  FIG. 50B
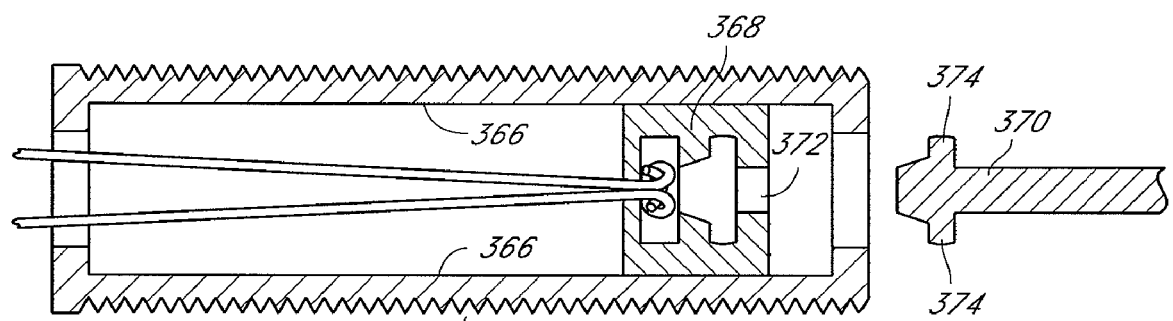
FIG. 50C
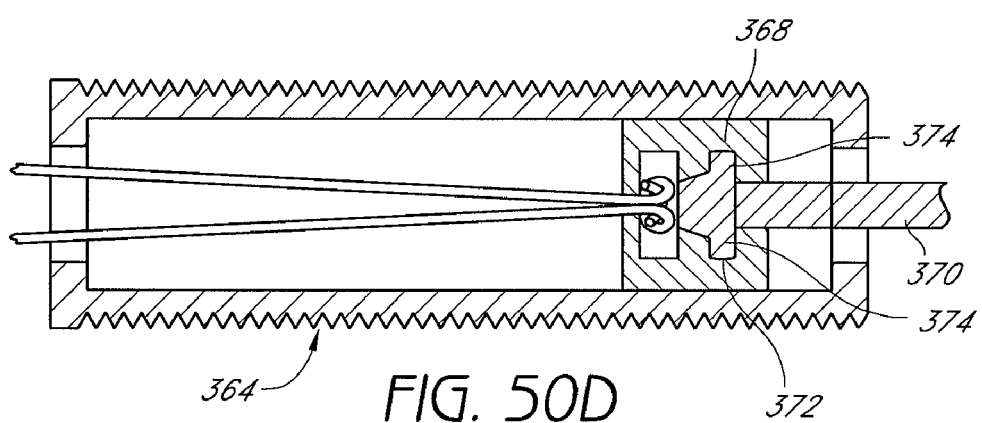
FIG. 50D

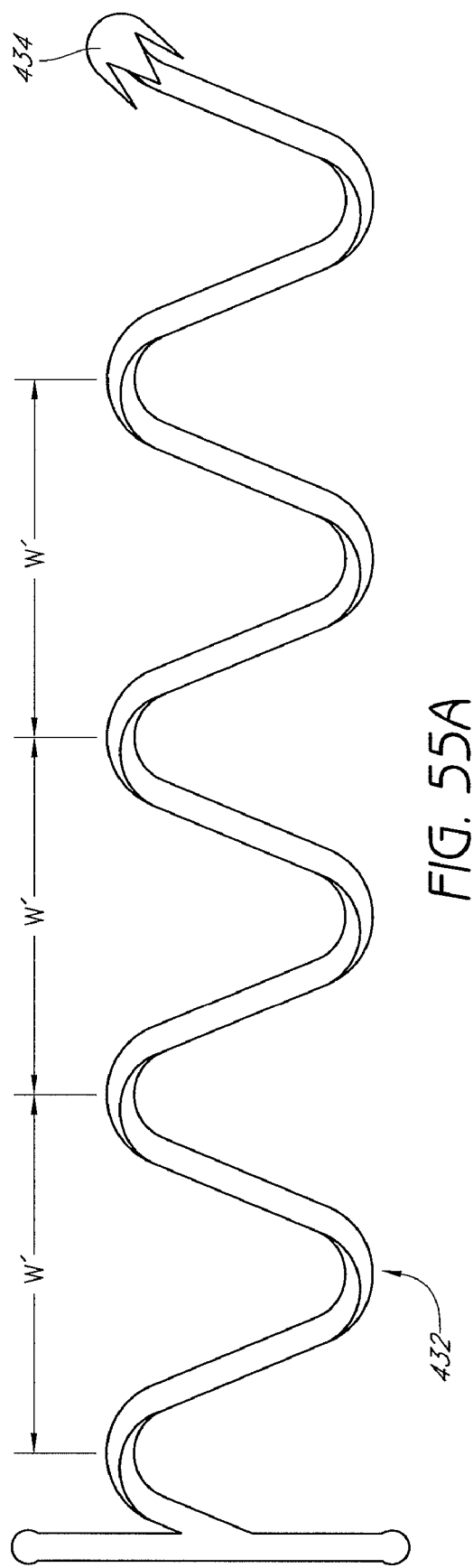
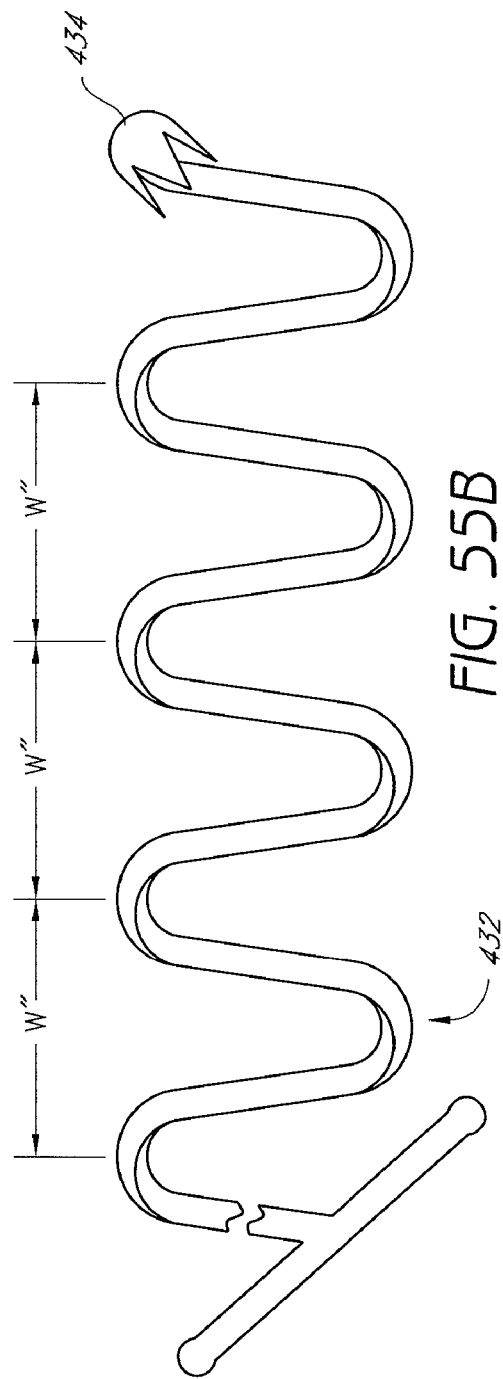
FIG. 55A
FIG. 55B

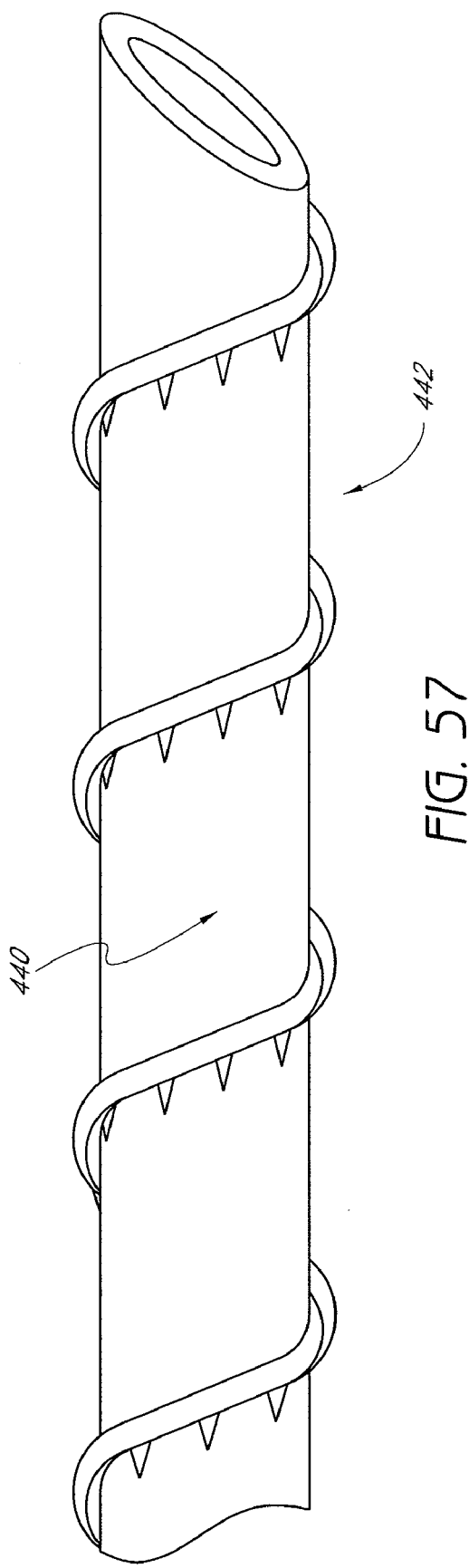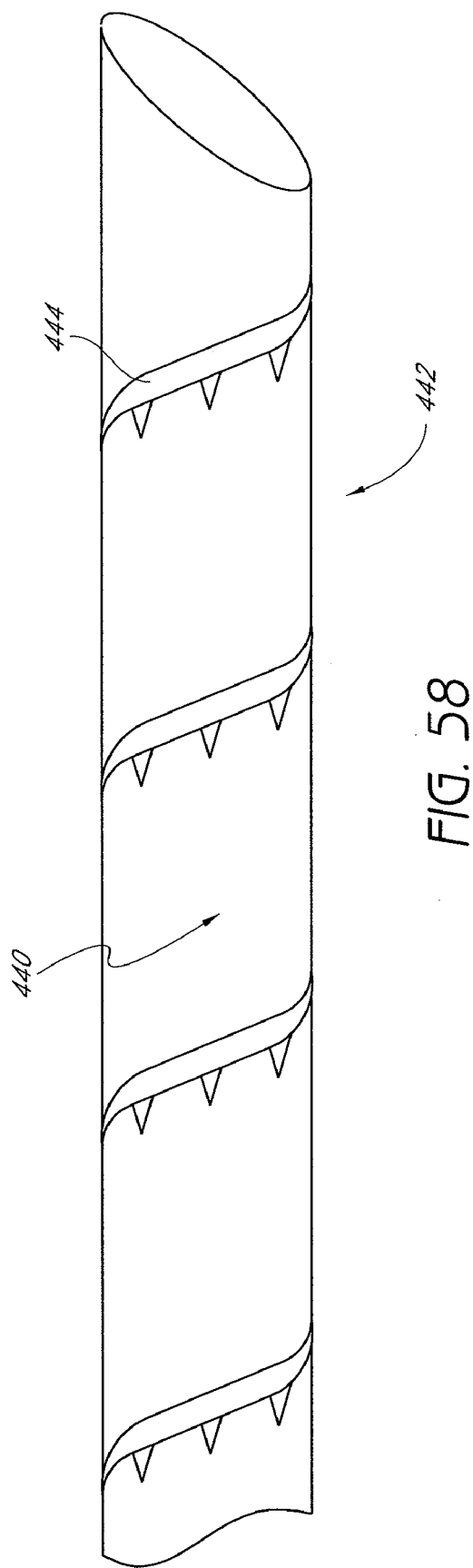
FIG. 57
FIG. 58

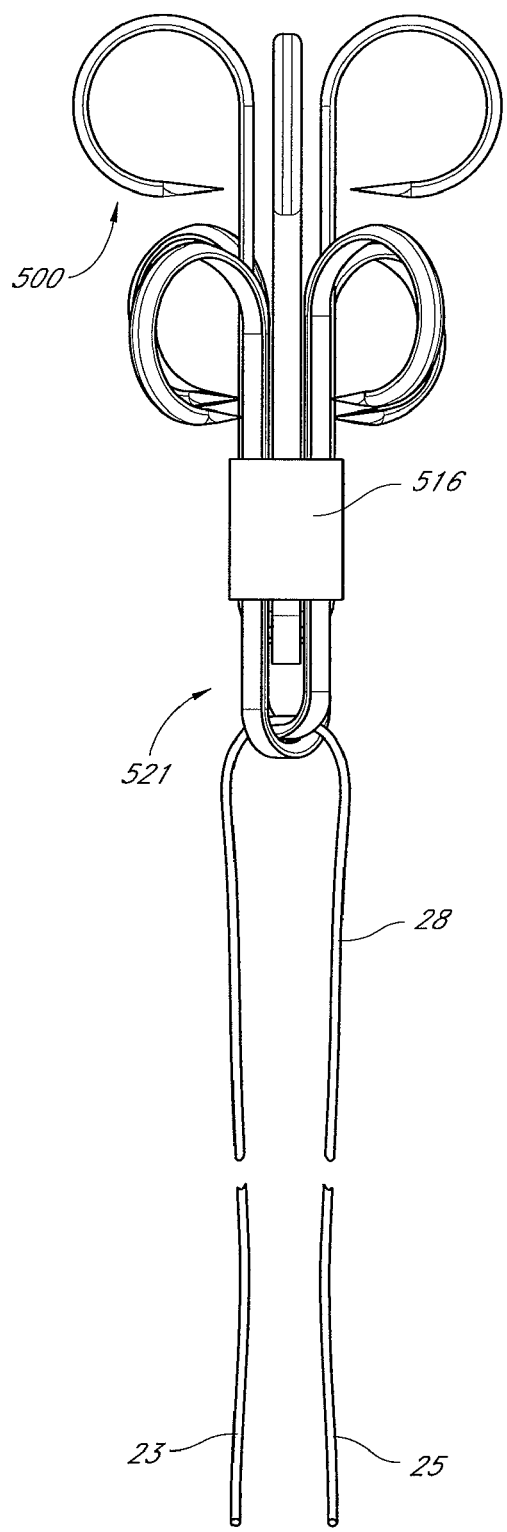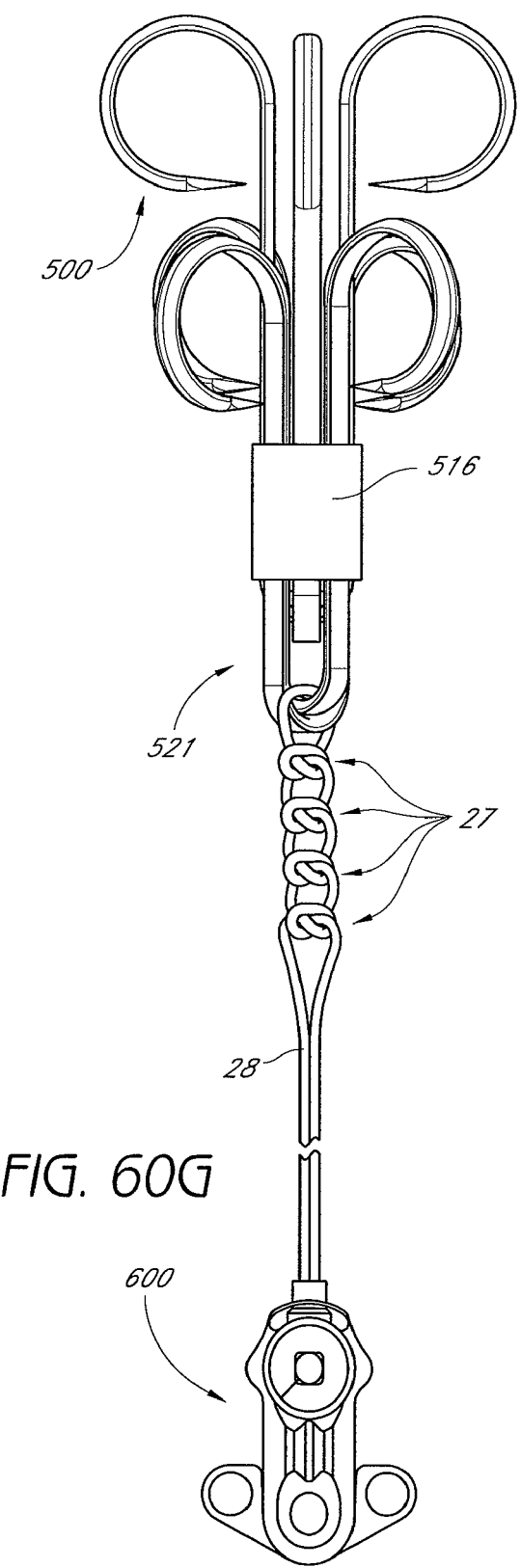
FIG. 60F
FIG. 60G

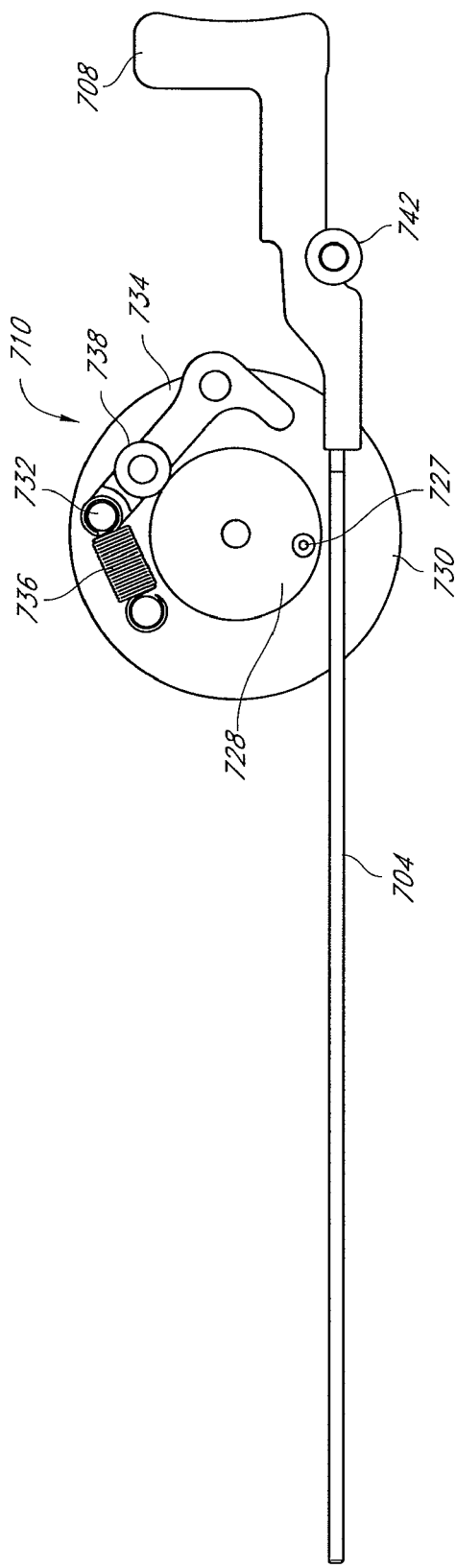
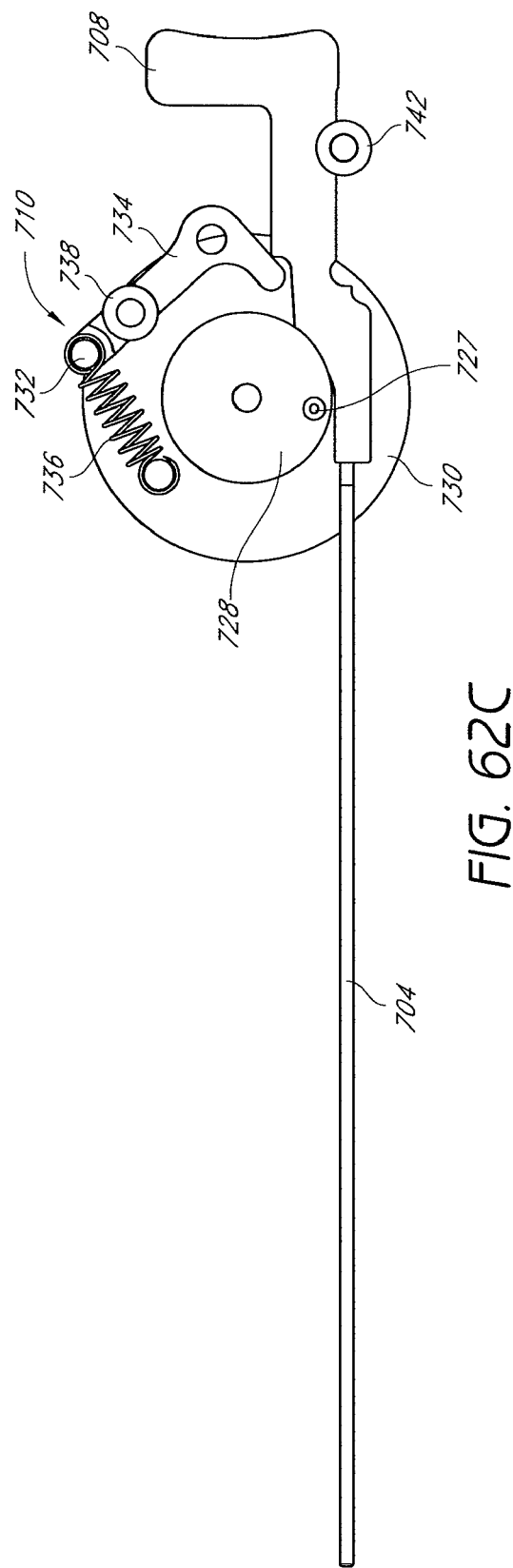
FIG. 62B
FIG. 62C

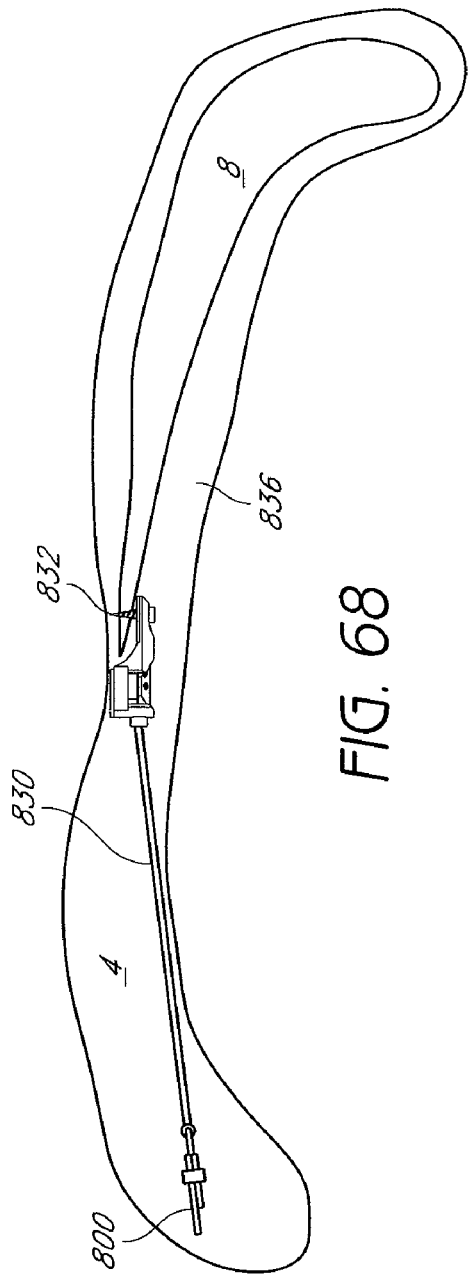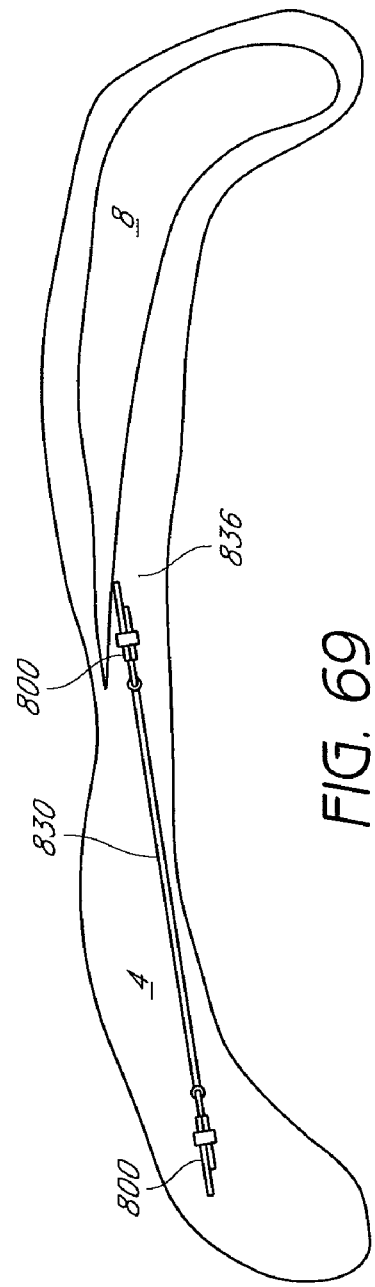

SYSTEM AND METHOD FOR TEMPORARY TONGUE SUSPENSION

INCORPORATION BY REFERENCE

This application claims priority under 35 U.S.C. §119(e) from provisional application Ser. No. 60/815,731 filed Jun. 21, 2006, the disclosure of which is incorporated by reference in its entirety. This application also incorporates by reference in their entirety each of the following: provisional application Ser. No. 60/650,867 filed Feb. 8, 2005, provisional application Ser. No. 60/726,028 filed Oct. 12, 2005, and utility application Ser. No. 11/349,067 filed Feb. 7, 2006.

BACKGROUND OF THE INVENTION

1. Field of the Invention

This invention relates generally to a system and method for treating upper airway obstruction, sleep disordered breathing, upper airway resistance syndrome and snoring by manipulating the structures of the oropharynx, including the tongue.

2. Description of the Related Art

Respiratory disorders during sleep are recognized as a common disorder with significant clinical consequences. During the various stages of sleep, the human body exhibits different patterns of brain and muscle activity. In particular, the REM sleep stage is associated with reduced or irregular ventilatory responses to chemical and mechanical stimuli and a significant degree of muscle inhibition. This muscle inhibition may lead to relaxation of certain muscle groups, including but not limited to muscles that maintain the patency of the upper airways, and create a risk of airway obstruction during sleep. Because muscle relaxation narrows the lumen of the airway, greater inspiratory effort may be required to overcome airway resistance. This increased inspiratory effort paradoxically increases the degree of airway resistance and obstruction through a Bernoulli effect on the flaccid pharyngeal walls during REM sleep.

Obstructive Sleep Apnea (OSA) is a sleep disorder that affects up to 2 to 4% of the population in the United States. OSA is characterized by an intermittent cessation of airflow in the presence of continued inspiratory effort. When these obstructive episodes occur, an affected person will transiently arouse, regain muscle tone and reopen the airway. Because these arousal episodes typically occur 10 to 60 times per night, sleep fragmentation occurs which produces excessive daytime sleepiness. Some patients with OSA experience over 100 transient arousal episodes per hour.

In addition to sleep disruption, OSA may also lead to cardiovascular and pulmonary disease. Apnea episodes of 60 seconds or more have been shown to decrease the partial pressure of oxygen in the lung alveoli by as much as 35 to 50 mm Hg. Some studies suggest that increased catecholamine release in the body due to the low oxygen saturation causes increases in systemic arterial blood pressure, which in turn causes left ventricular hypertrophy and eventually left heart failure. OSA is also associated with pulmonary hypertension, which can result in right heart failure.

Radiographic studies have shown that the site of obstruction in OSA is isolated generally to the supralaryngeal airway, but the particular site of obstruction varies with each person and multiple sites may be involved. A small percentage of patients with OSA have obstructions in the nasopharynx caused by deviated septums or enlarged turbinates. These obstructions may be treated with septoplasty or turbinate reduction procedures, respectively. More commonly, the oropharynx and the hypopharynx are implicated as sites of obstruction in OSA. Some studies have reported that the occlusion begins with the tongue falling back in an anterior-posterior direction (A-P) to contact with the soft palate and posterior pharyngeal wall, followed by further occlusion of the lower pharyngeal airway in the hypopharynx. This etiology is consistent with the physical findings associated with OSA, including a large base of tongue, a large soft palate, shallow palatal arch and a narrow mandibular arch. Other studies, however, have suggested that increased compliance of the lateral walls of the pharynx contributes to airway collapse. In the hypopharynx, radiographic studies have reported that hypopharyngeal collapse is frequently caused by lateral narrowing of the pharyngeal airway, rather than narrowing in the A-P direction.

OSA is generally diagnosed by performing overnight polysomnography in a sleep laboratory. Polysomnography typically includes electroencephalography to measure the stages of sleep, an electro-oculogram to measure rapid eye movements, monitoring of respiratory effort through intercostal electromyography or piezoelectric belts, electrocardiograms to monitor for arrhythmias, measurement of nasal and/or oral airflow and pulse oximetry to measure oxygen saturation of the blood.

Following the diagnosis of OSA, some patients are prescribed weight loss programs as part of their treatment plan, because of the association between obesity and OSA. Weight loss may reduce the frequency of apnea in some patients, but weight loss and other behavioral changes are difficult to achieve and maintain. Therefore, other modalities have also been used in the treatment of OSA, including pharmaceuticals, non-invasive devices and surgery.

Among the pharmaceutical treatments, respiratory stimulants and drugs that reduce REM sleep have been tried in OSA. Progesterone, theophylline and acetozolamide have been used as respiratory stimulants, but each drug is associated with significant side effects and their efficacy in OSA is not well studied. Protriptyline, a tricyclic antidepressant that reduces the amount of REM sleep, has been shown to decrease the frequency of apnea episodes in severe OSA, but is associated with anti-cholinergic side effects such as impotence, dry mouth, urinary retention and constipation.

Other modalities are directed at maintaining airway patency during sleep. Oral appliances aimed at changing the position of the soft palate, jaw or tongue are available, but patient discomfort and low compliance have limited their use. Continuous Positive Airway Pressure (CPAP) devices are often used as first-line treatments for OSA. These devices use a sealed mask which produce airflow at pressures of 5 to 15 cm of water and act to maintain positive air pressure within the pharyngeal airway and thereby maintain airway patency. Although CPAP is effective in treating OSA, patient compliance with these devices is low for several reasons. Sleeping with a sealed nasal mask is uncomfortable for patients. Smaller sealed nasal masks may be more comfortable to patients but are ineffective in patients who sleep with their mouths open, as the air pressure will enter the nasopharynx and then exit the oropharynx. CPAP also causes dry nasal passages and congestion.

Surgical treatments for OSA avoid issues with patient compliance and are useful for patients who fail conservative treatment. One surgery used for OSA is uvulopalatopharyngoplasty (UPPP). UPPP attempts to improve airway patency in the oropharynx by eliminating the structures that contact the tongue during sleep. This surgery involves removal of the uvula and a portion of the soft palate, along with the tonsils and portions of the tonsillar pillars. Although snoring is reduced in a majority of patients who undergo UPPP, the percentage of patients who experience reduced frequency of apnea episodes or improved oxygen saturation is substantially lower. Postoperatively, many patients that have undergone UPPP continue to exhibit oropharyngeal obstruction or concomitant hypopharyngeal obstruction. Nonresponders often have physical findings of a large base of tongue, an omega-shaped epiglottis and redundant aryepiglottic folds. UPPP is not a treatment directed at these structures. UPPP also exposes patients to the risks of general anesthesia and postoperative swelling of the airway that will require a tracheostomy. Excessive tissue removal may also cause velopharyngeal insufficiency where food and liquids enter into the nasopharynx during swallowing.

Laser-assisted uvulopalatopharyngoplasty (LAUP) is a similar procedure to UPPP that uses a CO2 laser to remove the uvula and portions of the soft palate, but the tonsils and the lateral pharyngeal walls are not removed.

For patients who fail UPPP or LAUP, other surgical treatments are available but these surgeries entail significantly higher risks of morbidity and mortality. In genioglossal advancement with hyoid myotomy (GAHM), an antero-inferior portion of the mandible, which includes the attachment point of the tongue musculature, is repositioned forward and in theory will pull the tongue forward and increase airway diameter. The muscles attached to the inferior hyoid bone are severed to allow the hyoid bone to move superiorly and anteriorly. Repositioning of the hyoid bone expands the retrolingual airspace by advancing the epiglottis and tongue base anteriorly. The hyoid bone is held in its new position by attaching to the mandible using fascia. Variants of this procedure attach the hyoid bone inferiorly to the thyroid cartilage.

A laser midline glossectomy (LMG) has also been tried in some patients who have failed UPPP and who exhibit hypopharyngeal collapse on radiographic studies. In this surgery, a laser is used to resect the midline portion of the base of the tongue. This involves significant morbidity and has shown only limited effectiveness.

In some patients with craniofacial abnormalities that include a receding mandible, mandibular or maxillomandibular advancement surgeries may be indicated for treatment of OSA. These patients are predisposed to OSA because the posterior mandible position produces posterior tongue displacement that causes airway obstruction. In a mandibular advancement procedure, the mandible is cut bilaterally posterior to the last molar and advanced forward approximately 10 to 14 mm. Bone grafts are used to bridge the bone gap and the newly positioned mandible is wire fixated to the maxilla until healing occurs. Mandibular advancement may be combined with a Le Fort I maxillary osteotomy procedure to correct associated dental or facial abnormalities. These procedures have a high morbidity and are indicated only in refractory cases of OSA.

Experimental procedures described in the clinical literature for OSA include the volumetric radiofrequency tissue ablation and hyoidplasty, where the hyoid bone is cut into several segments and attached to a brace that widens the angle of the U-shaped hyoid bone. The latter procedure has been used in dogs to increase the pharyngeal airway lumen at the level of the hyoid bone. The canine hyoid bone, however, is unlike a human hyoid bone because the canine hyoid bone comprises nine separate and jointed bones, while the human hyoid bone comprises five bones that are typically fused together.

Notwithstanding the foregoing, there remains a need for improved methods and devices for treating obstructive sleep apnea.

SUMMARY OF THE INVENTION

Methods and devices for manipulating soft tissue are provided. A tissue-engaging member is used to engage a region of soft tissue. The tissue-engaging member is attached to another site that is less mobile than the soft-tissue engaged by the tissue-engaging member. The less mobile site may be a bone or connective tissue attached to bone.

In some embodiments, methods and devices are disclosed for manipulating the tongue, and more particularly for temporarily suspending the tongue. One embodiment of the device comprises an elongate member with a retractable distal tissue-engaging tip that is movable within the lumen of tubular member configured for insertion into the tongue, preferably from an inferior surface of the jaw. The device may be used diagnostically assess the effect of performing tongue suspension in a patient prior to permanent implantation of a glossopexy device. The retractable distal tissue-engaging tip may be removed after diagnostic assessment, or left in place and attached to a temporary external securing device.

In one embodiment, a method for assessing airway obstruction is provided, comprising providing a glossopexy diagnostic system, the glossopexy diagnostic system comprising a cannula having a proximal end, a sharpened distal end, and a lumen therebetween, an elongate tissue anchor residing in the cannula lumen, the elongate tissue anchor having a proximal handle, a at least one distal outwardly biased barbs, and an elongate body therebetween, percutaneously inserting the cannula through the submental region of a patient toward the patient's tongue base, deploying the at least one barb in the tongue of the patient, pulling on the elongate tissue anchor from the chin to assess airway patency, repositioning the cannula with respect to the chin, maintaining cannula position with respect to the mandible by securing a clip relative to an external skin surface of the patient. The method may further comprise performing at least a portion of a sleep apnea study while maintaining the cannula position.

In another embodiment, a method for diagnosing airway obstruction is provided, comprising percutaneously inserting a tissue-engaging member through the submental region of a patient along a linear access pathway, engaging a tongue tissue site using the tissue-engaging member, forming tension in the tissue-engaging member, maintaining the tension in the tissue-engaging member by using a securing member pressed against the skin of the patient, and performing at least a portion of an apnea study on the patient while maintaining tension in the tissue-engaging member. The method may further comprise inserting a tubular member from a percutaneous insertion site toward the tongue tissue site, the tubular member comprising a proximal end, a sharpened distal end, and a lumen therebetween. The method may further comprise inserting the tissue-engaging member into the lumen of the tubular member. In some instances, the method may further comprise deploying the tissue-engaging member from the distal end of the tubular member. The method may also further comprise removing the tubular member from the patient before securing the repositioned tongue tissue site. The tubular member that is used may be a peel-away tubular member. The tissue-engaging member may comprise a proximal handle that is optionally a detachable proximal handle. The method may further comprise adjusting tension in the tissue-engaging member with the tubular member remaining within the patient. The tubular member or the elongate member may form a mechanical interfit with the securing member. In other embodiments, the tissue-engaging member forms a mechanical interfit with the securing member. The mechanical interfit may be a threaded interfit. Thus, in some embodiments, adjusting the tension in the tissue-engaging member comprises rotating the tubular member, securing member, or the tissue-engaging member. The method may also involve checking a plurality of indicia located on an external surface of the tubular member to determine the relative location of the tubular member in the tongue. The securing member may be pre-attached to the tissue-engaging member. In some embodiments, the securing member comprises a clamp or a blocking member having a threaded aperture. The blocking member may comprise a flexible pad.

In one embodiment, a system for performing tongue suspension is provided, comprising: a tissue-engaging assembly comprising a proximal handle, at least one distal tissue-engaging element having a linear non-deployed configuration and a non-linear deployed configuration, and a body therebetween, and an adjustable tensioning member configured to engage to the tissue-engaging assembly and press against an external skin surface of a patient. The proximal handle may be a detachable proximal handle, and the proximal handle and the adjustable tensioning member may be integrally formed. The adjustable tensioning member is configured to threadably engage to the tissue-engaging assembly. The system may further comprise a means for attaching the adjustable tensioning member to the patient's body. The tissue-engaging assembly may further comprise a cannula having a proximal handle, a sharpened distal end, and a lumen therebetween in which the body movably resides. The cannula may comprise indicia on an outer surface of the cannula. The adjustable tensioning member may comprise a clamp, which is optionally configured to clamp either the cannula or the body of the tissue-engaging assembly, or both.

In further embodiments, methods and devices are disclosed for manipulating the tongue. An implant is positioned within at least a portion of the tongue and may be secured to other surrounding structures such as the mandible and/or hyoid bone. In general, the implant is manipulated to displace at least a portion of the posterior tongue in an anterior or lateral direction, or to alter the tissue tension or compliance of the tongue.

In one embodiment of the invention, a method for treating a patient is provided, comprising the steps of providing a tongue remodeling system, the system comprising at least one tether support and at least one tongue element, the at least one tongue element having at least one anchor joined to at least one tether; accessing a region about the mandible; inserting the at least one anchor through a first pathway along the region about the mandible to a tongue; attaching at least one tether of the at least one tongue element to at least one tether support; positioning at least one tether support against the surface of the mandible; and fixing the at least one tether to the at least one tether support. The term "glossoplasty", as used herein, shall be given its ordinary meaning and shall also mean any change in the configuration and/or characteristics of the tongue and is also used interchangeably with the term "tongue remodeling". In some embodiments, at least a portion of the first pathway passes through the mandible. The method may further comprise the step of adjusting the tension of the at least one tether. The step of adjusting the tension of the at least one tether may comprise decreasing the tension or increasing the tension. In some instances, the at least one tether support of the providing step comprises an adjustable tether tension interface. In one embodiment, the method further comprises the steps of accessing the adjustable tether tension interface; and adjusting the tension of the at least one tether. In some embodiments, the first anchor of the providing step may comprise a wire coil, a T-tag, a polymer plug, or a fibrous or porous polymer plug. The first anchor of the providing step may also comprise a slotted tube having a distal end, a proximal end, and a plurality of expandable middle bands between the distal end and proximal end. The first tether may be secured to the distal end of the slotted tube or the proximal end of the slotted tube. In one embodiment, the slotted tube of the providing step may be self-expandable or expandable by shortening the slotted tube along its longitudinal length. The method may also further comprise the step of pulling the first tether to expand the slotted tube.

In embodiment of the invention, another method for treating a patient is provided, comprising the steps of providing a patient with an implanted adjustable tongue remodeling system, comprising an adjustment assembly and one or more tongue elements inserted through the tongue; wherein at least one tongue element comprises an anchor and a tether secured to the adjustment assembly at a securing point on the adjustment assembly; accessing the adjustment assembly; and adjusting the tension of one or more tongue elements by manipulating the adjustment assembly. The adjusting step may comprise altering the relative configuration of the adjustment assembly, moving the securing point relative to the adjustment assembly, releasing the tether from the adjustment assembly and resecuring the tether to the adjustment assembly, or altering the length of the tether.

In another embodiment, a method for treating a patient is provided, comprising the steps of providing a patient with an implanted tongue remodeling system comprising one or more tongue elements inserted through the tongue; wherein at least one tongue element comprises a first tissue anchor implanted within the tongue and a tether attached to the first tissue anchor; accessing the at least one tongue element; and withdrawing the tissue anchor from the tongue. The method may further comprise the step of deforming the tissue anchor.

In another embodiment, a method for treating a patient comprises engaging a first portion of the tongue and attaching said portion of the tongue to a bone using a tension element having a variable length, wherein the variable length of the tension element varies with the tension of the tension element.

In one embodiment, the invention comprises a method for treating a patient, the method comprises compressing tongue tissue, said compression being conducted by inserting a spiral structure into the tongue tissue. The spiral structure may comprise at least one tissue engagement structure.

In another embodiment, a method for treating a patient is provided, comprising changing tongue tissue compliance, said change being conducted by inserting a spiral structure into the tongue tissue.

In still another embodiment, a method for treating a patient is provided, comprising engaging a first portion of the tongue; engaging a second portion of the tongue; and altering the tissue compliance at least between the first portion and the second portion. The step of altering tissue compliance may comprise increasing the tissue tension. The method may also further comprise altering the tissue compliance about the first portion.

In another embodiment of the invention, a method for treating a patient is provided, comprising engaging a first portion of the tongue; engaging a second portion of the tongue; and changing the tissue compliance at least between the first portion and the second portion.

In another embodiment, a method for remodeling the tongue is provided, comprising the steps of providing a rigid elongate body having a shape; defining a non-linear pathway through the tongue; and inserting the rigid elongate body through the pathway. The rigid elongate body of the providing step may have a linear configuration. The method may further comprise the step of remodeling the tongue by reorienting the non-linear pathway with respect to the shape of the elongate body.

In one embodiment, a method for remodeling the tongue is provided, comprising the steps of providing an elongate body having a first configuration and a second configuration; inserting the elongate body in its first configuration through a pathway having a first configuration; and changing the elongate body from its first configuration to its second configuration. The method may further comprise the step of redistributing the tongue tissue about the pathway by changing the pathway to a second configuration. The first configuration of the pathway may be linear, non-linear, may comprise a curve or at least one convex segment and at least one concave segment.

In one embodiment of the invention, an implantable device for manipulating soft tissue is provided, comprising at least one tissue anchor; an elongate member attached to the at least one tissue anchor; and a securing assembly comprising a bony attachment structure and an elongate member securing structure, wherein the elongate member securing structure is adapted to be movable relative to the bony attachment structure while the elongate member is secured to the elongate member securing structure. The bony attachment structure may be adapted for insertion into the mandible. In some instances, the bony attachment structure has a cylindrical configuration and a threaded outer surface. The securing assembly may further comprise a moving interface component adapted to move the elongate member securing structure. In some embodiments, the bony attachment structure comprises an internal sealable cavity and the elongate member securing structure comprises a fluid seal adapted to provide a sliding seal within the internal sealable cavity of the bony attachment structure. The bony attachment structure may further comprise a pierceable membrane for accessing the internal sealable cavity. The bony attachment structure may also comprise a threaded cylindrical internal cavity and the elongate member securing structure may comprise a cylinder having outer threads complementary to the threaded cylindrical internal cavity of the bony attachment structure and a rotatably attached securing interface. The bony attachment structure may also further comprise a longitudinal groove and the rotatably attached securing interface comprises a protrusion having a complementary configuration to the longitudinal groove of the bony attachment structure. The bony attachment structure may comprise an internal friction cavity and the elongate member securing structure may comprise a friction surface configured to provide a frictional fit within the internal friction cavity of the bony attachment structure. In some embodiments, the elongate member securing structure is adapted to provide a sliding frictional fit within the internal friction cavity of the bony attachment structure. In other embodiments, the elongate member securing structure further comprises a manipulation interface adapted to reversibly engage a manipulation tool. In still other embodiments, the bony attachment structure comprises an internal tapered cavity and the elongate member securing structure comprises a base with at least two radially inwardly deflectable prongs adapted to engage the elongate member.

In one embodiment of the invention, a device for manipulating the tongue is provided, comprising a variable pitch spiral having a first portion with a first pitch and a second portion with a second pitch, the spiral comprising a biocompatible material dimensioned to fit within a tongue. The first portion may have a wide pitch and the second portion may have a narrow pitch. In other embodiments, the first portion has a narrow pitch and the second portion has a wide pitch.

In one embodiment, a device for manipulating the tongue is provided, comprising an elongate member having a first end, a second end, an middle section between the first end and the second end having at least one enlarged segment, wherein the first end is adapted to attach to a bony structure and the second end is adapted to attach to either a bony structure, the first end or the middle section, and wherein the at least one enlarged segment is adapted for positioning in the tongue. In some embodiments, the at least one enlarged segment may be at least partially formed in situ in the tongue, a tissue anchor, a sleeve or a coating.

In one embodiment, a method for manipulating the tongue is provided, comprising the steps of providing a tongue implant having a first portion with a first configuration and a second portion with a second configuration, the implant comprising a biocompatible material dimensioned to fit within a tongue; creating a pathway in the tongue by passing the first portion of the tongue implant; passing the second portion of the tongue implant into the pathway; and conforming the pathway in the tongue to the second portion of the tongue implant. The providing step may comprise providing a tongue implant that is a variable pitch spiral having a first portion with a first spiral pitch configuration and the second portion has a second spiral pitch configuration. The method may further comprise the steps of compressing the tissue about the pathway and/or stretching the tissue about the pathway.

In one embodiment, a method for treating a patient is provided, comprising: providing a tongue remodeling system, the system comprising at least one tether support and at least one tongue element, the at least one tongue element having at least one expandable tissue anchor joined to at least one tether; accessing a region about the mandible; inserting the at least one expandable tissue anchor through a first pathway along the region about the mandible to a tongue; attaching the at least one tether of the at least one tongue element to the at least one tether support; positioning the at least one tether support against the mandible; and fixing the at least one tether support to the mandible. The method may further comprise expanding the at least one expandable tissue anchor joined to the at least one tether. The expandable tissue anchor of the providing step may be self-expandable, may comprise a plurality of expandable elongate members, may comprise a plurality of expandable elongate piercing members, or may comprise a plurality of expandable tissue-grasping members. The fixing step may be performed before the attaching step. In some embodiments, at least a portion of the first pathway may pass through the mandible.

In another embodiment, a method for treating a patient is provided, comprising: providing a tongue element having an attachment end and an expandable tissue-anchoring end; inserting the expandable tissue-anchoring end into the tongue; and securing the attachment end of the tongue element to a body structure. The securing of the attachment end of the tongue element to the body structure may be performed with an adjustment assembly. The adjustment assembly may comprise a moving part, a non-moving part and a movement interface between the moving part and the non-moving part. The expandable tissue-anchoring end may comprise one or more tissue-grasping members. The expandable tissue-anchoring end may comprise at least two tissue-piercing members. In some embodiments, one or more tissue-grasping members may be metallic, and/or may be radially expandable elongate members. The expandable tissue-anchoring end of the providing step may comprise a wire coil, a T-tag, an expandable polymer plug, and/or a fibrous or porous expandable polymer plug. The expandable tissue-anchoring end may comprise a slotted tube having a distal end, a proximal end, and a plurality of expandable middle bands between the distal end and proximal end. The at least one tether may be secured to the distal end of the slotted tube the proximal end of the slotted tube. The slotted tube of the providing step may be self-expandable. The slotted tube may be expandable by shortening the slotted tube along its longitudinal length. The method may further comprise the step of pulling the at least one tether to expand the slotted tube.

In another embodiment, a method for treating a patient is provided, comprising: accessing a tissue anchor implanted in a tongue, the tissue anchor having a deployment configuration and a removal configuration; deforming the tissue anchor to the removal configuration; and withdrawing the tissue anchor from the tongue. The tissue anchor may further comprise a proximal tether. The method may further comprise exposing the proximal tether. Accessing the tissue anchor implanted in the tongue may comprise passing a tubular member along the proximal tether, the tubular member comprising a distal opening, a proximal opening and a lumen therebetween. Deforming the tissue anchor to the removal configuration may comprise collapsing the tissue anchor into the lumen of the tubular member. Withdrawing the tissue anchor from the tongue may comprise withdrawing the tubular member from the tongue. The tubular member may further comprise a longitudinal slot contiguous with the lumen of the tubular member. The longitudinal slot of the tubular member may be contiguous with the distal opening of the tubular member. The tubular member further may comprise a movable slot blocking member capable of blocking the distal portion of the longitudinal slot of the tubular member. The movable slot blocking member may be a slidable slot blocking member or a rotatable slot blocking member. The movable slot blocking member may be located within the lumen of the tubular member.

In one embodiment, a method for treating a patient is provided, comprising: providing a tongue remodeling system, the system comprising at least one tether support and at least one tongue element, the at least one tongue element having at least one tissue engaging structure joined to at least one tether having a length and a tension; accessing a region about the mandible; positioning the tissue engaging structure within a tongue; and attaching the at least one tether support to the mandible; wherein the at least one tether of the at least one tongue element may be attached to the at least one tether support, the at least one tether support comprising an adjustable tether interface. The method may further comprise: accessing the adjustable tether interface; and adjusting the length of the at least one tether between the tissue engaging structure and the adjustable tether interface. Adjusting the length of the at least one tether may comprise decreasing the tension of the at least one tether, increasing the tension of the at least one tether, or adjusting the dynamic response of the at least one tether. The at least one tether of the at least one tongue element may be releasably attached to the at least one tether support.

In another embodiment, a method for treating a patient is provided, comprising: accessing an adjustment assembly of a patient with an implanted adjustable tongue remodeling system comprising the adjustment assembly and one or more tongue elements inserted through the tongue; wherein at least one tongue element may comprise an anchor and a tether secured to the adjustment assembly at a securing point on the adjustment assembly; and adjusting one or more tongue elements by manipulating the adjustment assembly. Said adjusting may comprise altering the relative configuration of the adjustment assembly, moving the securing point of the adjustment assembly and/or altering the length of the tether between the anchor and the securing point of the adjustment assembly. Said adjusting may be performed without unsecuring the tether from the securing point of the adjustment assembly. The may further comprise securing the adjustment assembly to a mandible. The adjustment assembly may comprise a rotational component. The rotational component may comprise a spool.

In another embodiment, a method for treating a patient is provided, comprising: providing a tongue element having an attachment end and a tissue-engaging end; inserting the tissue-engaging end into the tongue; and securing the attachment end of the tongue element to a body structure using an adjustment assembly. The tongue element may comprise a tether having a length between the tissue-engaging end and the adjustment assembly, wherein the length is adjustable by the adjustment assembly. The adjustment assembly may be a rotation assembly, a spool assembly, a helical assembly, a slide assembly, a pivot assembly, or a combination thereof. The patient's tongue may be engaged with a tissue engaging structure attached about the first portion of the tether, or a tissue anchor that pierces through tongue tissue. Tension between the first and second portions of the tether may be adjustable while the first portion of the tether remains engaged with the patient's tongue and the second portion of the tether remains attached relative to the body structure. The body structure may be the mandible. The attachment end of the tongue element may be secured through a bone screw. The adjustment assembly may comprise a moving part, a non-moving part and a movement interface between the moving part and the non-moving part. The adjustment assembly may comprise a positionable tongue element attachment site. The adjustment assembly may comprise a locking member.

In another embodiment, a method for manipulating soft tissue is provided, comprising: accessing an adjustment structure attached to at least one tissue anchor by a connector, the at least one tissue anchor engaging the soft tissue and the adjustment structure being fixed relative to a body structure, the connector having a length between the at least one tissue anchor and the adjustment structure; and changing the length of the connector between the at least one tissue anchor and the adjustment structure by manipulating the adjustment structure without detaching the at least one tissue anchor from the adjustment structure. The tissue anchor may be at least partially located within the tongue. The adjustment structure may be fixed relative to a mandible. The tissue anchor may be at least partially located within the soft palate. The adjustment structure may be fixed relative to a hard palate.

In one embodiment, an implantable device for manipulating soft tissue is provided, comprising: at least one tissue engaging structure; an elongate member attached to the at least one tissue anchor; and a securing assembly comprising a bony attachment structure and a movable securing member, wherein the movable securing member may be adapted to be movable relative to the bony attachment structure while the elongate member may be secured to the movable securing member. The tissue engaging structure may be an anchor adapted to pierce the soft tissue. The movable securing member may be rotatable, slidable, and/or pivotable. The movable securing member may be a rotatable hub, or a spool. The bony attachment structure may be adapted for attachment to the mandible and/or for insertion into the mandible. The bony attachment structure has a cylindrical configuration and a threaded outer surface. The securing assembly further may comprise a moving interface component adapted to move the movable securing member. The bony attachment structure may comprise an internal sealable cavity and the movable securing member may comprise a fluid seal adapted to provide a sliding seal within the internal sealable cavity of the bony attachment structure. The bony attachment structure may further comprise a pierceable membrane for accessing the internal sealable cavity. The bony attachment structure may comprise a threaded cylindrical internal cavity and the movable securing member may comprise a cylinder having outer threads complementary to the threaded cylindrical internal cavity of the bony attachment structure and a rotatably attached securing interface. The bony attachment structure further may comprise a longitudinal groove and the rotatably attached securing interface may comprise a protrusion having a complementary configuration to the longitudinal groove of the bony attachment structure. The bony attachment structure may comprise an internal friction cavity and the movable securing member may comprise a friction surface configured to provide a frictional fit within the internal friction cavity of the bony attachment structure. The movable securing member may be adapted to provide a sliding frictional fit within the internal friction cavity of the bony attachment structure. The movable securing member further may comprise a manipulation interface adapted to reversibly engage a manipulation tool. The bony attachment structure may comprise an internal tapered cavity and the movable securing member may comprise a base with at least two radially inwardly deflectable prongs adapted to engage the elongate member.

In another embodiment, an implantable device for manipulating soft tissue is provided, comprising: at least one tissue anchor; an elongate member attached to the at least one tissue anchor; and a securing assembly comprising a bony attachment structure and a rotational securing structure. The rotational securing structure may be a spool.

In another embodiment, a device for manipulating the tongue is provided, comprising a variable pitch spiral having a first portion with a first pitch and a second portion with a second pitch, the spiral comprising a biocompatible material dimensioned to fit within a tongue. The first portion may have a wide pitch and the second portion has a narrow pitch, or the first portion may have a narrow pitch and the second portion has a wide pitch.

In another embodiment, an implantable device for manipulating soft tissue is provided, comprising: at least one tissue anchor; a securing assembly comprising a bony attachment structure; an elongate member attached to the at least one tissue anchor and having a length between the at least one tissue anchor and the securing assembly; and a means for adjusting the length of the elongate member. The securing assembly may further comprise the means for adjusting the length of the elongate member.

In another embodiment, a tissue anchoring system for engaging soft tissue is provided, comprising: at least one deformable hook element, the at least one hook element comprising an elongate body having a proximal portion and a sharp distal end, wherein the at least one hook element when unrestrained curls to form an arcuate structure; and a tether attached about the proximal portion of the at least one hook element. The at least one deformable hook element may be a plurality of deformable hook elements. The plurality of deformable hook elements may be arranged circumferentially, or in a generally planar configuration. The hook elements when unrestrained may curl back toward themselves to form a loop-like structure. The tissue anchoring system may further comprise a band about the proximal portions of the hook elements. The tissue anchoring system may further comprise a proximal group of hook elements and a distal group of hook elements. The hook elements may comprise symmetrical U-shaped planar structures with sharp distal tips on each end. The tissue anchoring system may further comprise a delivery device having a lumen adapted to receive and restrain the hook elements in a generally linear configuration, wherein the hook elements when advanced out of the delivery device curl back toward themselves to engage tissue.

In another embodiment, a tissue anchoring system for engaging soft tissue is provided, comprising: at least one means for expandable curled tissue engagement; and a tether attached to the at least one means for expandable curled tissue engagement.

In another embodiment, a tissue anchoring system for engaging soft tissue is provided, comprising: a plurality of deformable hook elements spaced circumferentially about each other, each of the hook element comprising an elongate body having a proximal portion and a sharp distal end, wherein the hook elements when unrestrained curls to form an arcuate structure; and a tether attached about the proximal portion of the hook elements. The plurality of deformable hook elements may comprise at least two pairs of deformable hooks elements joined together about the proximal portions of their elongate bodies. The at least two pairs of deformable hook elements may be joined proximally by a band. The at least two pairs of deformable hook elements may comprise four pairs of deformable hook elements. The at least two pairs of deformable hook elements may be arranged circumferentially, or in a generally planar configuration. The generally planar configuration may be a generally planar nested configuration or a generally planar stacked configuration.

In one embodiment, a method for treating a patient is provided, comprising: providing a palate remodeling system, the system comprising at least one tether support and at least one palate element, the at least one palate element having at least one expandable tissue anchor joined to at least one tether; accessing a region about a hard palate; inserting the at least one expandable tissue anchor through a first pathway along the region about the hard palate to a soft palate; attaching the at least one tether of the at least one palate element to the at least one tether support; positioning the at least one tether support about the hard palate; and fixing the at least one tether support about the hard palate. Fixing the at least one tether support about the hard palate may comprise fixing the at least one tether support to the hard palate, or to mucosal tissue overlying the hard palate.

In another embodiment, a method for treating a patient is provided, comprising: providing a soft palate element having an attachment end and an expandable tissue-anchoring end; inserting the expandable tissue-anchoring end into the soft palate; securing the attachment end of the palate element to a body structure. The body structure may be a palatine bone, a hard palate, or a nasal turbinate.

In another embodiment, a method for treating a patient is provided, comprising: accessing a tissue anchor implanted in a soft palate, the tissue anchor having a deployment configuration and a removal configuration; deforming the tissue anchor to the removal configuration; and withdrawing the tissue anchor from the soft palate.

In still another embodiment, a method for treating a patient is provided, comprising: accessing an adjustment assembly of a patient with an implanted adjustable soft palate remodeling system comprising the adjustment assembly and one or more soft palate elements inserted into the soft palate; wherein at least one soft palate element may comprise an anchor and a tether secured to the adjustment assembly at a securing point on the adjustment assembly; and adjusting one or more soft palate elements by manipulating the adjustment assembly.

BRIEF DESCRIPTION OF THE DRAWINGS

The structure and method of using the invention will be better understood with the following detailed description of embodiments of the invention, along with the accompanying illustrations, in which:

FIGS. 7I and 7J are detailed views of the distal anchors and removal tool in FIGS. 7G and 7H.

FIGS. 42A through 42D illustrate one embodiment of the invention comprising an adjustable mandible securing assembly with a non-rotating tether interface.

FIGS. 50A through 50F illustrate another embodiment of a mandible securing assembly comprising an inner resistance surface and tether interface.

FIGS. 55A and 55B represent another embodiment of the invention comprising a tissue compression coil.

FIG. 57 represents another embodiment of the invention comprising a barbed tissue compression coil positioned on an implantation needle.

FIG. 58 represents another embodiment of the invention comprising a barbed tissue compression coil positioned on a fitted groove implantation needle.

FIG. 60F illustrates a tether looped through the distal anchor and FIG. 60G illustrates the tether knotted to the distal anchor and the tether ends attached to a securing assembly.

FIGS. 61I and 61K illustrate an implanted distal anchor and securing assembly before and during adjustment of the securing assembly, respectively.

FIGS. 62B and 62C are left elevational views of the delivery tool without the delivery tool housing and delivery tube in the loaded and deployed configurations, respectively.

FIG. 68 is a schematic sagittal cross sectional view of the soft and hard palate with a palate anchor anchored to the hard palate.

FIG. 69 is a schematic sagittal cross sectional view of the soft and hard palate with a palate anchor anchored to the mucosal tissue overlying the hard palate.

FIGS. 71A to 71I are schematic views of one embodiment for recapturing an implanted anchor. FIG. 71C is a detailed view of FIG. 71B. FIG. 71E is a detailed view of FIG. 71D.

DETAILED DESCRIPTION OF THE PREFERRED EMBODIMENTS

A. Anatomy of the Pharynx

Figure 1:
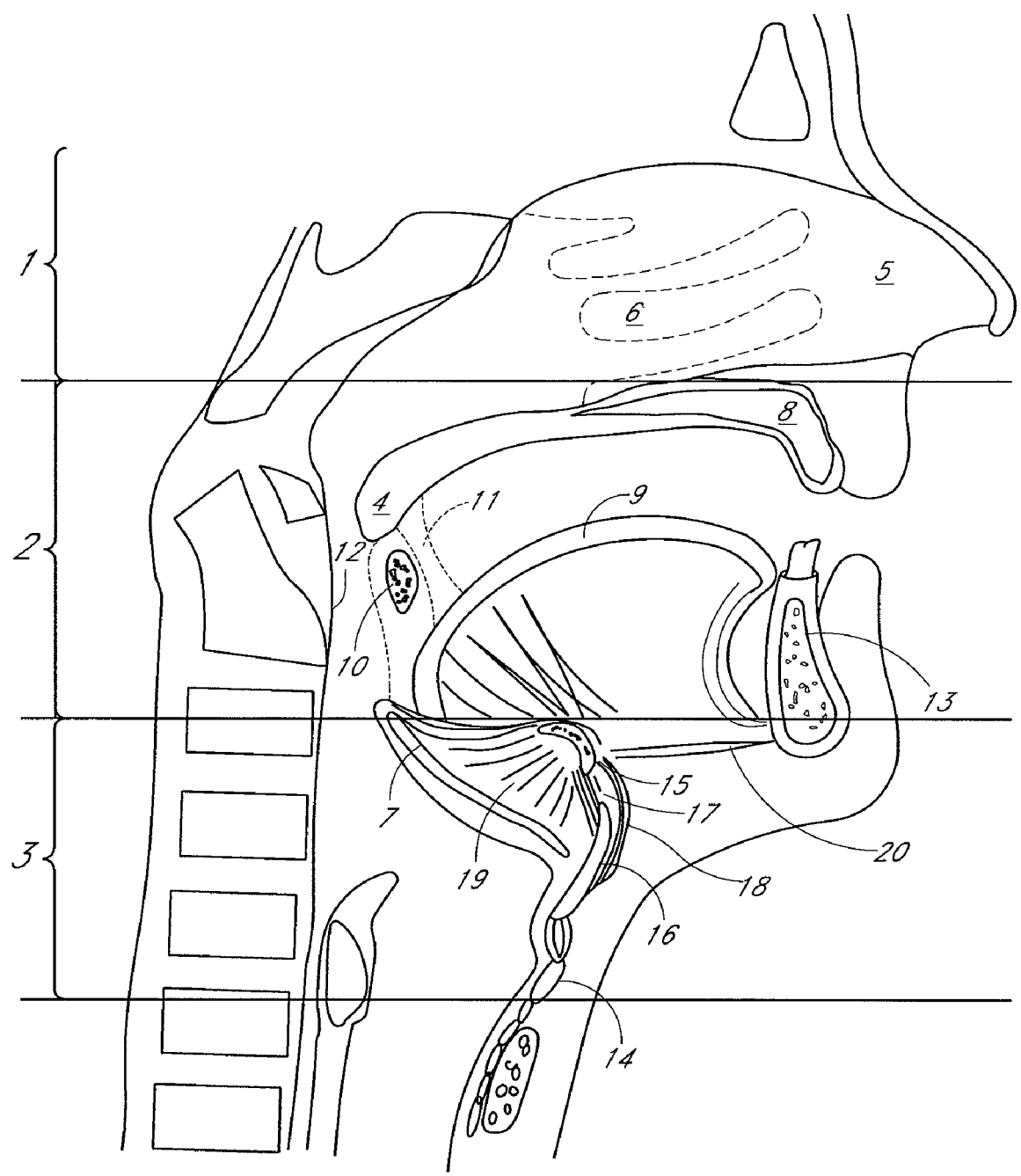
FIG. 1 is a schematic sagittal view of the pharynx.

FIG. 1 is a sagittal view of the structures that comprise the pharyngeal airway and may be involved in obstructive sleep apnea. The pharynx is divided, from superior to inferior, into the nasopharynx 1, the oropharynx 2 and the hypopharynx 3. The nasopharynx 1 is a less common source of obstruction in OSA. The nasopharynx is the portion of the pharynx above the soft palate 4. In the nasopharynx, a deviated nasal septum 5 or enlarged nasal turbinates 6 may occasionally contribute to upper airway resistance or blockage. Only rarely, a nasal mass, such as a polyp, cyst or tumor may be a source of obstruction.

The oropharynx 2 comprises structures from the soft palate 4 to the upper border of the epiglottis 7 and includes the hard palate 8, tongue 9, tonsils 10, palatoglossal arch 11, the posterior pharyngeal wall 12 and the mandible 13. The mandible typically has a bone thickness of about 5 mm to about 10 mm anteriorly with similar thicknesses laterally. An obstruction in the oropharynx 2 may result when the tongue 9 is displaced posteriorly during sleep as a consequence of reduced muscle activity during REM sleep. The displaced tongue 9 may push the soft palate 4 posteriorly and may seal off the nasopharynx 1 from the oropharynx 2. The tongue 9 may also contact the posterior pharyngeal wall 12, which causes further airway obstruction.

The hypopharynx 3 comprises the region from the upper border of the epiglottis 7 to the inferior border of the cricoid cartilage 14. The hypopharynx 3 further comprises the hyoid bone 15, a U-shaped, free floating bone that does not articulate with any other bone. The hyoid bone 15 is attached to surrounding structures by various muscles and connective tissues. The hyoid bone 15 lies inferior to the tongue 9 and superior to the thyroid cartilage 16. A thyrohyoid membrane 17 and a thyrohyoid muscle 18 attaches to the inferior border of the hyoid 15 and the superior border of the thyroid cartilage 16. The epiglottis 7 is infero-posterior to the hyoid bone 15 and attaches to the hyoid bone by a median hyoepiglottic ligament 19. The hyoid bone attaches anteriorly to the inferoposterior aspect of the mandible 13 by the geniohyoid muscle 20.

B. Tongue Remodeling

Embodiments of the present invention provide methods and devices for manipulating the airway. It is hypothesized that the laxity in pharyngeal structures contributes to the pathophysiology of obstructive sleep apnea, snoring, upper airway resistance and sleep disordered breathing. This laxity may be intrinsic to the oropharyngeal structures and/or may be affected by interrelationships between pharyngeal structures and other body structures. For example, in some studies, the cure rates in selected patients undergoing UPPP is as low as 5% to 10%. (Sher A E et al., "The efficacy of surgical modifications of the upper airway in adults with obstructive sleep apnea syndrome" Sleep, 1996 February; 19(2):156-77, herein incorporated by reference). These low cure rates may be affected by continued occlusion of the airway by structures unaffected by the surgery, such as the tongue. By biasing at least a portion of the posterior tongue or base of the tongue in at least a generally anterior and/or lateral direction, functional occlusion of the oropharynx may be prevented or reduced. Typically, this bias may be created by altering a distance or tension between a location in the tongue and an anchoring site, such as the mandible. In other instances, the bias may be created by altering the length or amount of a structure located in the tongue. In some instances, the bias provided to the tongue may only affect the mechanical characteristics tongue during tongue movement or in specific positions or situations. Thus, the dynamic response of the tongue tissue to mechanical forces or conditions may or may not occur with static changes, although static changes typically will affect the dynamic response of the tongue tissue. The embodiments of the invention described herein, however, are not limited to this hypothesis.

Although surgical and non-surgical techniques for biasing the tongue anteriorly are currently available, these techniques suffer from several limitations. For example, the Repose® system (InfluENT® Medical, New Hampshire) utilizes a bone screw attached to the lingual cortex of the mandible and a proline suture looped through the posterior tongue and bone screw, where the suture ends are tied together at some point along the suture loop to prevent posterior tongue displacement. In one study of 43 patients, four patients developed infections of the floor of the mouth and required antibiotics. One patient developed dehydration caused by painful swallowing, requiring intravenous fluids, and another patient developed delayed GI bleeding requiring hospitalization. (Woodson B T, "A tongue suspension suture for obstructive sleep apnea and snorers", Otolaryngol Head Neck Surg. 2001 March; 124(3):297-303). In another study of 19 patients undergoing combined UPPP and Repose® implantation, two patients developed submandibular infection requiring antibiotics, and one patient developed a hematoma in the floor of the mouth requiring drainage. In addition, one patient extruded the suture four weeks after implantation and another patient developed a persistent lump/globus sensation at the base of the tongue requiring removal of the Repose® system. (Miller F R et al., "Role of the tongue base suspension suture with The Repose® System bone screw in the multilevel surgical management of obstructive sleep apnea", Otolaryngol Head Neck Surg. 2002 April; 126(4):392-8).

By developing a tongue remodeling system that can be adjusted before, during and/or after the initial implantation procedure, a device and method for treating a patient with breathing problems may be better tolerated and less prone to treatment failure. For example, by adjusting the tension or bias of the implant, suture migration, suture extrusion, and/or dysphagia may be avoided or corrected. In another embodiment of the invention, the tongue remodeling system alters the structural characteristics of the tongue with an anterior or lateral bias force rather than a fixed length anchoring of the tongue to a body structure. This bias may reduce dysphagia or odynophagia associated with existing tongue suspension devices and procedures. In other embodiments, the tongue may be remodeled by altering the tissue compliance of at least a portion of the tongue. By inserting a prosthesis into the tongue tissue, tongue tissue compliance is changed and may alter the tongue response to forces acting during obstructive sleep apnea. The change in compliance may or may not be associated with a change in the position of the tongue. In some instances, embodiments of the tongue remodeling system can be implanted through an antero-inferior access site of the mandible. Implantation of the system that avoids the transoral route may improve infection rates that occur with other tongue related devices and procedures.

C. Tissue Anchor

Figure 2:
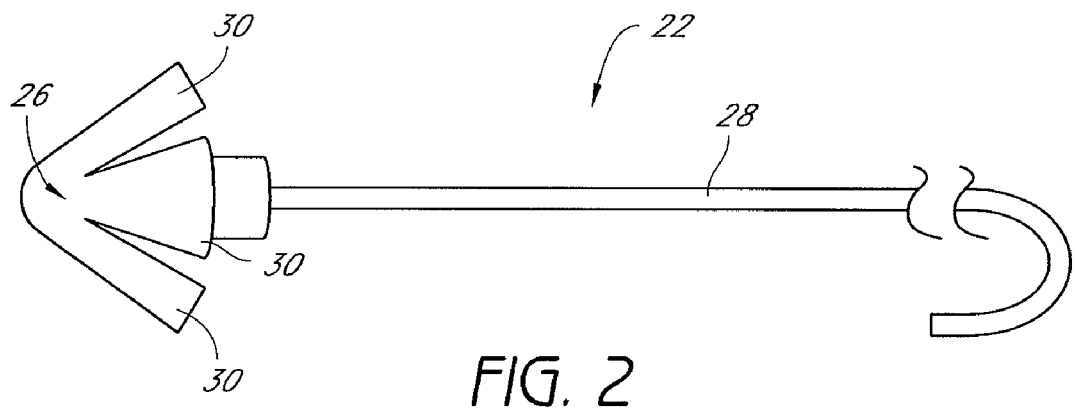
FIG. 2 is a schematic elevational view of one embodiment of a tongue element.
Figure 3A:
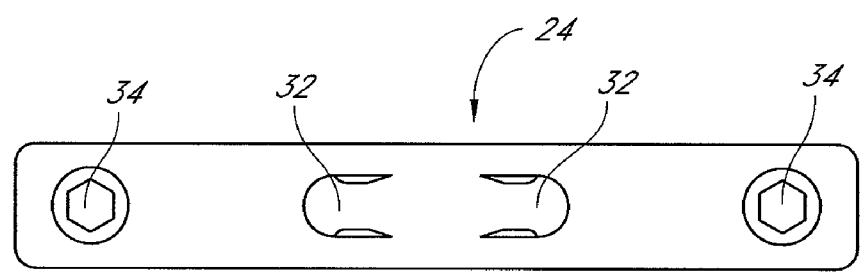
FIGS. 3A and 3B illustrate anterior and side elevational views of one embodiment of a mandible securing assembly.
Figure 3B:
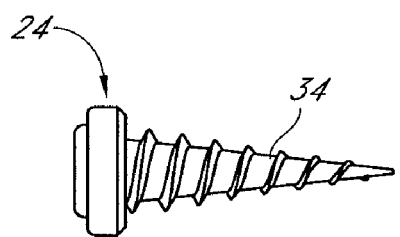

In one embodiment, depicted in FIGS. 2, 3A and 3B, the invention comprises a tongue remodeling system having one or more tongue elements 22 and at least one securing assembly 24. As depicted in FIG. 2, at least one tongue element 22 comprises a distal tissue anchor 26 attached to a proximal tether 28. The distal anchor 26 typically is a soft tissue anchor adapted for implantation within the tongue 9. The soft tissue anchor 26 may comprise any of a variety of structures capable of engaging the surrounding tissue. These structures may have pointed, sharp or blunt tissue engagement structures 30. In some instances, the distal anchor 26 has a first reduced diameter configuration for delivery into the tongue tissue and a second expanded diameter configuration for engaging the surrounding tissue. In other embodiments, the distal anchor 26 has a fixed configuration.

The securing assembly 24 is configured to provide a stable position about the mandible 13 or other structure adjacent to the mandible 13 and comprises one or more securing interfaces 32 to which one or more proximal tethers 28 may be secured. In some embodiments, the securing assembly 24 may comprise a bone anchor or bone screw, a clip, or a staple for attaching the proximal tether 28 to the bone. In other embodiments, as illustrated in FIGS. 3A and 3B, the securing interface 32 may provide a friction fit or mechanical interfit with the proximal tether 28 that may be reversed or altered without disengaging or loosening the securing assembly 24 from the bone. The securing assembly in turn is attached to the bone using bone screws or anchors 34. In some embodiments, the friction fit or mechanical interfit is adjustable in one direction. In other embodiments, the friction fit or mechanical interfit is capable of bidirectional adjustment. In some embodiments, the proximal tether 28 and the securing assembly 24 may be integrated together. Various embodiments of the securing assembly 24 are described in further detail below. Preferably, the remodeling system comprises one securing assembly 24 and one to three tongue elements 22, but one skilled in the art may select other combinations of securing assemblies and tongue elements, depending upon the patient's anatomy and the desired result.

By implanting one or more tongue elements 22 within the tongue 9, creating tension in the proximal tethers 28, and attaching the proximal tethers 28 to a securing assembly 24 located peripherally to the distal anchors 26, a directional bias may be created in the tongue 9 to resist posterior displacement. There need not be continuous tension present in the proximal tethers 28. In some embodiments, tension is generated in one or more proximal tethers 28 only when the tongue 9 has been displaced a particular distance and/or a range of directions. The peripheral site of the securing assembly is typically located about an anterior portion of the mandible 13 and may involve the external, internal or inferior surface of the mandible 13 or a combination of these surfaces. In some embodiments, a lateral or anterolateral location about the mandible 13 may be used.

Figure 4A:
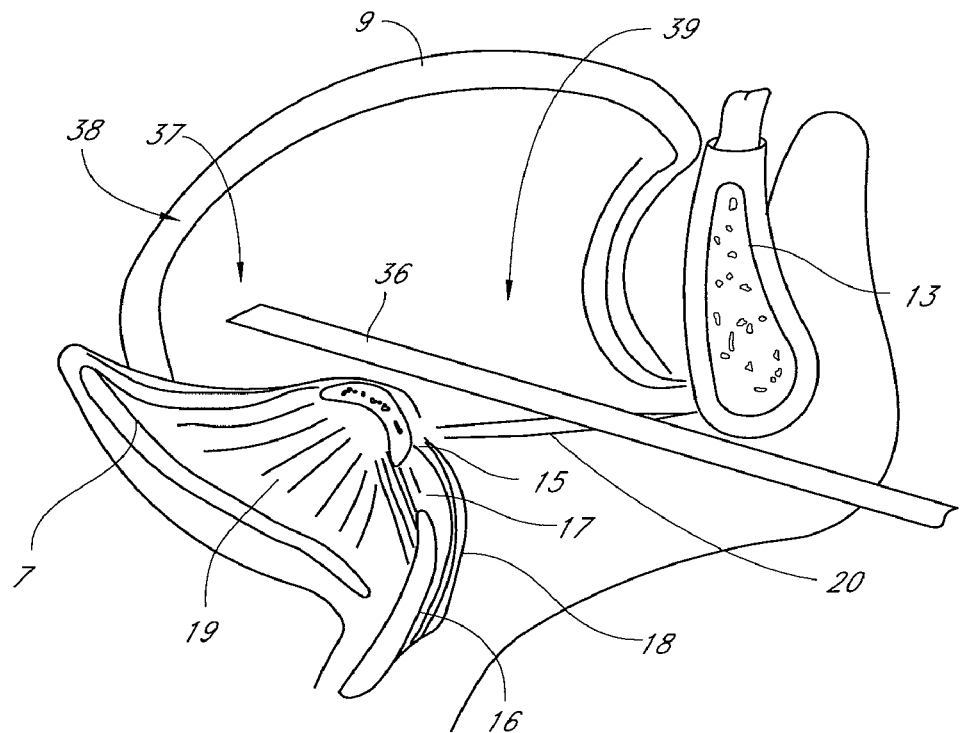
FIGS. 4A through 4D are cross sectional views through the oropharynx and mandible depicting implantation of one embodiment of the invention.
Figure 4B:
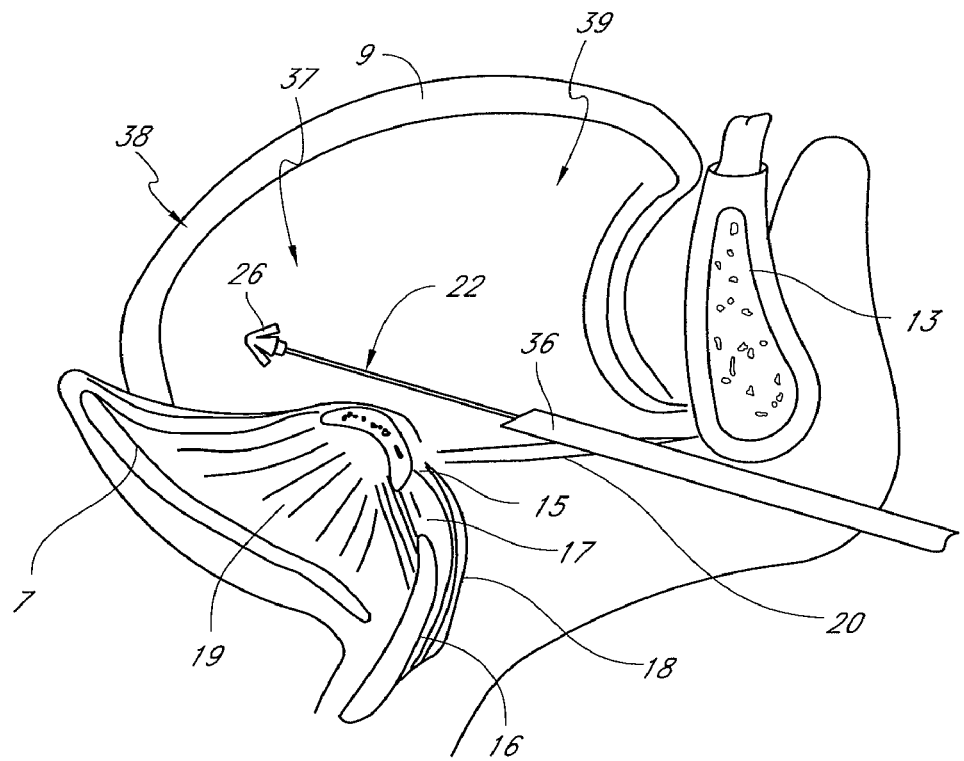
Figure 4C:
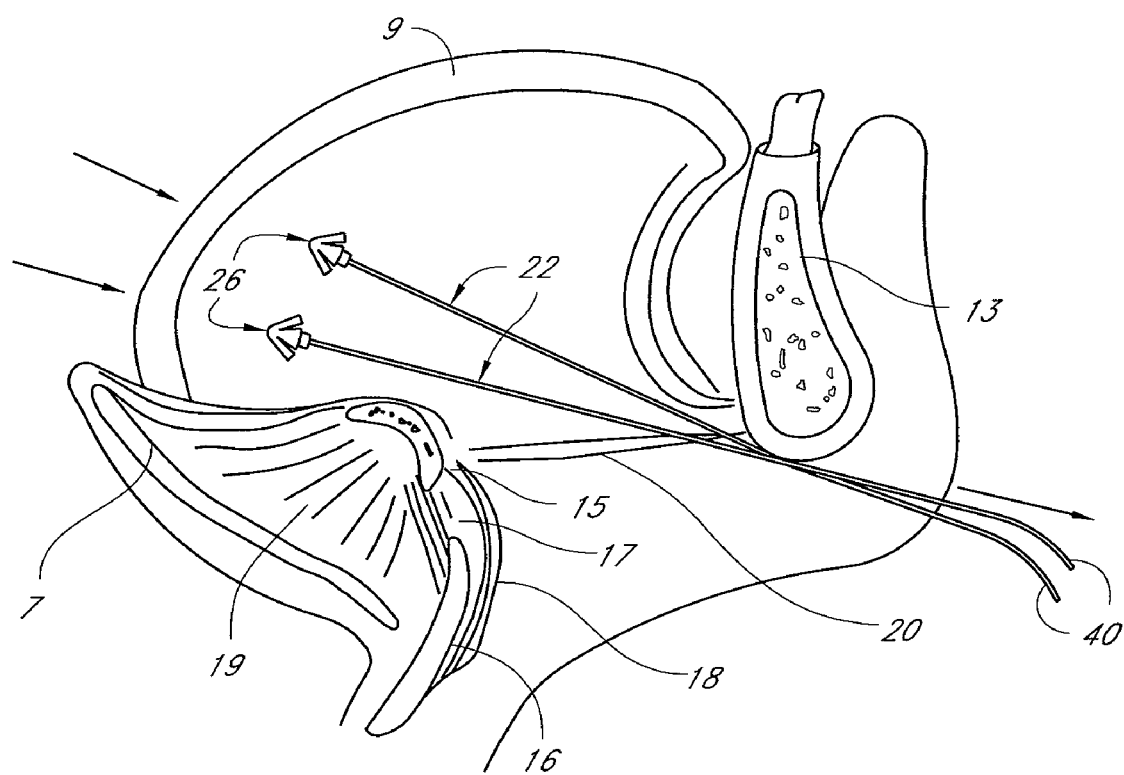
Figure 4D:
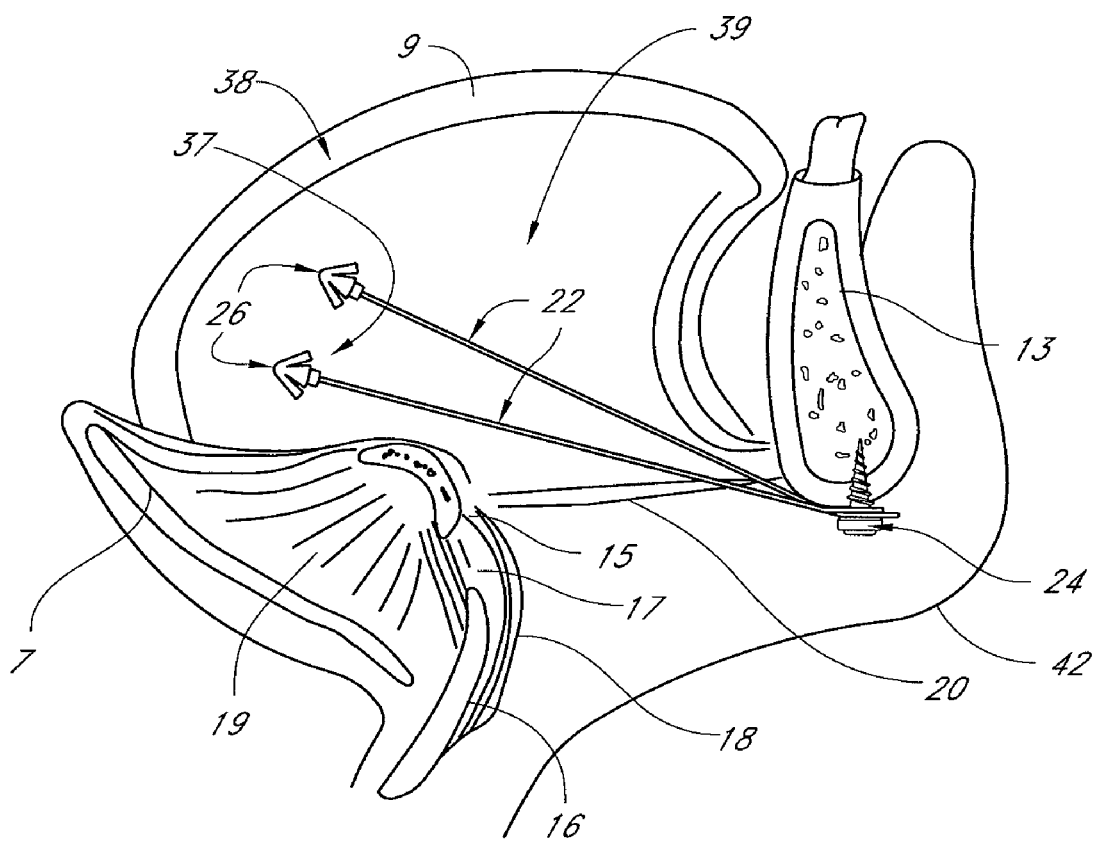

FIGS. 4A to 4D depict one embodiment of the invention where the tongue elements 22 are inserted into the tongue 9 through an insertion site inferior to the mandible 13, preferably but not always about the anterior portion of the mandible 13. In other embodiments, the implantation pathway may originate from a location anterior or lateral to the mandible 13, and in still other embodiments, may also pass through the mandible 13. The tongue elements 22 may be implanted percutaneously into the tongue 9 using a hypodermic needle 36 or other piercing delivery tool known in the art. In some instances, the distal anchors 26 of the tongue elements are positioned about the base of the tongue, which is the portion of the tongue posterior to the circumvallate papillae (not shown), but other locations within the tongue 9, such as the anterior portion 39, may also be used. For example, the distal anchors 26 may also be positioned in the dorsal region 38 of the tongue 9. This position may have a better effect on resisting posterior tongue displacement against the pharyngopalatine arch. Once positioned, the distal anchor 26 is released from the delivery tool 36. As shown in FIG. 4C, additional anchors 26 may be deployed, if desired. The delivery tool 36 is then withdrawn, leaving the proximal tether 40 trailing from the distal anchor 26 and accessible by the physician. A securing assembly 24 may be attached to the mandible 13 using minimally invasive techniques and the proximal tethers 40 of the tongue elements 22 are adjusted to an initial tension and secured to the securing structures 32 on the securing assembly 24. In some embodiments, the initial tension is zero but increases with changes in tongue position. In some embodiments, the securing assembly 24 is preferably secured to the inferior or inner surface of the mandible 13 to reduce visibility of the securing assembly beneath the skin 42. The securing assembly 24 may be adapted to penetrate and attach to the mandible 13, as depicted in FIG. 4D, or attach to the mandible surface with the use of an adhesive or tissue welding. In some embodiments, the securing structures may also be adjusted through an adjustment interface, described below, to further alter the tension in the proximal tether.

Figure 5A:
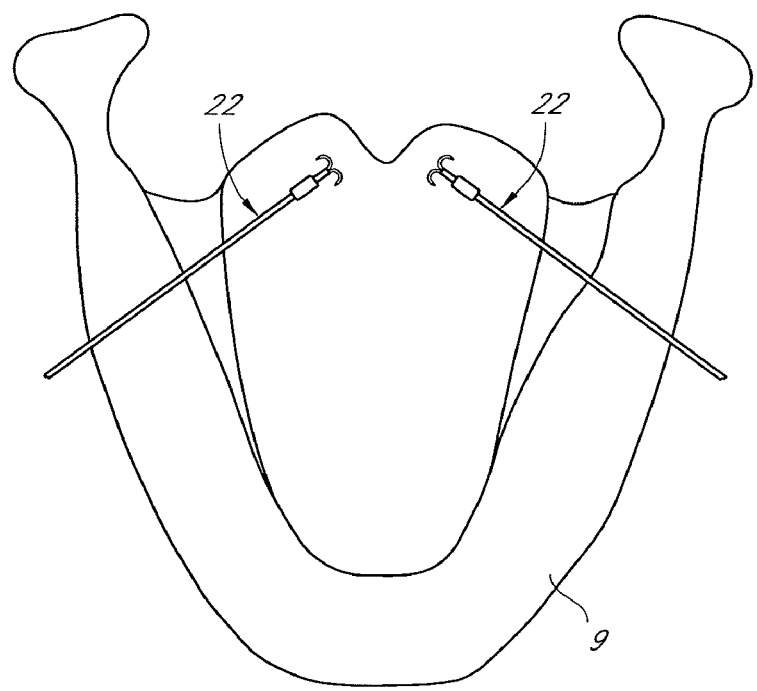
FIGS. 5A through 5C are cross sectional views through the oropharynx and mandible depicting another embodiment of the invention wherein the tongue elements are engaged to the lateral portions of the mandible.
Figure 5B:
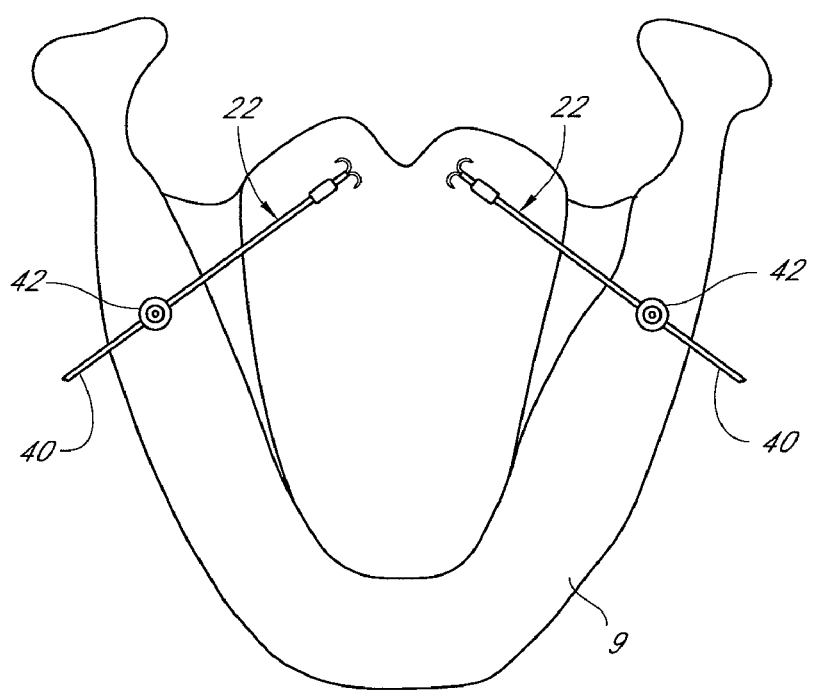
Figure 5C:
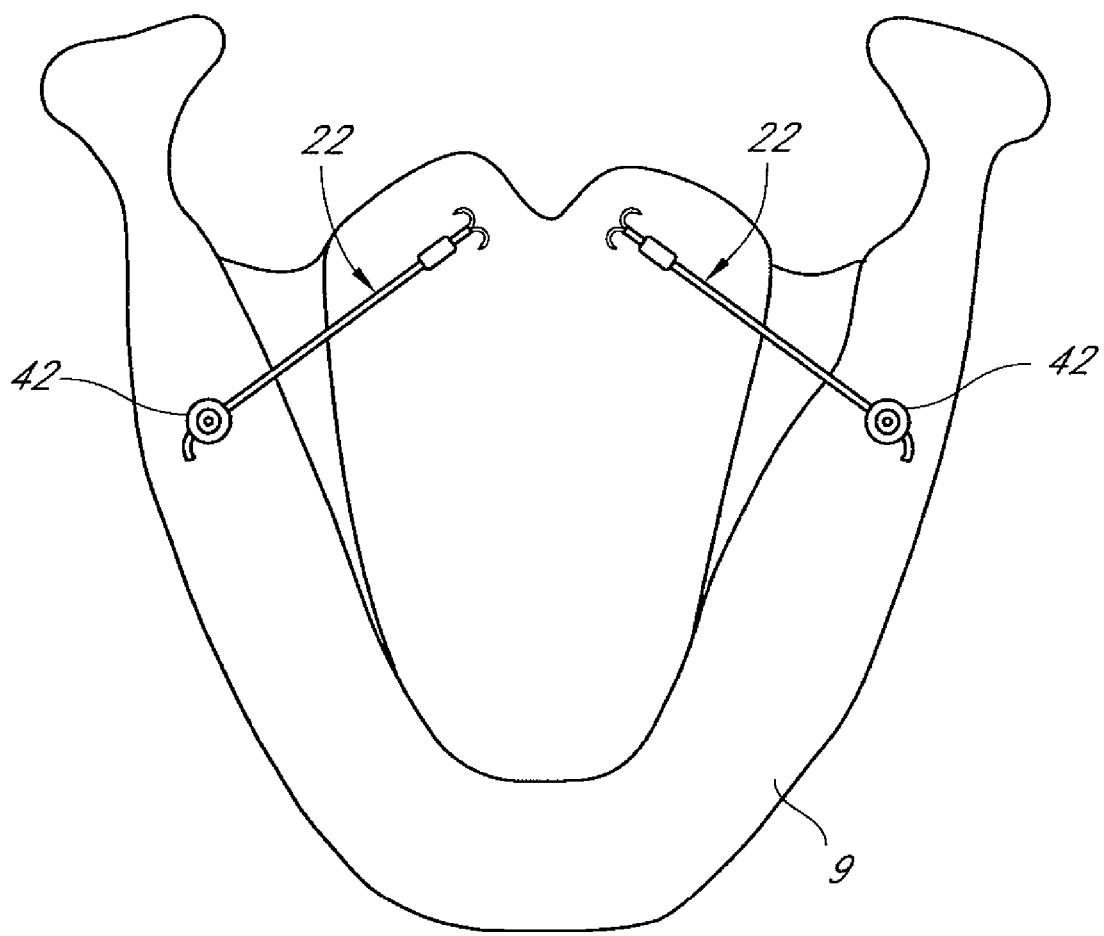

FIGS. 5A through 5C are inferior schematic views of an embodiment of the invention where the tongue elements 22 have been inserted into the posterior tongue bilaterally and attached to securing assemblies 42 located on the inferior surface of the bilateral mandible 13. Continuous or intermittent tension created within the tongue elements 22 causes remodeling of the posterior tongue not only in an anterior direction but also a lateral direction. This may be advantageous by increasing tissue tension in the posterior tongue with less limitation of tongue movement in the antero-posterior direction.

Figure 6A:
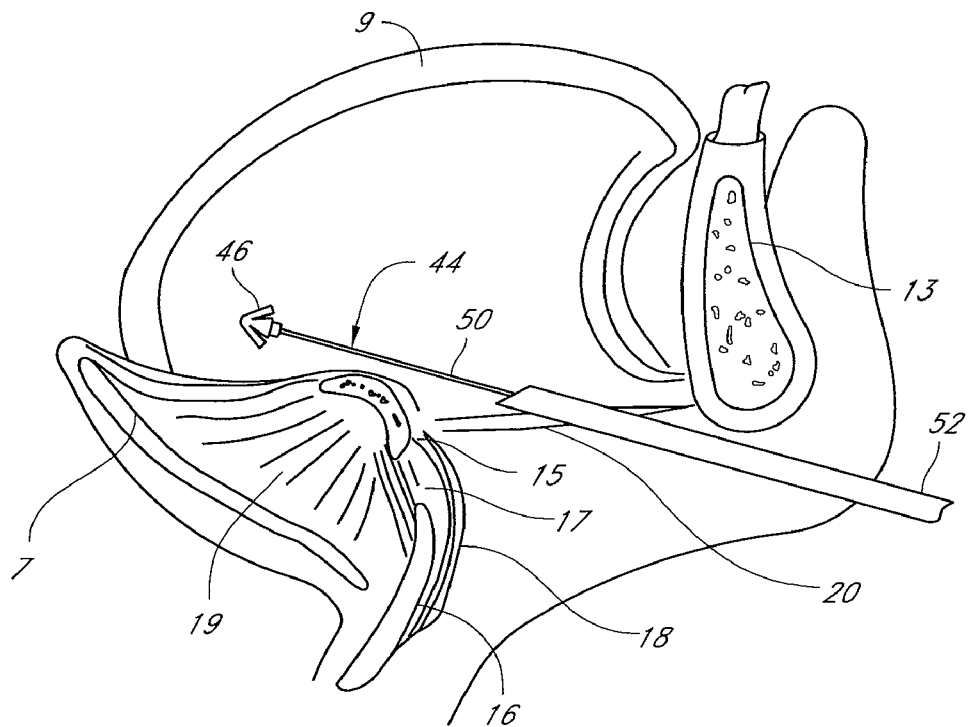
FIGS. 6A and 6B are cross sectional views through the oropharynx and mandible illustrating another embodiment of the invention comprising a dual-anchor device.
Figure 6B:
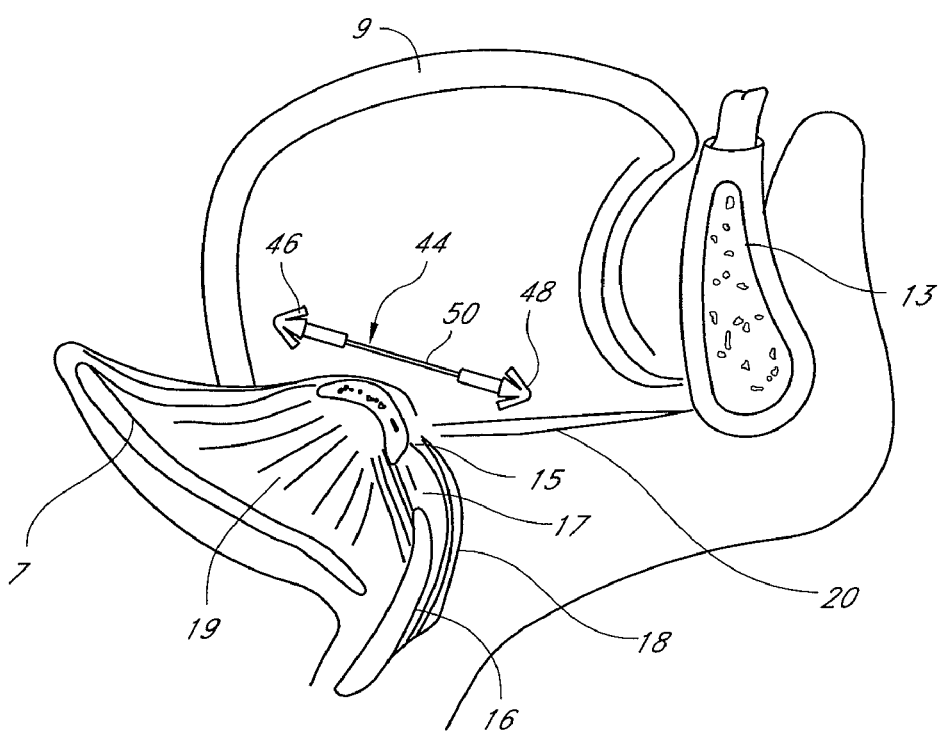

FIGS. 6A and 6B depict another embodiment of the invention comprising a tongue element 44 having a distal tissue anchor 46 and a proximal tissue anchor 48 joined by a tether 50. This device can be inserted into the tongue tissue using a single cutaneous delivery device 52 and access point without accessing or inserting into the mandible or other bone. To implant a dual-ended tongue element 44, the needle or delivery tool 52 is inserted percutaneously into the tongue 9 to a desired distal location and in a direction along the desired tension pathway. The distal anchor 46 is released from the delivery tool 52 into the tongue tissue. The delivery tool 52 is withdrawn, gradually exposing the tether 50. By applying proximal force to the delivery tool 52, tension may be formed within the tether 50. In some embodiments, the release mechanism for the proximal tissue anchor 48 further comprises a force measurement component that may assist the physician in determining the appropriate release position for the proximal tissue anchor 48. The measurement component may comprise a calibrated spring or a piezoelectric crystal with an analog or digital readout. When the desired tension and/or location for the proximal tissue anchor 48 are reached, the proximal tissue anchor 48 may be released from the delivery tool by withdrawal of an outer sheath on the delivery tool 52 to expose the proximal tissue anchor 48, or by release of an engagement structure, such as a suture or deflection of one or more biased prongs, that are engaged to the proximal tissue anchor 48. The tether tension allows the distal and proximal tissue anchors 46, 48 to come closer together, thereby compressing the tongue tissue between the anchors 46, 48 and altering the tongue configuration. In other embodiments, the dual-ended tongue element 44 is implanted within the tongue 9 and creates intermittent rather than continuous tissue compression, depending on tongue position.

Figure 7A:
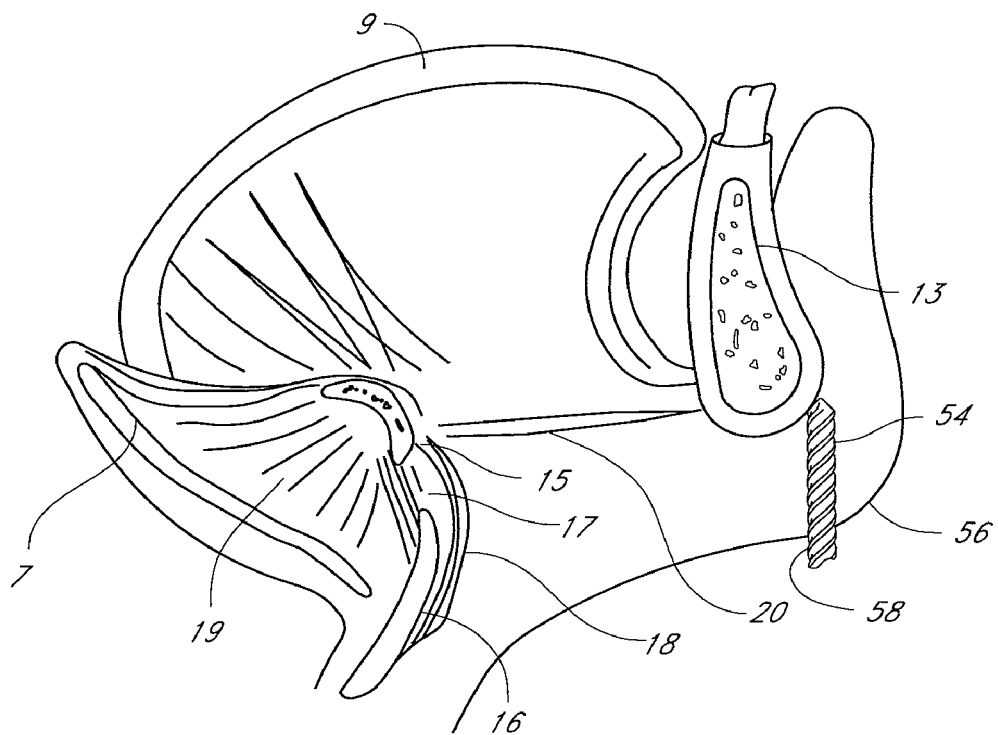
FIGS. 7A through 7F are cross sectional views through the oropharynx and mandible depicting transmandibular implantation of one embodiment of the invention.
Figure 7B:
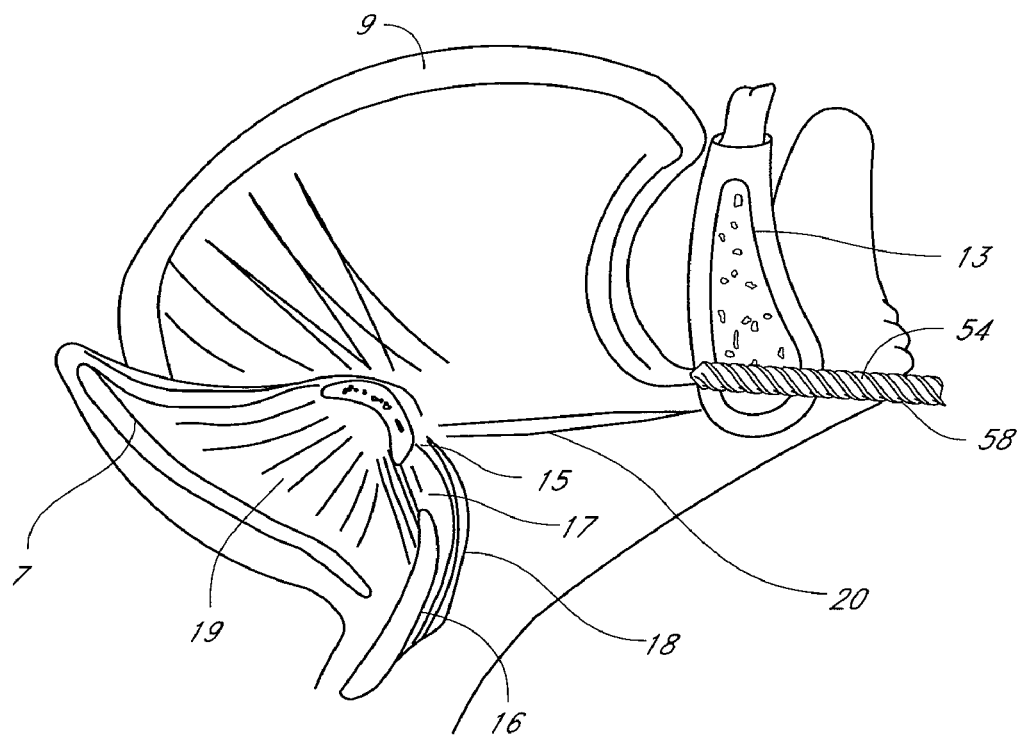
Figure 7C:
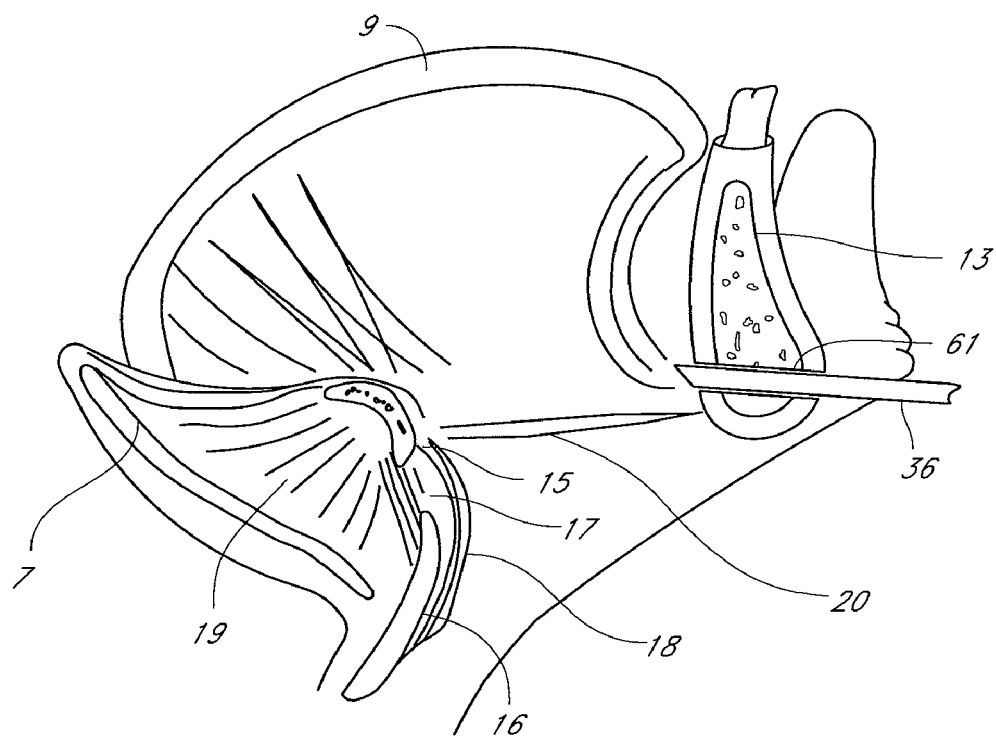
Figure 7D:
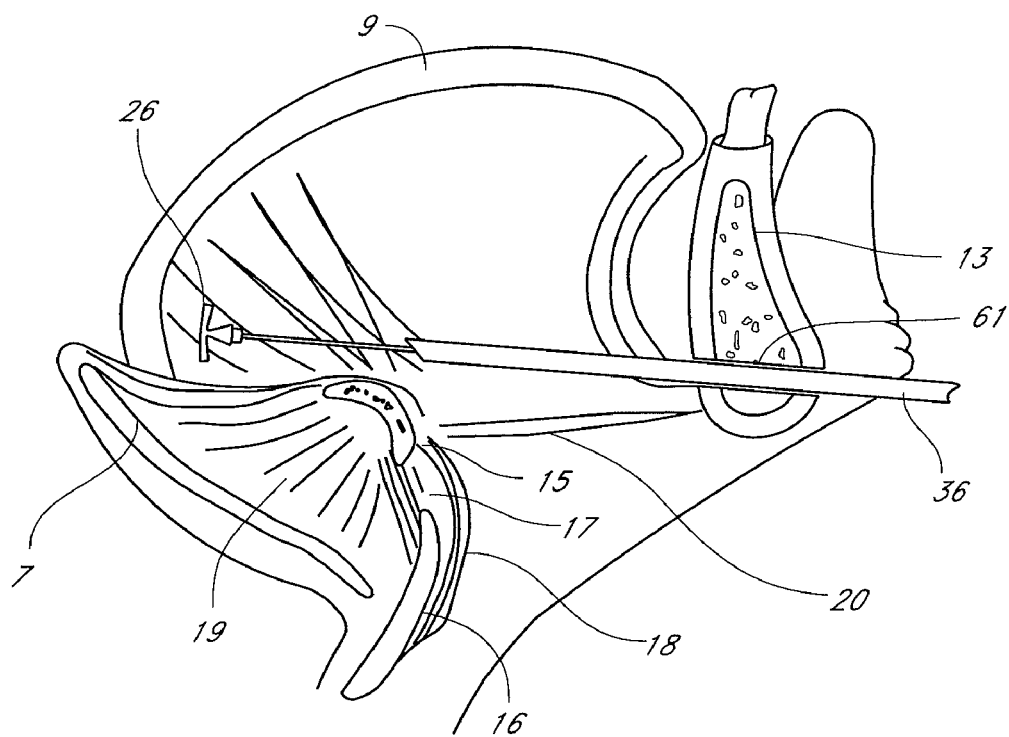
Figure 7E:
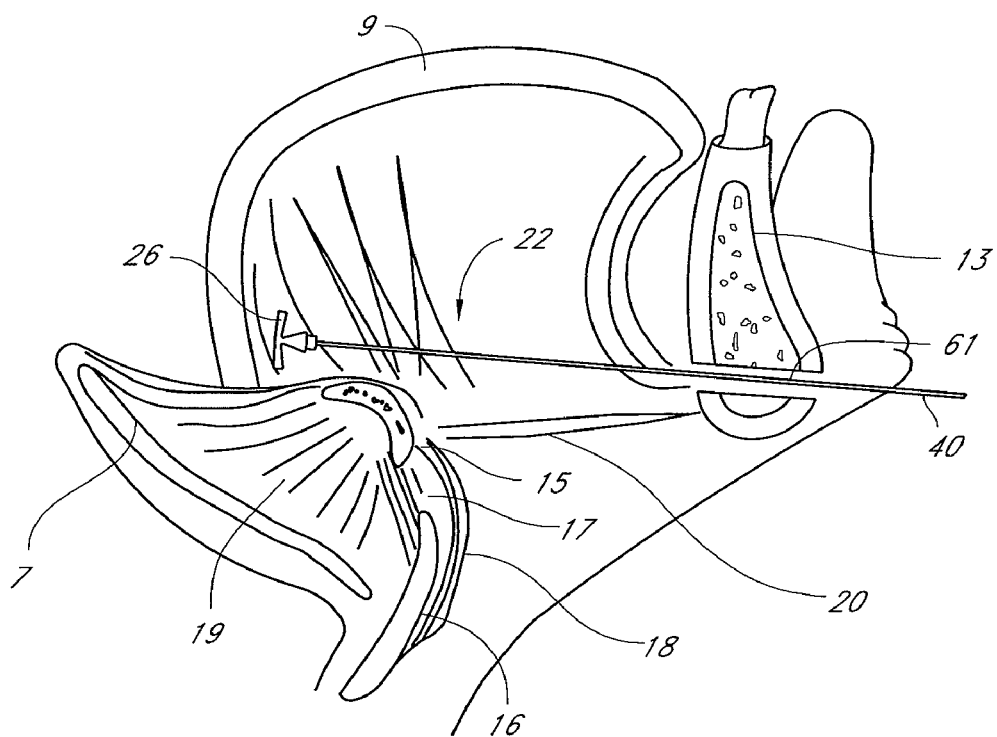
Figure 7F:
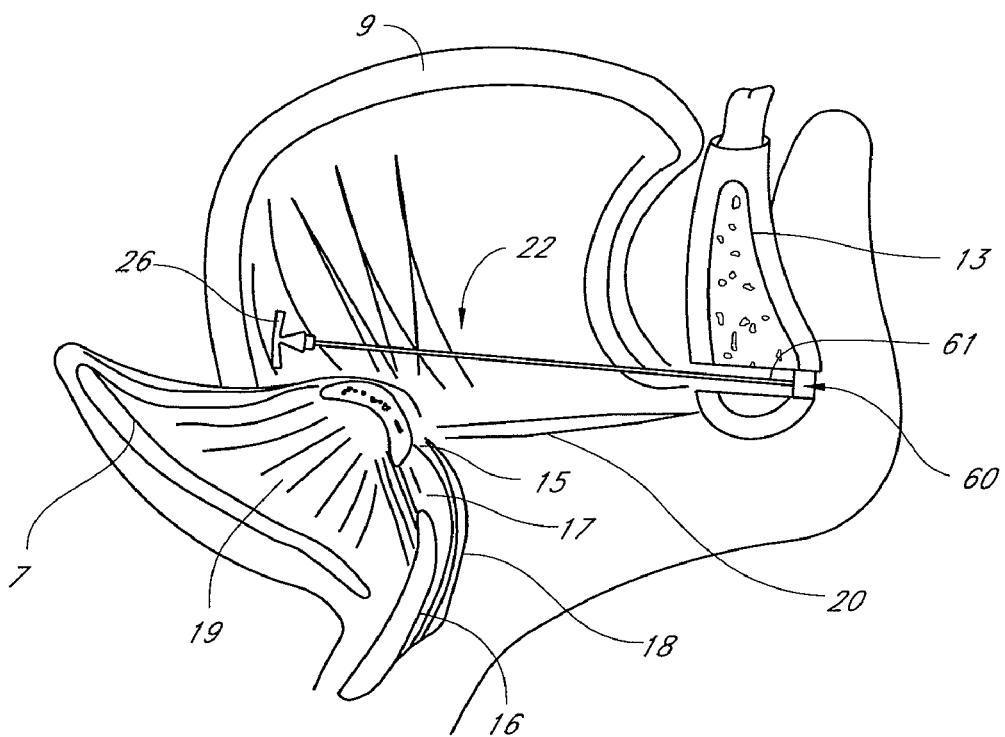

FIGS. 7A through 7F depict another embodiment of the invention, where the implantation pathway passes through the mandible 13 to access the tongue 9. A pathway or conduit through the mandible 13 or other bone may be created using a bone drill 54 or other device known in the art. As illustrated in FIGS. 7A and 7B, in some instances, the inferior skin 56 of the lower jaw is drawn toward the anterior chin prior to accessing the anterior mandible 13. Displacing the skin anteriorly provides access through skin that normally faces inferiorly, thereby hiding the skin access site 59 at the inferior surface of the mandible 13 once the procedure is complete. Referring to FIGS. 7C and 7D, once a pathway is created through the mandible 13, the delivery tool 36 may be used to insert one or more tongue elements 22 into the tongue 9. A sheath or retractors may be inserted through the skin and bone conduit to maintain access and/or exposure to the bone during the procedure. In one embodiment, a delivery tool 36 with a tongue element 22 is inserted generally through the mandible 13 to a desired location in the tongue 9, deployed and released from the delivery tool 36. Deployment of the distal anchor 26 may also include expansion of the distal anchor 26, if needed. In FIG. 7E, the delivery tool 36 is then withdrawn, leaving the proximal tether 40 trailing from the distal anchor 26 and accessible by the surgeon. Additional anchors 26 may be deployed, if desired. In some embodiments, an intra-mandible securing assembly 60, shown in FIG. 7F, may be attached or partially attached to the bone before, during and/or after the implantation of the tongue elements 22. In one embodiment, the proximal tethers 40 are attached to a securing assembly 60 and the tension of the proximal tether 40 is adjusted as needed and secured to the securing assembly 60. In some embodiments, the securing assembly 60 may be engaged to the mandible surface or conduit surface. In other embodiments, the tension of the tongue element(s) 22 alone is sufficient to keep the securing assembly against the mandible 13. In some embodiment, a portion of the securing assembly may be inserted prior to implantation of the tongue elements 22. In FIG. 7C, for example, a conduit portion 61 of the securing assembly 60 is inserted through the mandible 13 prior to use of the delivery tool 36.

In addition to securing the proximal tethers 40 of the tongue elements 22 to the anterior portion of the mandible 13, other securing sites are also envisioned, including the lateral portions of the mandible 13, the hyoid bone 15, the occiput, the thyroid cartilage 16, the tracheal rings and any other structure about the head or neck.

The embodiments of the invention described above may be combined with other treatments for OSA, sleep disordered breathing, upper airway resistance syndrome and snoring. These other treatments may also include external devices such as CPAP, medications such as modafinil, other surgical procedures, as well as other treatments of the tongue, including various forms of tongue debulking using RF ablation such as Coblation® by ArthroCare® ENT.

1. Distal Anchor

The distal anchor may have any of a variety of shapes adapted for implantation within the tongue 9 and to resist migration, typically comprising one or more tissue engaging structures 30. Expandable anchors may include expandable slotted tubes, fibrous or porous polymer plugs or structures, coilable wires, expandable barb structures or any other deformable or expandable structure or combinations thereof. In other embodiments, the distal anchor 26 has a fixed configuration but is adapted to facilitate its insertion in one direction through the tongue 9 or other soft tissue and to resist migration or displacement in at least the opposite direction. Distal anchors 26 with a fixed configuration may have barbs, angled pins, hooks or other angled or ramped structures capable of engaging surrounding tissue. The distal anchors may also be self-expandable or may require the application of force to expand in size or surface area. For instance, in some embodiments of the invention, the distal anchor may have one or more deformable tissue engagement structures that self-expand upon release of the distal anchor from the delivery tool to engage the surrounding tissue. In other embodiments, the distal anchor may engage or expand into the surrounding tongue tissue upon the application of tension to the proximal tether of the tongue element.

In some embodiments, the distal anchor has a first configuration with a reduced cross-sectional profile to facilitate implantation of the distal anchor within the tongue, and a second configuration with an expanded cross-sectional profile to engage the surrounding tissue and/or resist migration of the anchor within or out of the tongue. In further embodiments of the invention, the distal anchor may have a third configuration to facilitate removal of the distal anchor from the tongue. The third configuration may result from deformation of the distal anchor to facilitate disengagement from the surrounding tongue tissue and/or to reduce the cross-sectional profile. Deformation of the distal anchor may occur at one or more pre-engineered failure points or deformation points on the distal anchor. One skilled in the art can design a failure point to deform with a force greater than the upper limit of forces generally acting on the distal anchor in its intended use.

Figure 7G:
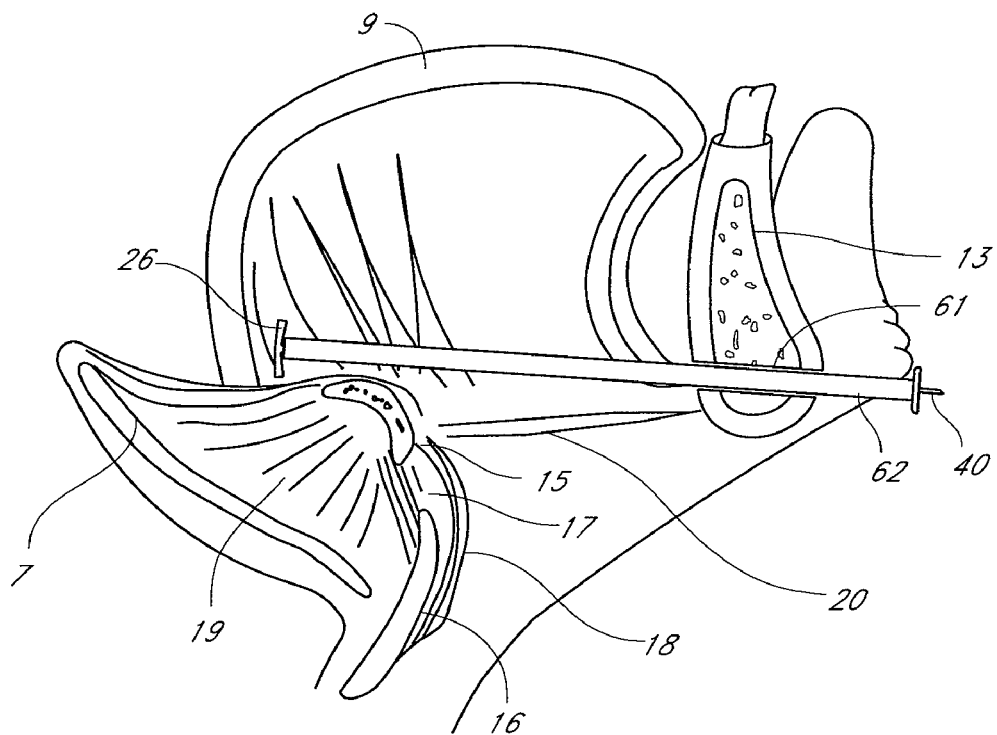
FIGS. 7G through 7J are schematic cross sectional views depicting the removal of an embodiment of the invention.
Figure 7H:
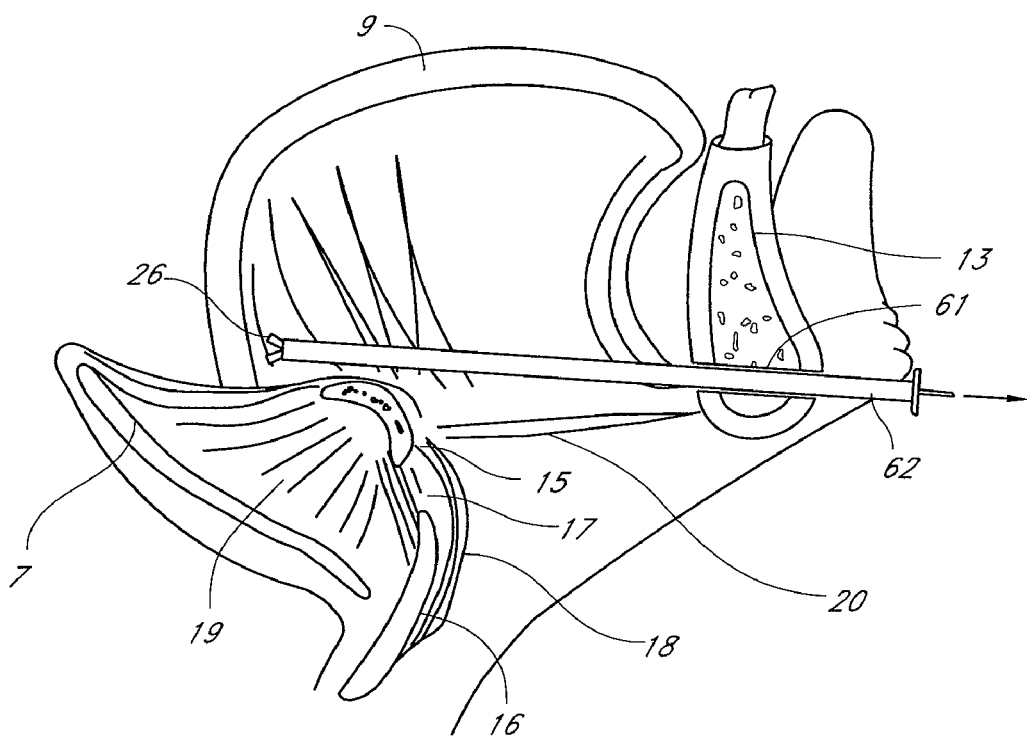
Figure 7I:
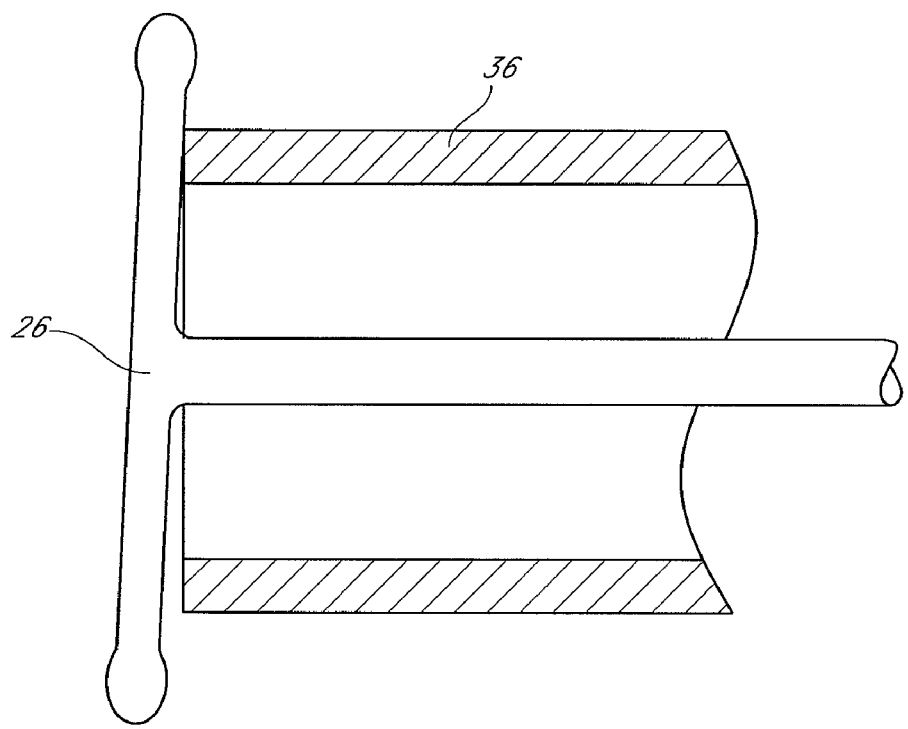
Figure 7J:
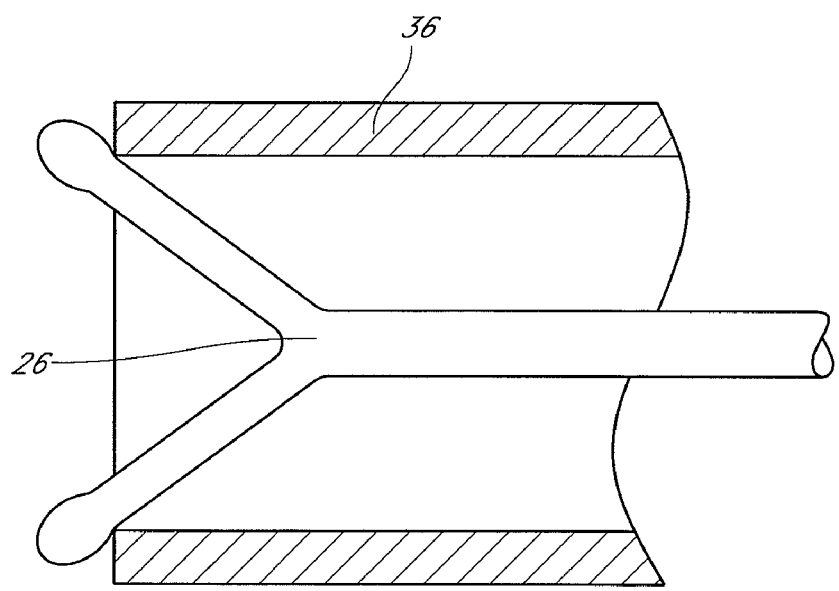

FIGS. 7G through 7J depict the removal of an anchor previously inserted in FIGS. 7A through 7F. In FIG. 7G, the proximal tether 40 is disengaged from the securing assembly 60 and a removal tool 62 is passed along the proximal tether 40 to the distal anchor 26. In FIG. 7H, the distal anchor 26 is deformed such that the distal anchor 26 has a reduced cross sectional profile and/or disengages the surrounding tongue tissue. The deformation may occur by stabilizing or pulling on the proximal tether and distal anchor while pushing and/or stabilizing the removal tool against the distal anchor. FIG. 7I depicts a cross sectional expanded view of the distal anchor 26 and removal tool 62 from FIG. 7G as the removal tool 62 abuts the distal anchor 26. FIG. 7J depicts the distal anchor and removal tool from FIG. 7I following deformation of the distal anchor. After deformation, the removal tool 62 may be withdrawn from the tongue separately from the distal anchor 26 or together with the distal anchor 26. In some embodiments, the removal tool 62 surrounds the distal anchor 26 to reduce the risk of breakage or snagging of the distal anchor 26 during withdrawal from the tongue. The removal tool may include any of a variety of structures capable of exerting sufficient force against the distal anchor 26 to cause deformation. In some instances, the removal tool 62 may be a catheter or large gauge needle. Preferably, the removal tool 62 is further adapted to slide or interface with the proximal tether 40 of the distal anchor to guide the removal tool 62 to the distal anchor 26. The adaptation may include a groove, channel or a lumen that can be placed about the proximal tether 40.

Figure 8A:
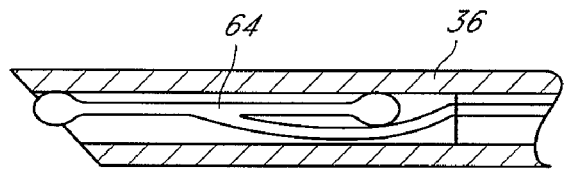
FIGS. 8A and 8B depict one embodiment of the invention comprising a glossoplasty device with a T-shaped tissue anchor.
Figure 8B:
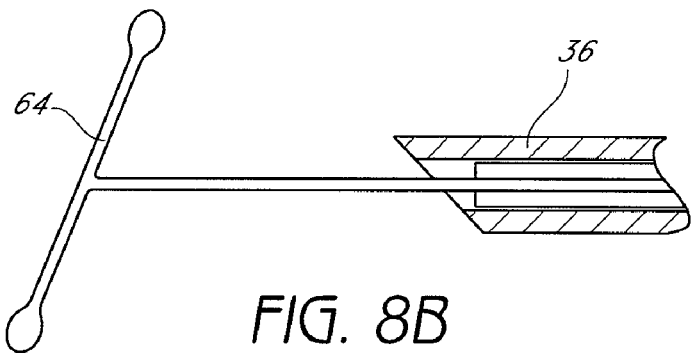
Figure 9A:
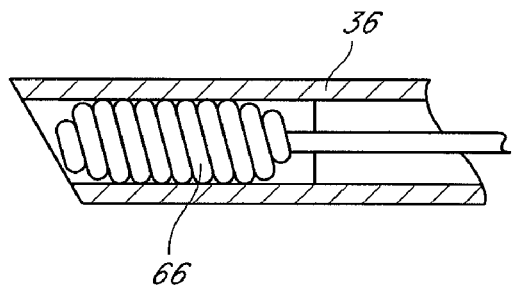
FIGS. 9A and 9B depict one embodiment of the invention comprising a glossoplasty device with a spiral tissue anchor.
Figure 9B:
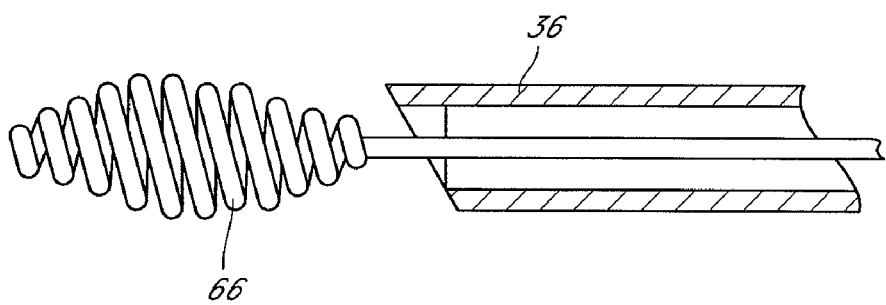
Figure 10A:
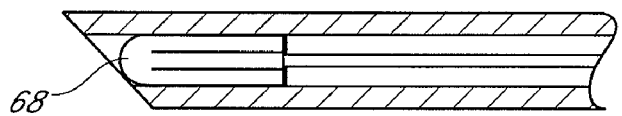
FIGS. 10A and 10B depict one embodiment of the invention comprising a glossoplasty device with a flat pronged tissue anchor.
Figure 10B:
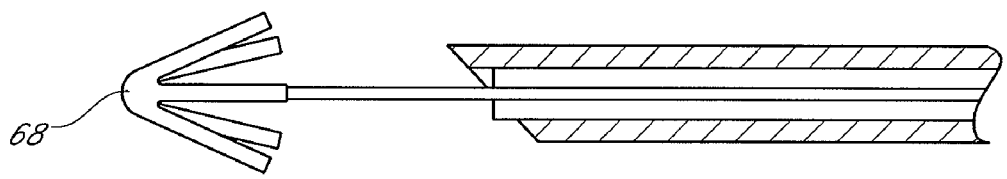
Figure 11:
FIG. 11 illustrates one embodiment of the invention comprising a glossoplasty device with a pointed prong tissue anchor.
Figure 12:
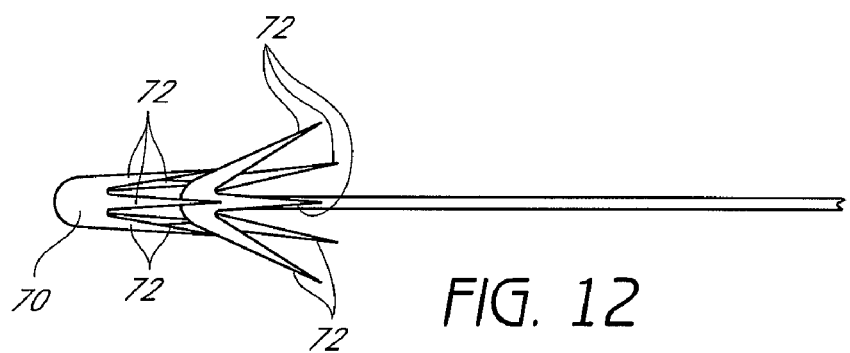
FIG. 12 illustrates one embodiment of the invention comprising a glossoplasty device with a dual pointed prong tissue anchor.

In some embodiments of the invention, the distal anchor may resist migration by having an enlarged surface area that creates a frictional or mechanical interface with the surrounding tissue, but is not limited to this sole mechanism to resist migration. Examples of such distal anchors include a T-shaped anchor 64 depicted in FIGS. 8A and 8B, a coil-shaped anchor 66 in FIGS. 9A and 9B, and the flat-ended prong anchor 68 illustrated in FIGS. 10A and 10B. Tissue anchors having an enlarged surface area may be advantageous by reducing or avoiding tissue laceration that may be associated with piercing-type anchors. In other embodiments of the invention, the distal anchor comprises one or more coils that are drawn taut during the implantation procedure and resume a coiled configuration upon release of tension on the wire coil. In embodiments of the distal anchor comprising multiple coils, the coils lengths may be distinct or intertwined with other coils of the same or different anchor. The ends of each coil may be attached to the same or different point on the tether or coils of the tether. However, a piercing anchor 70 with hooks or barbs 72, as shown in FIG. 11, may also be used. The piercing structures need not be arranged on the distal anchor about the same circumference. FIG. 12 illustrates another embodiment of the invention where the piercing structures 72 are located at two separate circumferences of the distal anchor 70, but in other embodiments, the piercing structures may be staggered anywhere along the length of the distal anchor.

Figure 13:
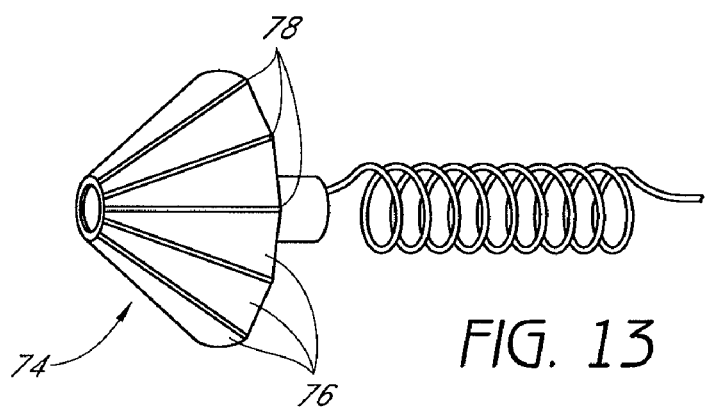
FIG. 13 illustrates another embodiment of the invention comprising a glossoplasty device with an umbrella tissue anchor.

In some embodiments of the invention, the distal anchor 74 may further comprise one or more polymeric sheets 76 between or engaged to the tissue engagement structures 78 of the distal anchor 74. In one example depicted in FIG. 13, the polymeric sheets 76 may be attached to the tissue engagement structures 78 generally about one end of the distal anchor 74, thereby forming an umbrella-like structure upon expansion that provides an increased surface area for resisting the migration of the distal anchor 74. In other embodiments, the polymeric sheets may span from one end of the distal anchor to the other end, thereby forming a generally enclosed shape.

Figure 14A:
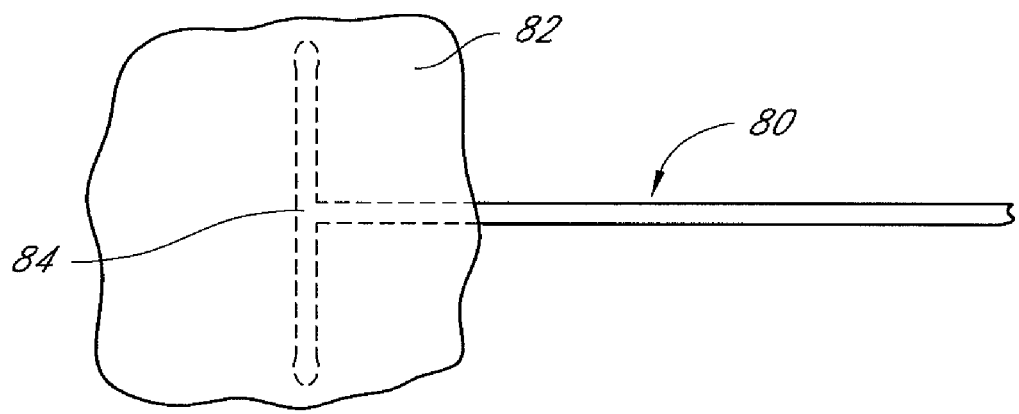
FIGS. 14A and 14B depict embodiments of the invention comprising a distal anchor having a foam plug and T-tag core. The foam plug fully encapsulates the T-tag in FIG. 14A and partially encapsulates the T-tag in FIG. 14B.
Figure 14B:
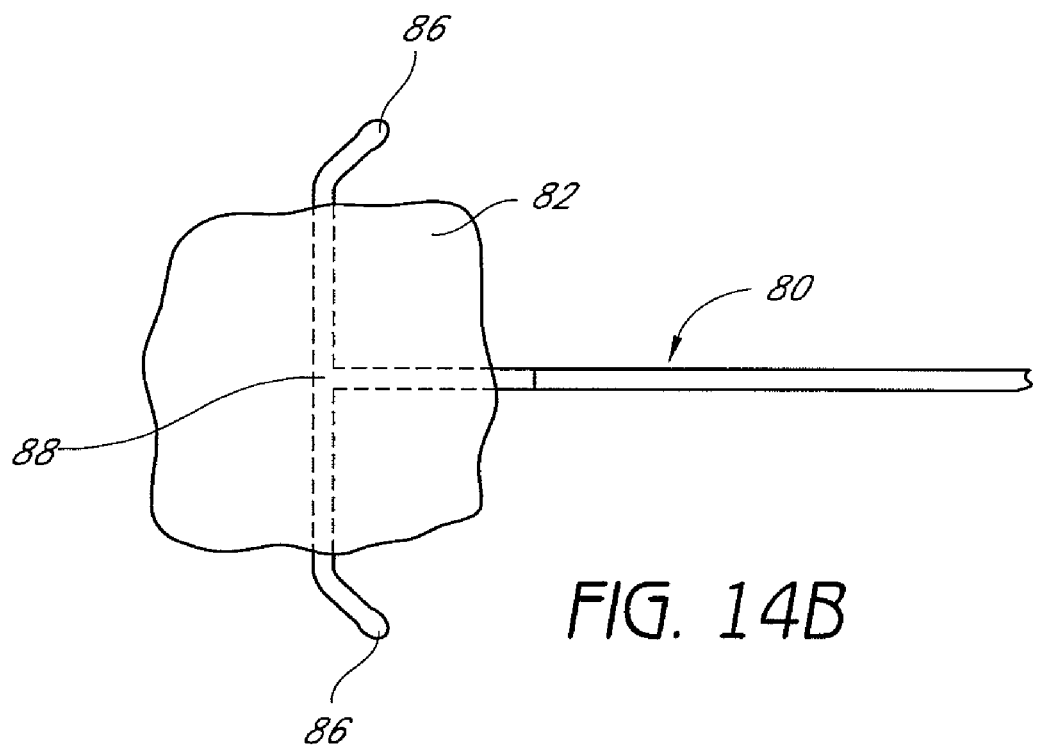

Referring to FIGS. 14A and 14B, in one embodiment of the invention, at least a portion of the distal anchor 80 may comprise a plug structure 82. The term plug is used to describe any of a variety of space-occupying structures, including lattice, reticular, fibrous or porous plugs, discs or other structures. The plug 82 may comprise a polymer, a metal, a ceramic or combination thereof. The polymer may optionally be a resorbable polymer. The plugs may be expandable or non-expandable. Expandable plugs may be self-expandable through the use of a shape memory material, a compressible material such as a foam, or an absorptive material that may expand in the presence of liquid. The plugs may or may not be filled or saturated with one or more therapeutic agents that may alter tissue ingrowth, scarring or other physiological effect, either systemically or locally about the tongue 9. These agents may include but are not limited to an antibiotic, a sclerosing agent, an anti-proliferative agent, growth factors, hormones and other therapeutic agents known in the art. The plug structure 82 may also be combined with other distal anchor designs discussed herein. FIGS. 14A and 14B represent embodiments of a distal anchor 80 comprising an expandable foam plug 82 with a T-tag core 84. The T-tag 84 may be fully encapsulated by the foam 82 as shown in FIG. 14A, or some portions 86 of the T-tag 88 may protrude from the foam plug 82, as shown in FIG. 14B.

Figure 15A:
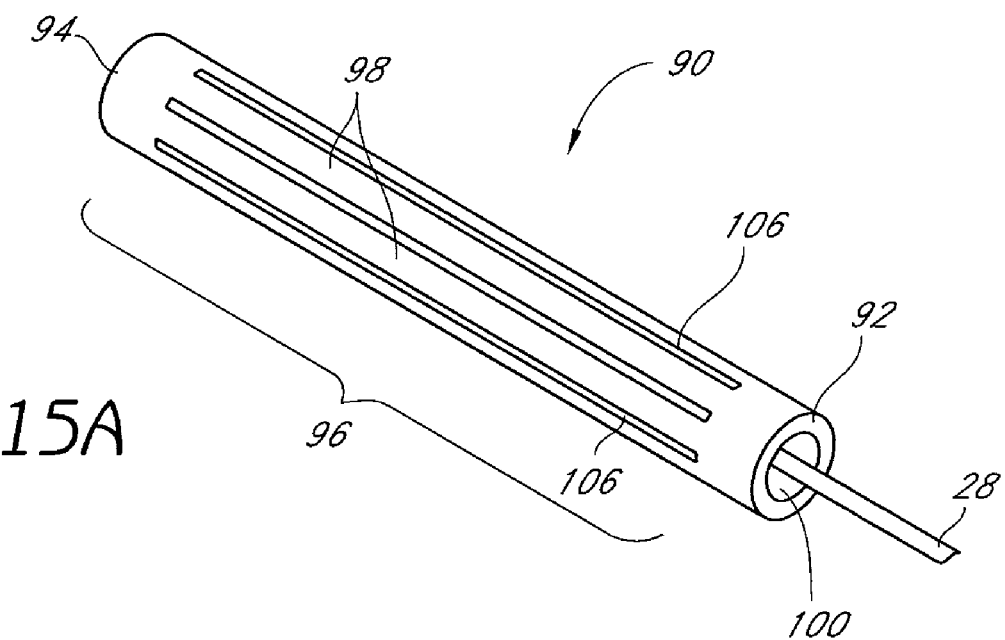
FIGS. 15A through 15C depict another embodiment of the invention comprising a glossoplasty device with a radially expandable slotted tissue anchor.
Figure 15B:
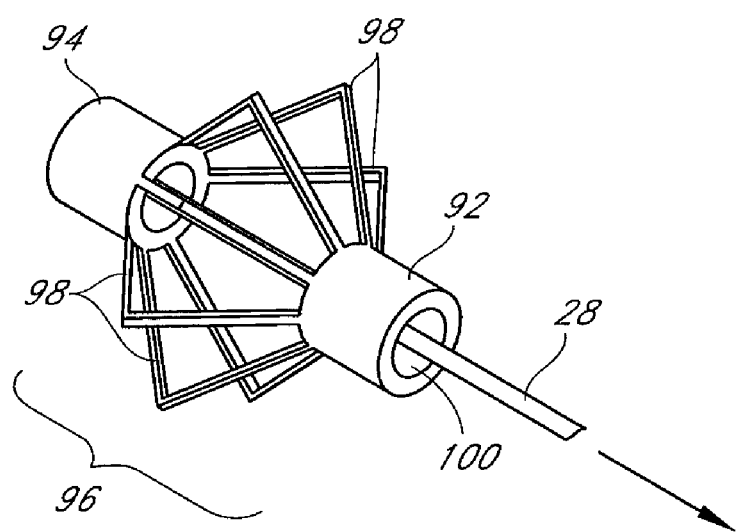

Other distal anchor designs that may be used are shown in FIGS. 15A though 22B. FIGS. 15A and 15B depict one embodiment of the invention comprising a tubular distal anchor 90 having a proximal end 92, a distal end 94 and at least one deformable zone 96 between the proximal end 92 and the distal end 94. The deformable zone 96 is configured to deform radially outward and may comprise any of a variety of deformable structures, including but not limited to struts 98, prongs, lattice, reticular, coiled or spiral structures. The deformation may occur as a result of elastic deformation of the distal anchor 90, shape memory effects, or particular mechanical effects of the distal anchor configuration in response to applied force. In some embodiments, when the distal end 94 and/or proximal end 92 of the distal anchor 90 are pushed or pulled closer together, the deformable zone 96 bends in a radially outward direction. In one embodiment, the tether 28 is located through a lumen in the proximal end 92 of the distal anchor 90 and the deformable zone 96 and attaches to the distal end 94 of the distal anchor 90. Referring to FIG. 15B, by pulling on the tether 28, the tether 28 moves in a proximal direction and brings the distal end 94 of the distal anchor 90 closer to the proximal end 92, causing radial expansion of the deformable zone 96.

Figure 15C:
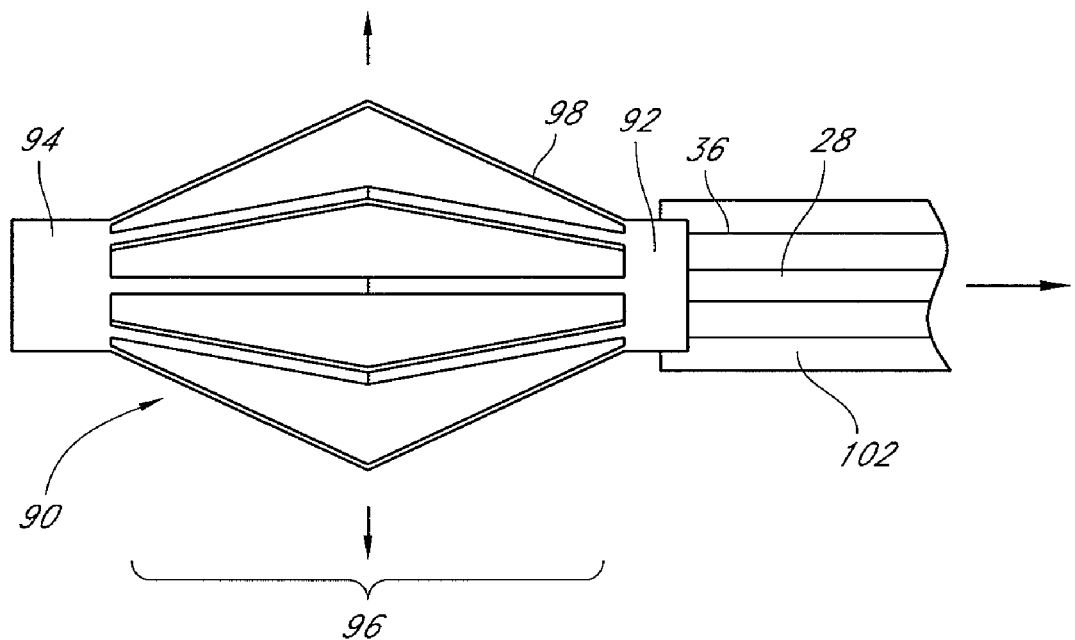
Figure 16:
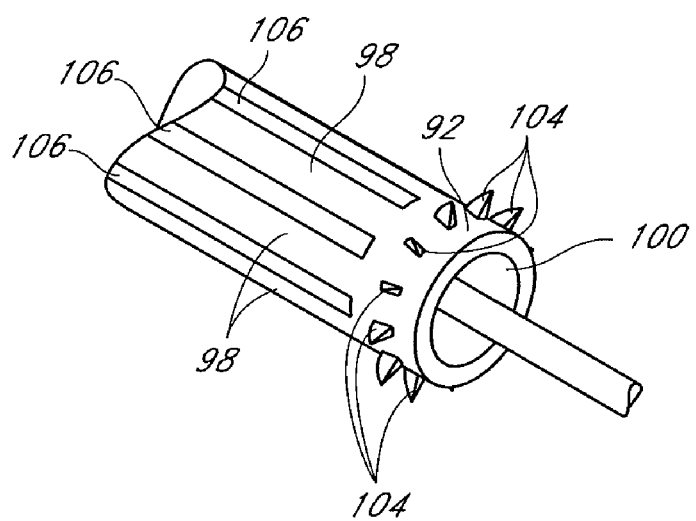
FIG. 16 depicts one embodiment of the invention where the proximal end of the tissue anchor comprises barbs for engaging tissue.

In one embodiment, shown in FIG. 15C, the position of the proximal end 92 is maintained during the expansion of the deformation zone 96, by abutting a portion of the delivery tool 36 against the proximal end 92 of the distal anchor 90 to provide leverage and to resist proximal displacement during the expansion process. The delivery tool 36 may comprise a sheath 102 for retaining the proximal end 92 of the distal anchor 90 during expansion to prevent angular displacement of the anchor 90 as force is applied through the tether 28. In other embodiments, sufficient resistance is provided by the contact between the proximal end 92 of the distal anchor 90 and the tongue tissue to limit displacement of the proximal end 92 with tension of the tether 28 and thereby allow deformable zone expansion. Referring to FIG. 16, resistance between the proximal end 92 of the anchor 90 and the tongue tissue may be enhanced by tissue engagement members 104 on the proximal end, such as small hooks, barbs, or any of a variety of ramped surfaces inclined radially outwardly from a distal to proximal direction.

Figure 17A:
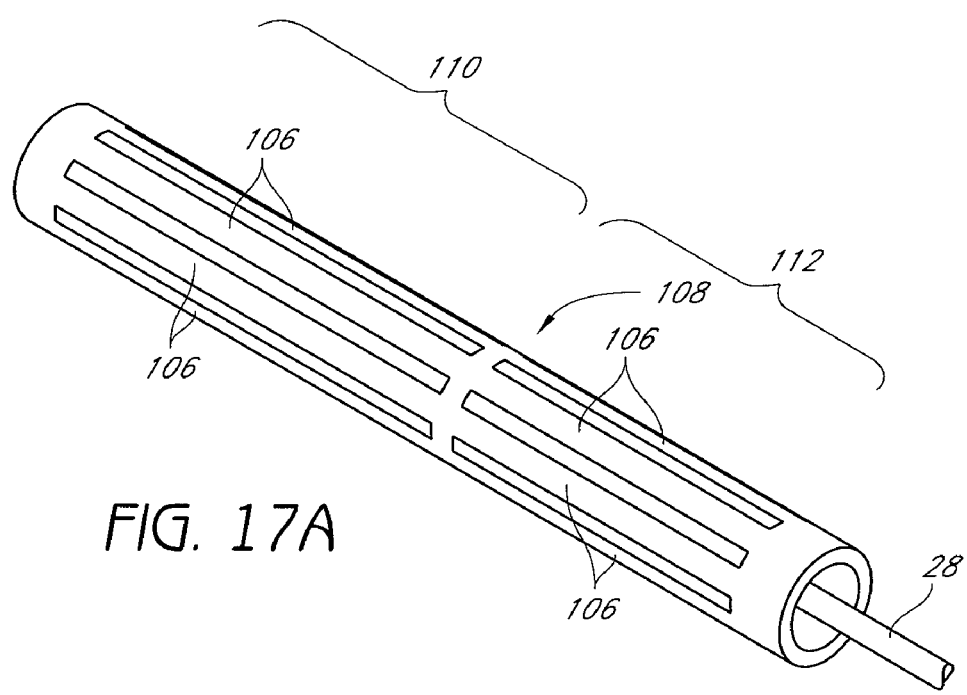
FIGS. 17A and 17B depict another embodiment of the invention comprising a glossoplasty device with a dual radially expandable slotted tissue anchor.
Figure 17B:
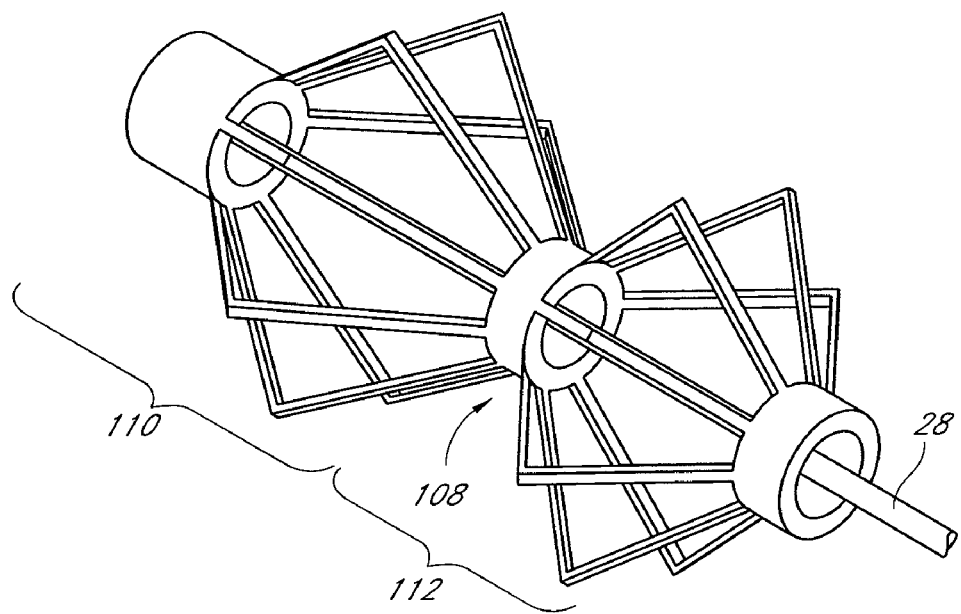

One skilled in the art can configure the deformable zone to provide any of a variety of desired expanded anchor shapes. In addition to a plurality of longitudinally oriented circumferentially spaced slots 106 depicted in FIGS. 15A and 15B, the slots 106 may also be arranged serially along the longitudinal axis of the distal anchor 108, as depicted in FIGS. 17A and 17B, to create two or more deformable zones 110, 112. Each deformable zone 110, 112 need not have the same deformation characteristics. The first deformable zone, for example, may be configured for a larger expanded diameter compared to the second deformable zone.

Figure 18A:
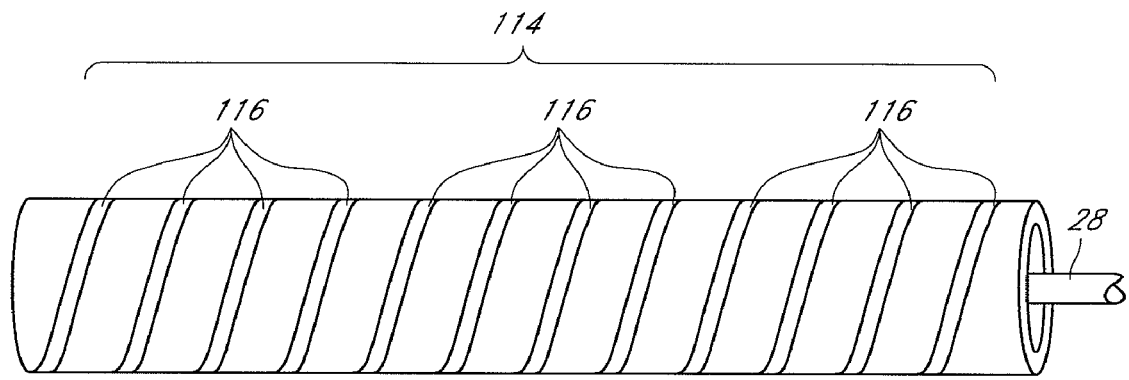
FIGS. 18A and 18B depict another embodiment the invention comprising a radially expandable tissue anchor before and after expansion.
Figure 18B:
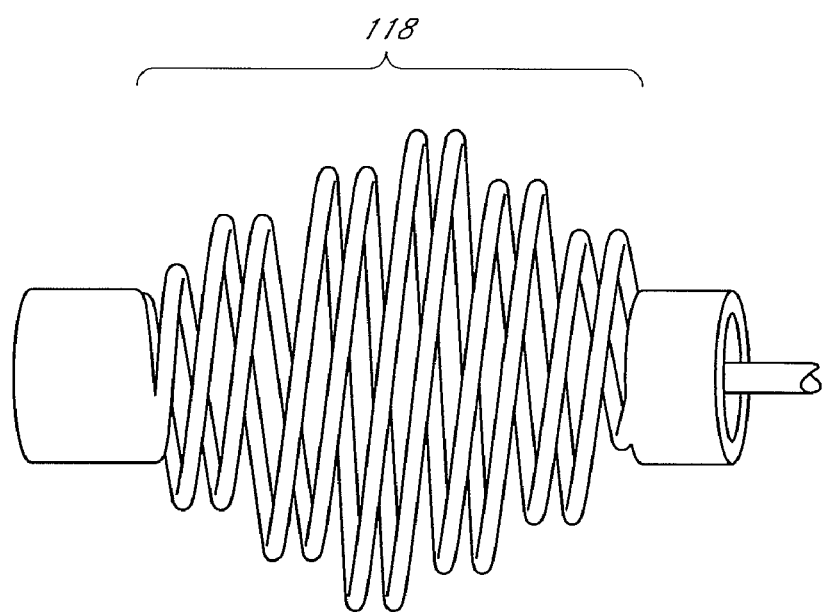
Figure 19:
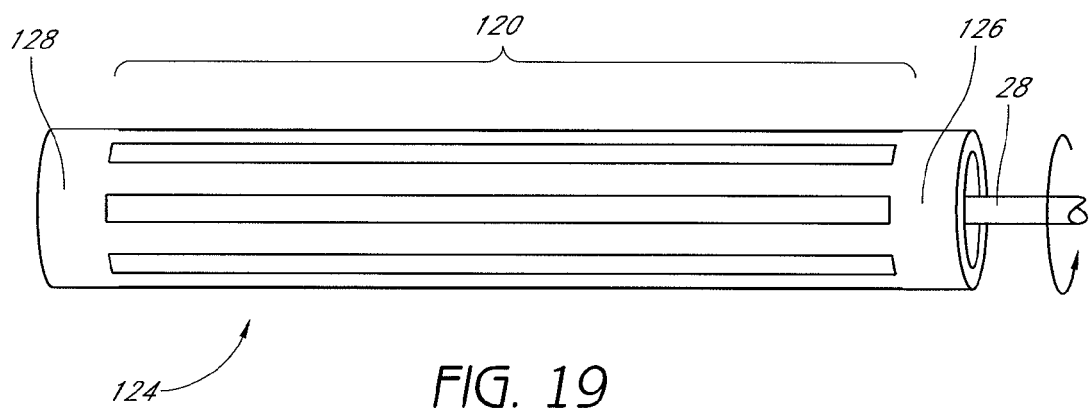
FIG. 19 depicts still another embodiment the invention comprising a radially expandable tissue anchor.

Referring to FIG. 18A, in another embodiment, the deformable zone 114 comprises angled circumferential slots 116, which, when expanded as shown in FIG. 18B, result in a spirally oriented deformation zone 118. FIG. 19 illustrates a spirally oriented deformable zone 120 of an anchor 124 configured to maintain the position of the one end of the anchor 124 while rotating the other end of the anchor. In one embodiment, the proximal end 126 of the distal anchor 124 is held in position by a delivery tool or catheter while the distal end 128 of the distal anchor 124 is pulled and rotated proximally. In some instances, the tether 28 has sufficient stiffness such that rotation of a tether 28 joined to the distal end 128 of the anchor 124 is sufficient to cause twisting of the anchor 124. In other instances, the tether 28 attached to the distal anchor 124 may lack sufficient stiffness to transmit sufficient torque to the distal anchor 124. To facilitate torque transmission to the distal anchor 124, a stiff inner core of the delivery tool may extend into the distal anchor to form a mechanical interfit with the distal end 128 of the anchor 124 and that is adopted to rotate and deploy the anchor 124 with rotation in one direction of the delivery tool and disengage from the anchor 124 when rotated in the other direction. After expansion, the inner core may be disengaged from the distal anchor 124 and withdrawn.

Figure 20:
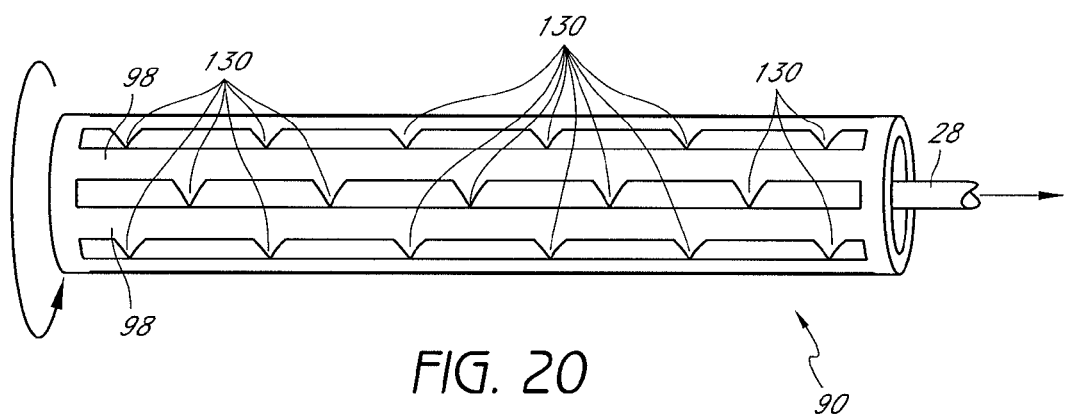
FIG. 20 depicts still another embodiment the invention comprising a radially expandable tissue anchor with barbs.

One or more surfaces of an anchor may also be further configured with protrusions, indentations or one or more porous layers to further engage the surrounding tissue. FIG. 20 is a further embodiment of the invention comprising teeth or pointed members 130 protruding from the struts 98 of the distal anchor 90 that may further enhance the tissue engagement characteristics of the distal anchor 90. In another embodiment, one or more surfaces of a strut 98 may be polished by methods known in the art. In still another embodiment, portions of the distal anchor 90 may comprise a drug-eluting surface. Preferably, the drug-eluting anchor may be used to release agents that alter the tissue and scar formation about the anchor. In some embodiments, fibrous tissue growth is encouraged to reduce the friability of the tissue surrounding the anchor. In other embodiments, anti-proliferative agents such as rapamycin or corticosteroids may be used to limit tissue growth. Other therapeutic agents may also be used, including antimicrobials, clot inhibitors, sclerosants, growth factors, hormones and other therapeutic agents known in the art. More than one therapeutic agent may be eluted from the drug-eluting surface, if desired. As mentioned previously, the distal anchor may also be covered with a bioabsorbable coating. The bioabsorbable coating may result in inflammation and/or fibrous tissue formation about the distal anchor. The fibrous tissue formation may also alter the tension or compliance characteristics of the tongue element or surrounding tongue tissue, and may be beneficial in reducing the risk of anchor extrusion or migration.

Figure 21A:
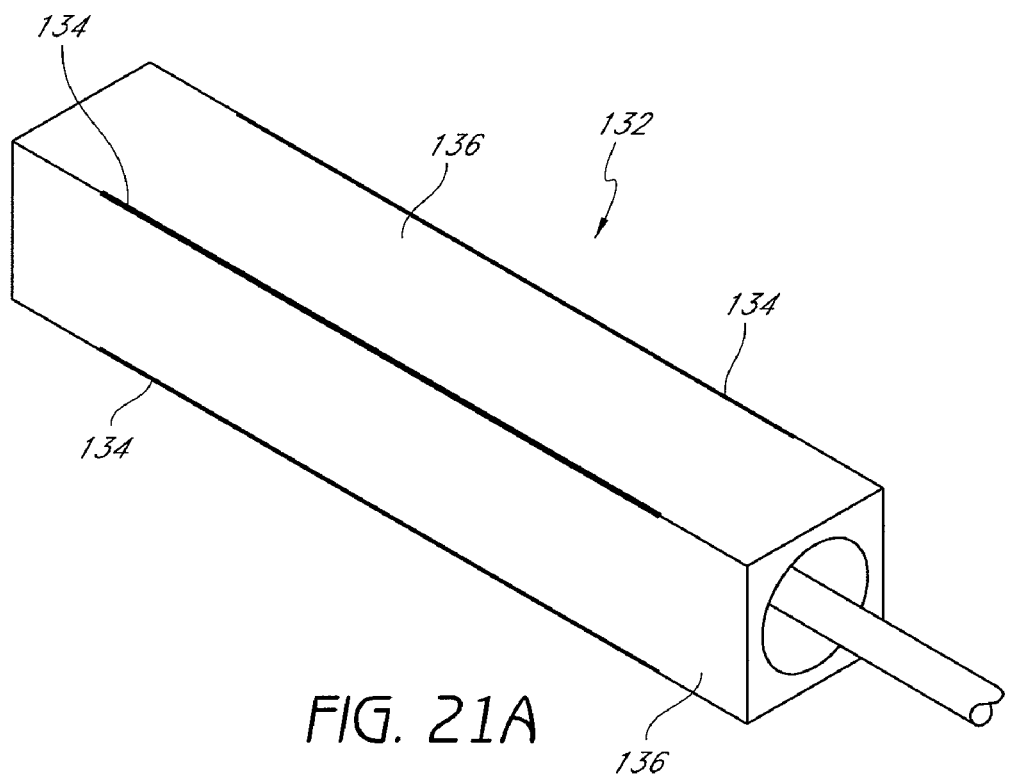
FIGS. 21A and 21B depict another embodiment the invention comprising a radially expandable tissue anchor before and after expansion.
Figure 21B:
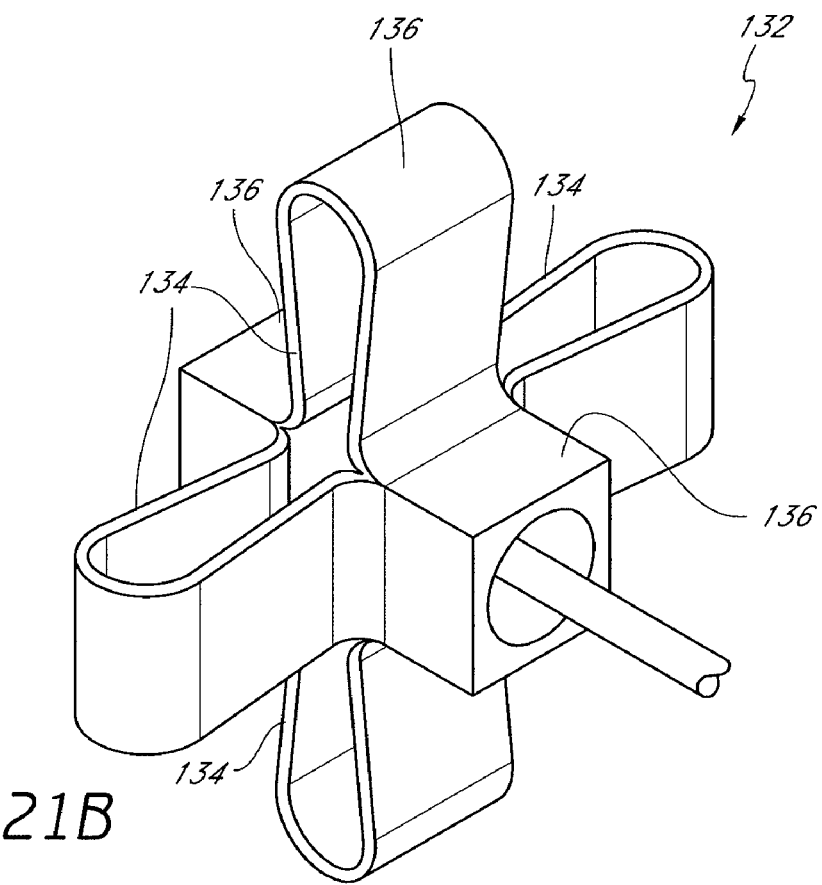

Although a distal anchor having a circular cross-sectional shape may be used in some embodiments of the invention, other cross-sectional shapes of distal anchors may also be used, including, triangular, rectangular, oval, polygonal or any other shape. The distal anchor need not have the same cross-sectional shape or size along its length. FIG. 21A depicts one embodiment of the distal anchor 132 comprising a square cross-sectional shape with slots 134 between each surface 136 of the anchor 132. When expanded, the anchor forms an X-shaped anchor as shown in FIG. 21B. The slots, however, may be positioned in a variety of configurations on the anchor as desired to achieve a particular expanded shape. In other embodiments, slots may be located within a surface 136 of the anchor 132, in addition to or in lieu of slots between the surfaces 136.

Figure 22A:
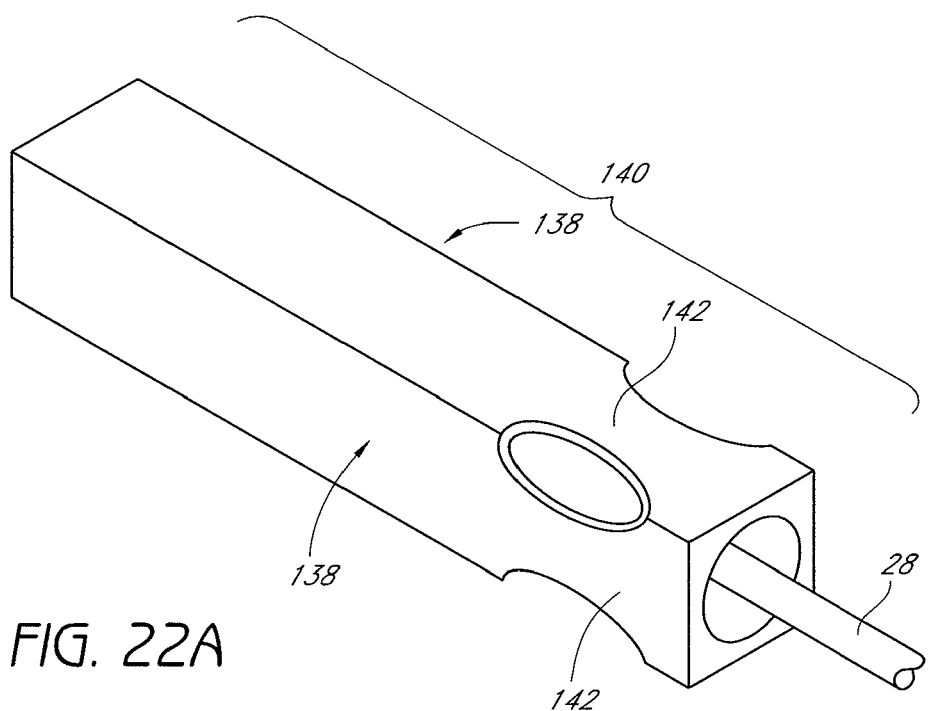
FIGS. 22A and 22B depict another embodiment the invention comprising a radially expandable tissue anchor before and after expansion.
Figure 22B:
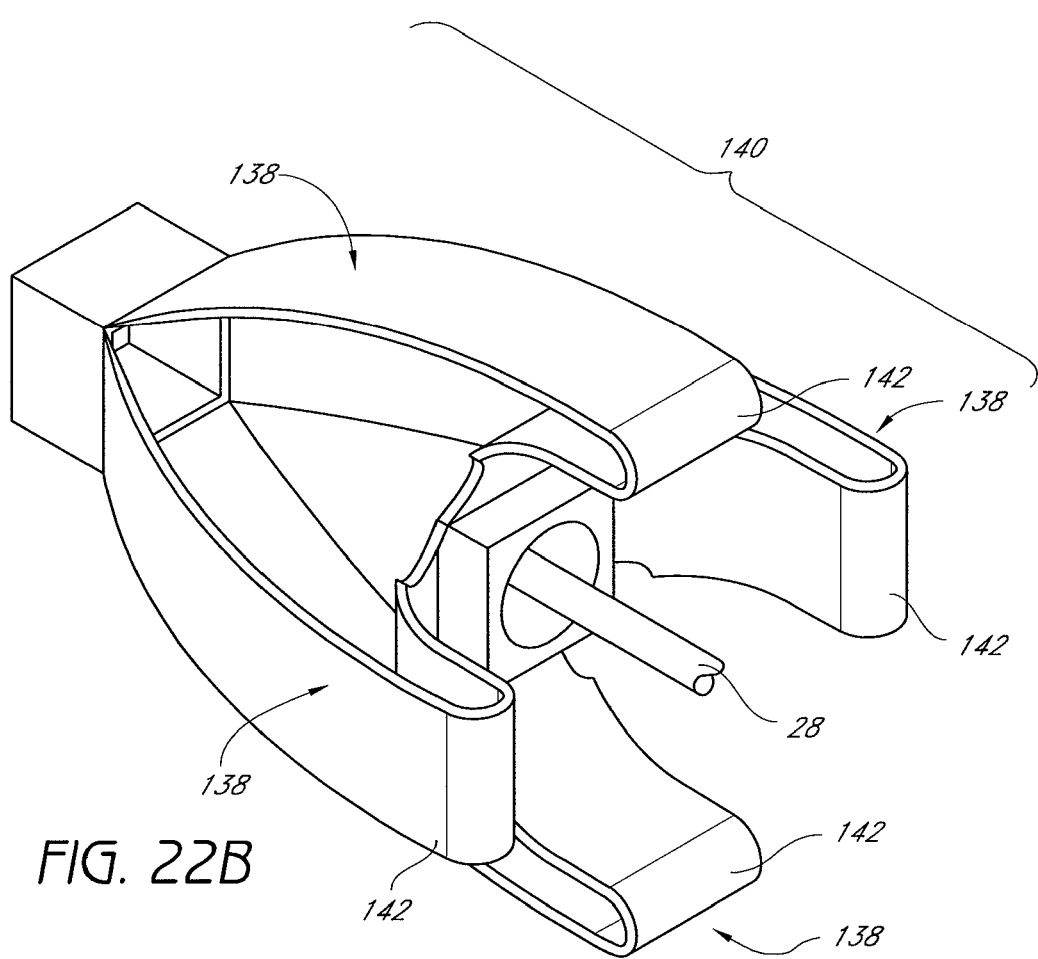

The shape of the slot and/or strut of the deformable zone need not be constant along the length of the slot or strut, or between the slots and/or struts of the same anchor. The struts may also be configured to control the shape of the deformation by varying the strut dimensions along the length of the strut. In some embodiments, indentations or creases in the struts may be used to cause an angular deformation of the strut with expansion. In other embodiments, the struts may deform in a curved or looped fashion. For example, variations in the cross-sectional shape, thickness and width of the struts may be used to provide a distal anchor that deforms asymmetrically in as least one dimension. This may be advantageous for resisting migration of the anchor in a particular direction. In FIGS. 22A and 22B, for example, struts 138 of the deformable zone 140 expands with a proximal bias because of proximal regions 142 of narrower widths, which may be beneficial in resisting migration from the proximal tension exerted through the tether 28.

Figure 23A:
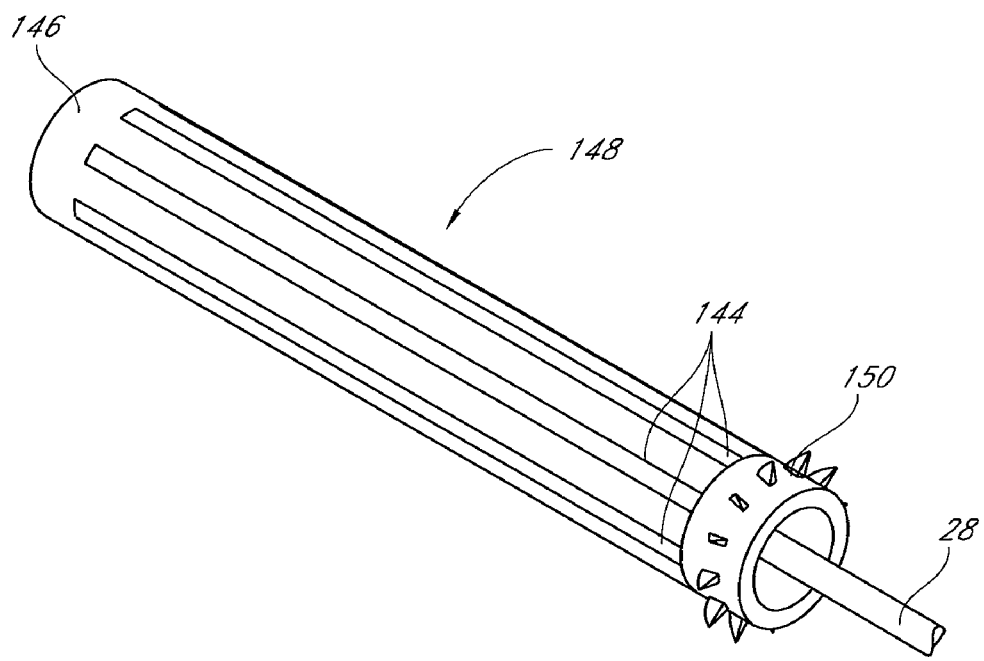
FIGS. 23A and 23B depict one embodiment the invention comprising a splayed tissue anchor before and after expansion.
Figure 23B:
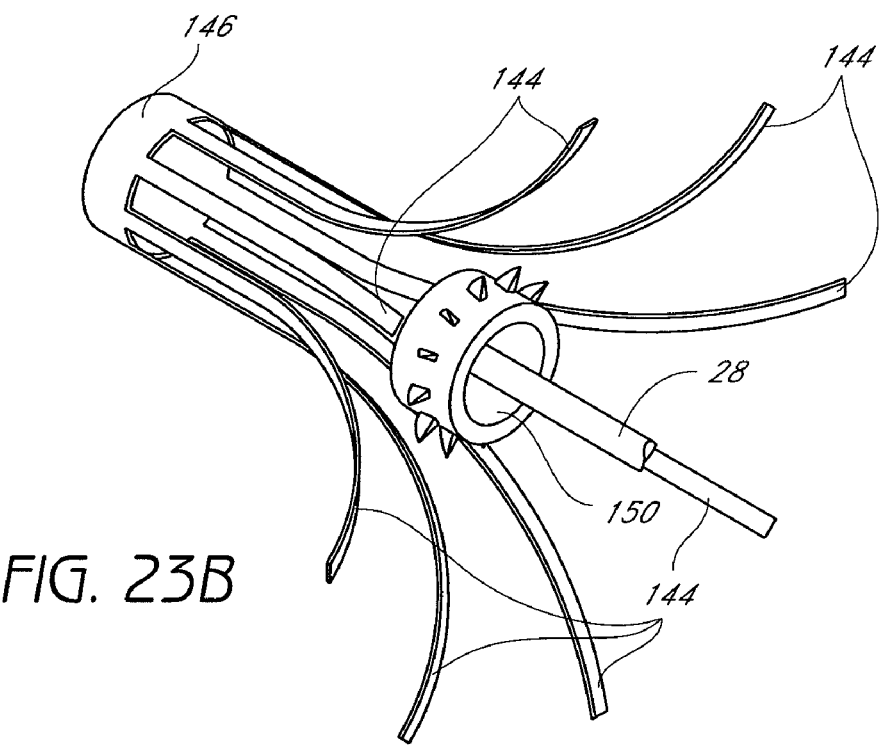
Figure 24A:
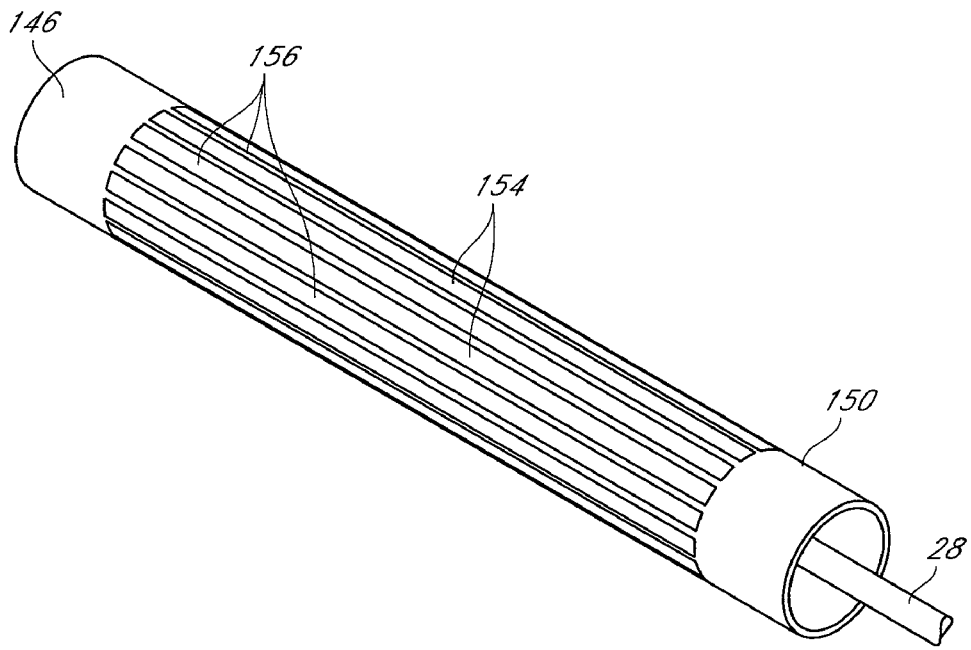
FIGS. 24A and 24B depict one embodiment the invention comprising a dual splayed tissue anchor before and after expansion.
Figure 24B:
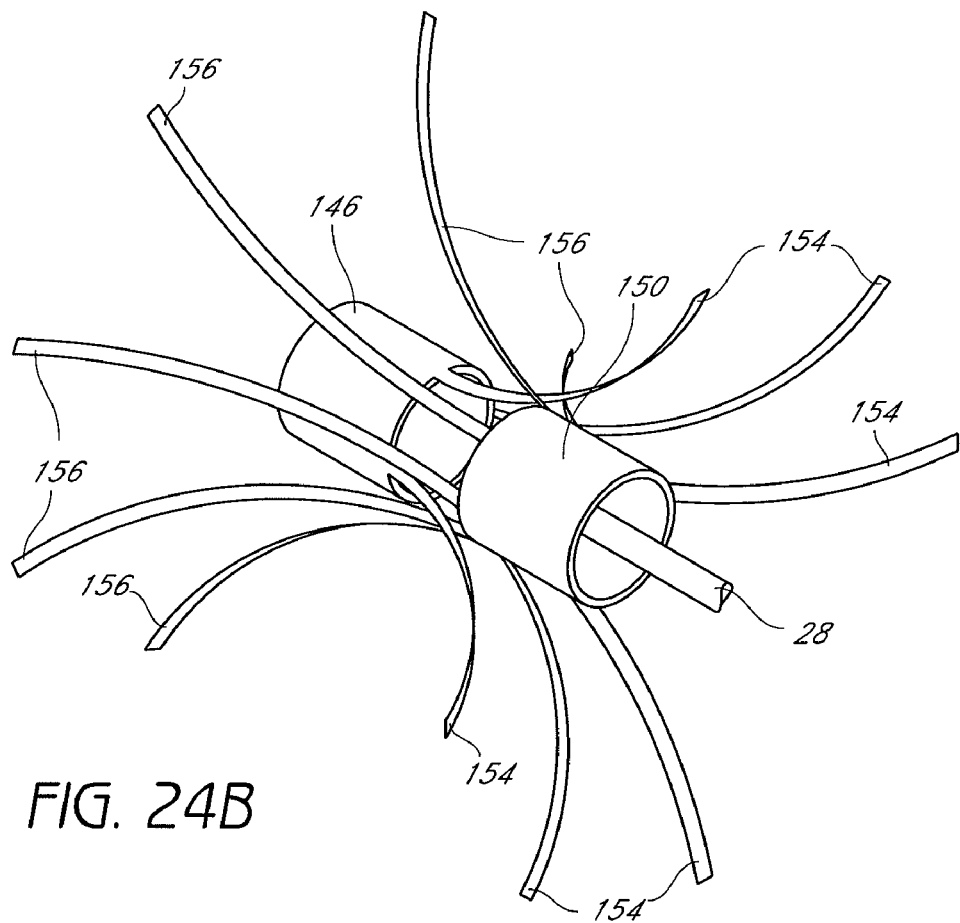

In some embodiments of the invention, the deformable zone may comprise at least one prong with one end that is not joined to either the distal end or proximal end of the tube segment. When the distal end and proximal end of the tube segment is brought closer together, the free end of the prong is able to splay outward and engage the tongue tissue. The strut may or may not have an intrinsic outward bias. FIGS. 23A and 23B depict one embodiment of the invention comprising prongs 144 attached to the distal end 146 of the anchor 148. When proximal tension is placed upon the tether 28, the prongs 144 contact and slide away from the proximal end 150 of the anchor 146, thereby splaying in a radially outward direction to engage the tongue tissue. In other embodiments, the anchor 152 comprises an alternating or other arrangement of multi-directional prongs 154, 156. In FIGS. 24A and 24B, alternating distal end and proximal end prongs 154, 156 are provided to engage the surrounding tissue from multiple directions. Although the prongs depicted in FIGS. 23A through 24B are flat prongs 144, 154, 156, the prongs may have any of a variety of cross-sectional shapes, including triangles, circles, square or any of a variety of other shapes. The end of each prong may be also configured with additional structures to modify the tissue engagement characteristics of the anchor. In some embodiments, the prong ends may be configured with spheres or other smooth surfaces to reduce the risk of tissue laceration from chronic tension exerted by the tether. In other embodiments, the prong ends are configured with barbs or hooks to further enhance tissue engagement. One skilled in the art can configure or select the prongs with the desired features for a given patient's anatomy and pathophysiology.

In another embodiment of the invention, the distal anchor 500 comprises at least one deformable hook element, and preferably a plurality of deformable hook elements 502, 504. The plurality of hook elements 502, 504 may be spaced circumferentially and/or longitudinally on the distal anchor 500 in any of a variety of configurations, at regular or irregular positions. The hook elements 502, 504 may be arranged individually about the distal anchor or placed in one or more groups about the distal anchor 500. A tether is typically attached to the distal anchor 500 about its proximal end 521. In the specific embodiment illustrated in FIGS. 60A to 60D, the distal anchor 500 comprises a proximal group 506 of four hook elements 502 and a distal group 508 of four hooks 504. The hook elements 502, 504 within each group 506, 508 are spaced about 90 degrees apart and the proximal group 506 is offset from the distal group 508 by about forty-five degrees. In other embodiments, one or more of the angles between the hook elements 502, 504 and/or hook groups 506, 508 may be different. For example, the hook elements may be spaced such that the distal anchor has a left/right symmetry but a smaller vertical profile than horizontal profile when fully deployed into tissue. In still other embodiments, the hook elements may or may not have a left/right symmetry, and/or may have similar or dissimilar sizes, shapes and/or lengths. The hook elements 502, 504 may be provided with sharp or tapered distal ends 510, 512 as depicted in FIGS. 60A to 60E, but in other embodiments, the ends may have blunt or have other configurations. Each end of the hook element need not have the same configuration. The distal anchor 500 illustrated in FIGS. 60A to 60D may also be combined with other features and structures described herein, including but not limited to biocompatible or biodegradable coatings.

Figure 60A:
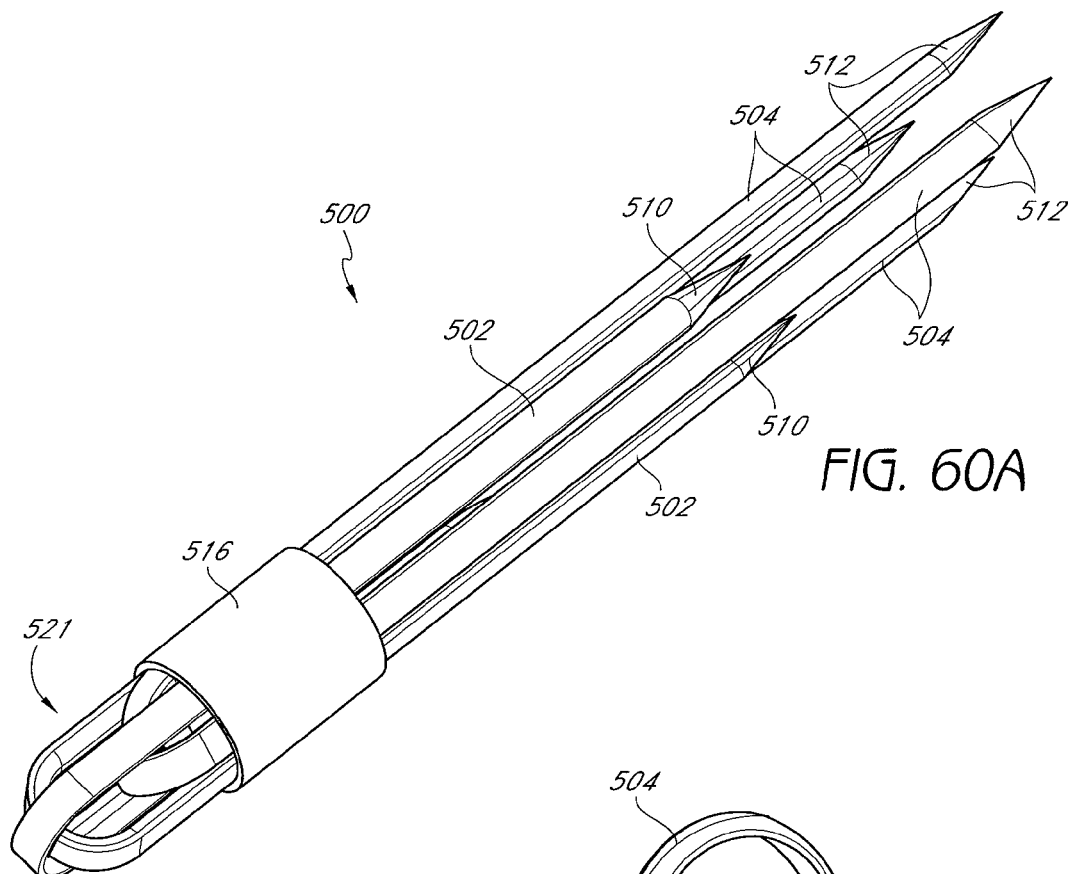
FIGS. 60A and 60B are perspective views of another embodiment of a distal anchor in the delivery and deployed configurations, respectively.
Figure 60B:
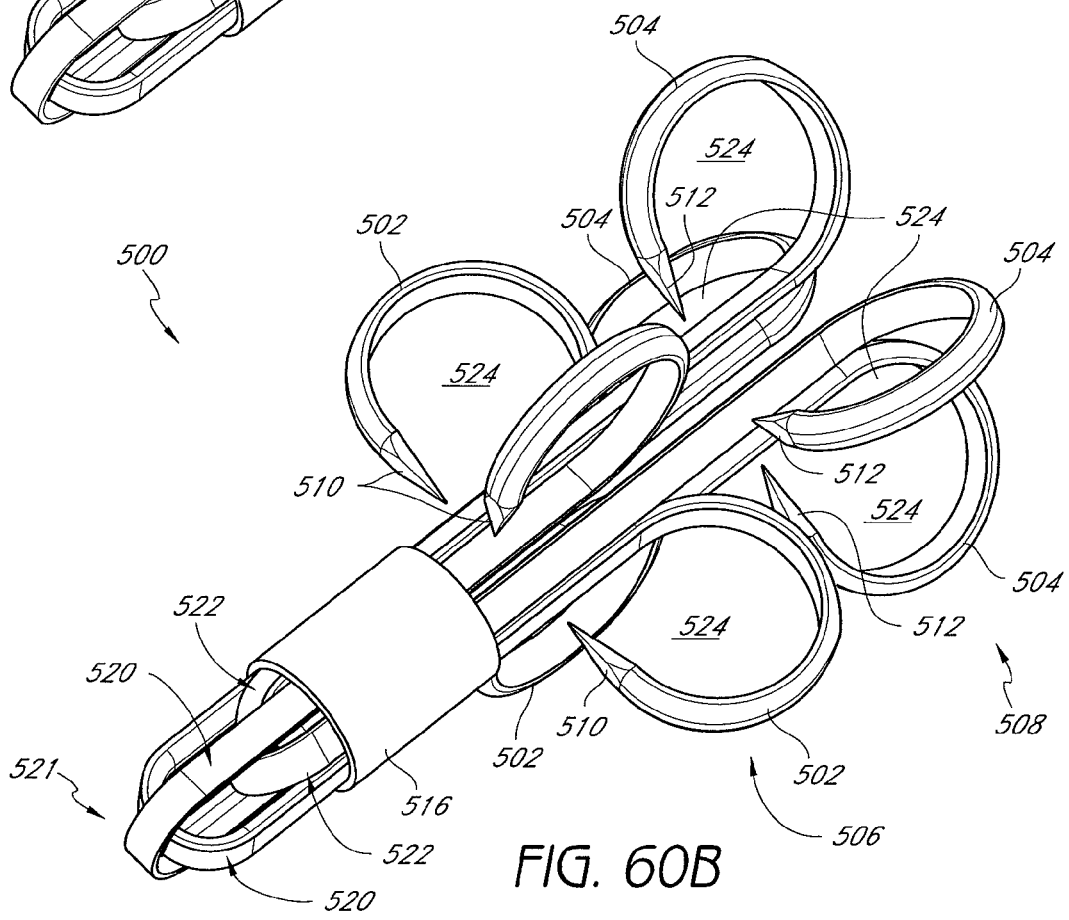
Figure 60C:
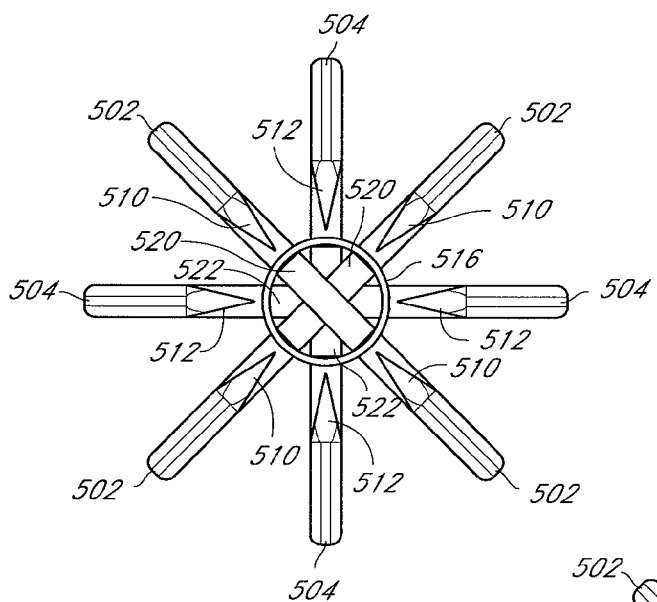
FIGS. 60C and 60D are rear and frontal views of the distal anchor in FIG. 60B.
Figure 60D:
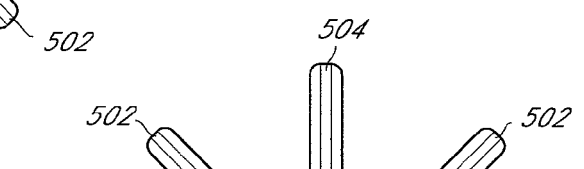
Figure 60E:
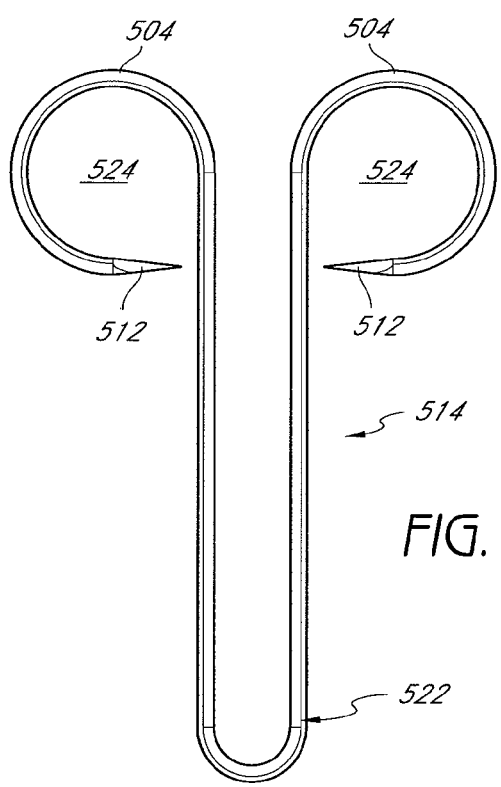
FIG. 60E depicts a subcomponent of the distal anchor in FIGS. 60B to 60D.

The distal anchor 500 in FIGS. 60A to 60D comprise groups 506, 508 of symmetrical U-shaped planar structures 514 with one hook element on each end, as depicted in FIG. 60E, and restrained by a band 516 and an inner core 518 about their proximal ends 520, 522, as depicted in FIGS. 60C and 60D. One of skill in the art can produce any of a variety of expandable hook structures for deployment in the tongue without undue experimentation and will understand that the embodiments of the invention are not limited to the arrangements of U-shaped symmetrical hook element structures. For example, in other embodiments, the distal anchor may have a unibody construction, or may comprise a plurality of non-symmetrical and/or multi-planar components. In one specific embodiment, the plurality of piercing or grasping elongate members may be provided using one or more X- or asterisk-like structure formed into a multi-planar structure. Each group may be formed from the same or a different X or asterisk-like structure.

Figure 62A:
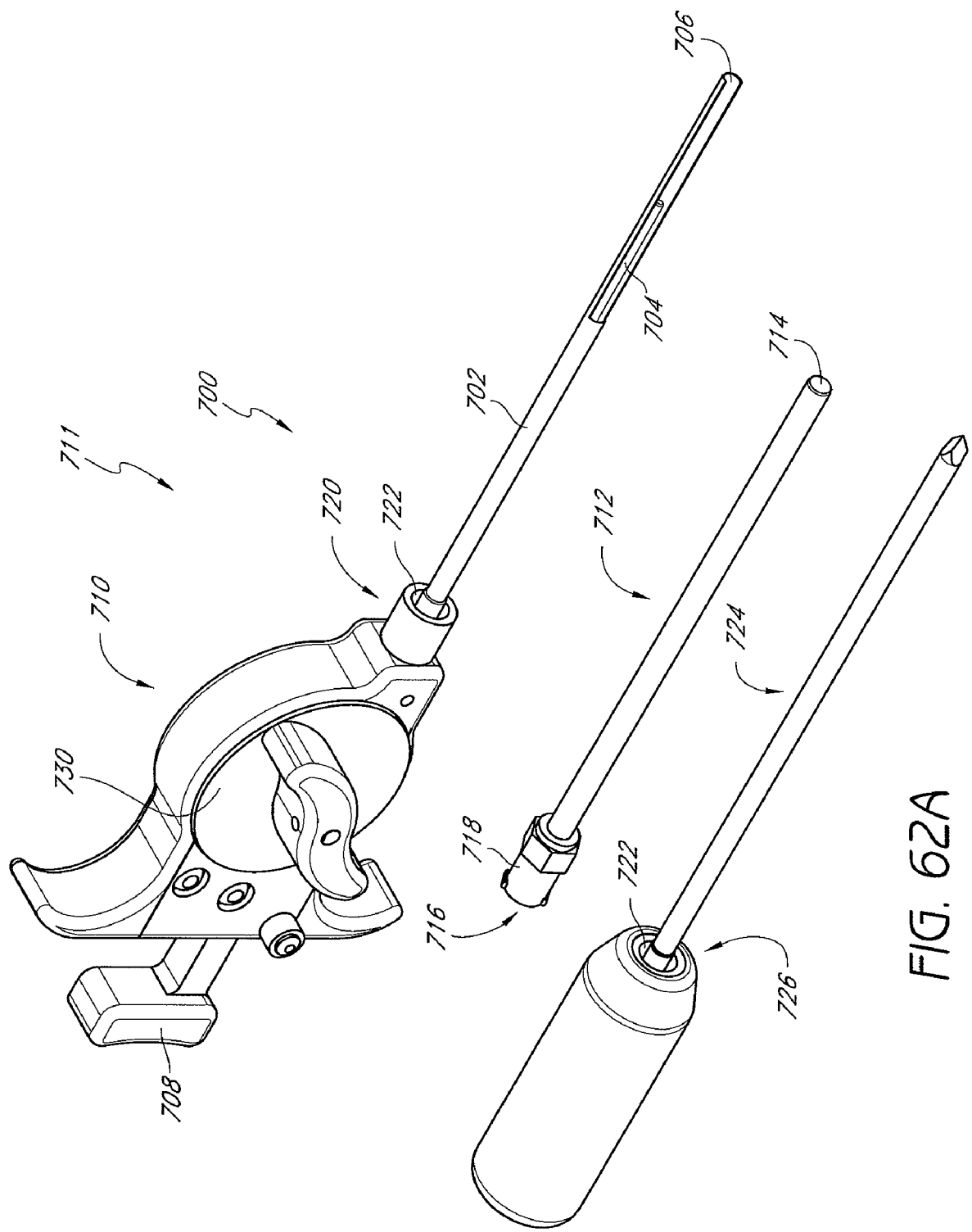
FIG. 62A is a superior isometric view of one embodiment of a delivery tool system with a partial cut-away of the delivery tube of the delivery tool.

As shown in FIG. 60A, the distal anchor 500 may comprise a low-profile delivery configuration to facilitate minimally invasive implantation of the distal anchor 500 and, as shown in FIG. 60B, an expanded deployment configuration to engage the surrounding soft tissue. In the low-profile delivery configuration, each hook element 502, 504 generally has a straighter configuration to facilitate insertion of the distal anchor 500 into the soft tissue using a delivery device. The delivery device may be configured to restrain the hook elements in the straighter low-profile configuration until the distal anchor is deployed. As illustrated in FIG. 62A, one embodiment of the delivery device 700 for deploying a distal anchor comprises a tubular body 702 with a pushrod 704, spring structure or other structure for displacing a distal anchor out of the distal opening 706 of the tubular body 702. In other embodiments, the tubular structure may be retracted or withdrawn relative to the pushrod. One embodiment of a delivery device is discussed in greater detail below.

As each hook element is exposed relative to the distal opening 706 of the tubular body 702, the distal tip of each hook element is no longer restrained and can revert back to its deployment configuration to engage the surrounding tissue. In the embodiment depicted in FIG. 60B, the distal ends 510, 512 of the hook elements 502, 504 are configured to curl back onto themselves to form a loop-like structure 524. In other embodiments, the hook elements may curl to a greater or lesser extent, have a tighter or looser curl, and/or may have a more angular configuration when deployed. In some embodiments, due to the expansion bias of the hook elements 502, 504 in the deployment configuration, as the distal ends 510, 512 of the hook elements 502, 504 are partially exposed from the delivery tool, the expansion of the hook elements 502, 504 may cause the proximal portions 520, 522 of the distal anchor 500 to be quickly pulled out of the delivery tool unless restrained or controlled in some manner. In some instances, the rapid expansion of the hook elements 502, 504 out of the delivery tool may facilitate its engagement of the surrounding tongue tissue by virtue of the rate with which the hook elements pierces or grabs the surrounding soft tissue. With a slower deployment speed, the soft tissue may get pushed away or displaced from the curling hook elements 502, 504, rather than being engaged, captured, pierced or grasped. Additional features on the hook elements, including but not limited to tissue ingrowth surfaces or barbs, may be used to enhance engagement of the tissue anchor to the surrounding tissue in some instances when a slower delivery speed is desirable but provides inadequate tissue engagement. Preferably, the deformable or expandable piercing or grasping members of the distal anchor comprise a metal such as Nitinol or superelastic Nitinol, but other materials may also be used and are described in greater detail below.

Although the distal anchor structure shown in FIGS. 60A to 60D and in other figures are described in the context of tongue manipulation, such structures may be applicable to a variety of other tissue structures, anatomical locations and treatments. Other tissue structures may include bone, fat, ligament, tendon, liver, striated and smooth muscle. Other anatomical locations may include the nasopharynx, soft palate, hard palate, pharyngeal wall, GI tract, bronchial tree, biliary tree, and genitourinary tract.

Figure 25A:
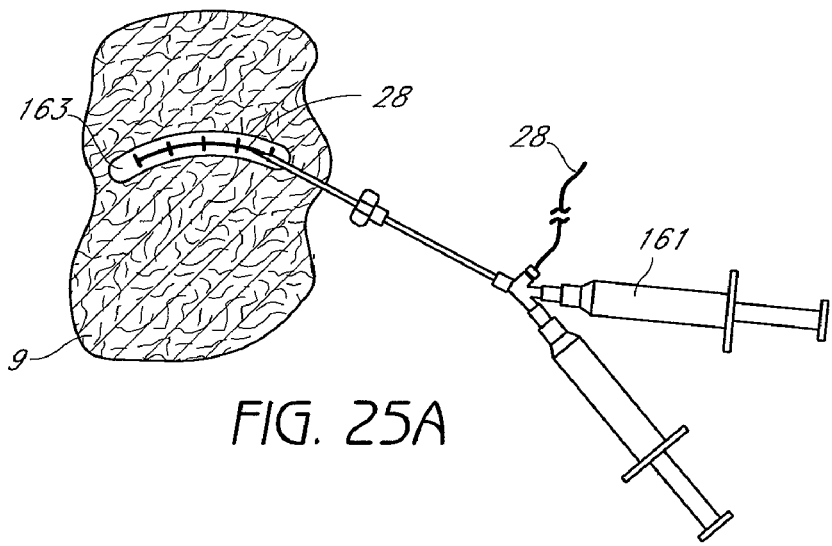
FIGS. 25A through 25C illustrate one embodiment of the invention comprising an in situ formed anchor or plug.
Figure 25B:
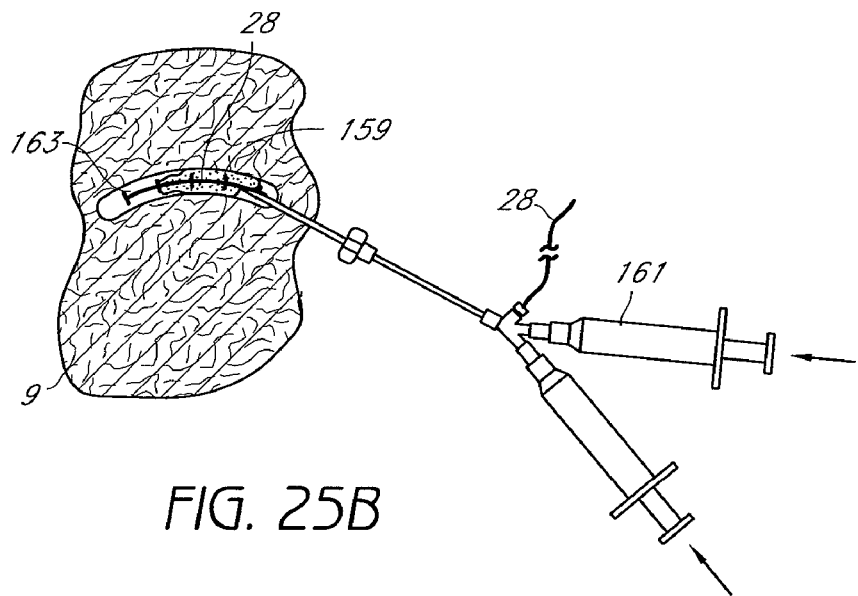
Figure 25C:
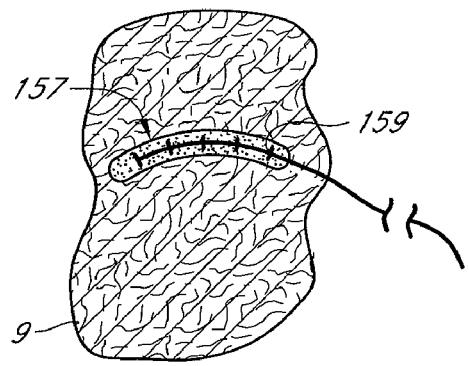

Referring to FIGS. 25A through 25C, in another embodiment of the invention, the anchor or plug 157 may be at least partially formed in situ within the tongue 9. As shown in FIG. 25C, an injectable material 159 may be formulated to set in situ, to form the anchor 157 or plug, possessing the desired shape, position and mechanical properties to engage or resist migration from the surrounding tongue 9 or other soft tissue. A tether 28 may be positioned at the site of formation before, during or after the injection of the material 159. The portion of the tether embedded in the anchor or plug 157 may be configured to resist separation from the material 159, typically by one or more transverse elements, but one skilled in the art will understand that any of a variety of protrusions or other three-dimensional structures may be used.

The anchor 157 may comprise an injectable material 159 having one or more biocompatible liquid components, or one or more solid biocompatible components carried in one or more liquid biocompatible components. As depicted in FIG. 25B, the material 159 may be injected as a liquid or slurry into the tongue 9 or other soft tissue region by a syringe or other delivery tool 161. Upon mixing, the components cross-link, polymerize, or otherwise chemically react to create the in situ biocompatible, non-liquid, static mechanical anchor 157 or plug, as shown in FIG. 25C. In one embodiment, the delivery tool 161 has at least two injection lumens for delivering the components separately to the target site to prevent premature reaction of the components within the delivery tool 161 or elsewhere.

Referring to FIG. 25A, in some embodiments, prior to injection of the material 159, the targeted tissue region may be dilated by use of a trocar, balloon catheter or other expandable structure, to open a tissue space 163 in the tongue 9 to receive the injectable material 159. During dilation, the tissue space 163 may be deliberately sized and shaped, so that the resulting material 159 injected into the tissue space 163 will possess the size, shape, and physical characteristics to resist migration within the surrounding soft tissue.

The biocompatible liquid component may comprise, e.g., an Elastin™ media. Alternatively, the liquid component may comprise an oil or low viscosity liquid that is biocompatible to impart the desired features and/or shape to the anchor 157. The solid component may be a polyvinyl acetate (PVA) or foam that is appropriately sealed to provide biocompatibility. Other materials such as silicone rubber, elastomeric polymers and polytetrafluoroethylene (Teflon® Material, from DuPont) may also be selected. Alternatively, a powder, small spheres, microtubules or shavings of solid material can be mixed with a slurry or liquid.

Figure 26A:
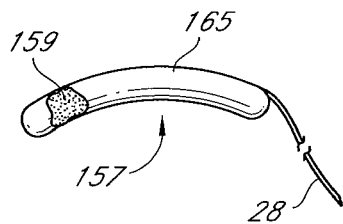
FIGS. 26A through 26D illustrate one embodiment of the invention comprising a fillable anchor or plug.
Figure 26B:
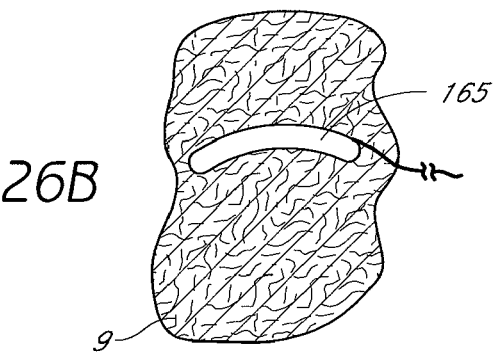

Referring to FIGS. 26A and 26B, alternatively, the injectable material 159 may be injected into a fillable structure 165 that is itself implanted in a targeted tissue region. The fillable structure is preferably pre-shaped, expandable to assume the desired inflated shape, position, and mechanical properties. A tether 28 may or may not be integrated with the fillable structure 165.

Figure 26C:
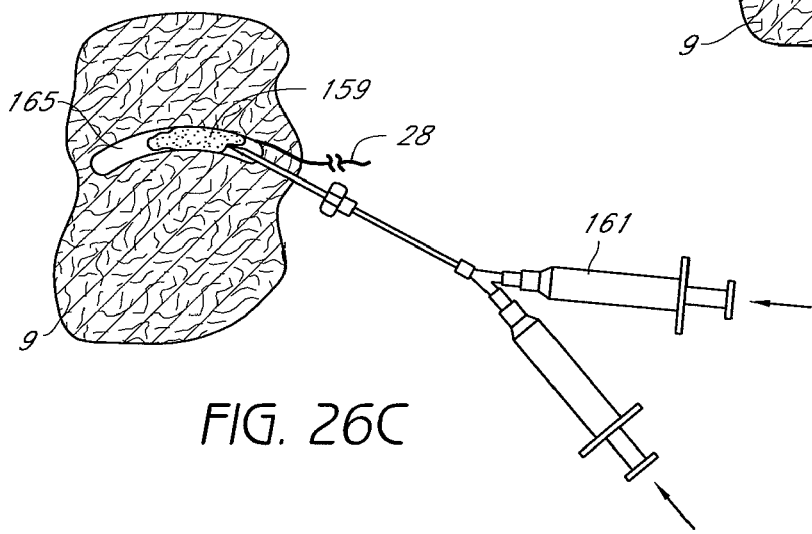
Figure 26D:
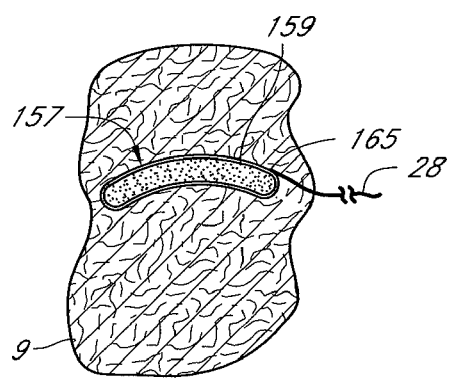

As illustrated in FIGS. 26C and 26D, once suitably implanted, the fillable structure 165 is inflated by infusion of the injectable material 159, which is dispensed from a syringe or other delivery tool 161. In one embodiment, the injectable material 159 may be formulated to set in situ within the fillable structure 165, the finable structure 165 and its contents serving as an anchor 157 or plug, possessing the shape, position and mechanical properties to resist migration. It should be appreciated that, when an expandable fillable structure 165 is used to house the injectable material 159, a fluid (e.g. saline) or slurry that does not set or cure in situ may be also used to form an anchor 157 or plug. Furthermore, the injectable material 159 may be formulated to be injected as a gel that need not set or cure to perform its desired function.

The fillable structure 165 may comprise a bioresorbable material, such as polyglycolic acid, a polymer used for resorbable sutures and other devices within the body. In this arrangement, once expandable fillable structure 165 is resorbed, only the core of injectable material 159 will remain to serve as the anchor or plug. The fillable structure 165 may also have one or more porous regions. Each porous region may be full thickness or partial thickness porous regions. One or more full thickness porous regions may allow escape of trapped air, if any, during the injection procedure. Depending on the pore size, the full thickness porous regions may also allow partial extrusion of one or more components of the injectable material 159 from the fillable structure 165 to interface with the surrounding tissue.

One or more partial thickness porous regions on the outer surface of the fillable structure 165 may allow tissue ingrowth into the fillable structure 165 or increase the frictional resistance between the fillable structure 165 and the surrounding tissue to further resist migration. One or more porous regions may also be provided on the inner surface of the fillable structure 165 to allow the injectable material 159 to form an interlocking configuration with fillable structure 165 which can resist separation or movement at the interface between the fillable structure 165 and the core formed in situ by the injectable material.

In one embodiment of the invention, the anchor is integral with a tether and comprises a tubular elastic member wherein one or more regions of the elastic member are configured to expand and occupy a larger space when the tubular elastic member is filled or pressurized with the injectable material. In one embodiment the anchor portion of the tubular elastic member comprises a thin walled region configured to expand to a greater size than other portion of the tubular elastic member.

2. Tether

In some embodiments of the invention, the tethers of the tongue elements comprise sutures or wires that are well known in the art. Such materials are generally inelastic and may be useful to fix the distance between the distal anchor and the proximal anchor or securing assembly. For reasons previously mentioned, however, a tether with elastic properties or comprising structures that provide a length/tension relationship may be preferred in some instances. A tether capable of lengthening in response to increased load or tension may be optimized to provide sufficient bias to reduce the effects of oropharyngeal occlusion while providing a more physiologic range of tongue motion than that produced by fixed length tethers. Fixed length glossoplasty or suspension of the tongue may be the cause of odynophagia, dysphagia and deglutition problems seen with existing tongue remodeling devices, but the current invention is not limited to this purpose. A tether with elastomeric properties may be provided by using materials such as but not limited to urethane or silicone. One skilled in the art can select the particular material, tether length, diameter, cross-sectional shape and other features based upon the desired effect, tolerances, and the particular patient's anatomical characteristics. Other materials that may comprise the tether include but are not limited to Nitinol, spring steel, tantalum, polyethylene, polyester, silk, polypropylene, polyolefin or a combination thereof.

Other tether configurations that may be used include passive and active variable length or bias structures such as braided or woven structures, electropolymers, springs, coils, magnets or solenoids. Thus, in some of the embodiments, the tether configuration may actively change in length in length or configuration resulting from the application of external energy or force such as electrical current or magnets. These active tether configurations may be further configured with local or distal sensor components that may modulate the activity of the external energy or force acting on the active tether. The modulation may be influenced or triggered by detection of diaphragm movement or depolarization activity, nerve depolarization, pressure changes and/mechanical contact in the airway.

The tether may also be covered by a lubricious biocompatible coating. In another embodiment, the tether comprises a bioabsorbable coating that may cause scar or connective tissue formation about the tether. Scar tissue formation may further enhance the effect of the glossoplasty implant by tightening the tongue tissue and/or to resist migration of the implant.

In some embodiments, the proximal tether of the tongue element may be configured with one or more structures or surfaces capable of engaging at least a portion of the tongue tissue surrounding the tether so that a distal anchor is not required, or to distribute the tissue engagement. In still other embodiments, the tongue element may comprise multiple distal anchors and multiple tethers arranged in a serial or branching fashion.

Figure 27:
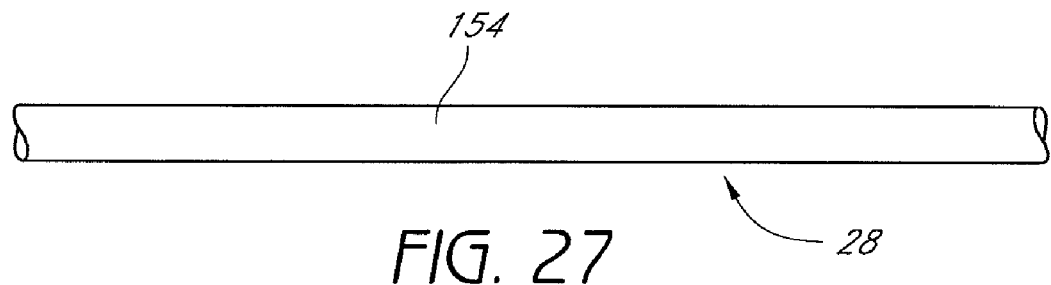
FIG. 27 represents one embodiment of the invention comprising an elastomeric tether.
Figure 28:
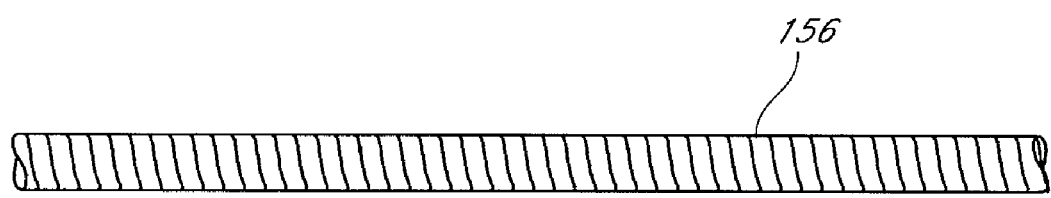
FIG. 28 represents one embodiment of the invention comprising a wound wire.
Figure 29:
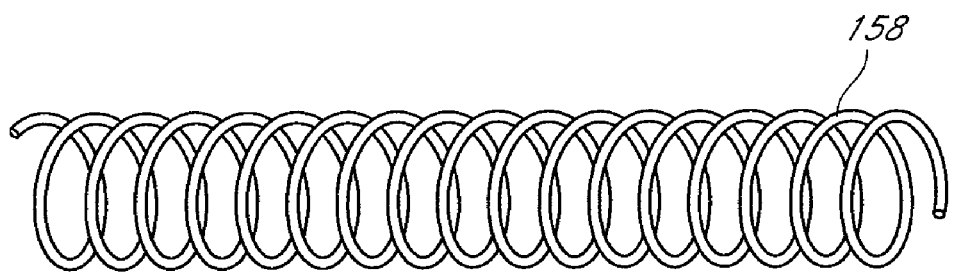
FIG. 29 represents one embodiment of the invention comprising a spring coil.

FIG. 27 depicts one embodiment of the invention comprising an elastomeric cord that may be used for the tether 28. The elastomeric cord 154 may comprise single or multiple tightly wound elastomeric members 156, as shown in FIG. 28. Referring to FIG. 29, in other embodiments, the tether may comprise a structure having spring-like or resilient properties, such as a braided structure, a woven structure, or a metallic or polymeric coil 158.

Figure 30:
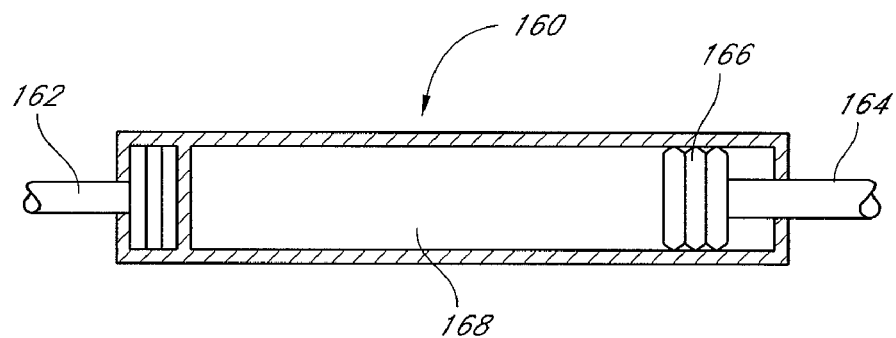
FIG. 30 represents one embodiment of the invention comprising one-sided pneumatic tension assembly.
Figure 31:
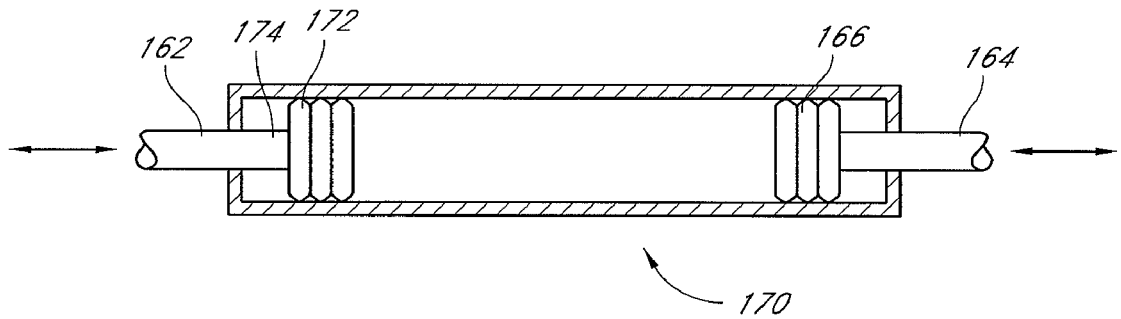
FIG. 31 represents another embodiment of the invention comprising two-sided pneumatic tension assembly.

The tether may also comprise a variety of other tension structures that provide length/tension relationships. FIG. 30 depicts one embodiment of the invention comprising a pneumatic casing 160 with a first tether 162 fixed to one end of the pneumatic casing 160 and a second tether 164 attached to a movable piston 166 within the casing 160 which is capable of reversible movement within the pneumatic casing 160 depending upon tension exerted through the first and second tethers 162, 164. A vacuum chamber 168 provides a shortening bias to the second tether 164. In another embodiment of the invention, shown in FIG. 31, the pneumatic casing 170 comprising a first movable piston 166 attached to a first tether 164 and a second movable piston 172 attached to the second tether 174. By having two movable pistons 166, 172 incorporated into the pneumatic casing 190, the casing 170 can remain in a fixed position within the tongue 9 while distributing changes in distance between both the first and second tether 164, 174, which may reduce the irritation and inflammation caused by excessive movement of any one part of the tether system.

Figure 32:
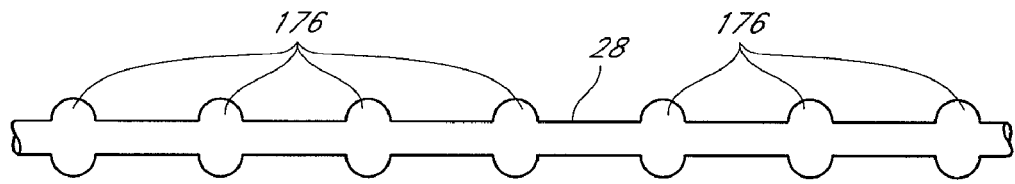
FIG. 32 represents one embodiment of the invention comprising a beaded tether.
Figure 33:
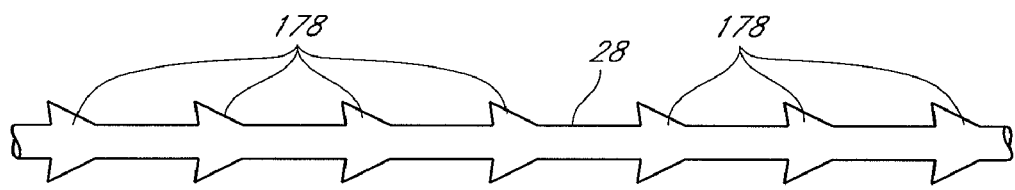
FIG. 33 represents one embodiment of the invention comprising a barbed tether.

The tether may be further configured to provide one or more structures for adjustable mechanical interfacing with the securing structure of the implant. These structures may include bead structures 176, as shown in FIG. 32, or ramped structures 178 as shown in FIG. 33. The particular structure on the tether 28 can be selected by one skilled in the art based upon particular interface characteristics desired with the securing assembly.

Figure 34:
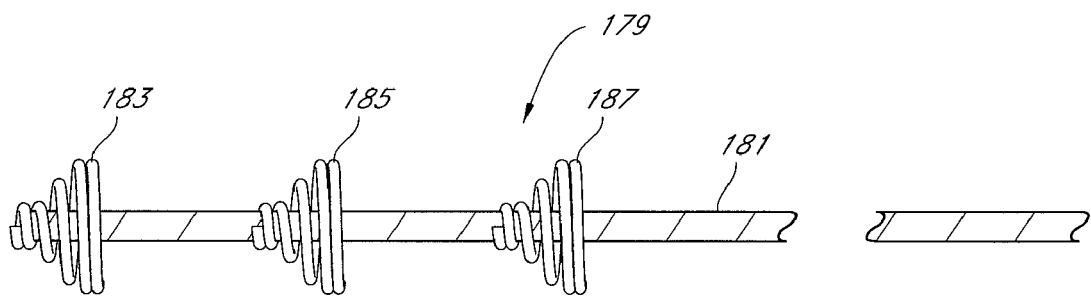
FIG. 34 depicts one embodiment of a tether having a serial arrangement of anchors.
Figure 35:
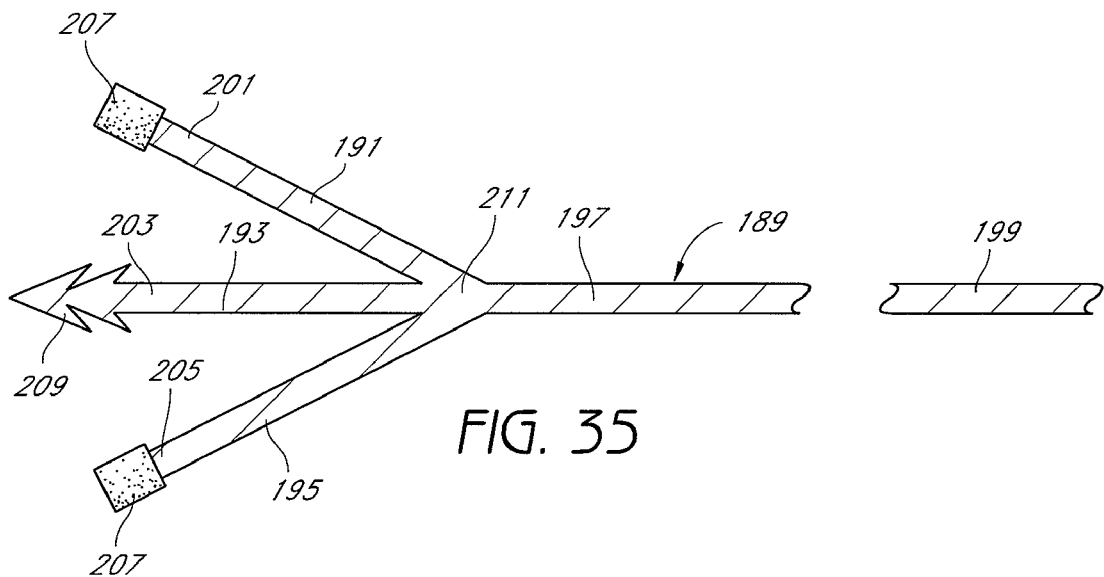
FIG. 35 illustrates one embodiment of a branched tether with anchors.

Although in some embodiments of the invention, the tongue element comprises a single elongate tether having one proximal end, one distal end, and a single distal anchor attached to the distal end of the tether, other configurations of the tongue element are also envisioned. In one embodiment, depicted in FIG. 34, the tongue element 179 comprises a tether 181, a distal anchor 183, and at least one additional anchor 185, 187 along the length of the tether 181, arranged serially. The multiple anchors 183, 185, 187 need not be of the same configuration and need not be spaced regularly along the segment or length of tether 181. In another embodiment, depicted in FIG. 35, the tether 189 may have one or more branches, 191, 193, 195. The branches 191, 193, 195 may originate from the main tether trunk 197, or may branch from other branches 191, 193, 195 of the tether 189. In one embodiment, the branching tether 189 had a single proximal end 199 and two or more distal ends 201, 203, 205. Tissue anchors 207, 209 may be located along a branching tether 189 at the distal ends 201, 203, 205, a branch point 211, or any other position along the branching tether 189. The branches 201, 203, 205 of the tether 189 need not be symmetrical in branch length, diameter, elasticity, branch configuration or other characteristics.

Figure 36:
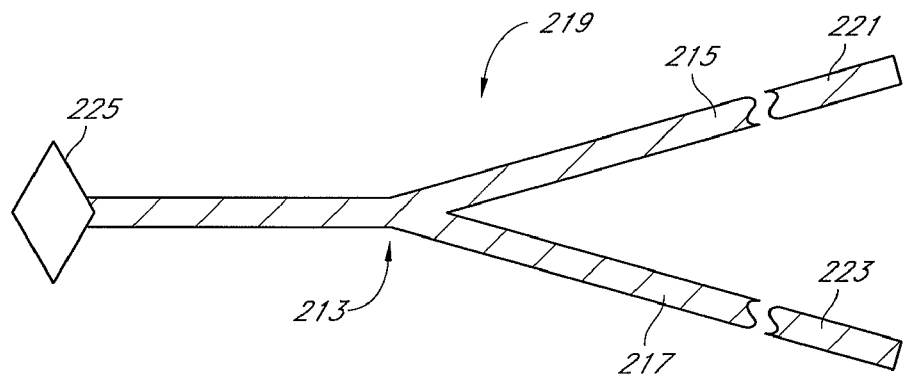
FIG. 36 depicts a tether having two proximal ends.

In another embodiment, shown in FIG. 36, the tether 213 may comprise two or more proximal ends 215, 217, that are attachable to the same or different anatomical structures. A tongue element 219 having two or more proximal attachments 221, 223 may be beneficial in limiting tongue movement or distal anchor 225 movement in more than one direction. The various features of the tongue element described above may be used in various combinations to achieve the desired effect from the glossoplasty system.

Figure 37:
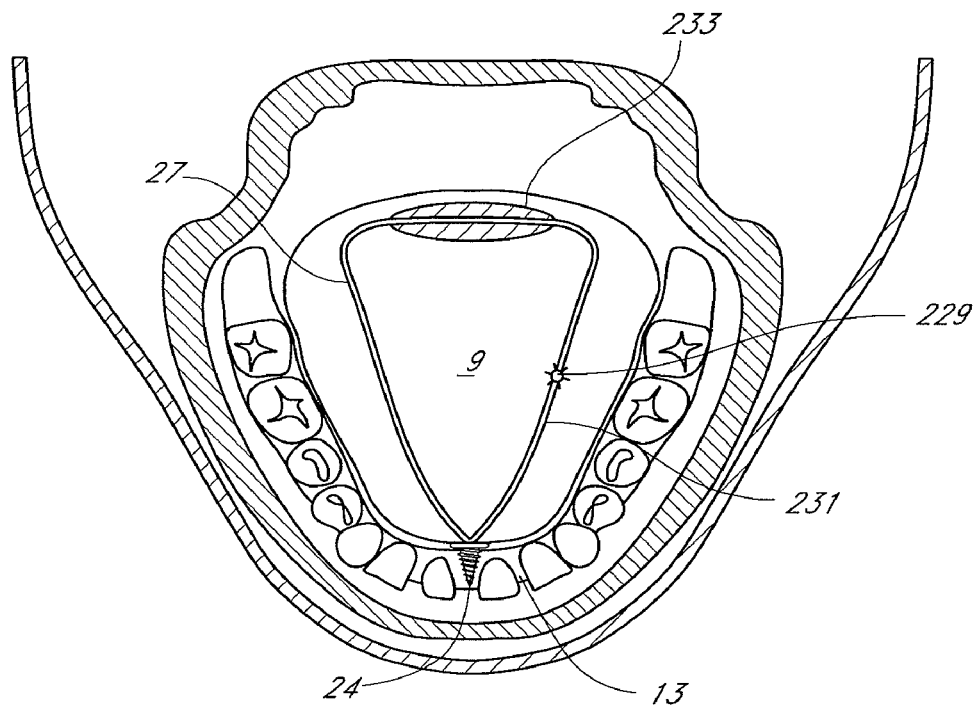
FIG. 37 is a cross sectional view of one embodiment of the invention comprising a tether loop with an enlarged section.

FIG. 37 depicts another embodiment comprising a tether loop 227 having two ends 229, 231 wherein the two ends 229, 231 are joined and the tether loop 227 is engaged to a securing assembly 24. The tether loop 227 may comprise one or more regions 233 of an expanded diameter or size to reduce the risk of the loop 227 cutting through the tongue 9 due to chronic tether tension and with tongue movement. The tether loop 227 may have a fixed region of increased diameter, a self-expanding region, a balloon or fluid expanding region or an in situ formed expanded region.

Figure 38:
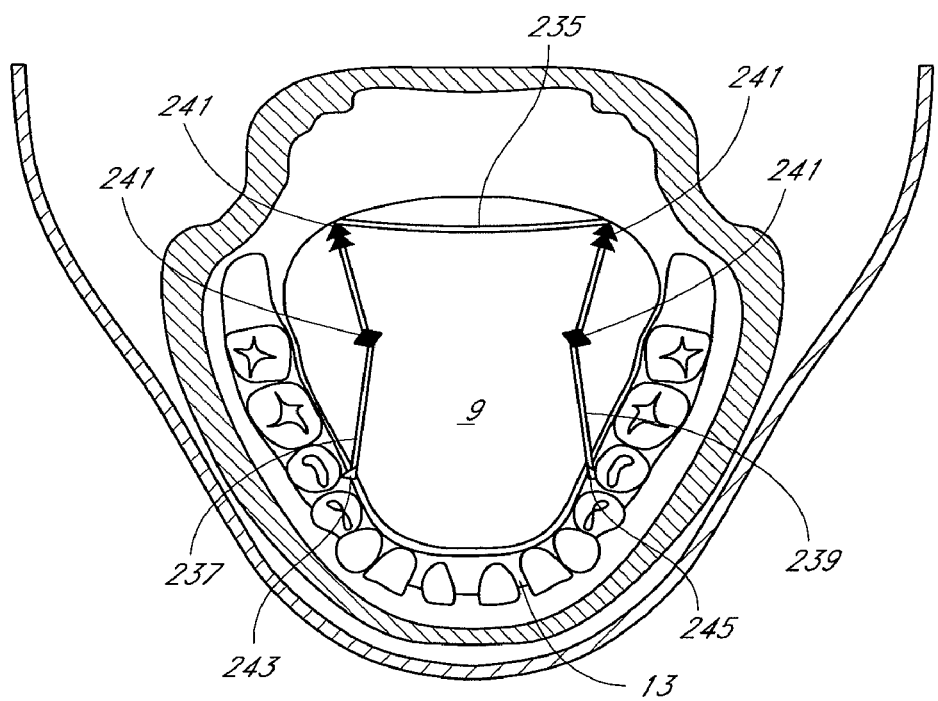
FIG. 38 is a cross sectional view of one embodiment of the invention comprising a tether loop with tissue anchors along the tether loop.

FIG. 38 illustrates another embodiment of the invention comprising a tether 235 with two ends 237, 239 and at least one tissue anchor 241 attached to the tether 235 between the two ends 237, 239. The two ends 237, 239 of the tether 235 may be attached to the same site or same securing assembly, or at two different sites 243, 245. Although the relative locations of the two sites 243, 245 as shown in FIG. 38 are symmetrical with respect to the midline of the tongue 9 and mandible 13, in other embodiments the location may be asymmetrical.

FIG. 60F depicts another embodiment of the invention, comprising a tether 28 that is looped or threaded through the proximal end 521 of the distal anchor 500 from FIG. 60B. Typically, the proximal end of the distal anchor 500 is positioned about halfway between the first end 23 and second end 25 of the tether 28, but may also be positioned at other locations between the first and second ends 23, 25. Referring to FIG. 60G, one or more knots 27 are optionally provided to resist slippage of the distal anchor 500 along the length of the tether 28. One or more knots 27 and/or other securing methods (e.g. gluing or melting the elongate member to itself) may also be used to prevent the distal anchor 500 from separating from the tether 28 should a section of the tether 28 between the knot(s) 27 and one of the ends 23, 25 be severed. The optional knot(s) 27 will keep the distal anchor 500 secured to the tether 28 and allow the remaining intact section of the tether 28 to maintain its connection to the securing assembly 600. The connection of the tether 28 to the distal anchor 500 is typically performed at the point of manufacture, but in other embodiments of the invention, one or more attachments may be performed at the point of use to allow customization of the tongue element. As mentioned previously, the distal anchor 500 is preferably implanted into the tongue prior the attachment of the first and second ends 23, 25 of the tether 28 to the securing assembly 500, but in other embodiments, the distal anchor 500 and tether 28 are pre-attached to the securing assembly 600 when the distal anchor 500 is implanted.

3. Securing Assembly

As mentioned previously, bone anchors or screws, clips, staples and other devices well known in the art may be used for directly attaching a tongue element 22 to a mandible 13 or other rigid structure. Preferably, however, a tether securing assembly 24 is provided to facilitate attachment, removal and/or adjustment of the tether 28 to an attachment structure. More preferably, tether securing structures 24 that allow adjustment in a minimally invasive manner are used. In some embodiments, one tether securing structure is provided for each tongue element 22 of the glossoplasty system. In other embodiments, more than one tongue element 22 may be secured to each retaining structure.

Figure 39:
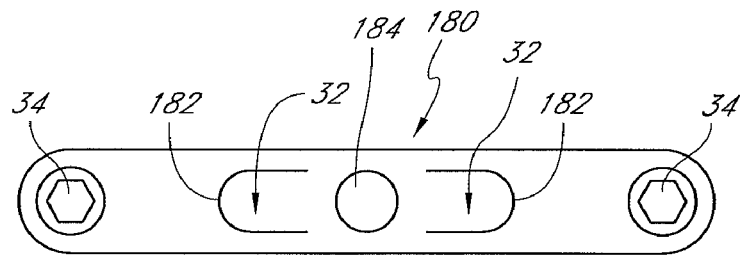
FIG. 39 illustrates one embodiment of the invention comprising a mandible securing assembly with a lumen.

FIG. 39 depicts one embodiment of an attachment structure 180. The attachment structure 180 comprises one or more bone engaging elements to attach the attachment structure to a bone or other structure such as a bone screw or anchor 34. Angled protrusions or tabs 182 projecting from the attachment structure 180 provide securing interfaces 32 may be used to lodge and retain one or more tethers 28 through frictional resistance. The tether 28 may be wound between the two angled protrusions 182 to further enhance the frictional resistance between the protrusions 182 and tether 28, and also to localize excess tether material for access at a later date. If the tongue element 22 was secured with excessive tension, the excess tether material may be unwound, loosened to a desired tension and rewound onto the protrusions 182. Once the desired tension is determined over the course of days, weeks or months post-implantations, any excess tether material not required to secure the tether 28 to the attachment structure 180 may be removed to reduce the infection risk from unnecessary foreign body material. In some embodiments of the invention, a conduit or bore hole is provided in the mandible 13 or other bone, an access hole 184 may be provided in the attachment structures 180 and the attachment structure 180 may be positioned directly over the conduit or bore hole.

Figure 40A:
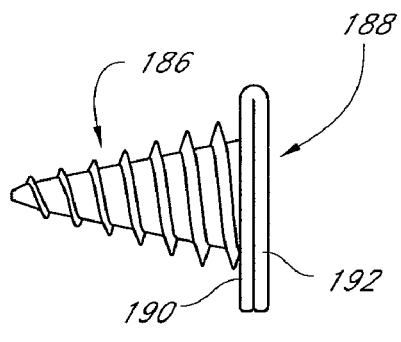
FIGS. 40A through 40C represents one embodiment of the invention comprising a mandible securing assembly with a clipping interface.
Figure 40B:
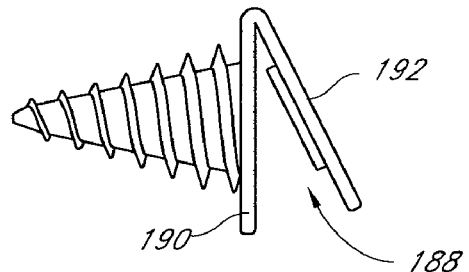
Figure 40C:
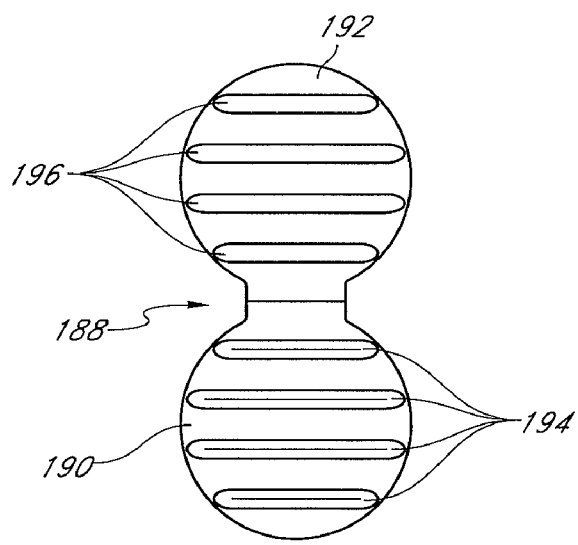

FIGS. 40A through 40C depict another embodiment of attachment structure comprising a bone screw 186 with a clamping interface 188 for retaining tethers 28. The clamping interface 188 comprises two opposing surfaces 190, 192 or structures that are adapted to provide a frictional or mechanical interface with tethers 28 or other elongate members inserted within the clamping interface 188. The clamping interface 188 has an open configuration depicted in FIGS. 40B and 40C to allow positioning of one or more tethers 28 within the interface 188 and a closed configuration shown in FIG. 40A for retaining the tethers 28. The closed configuration may be achieved by crimping the two opposing surfaces 190, 192 or by further structures of the clamping interface, such as complementary clasps or clip structures that are well known in the art to fix the opposing surfaces 190, 192 together. Referring to FIG. 40C, the clamping interface 188 may further comprise complementary indentations 194 and protrusions 196 to further enhance the frictional resistance of the interface in the closed configuration. The opposing surfaces or structures of the clamping interface may also be configured with frictional surfaces that are well known in the art through the use of various materials, surface treatments or configurations. Frictional surface configurations may also include cross hatched surfaces or irregular porous surfaces.

Figure 41A:
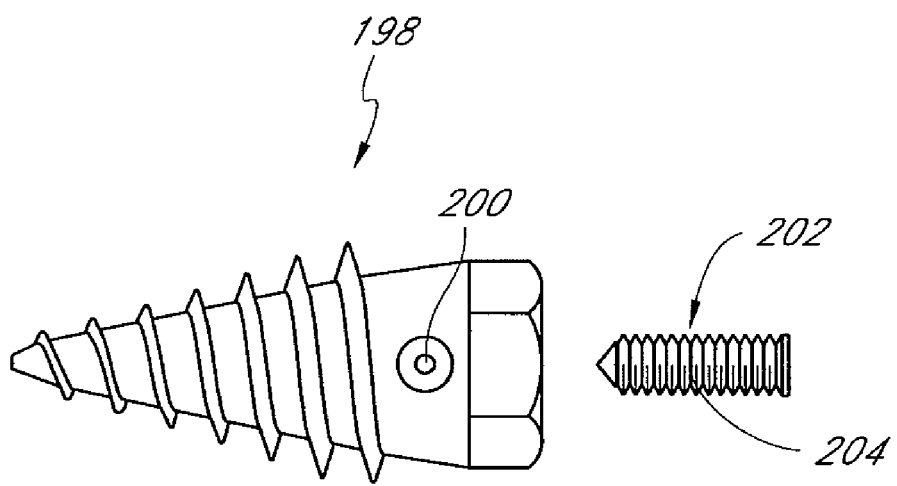
FIGS. 41A and 41B illustrate one embodiment of the invention comprising a mandible securing assembly with a tether securing bolt.
Figure 41B:
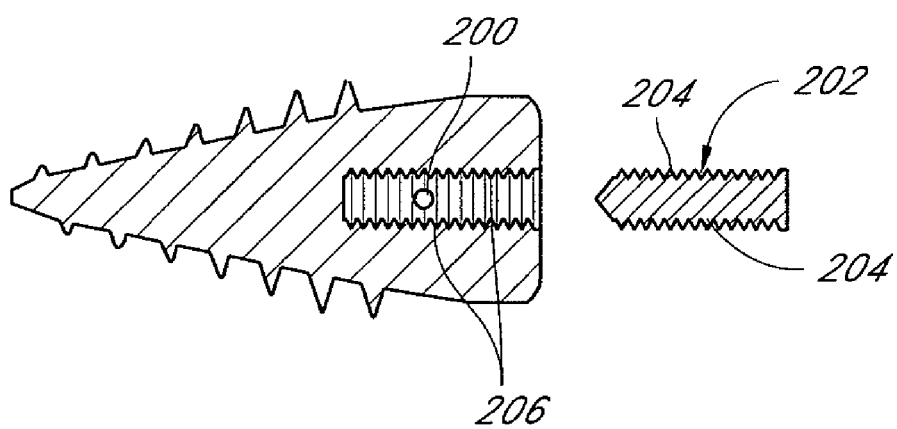

FIGS. 41A and 41B illustrate another embodiment of the attachment structure 198 comprising a retaining lumen 200 for inserting one or more tethers 28 and accepting a retaining bolt 202 for securing the tethers 200 within the retaining lumen 200. Typically the retaining bolt 202 will comprise a threaded surface 204 that is complementary to a threaded surface 206 of the retaining lumen 200.

In some embodiments of the invention, the securing assembly is capable of adjusting the tension acting on the tether without directly accessing and manipulating the tether. This may reduce the need to perform an open procedure to access the securing assembly and locate small, hard-to-find tether ends. Preferably, the tension adjustment may be facilitated through an adjustment tool interface that can be accessed in a minimally invasive manner.

As previously illustrated in FIGS. 7A through 7F, in some embodiments of the invention, the securing assembly 60 is adapted for insertion into a conduit created through the mandible 13 or other bone. A securing assembly 60 with a reduced or flush profile may be beneficial by minimizing or eliminating any palpability or visibility of the implant. Some patients may find that palpable or visible surface landmarks of the implant are psychologically or cosmetically unacceptable. Although the securing assemblies described below are described in the context of insertion into a conduit through the mandible, these securing assemblies may adapted for attachment to the exterior of the bone by providing an attachment structure with an aperture on the exterior surface of the securing structure capable of accepting a bone screw.

Referring to FIGS. 42A through 42D, in one embodiment of the invention, a securing assembly 217 comprises an elongate body 208 with a lumen 210 and an inner threaded surface 212, and a core 214 with external surface threads 216 complementary to the threaded lumen surface 212 of the lumen 210 and capable of forming a rotational interface with the elongate body 208. The core 214 may be directly attached or attachable to one or more tethers 216 of the glossoplasty system. After implantation of the distal anchor in the tongue, tether tension can be adjusted by rotating the core 214 within the threaded lumen 210 which in turn adjusts the distance between the distal anchor and the core 214 within the lumen 210 of the elongate body 208. In one embodiment, where the tether 216 is directly attached to the core 214, rotation of the core 214 with a rotation tool 240 will adjust the tether tension and result in translation of the core rotation into torque acting on the tether 216 and distal anchor, which may or may not result in unacceptable rotation of the tether 216 and distal anchor. This torque effect may cause increased tension in the tether 216 from twisting causing further reduction in the distance between the core and the distal anchor. The torque effect may cause rotational laceration of the tongue tissue about the distal anchor. In other embodiments, however, the torque effect may be advantageous in taking up excess slack in the tether.

The securing assembly 217 may be threaded on its external surface 222 to allow secure positioning of the elongate body 208 within the bone conduit of a bone. Although the lumen 210 is generally circular in cross section, the cross sectional shape of the external surfaces 222 of the elongate body 208 need not be circular, and could be oval, rectangular, square, polygonal or any other of a variety of cross sectional shapes. The external surface 222 may also have other surface characteristics or structures to resist migration, including but not limited to ridges, barbs, hooks, and/or porous surfaces for bone ingrowth. The elongate body 208 may also comprise a flange on the proximal end 218 to resist migration of the elongate body 208 in the distal direction. The proximal end 218 of the elongate body 208 is typically open ended to allow insertion of the threaded core 214 after implantation of the elongate body 208. In other embodiments, the proximal end 218 of the elongate body 208 is partially closed and is configured to accept the threaded core 214 at the distal end 220. In still other embodiments, the elongate body 208 is open at both ends. Preferably, the distal end 220 of the elongate body 208 is partially closed to prevent accidental release and loss of the threaded core if the core is overadjusted while still open sufficiently to allow passage of one or more tethers into the elongate body. In some embodiments of the invention, a slip interface is provided at the attachment of the tether to the distal anchor to resist rotation of the distal anchor with adjustment of tether tension.

As shown in FIG. 42A, the threaded core 214 is a cylindrical component with a proximal end 224, distal end 220, and a threaded external surface 228 complementary to the threaded inner lumenal surface 212 of the elongate body 208. The threaded core 214 further comprises a first partial slot 230 that is generally perpendicular to the longitudinal axis of the core 214 and a second slot 232 that is generally between the first slot, the external surface and the distal end of the core. The second slot 232 is dimensioned to allow passage of at least the diameter of one tether 216 but to resist passage of the tether 216 when the external surface of the core 214 is in contact with the inner lumenal surface 212 of the elongate body 208 and where the proximal end 234 of the tether 216 is configured to with an increased diameter, in some examples, by tying the tether end 234 into one or more knots, or to attach the tethers end 234 to an enlarged surface area slippage component, such as a rod, disc 236 or plate. The first and second slots 230, 232 are generally dimensioned to align the center of the disc 236 with the center of the distal end 226 of the core 214, but it is not required. Alignment of the centers allows the tether 216 to maintain a generally stable position while the core 214 is rotated. If either the first or second slot 230, 232 does not include the center of the core 214, the tether may wobble eccentrically when the core 214 is rotated. FIG. 42B illustrates one embodiment of the securing assembly where the tether 216 is attached to a disc 236, which is then passed through the second slot 232 and into the first slot 230. Although it is preferred that the first slot 230 be generally perpendicular to the longitudinal axis of the core 214 to evenly distribute frictional forces between the core and tether end, this is not required. In some embodiments, the first slot 230 may be oriented within the range of about zero degrees to about 180 degrees with respect to the longitudinal axis of the core 214. In other embodiments, the first slot 230 is oriented between about 45 degrees and 135 degrees, and in still other embodiments to about 75 degrees to about 110 degrees. The core 214 further comprises a mechanical interface 238 on its proximal end 224 for engaging a rotational tool 240. As shown in FIGS. 42C and 42D, when the core 214 is rotated within the lumen 210, the position of the core 214 with respect to the lumen 210 is changed, thereby adjusting the tension in the tether 216. The first slot 230, second slot 232, and/or slippage component 236 may be covered with PTFE or another lubricious coating to minimize rotation of the tether 216 from rotation of the core 214 due to friction between the tether/slippage component 236 and core 214.

Figure 43A:
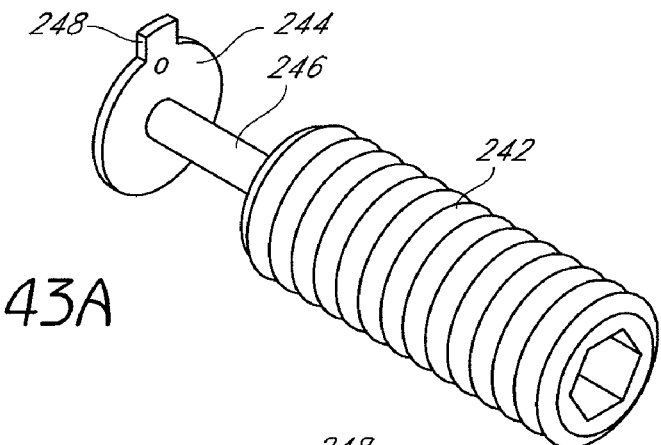
FIGS. 43A through 43E illustrate another embodiment of the invention comprising a keyed tether interface.
Figure 43B:
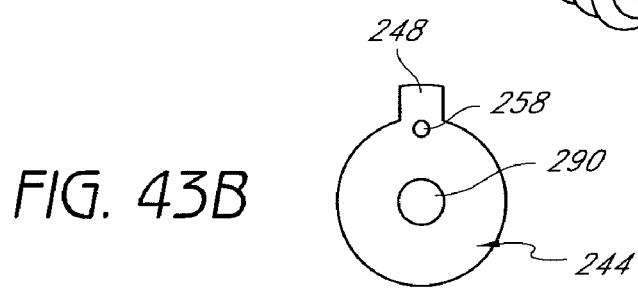
Figure 43C:
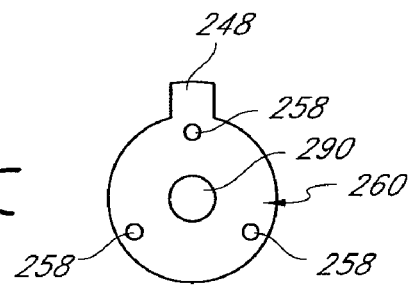
Figure 43D:
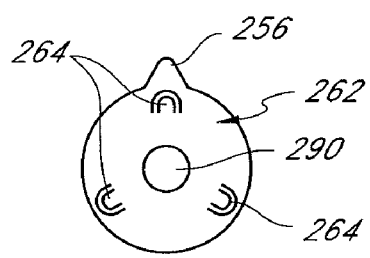
Figure 43E:
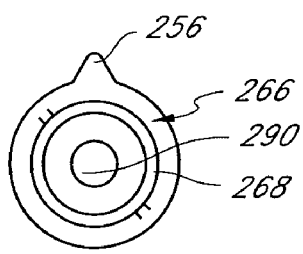
Figure 44A:
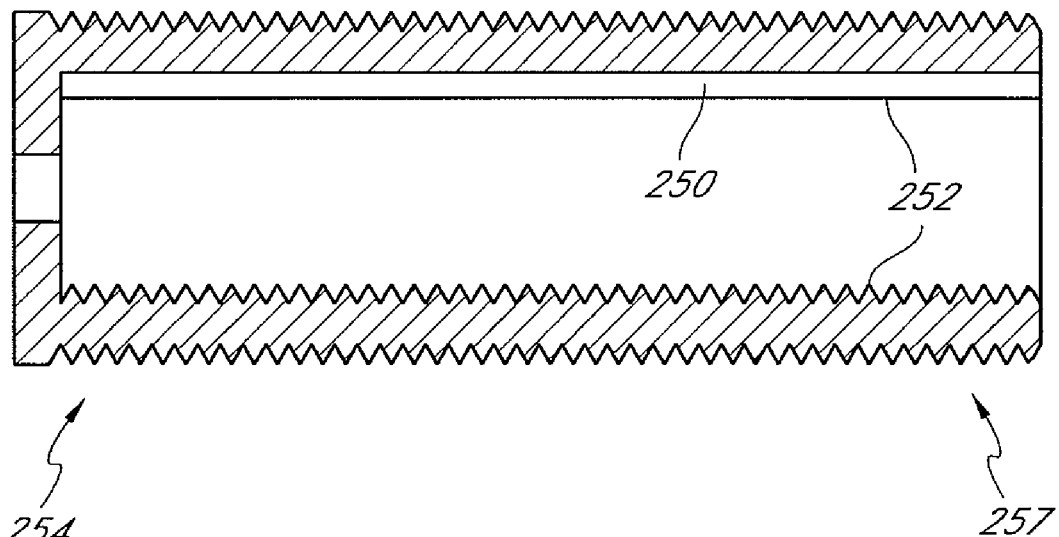
FIGS. 44A and 44B illustrate an embodiment of an adjustable mandible securing assembly with a keyed interface usable with the keyed tether interface in FIGS. 41A through 41E.
Figure 44B:
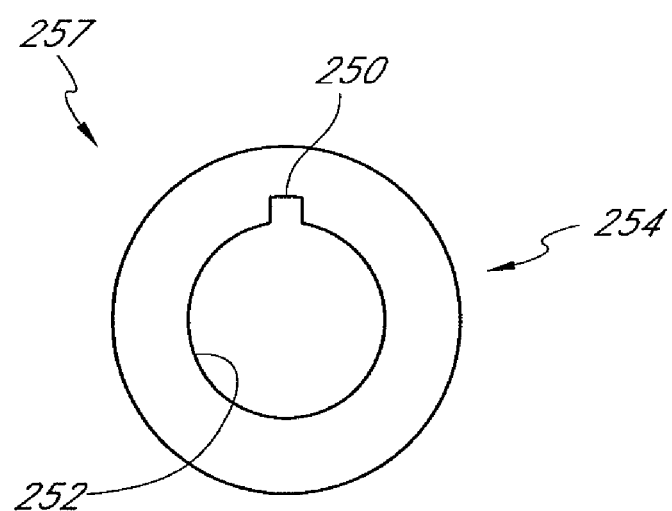

FIGS. 43A through 43E depict another embodiment of the invention for restricting rotation of the tether. Here, the core 242 is rotatably attached to an intermediate tether interface 244 by a rod 246 or other structure. The intermediate tether interface 244 may be any structure that is rotatably attached to the core 242 and comprises one or more keyed structures 248 that form a partial mechanical interfit with a complementary groove or track 250 on the inner threaded surface 252 of the elongate body 254 that allows sliding of the intermediate tether interface 244 along the longitudinal axis of the elongate body 254 while restricting rotation of the intermediate tether interface 244. The groove 250 typically has a generally linear configuration oriented parallel to the longitudinal axis of the elongate body 254, but the groove 250 may also have other configurations and orientations. In some embodiments, the groove may have a spiral configuration within the inner threaded surface 252 of the elongate body, thereby allow some torque transmission to the tether. The pitch of the spiral configuration may be constant or variable. For example, in some embodiments, the groove may have a tighter pitch proximally, so that it the keyed structure can impart greater rotation to the tether as the longitudinal displacement range limit is reached. The keyed structure 248 may comprise any of a variety of shapes sufficient to restrict rotation and need not be exactly matched in cross sectional shape and/or surface area to the groove or tract. The keyed structure 248 and/or the groove of the elongate body 250 may be coated with PTFE and/or other lubricious coating to reduce friction and promote sliding of the keyed structure 248 long the groove 250. The keyed structure 248 depicted FIGS. 43B and 43C are square shaped, while the keyed structures 256 depicted in FIGS. 43D and 43E are triangular. FIGS. 44A and 44B are cross sectional and end elevational views of one embodiment of the securing assembly 257 configured with a keyed groove 250 and inner threaded surface 252 to accept a threaded core 242 attached to a keyed intermediate tether interface 244.

The intermediate tether interface 244 may be configured with a variety of structures to which one or more tethers may be attached. FIG. 43B depicts a tether interface 244 configured with a single hole 258 to accept a single tether, while FIG. 43C depicts another tether interface 260 configured with three holes 256 capable of accepting up to three tethers. FIG. 43D depicts still another tether interface 262 with three eyelet attaching sites 264, while FIG. 43E illustrates a tether interface 266 with circular post 268 capable of engaging a number of attached tethers.

Figure 45A:
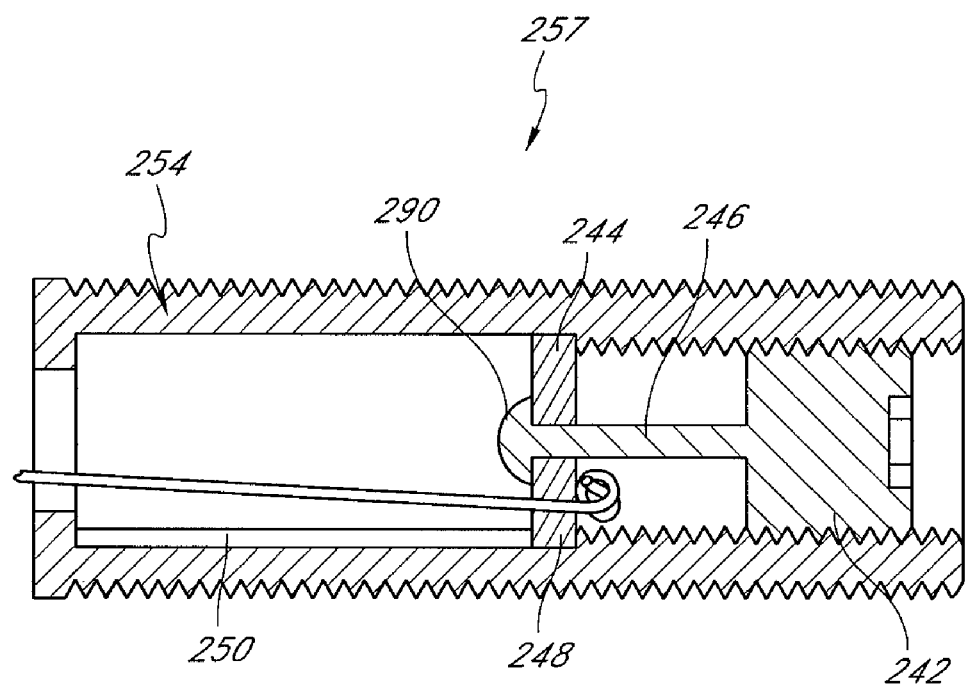
FIGS. 45A and 45B are cross sectional views of the adjustable mandible securing assembly of FIGS. 42A and 42B before and after an adjustment.
Figure 45B:
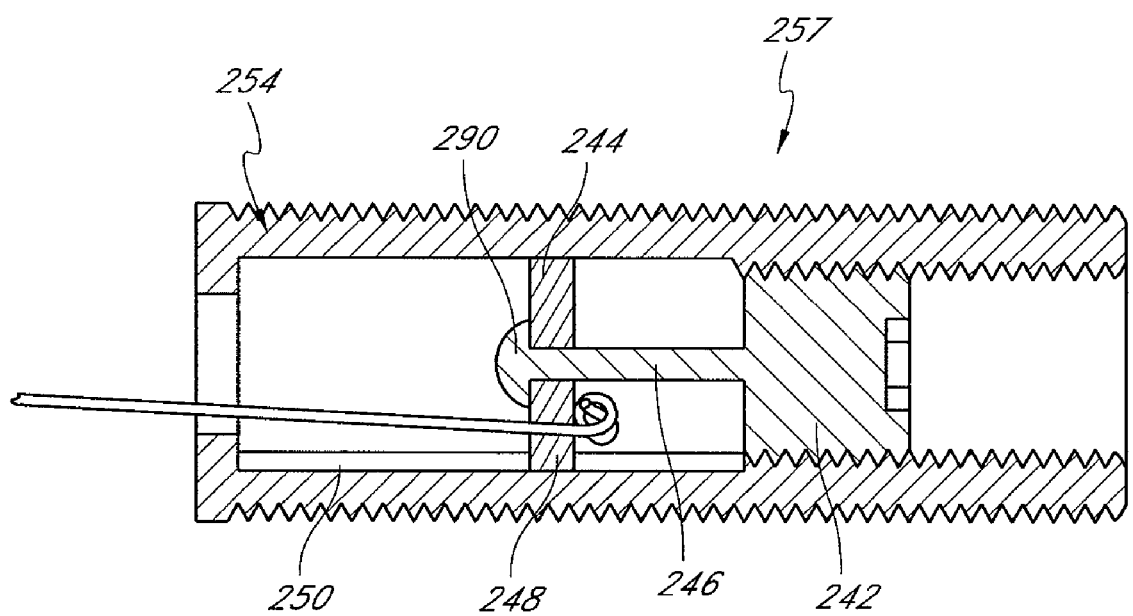

FIGS. 45A and 45B depict one embodiment of the invention utilizing the core 242 and tether interface 244 depicted in FIG. 43A and the securing assembly 257 shown in FIGS. 44A and 44B. The keyed structure 248 of the tether interface 244 remains in the groove 250 or tract of the elongate body 254 to restrict rotation of the interface 244. The rod 246 of the threaded core 242 and/or the rod lumen 290 of the tether interface 244 may be coated with PTFE and/or other lubricious coating to reduce friction at the rod rotation site.

Figure 46A:
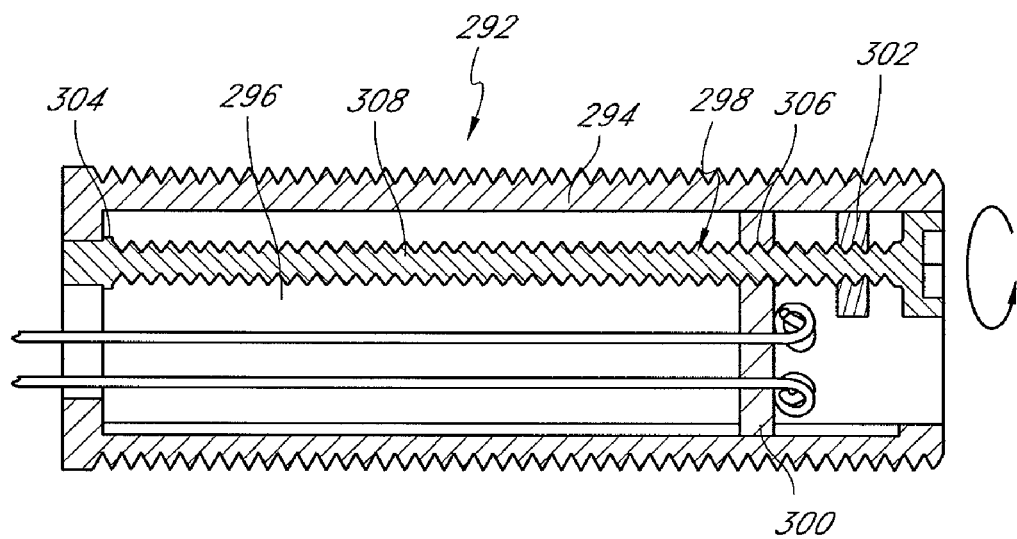
FIGS. 46A and 46B illustrate an embodiment of an adjustable mandible securing assembly with a keyed interface.
Figure 46B:
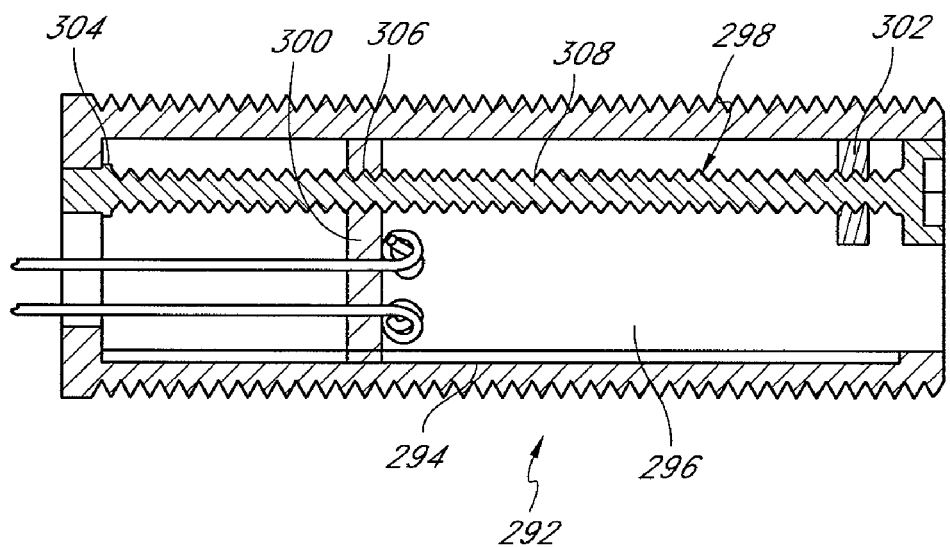

In another embodiment of the invention, shown in FIGS. 46A and 46B, a securing assembly 292 comprises an elongate body 294 with an unthreaded lumen 296 containing a drive screw 298 and a keyed tether interface 300. The drive screw 298 is supported within the unthreaded lumen 296 by threadless supports 302, 304 that allow the drive screw 298 to remain in the same general location when rotated. The keyed tether interface 300 is manipulable using a drive screw 298. The keyed tether interface 300 has a threaded opening 306 that is complementary to the threads 308 of the drive screw 298. Rotation of the drive screw 298 causes movement of the keyed tether interface 300 along the longitudinal axis of the unthreaded lumen 296 of the securing assembly 292. Although the embodiment shown in FIGS. 46A and 46B depict a drive screw 298 located off-center from the longitudinal axis of the elongate body 294, the drive screw 298 may be configured with respect to the elongate body 294 and tether interface 300 at any of a variety of locations relative to the central longitudinal axis. One skilled in the art can select the diameter of the drive screw 298 and the thread pitch of the drive screw 298 and threaded lumen 306 of the tether interface 300 to achieve the desired adjustment characteristics.

Figure 47A:
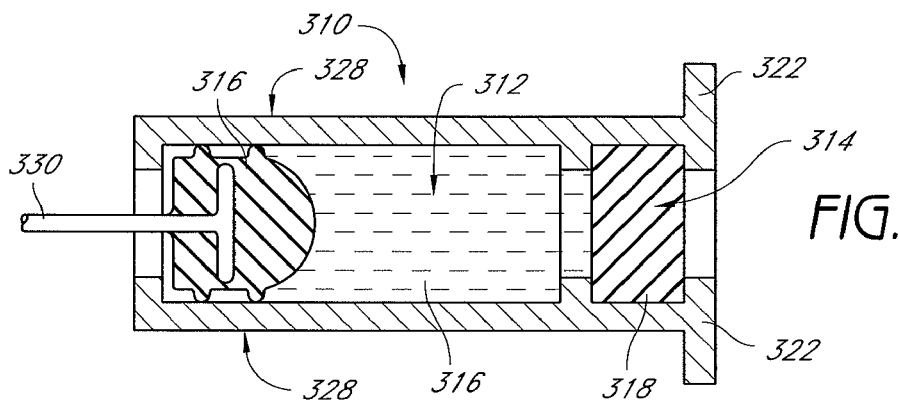
FIGS. 47A through 47D illustrate an embodiment of an adjustable mandible securing assembly with a pierceable membrane.
Figure 47B:
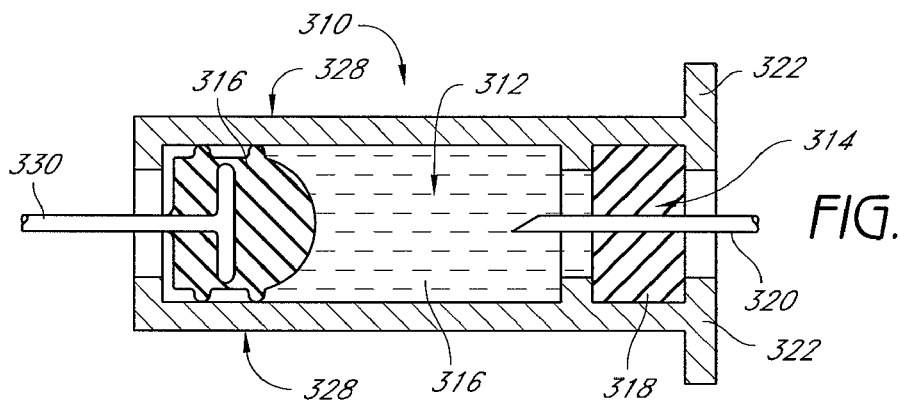
Figure 47C:
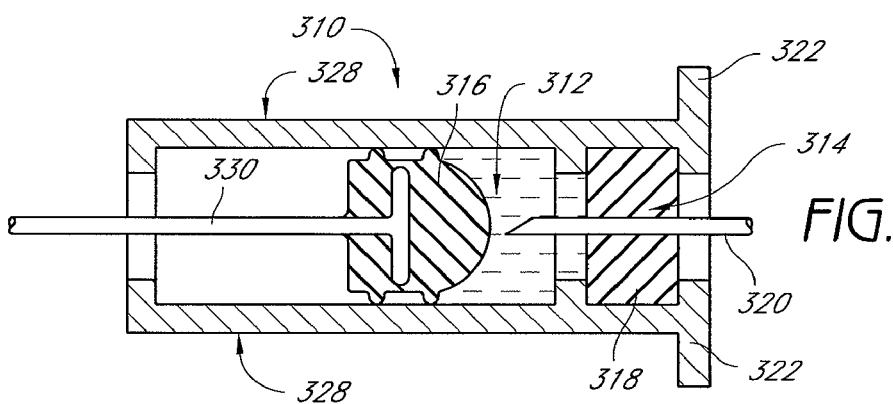
Figure 47D:
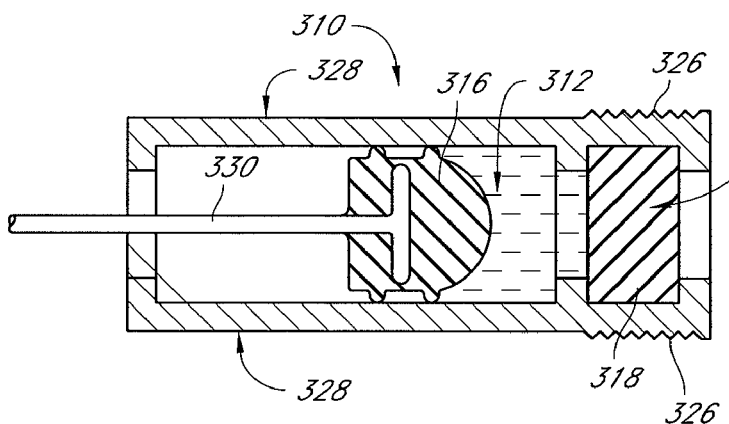

Referring to FIGS. 47A through 47D, in one embodiment of the invention, the securing assembly 310 comprises a sealed cavity 312 wherein one section of the sealed cavity 312 comprises a sealed access interface 314 and a second portion of the sealed cavity comprises a sliding seal 316 attached to a tether 28. The sealed cavity 312 may be filled with a volume of gas or preferably a liquid 316 that can be changed by adding or removing the fluid through the access interface 314. The sliding seal 316 is configured to move with changes in fluid volume of the sealed cavity 312. As shown in FIGS. 47B and 47C, the access interface 314 is preferably configured as a self-sealing pierceable membrane 318 so that the sealed cavity may be accessed with a hypodermic needle 320 that is percutaneously inserted through the membrane 318 in a minimally invasive fashion. Alternatively, the access interface 314 may comprise any of a variety of sealed mechanical valves or other interfaces that are well known in the art. The securing assembly 310 shown in FIGS. 47A through 47C further comprise a flange 322 at the proximal end of the securing assembly to restrict further distal migration of the securing assembly. FIG. 47D depicts an alternative embodiment of the securing assembly 324 lacking a flange and comprising a threaded or frictional surface 326 on at least a portion of the external surface 328. Limiting the threaded or frictional surface 326 to only a portion of the external surface 328 may facilitate insertion of the securing assembly 310 into a bony conduit while still providing sufficient friction to resist migration of the assembly 310. Although the tether 330 depicted in FIGS. 47A through 47D is embedded into the sliding seal 316 of the securing assembly 310, the sliding seal 316 may also be configured with any of a variety of attachment structures to allow attachment of one or more tethers to the sliding seal 316.

Figure 48A:
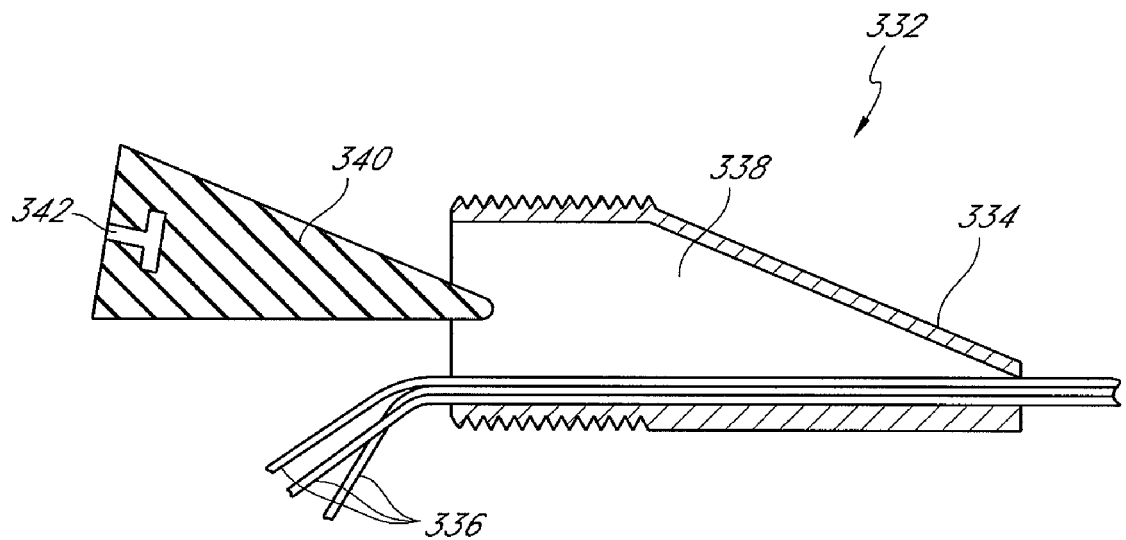
FIGS. 48A and 48B illustrate an embodiment of a mandible securing assembly with a resistance plug.
Figure 48B:
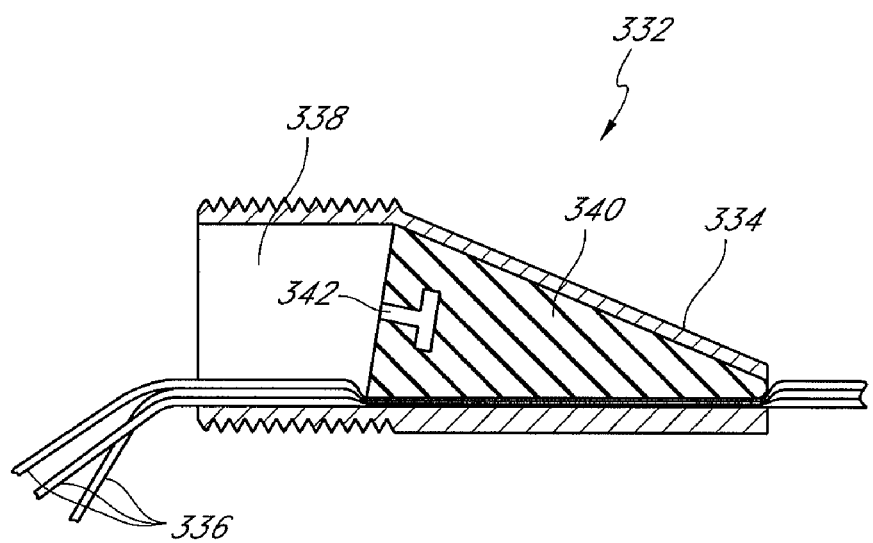

In one embodiment of the invention, illustrated in FIGS. 48A and 48B, a securing assembly 332 comprises a tapered elongate body 334 through which one or more tethers 336 may be passed into or through the lumen 338 of the elongate body 334. The tethers 336 may be secured to the securing assembly 332 by a frictional core 340 that can be snugly inserted into the tapered lumen 338 of the tapered elongate body 334. The frictional core 340 may comprise any of a variety of frictional materials, including silicone, rubber, metal, polymers or a combination thereof. While the frictional core 338 forms a friction fit with the tether 336, the fit to the tapered lumen 338 may be frictional or mechanical. The surface of the lumen 338 may or may not be coated with frictional materials to further enhance the frictional securing of the tethers 336 between the core 340 and lumen 338. The frictional core 340 may be inserted and removed through a recessed interface 342 that is configured to accept a complementary core attachment tool. Alternatively or additionally, the frictional core 340 may also comprise a patterned, rough or porous surface, such as a knurled or grooved surface. Alternatively, the frictional core 340 may comprise a protruding structure with can be engaged with forceps or other grasping tool for insertion and/or removal.

Figure 49A:
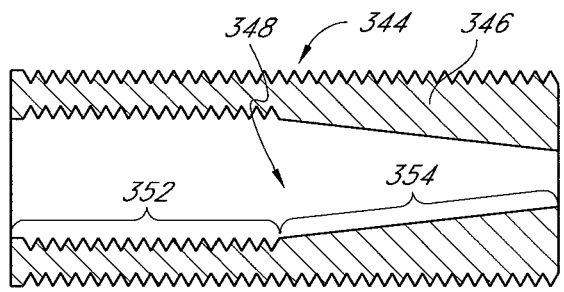
FIGS. 49A through 49D illustrate an embodiment of a mandible securing assembly usable with a beaded tether.
Figure 49B:
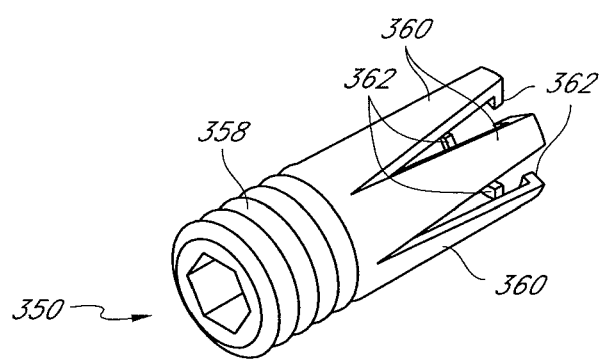
Figure 49C:
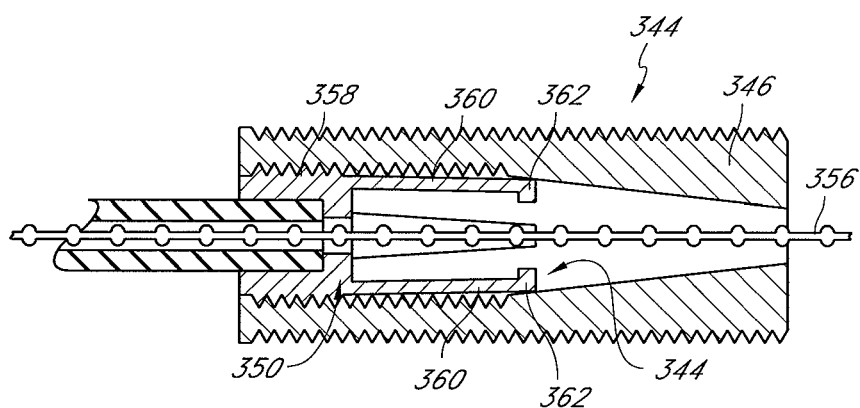
Figure 49D:
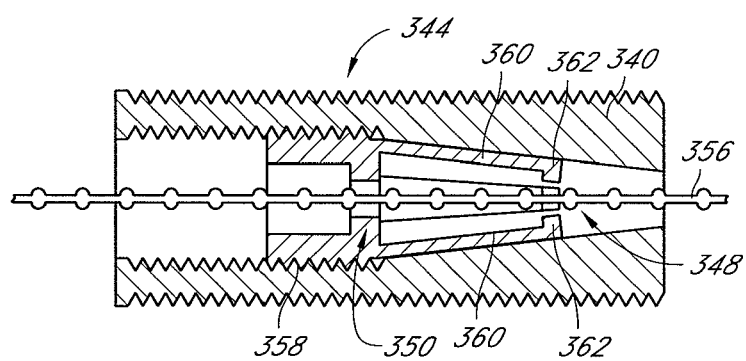

In one embodiment of the invention, shown in FIGS. 49A through 49D, a securing assembly 344 comprises an elongate body 346, a tapered lumen 348, and a pronged core 350 capable of forming a mechanical stop or frictional surface to restrict movement of one or more tethers 352. The tapered lumen 348 comprises a proximal threaded lumen 352 and a distal tapered lumen 354 through which a tether 356 may be passed. The pronged core 350 comprises a proximal threaded external surface 358 that is complementary to the proximal threaded lumen 352 of the elongate body 346, and one or more distal prongs 360 that are capable of inward deflection. When the pronged core 350 is inserted into the elongate body 346, as depicted in FIG. 49C, as the pronged core 350 is rotated and advanced distally, the prong or prongs 360 are deflected radially inward by the tapered lumen 354. In some embodiments, shown in FIGS. 49B through 49D, the distal ends 362 of at least some prongs may be curved or angled inward to form a mechanical stop interface capable of restricting a beaded tether 356 or other similarly configured tethers with segments of increased cross sectional area. In other embodiments, the distal ends 362 of the prongs 360 are capable of reducing sufficiently to form a frictional aperture that is capable of resisting sliding of a tether about the prong ends 362.

Figure 50E:
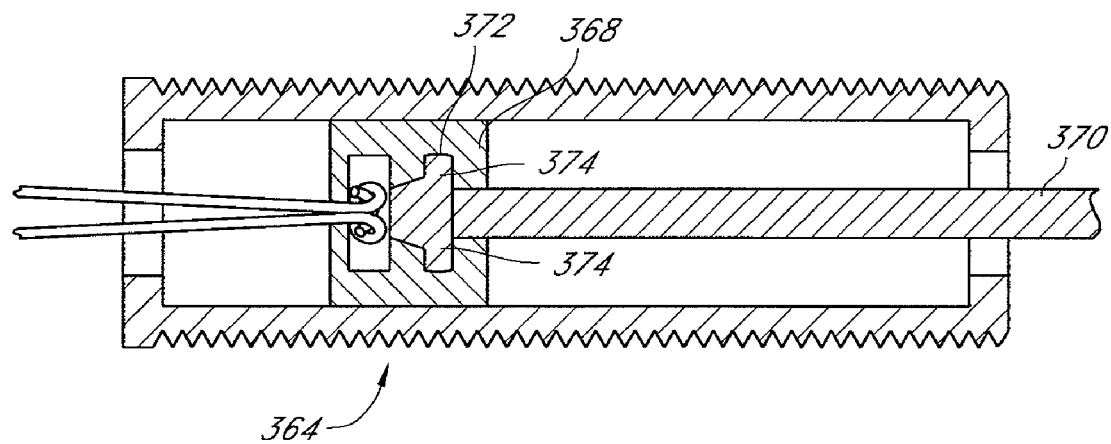
Figure 50F:
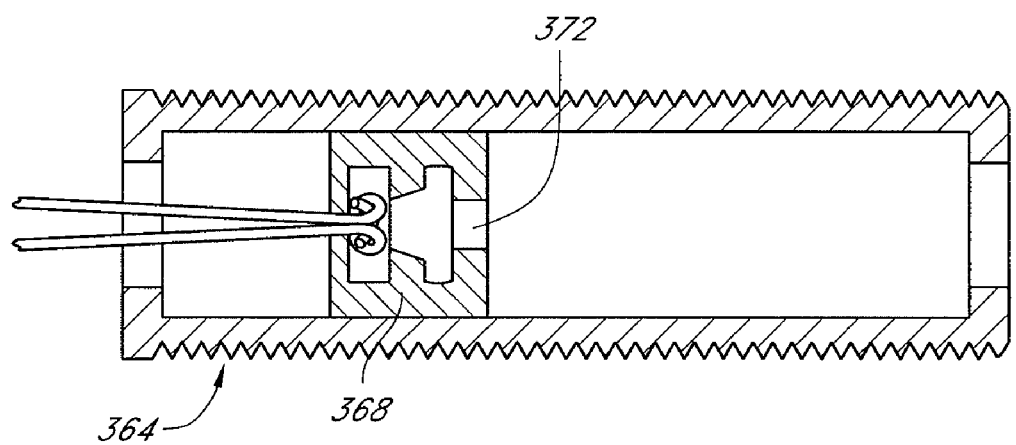

Referring to FIGS. 50A through 50F, another embodiment of the invention comprises an elongate body 364 with a frictional internal lumenal surface 366 and a frictional core 368. The frictional core 368 is configured to resist movement within the internal lumenal surface 366 by exertion of force within the broad range of force expected by physiologic activities acting on one or more attached tongue elements, but is also capable of movement with the application of supraphysiologic forces through a frictional core movement tool 370. One embodiment of the movement tool 370 is depicted in FIG. 50B. The interface 372 between the movement tool 370 and the frictional core 368 may comprise any of a variety of mechanical interfaces known in the art sufficient to transmit adequate pulling and pushing force to the frictional core. The interface 372 shown in FIGS. 50A and 50C though 50F allow engagement of the frictional core 368 following insertion and rotation of the movement tool 370 with one or more arms 374 capable of resisting dislodgement from the frictional core 368 when in the rotated position.

Figure 51A:
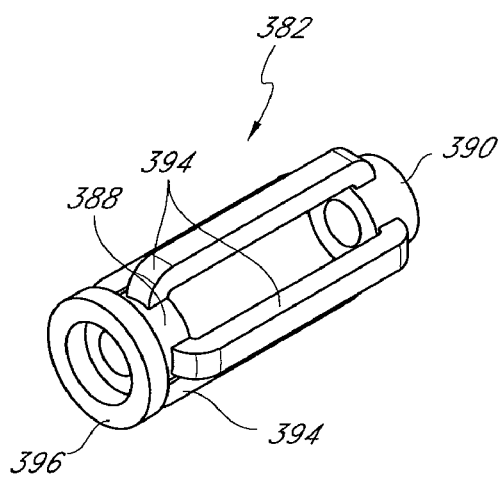
FIGS. 51A through 51E illustrate another embodiment of a mandible securing assembly comprising an expandable tether interface.
Figure 51B:
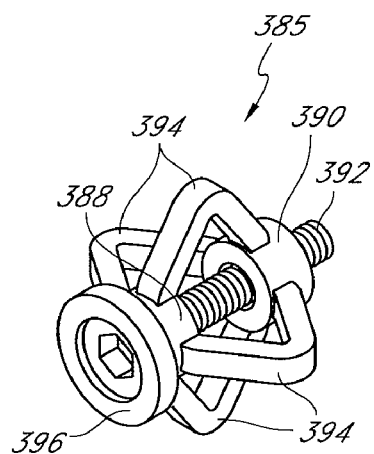
Figure 51C:
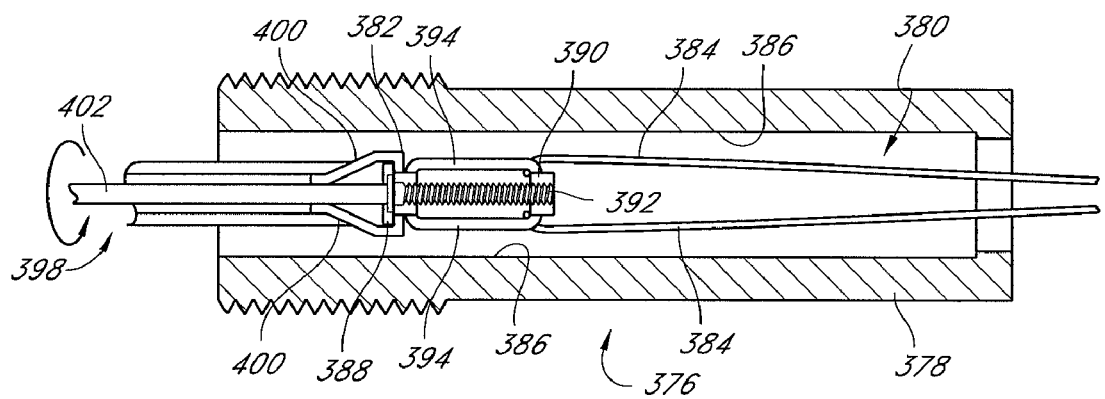
Figure 51D:
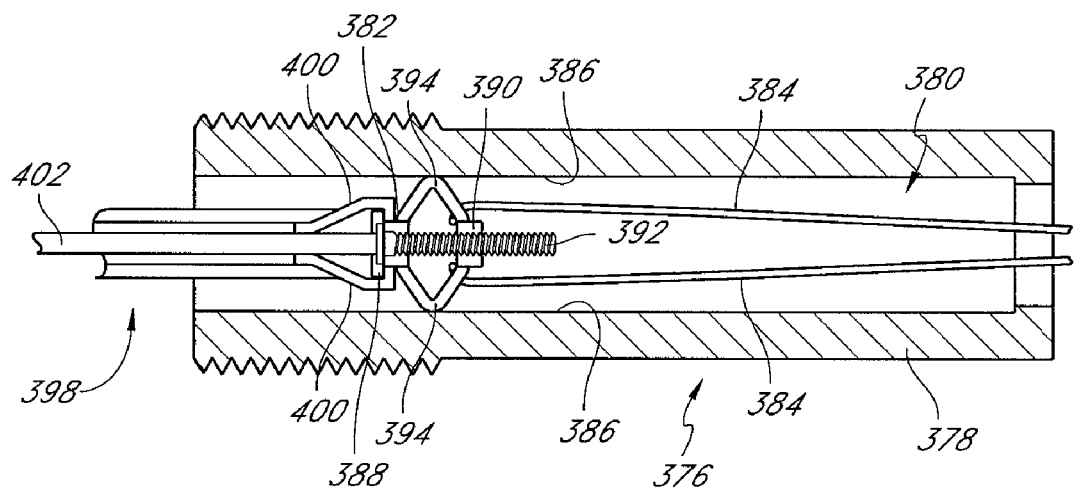
Figure 51E:
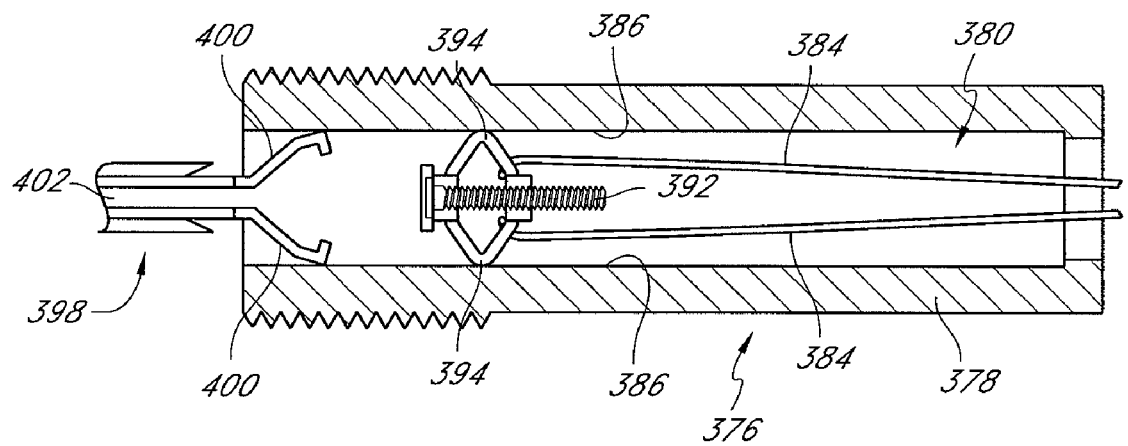

In still another embodiment of the invention, illustrated in FIGS. 51A to 51E, the securing assembly 376 comprises an elongate body 378 with a lumen 380 and an expandable tether core 382. The expandable tether core 382 is configured to allow attachment of one or more tethers 384 and to also reversibly radially expand and contract such that the expanded radius of the core 382 is capable of forming a frictional and/or mechanical fit with the lumen wall 386 of the elongate body 378. In one embodiment of the invention, depicted in FIGS. 51A through 51E, the expandable core 382 comprises a proximal end 388 and a threaded distal end 390, a threaded drive screw 392 through the proximal end 388 and threadably engaged to the threaded distal end 390, and one or more expandable members 394 between the proximal end 388 and distal end 390. When the drive screw 392 is rotated, as shown in FIG. 51C, the distal end 390 of the expandable core 382 is brought closer to the proximal end 388, causing deformation of the expandable members 394 which can then engage the lumen wall 386, as shown in FIG. 51E. The proximal end 388 of the expandable tether core 382 may have a flange 396 to facilitate engagement by a deployment tool 398. The deployment tool 398 have grasper 400 adapted to engage and hold the flange 396 while an extendable shaft 402 can form an interfit with the drive screw 392 and rotate the drive screw 392.

In another embodiment of the invention, the securing assembly comprises a spool or rotation assembly for adjusting the tether length or tether tension between the securing assembly and distal anchor. Referring to FIGS. 61A to 61I, in one embodiment of the invention, the securing assembly 600 comprises a fastener interface 602 for attaching the securing assembly 600 to a bone or other tissue and a spool assembly 604, the spool assembly 604 comprising a spool 606 and a spool lock 608. The spool lock 608 allows the rotation of the spool 606 to take up or release a portion of the tether when desired, while resisting unintentional uptake or release of the tether at other times. In the specific embodiment depicted in FIGS. 61A to 61I, the spool 606 comprises one or more spool hubs 610 onto which one or more tethers may be wound or unwound. Optionally, one or more flange structures 612, 614 are provided on the spool 606 to help maintain the tether on the spool hub 610. In other embodiments, grooves or a slip-resistant surface on the spool hub may be used to maintain the tether on the spool hub, with or without spool flanges. Typically, two flange structures 612, 614 are provided, but in other embodiments of the invention, only one flange structure is needed as other portions of the securing assembly housing 616 may act to maintain the tether on the spool hub 610. The spool hub 610 typically has a circular cross-section, but any of a variety of other cross-sectional shapes may also be used. Furthermore, although the spool hub 610 described, for example, in FIG. 61G comprises a cylindrical surface, the spool hub may be any structure capable of winding a tether about it, e.g. in some embodiments, the spool hub may be the region where two flanges are joined.

The spool may further comprise one or more engagement structures for engaging the tether or elongate element. For example, in FIG. 61D, the inferior flange 612 of the spool 606 comprises one or more holes 618 for attaching the tether. One of skill in the art will understand that any of a variety of alternative engagement structures may be provide on the spool, spool flange or spool hub, including hooks, clips, clasps, crimp structures or any combination thereof.

In a further embodiment of the invention, the spool assembly may comprise two or more spools for winding the tether. Use of multiple spools may allow the use of smaller spools and/or use of non-circular tether uptake paths, which may allow the construction of securing assemblies having a reduced profile compared to securing assemblies comprising a single large spool.

Figure 61A:
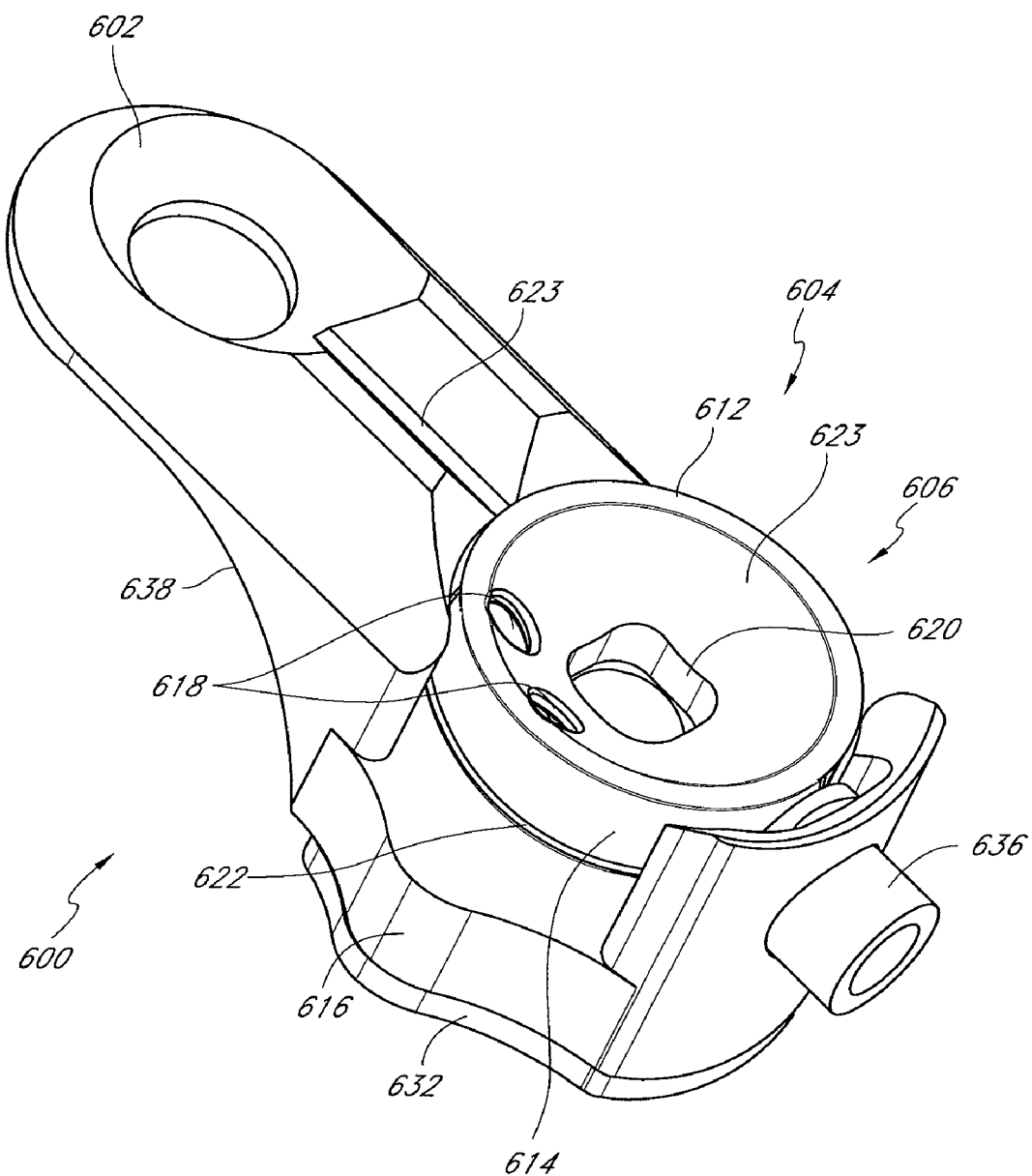
FIGS. 61A and 61B are inferior and superior perspective views of another embodiment of the securing assembly, respectively.
Figure 61B:
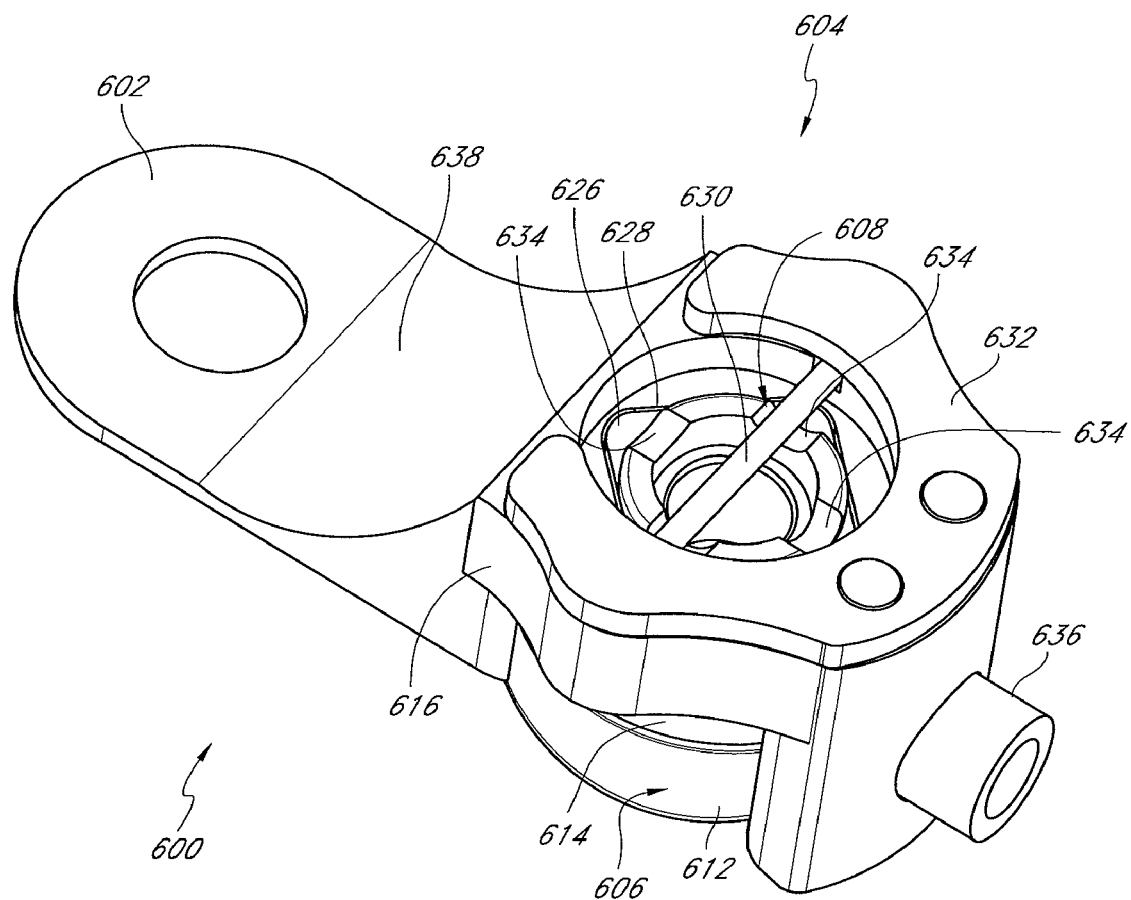
Figure 61C:
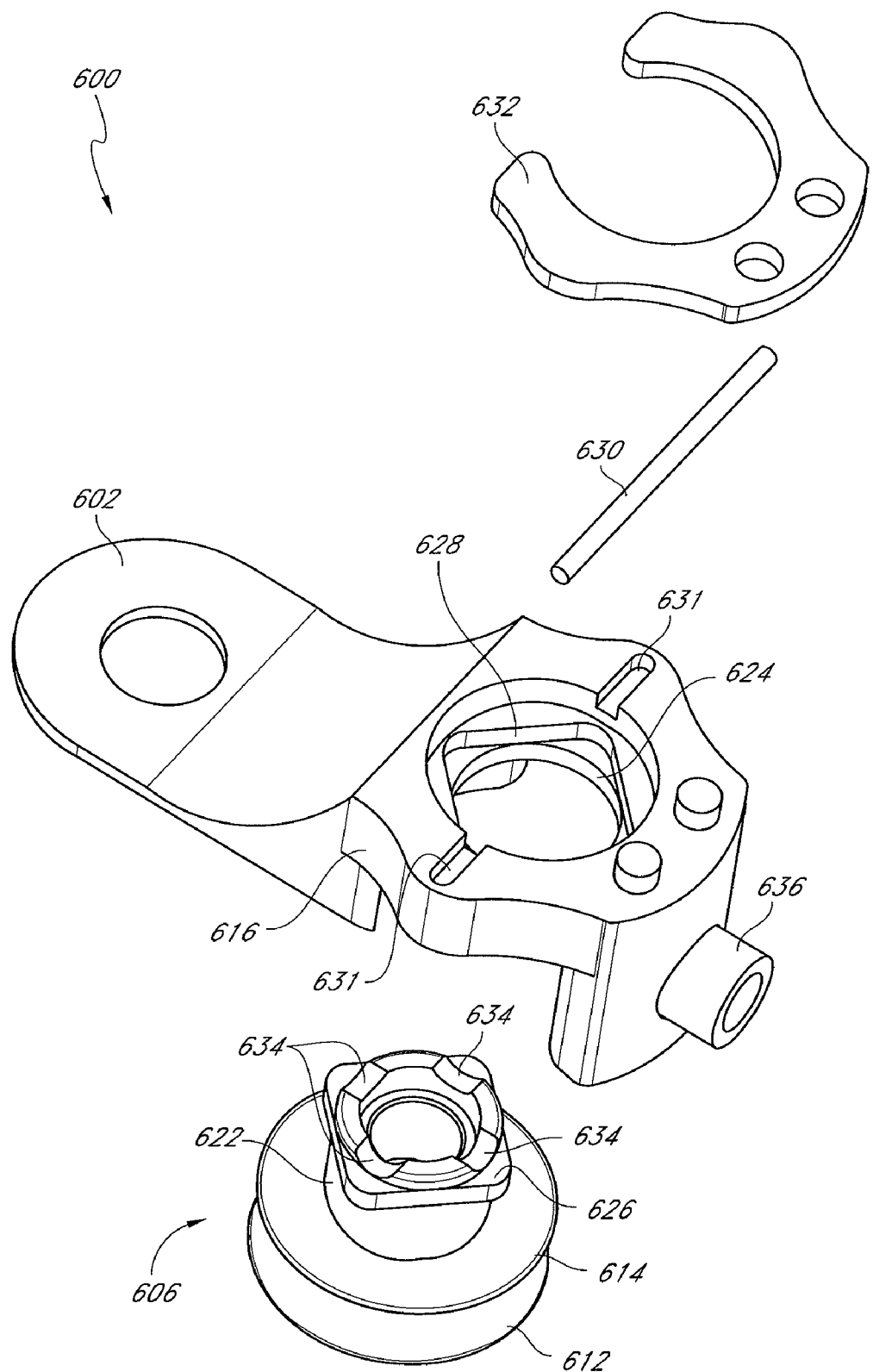
FIG. 61C is an exploded superior perspective view of the securing assembly in FIG. 61B.
Figure 61D:
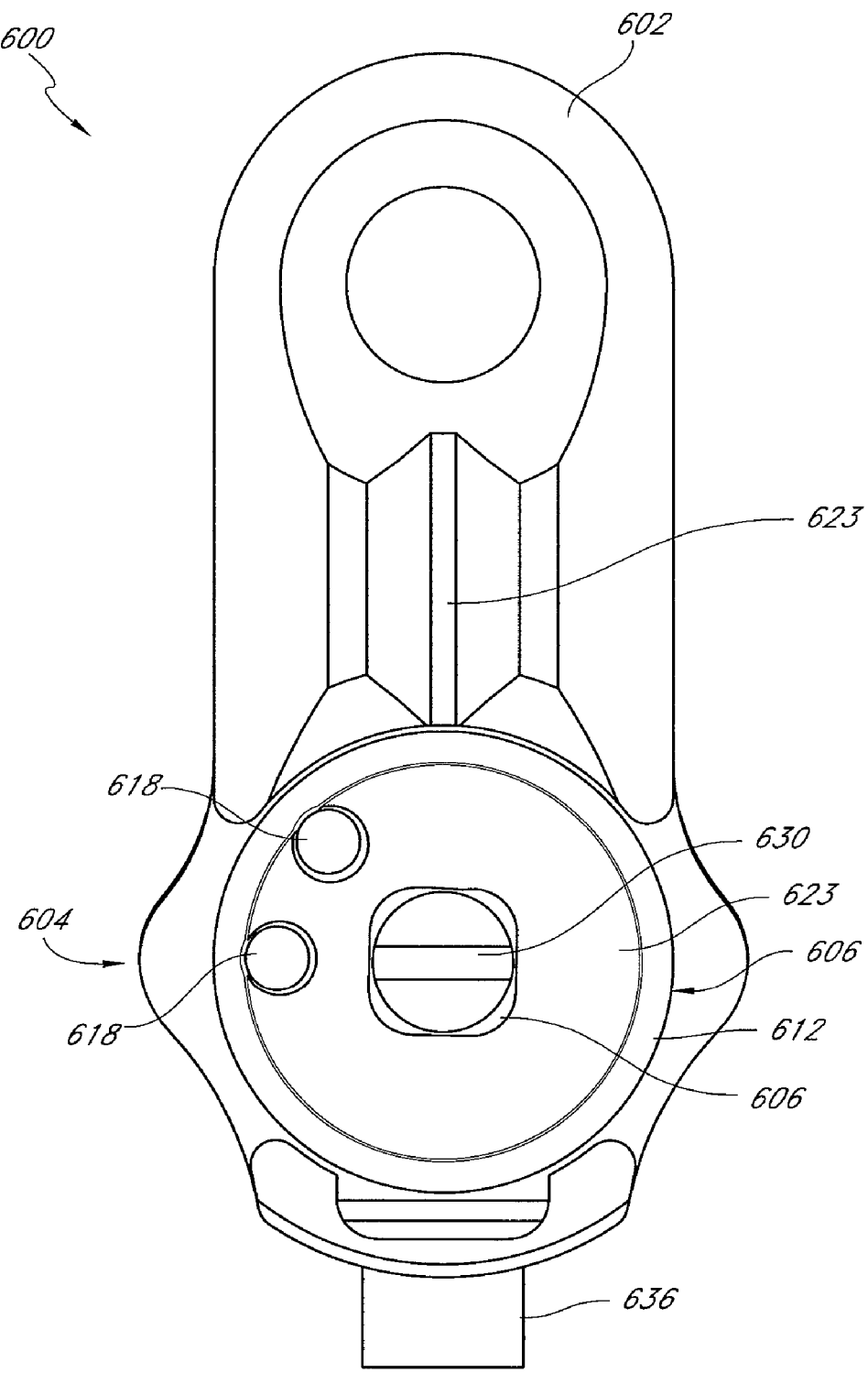
FIGS. 61D to 61F are inferior, superior and side elevational views of the securing assembly, respectively.

The spool assembly 604 may further comprise a spool adjustment interface 620. Referring to FIGS. 61H and 61I, the spool adjustment interface 620 is typically located at the center of the spool 606 and is configured to form an interfit with an adjustment tool 621 for rotating the spool 606. The adjustment tool 621 may optionally have a sharp distal end so that the adjustment tool may also be used to provide direct access to the spool 606 without the preforming the access pathway, or having to use a cannula, introducer, trocar or access needle first. In further embodiments, the adjustment tool 621 may also be used to displace the spool 606 in one or more directions. Spool displacement, whether perpendicular to its rotation axis or longitudinally along its rotation axis, as depicted in FIGS. 61H and 61I, may be used to switch the spool between its locking and rotation configurations. In other embodiments, spool displacement may be used to wind the tether onto a secondary spool hub of the spool having a different diameter to provide a different rate of tether winding per rotation, for example, on a frusta-conical spool hub.

To facilitate the insertion of the adjustment tool 621 into the spool adjustment interface 620, the adjacent flange 612 may have a tapered or conical surface 623 to help guide an adjustment tool 621 into the spool adjustment interface 620. Other tapered or grooved structures 623 on the securing assembly 600 may also be provided to guide the adjustment tool 621 from other locations about the securing assembly 600.

In other embodiments, the spool adjustment interface may be provided on a cog or disc, which in turn is configured to rotate the spool for adjusting the tether. Likewise, the cog may also be reversibly displaceable along its rotation axis and/or off its rotation axis to lock rotation of the spool.

The interface between the spool and the spool housing may be configured in a number of ways. As depicted in FIG. 61C, spool rotation is provided by a generally cylindrical or circular rotation surface 622 that rotates in or about a hole 624, lumen or other arcuate surface of the spool housing 616 to provide rotation. The circular rotation surface 622 may be located on the spool hub 610, spool flanges 612, 614 or other section of the spool 606. In other embodiments, the spool may comprise a tubular lumen which rotates about a pin or an axle structure of the spool housing. The tubular lumen may be concentric or eccentric with the spool hub.

In some embodiments of the invention, the interface between the spool and the spool housing provides sufficient mechanical or frictional force to generally resist undesired rotation, in one or both directions, related to physiological forces acting on the distal anchor, tether and/or securing assembly. In other embodiments of the invention, the securing assembly may further comprise a reversibly engageable spool lock to resist undesirable spool rotation. Referring to the embodiment shown in FIGS. 61A to 61I, the spool lock 608 may comprise a four-sided locking flange 626 that prevents rotation of the spool 606 when the locking flange 626 is positioned within a corresponding four-sided locking cavity 628 of the spool housing 616. In some embodiments of the invention, the locking flange may also serve the function of a spool flange. To rotate the spool 606 when desired, the four-sided locking flange 626 may be displaced out of the four-sided locking cavity 628 of the spool housing 616, longitudinally along the rotation axis of the spool 606. Longitudinal displacement along the rotation axis of the spool 606 is provided because the cylindrical rotation surface 622 of the spool 606 has an axial length that is greater than the axial length of arcuate rotation surface or hole 624 of the spool housing 616. The spool 606 may be biased to its locked position by a bias structure 630 that applies an axial force on the spool to maintain or push the four-sided locking flange 626 into the four-sided locking cavity 628 of the spool housing 616. This bias structure 630 may be a coil or leaf spring, an elastically deformable wire or other similar structures known in the art. The bias may be attached or retained in the spool housing in any of a variety of ways, including bonding, or retention within a cavity 631, with or without a retaining plate 632, as illustrated in FIGS. 61A to 61I. To move the spool 606 from the locked position to the adjustment position, in the embodiment depicted in FIGS. 61H and 61I, the adjustment tool 621 is inserted into the spool adjustment interface 620 with sufficient force to overcome the force exerted by the bias structure 630.

Figure 61E:
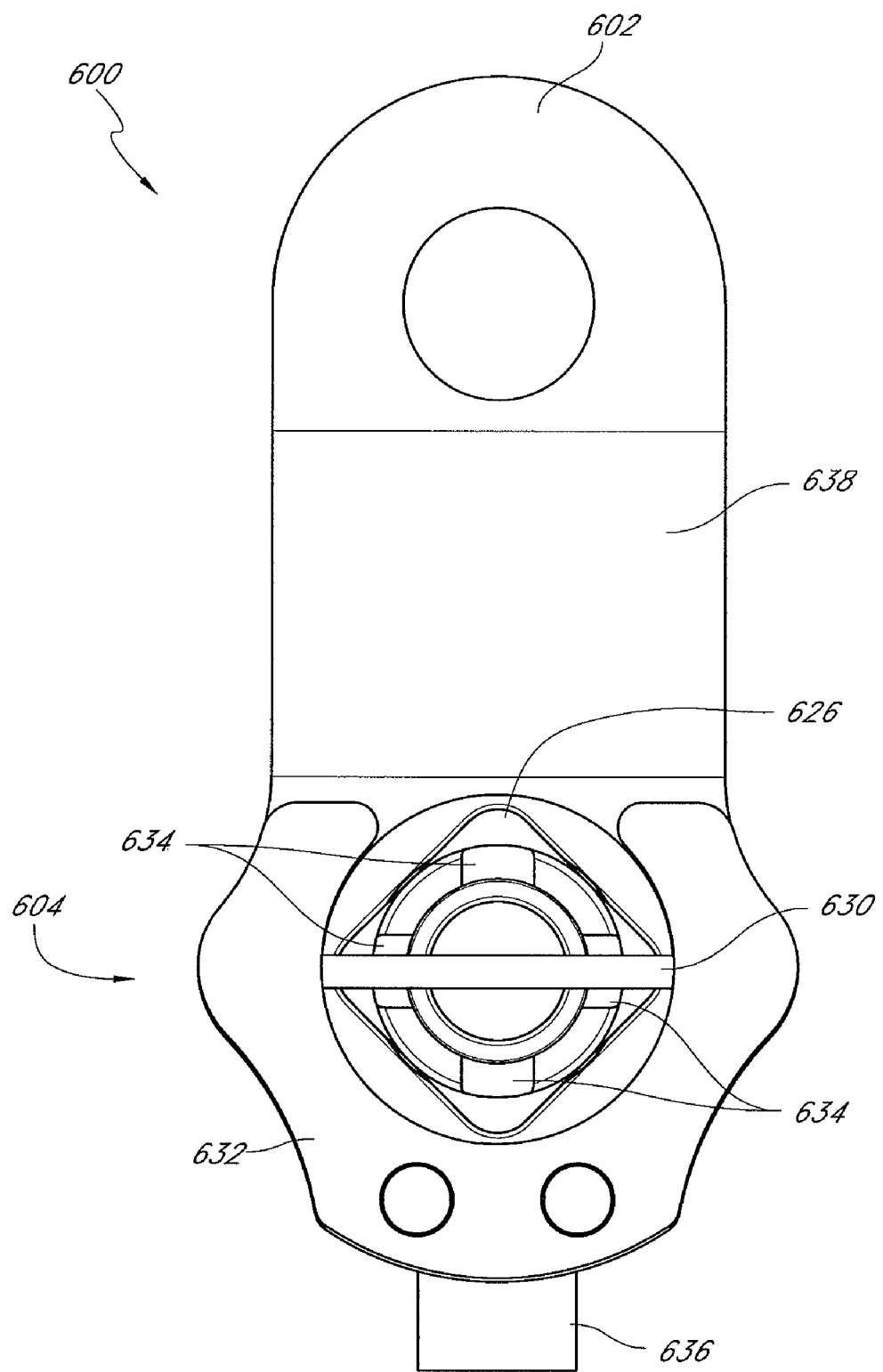
Figure 61F:
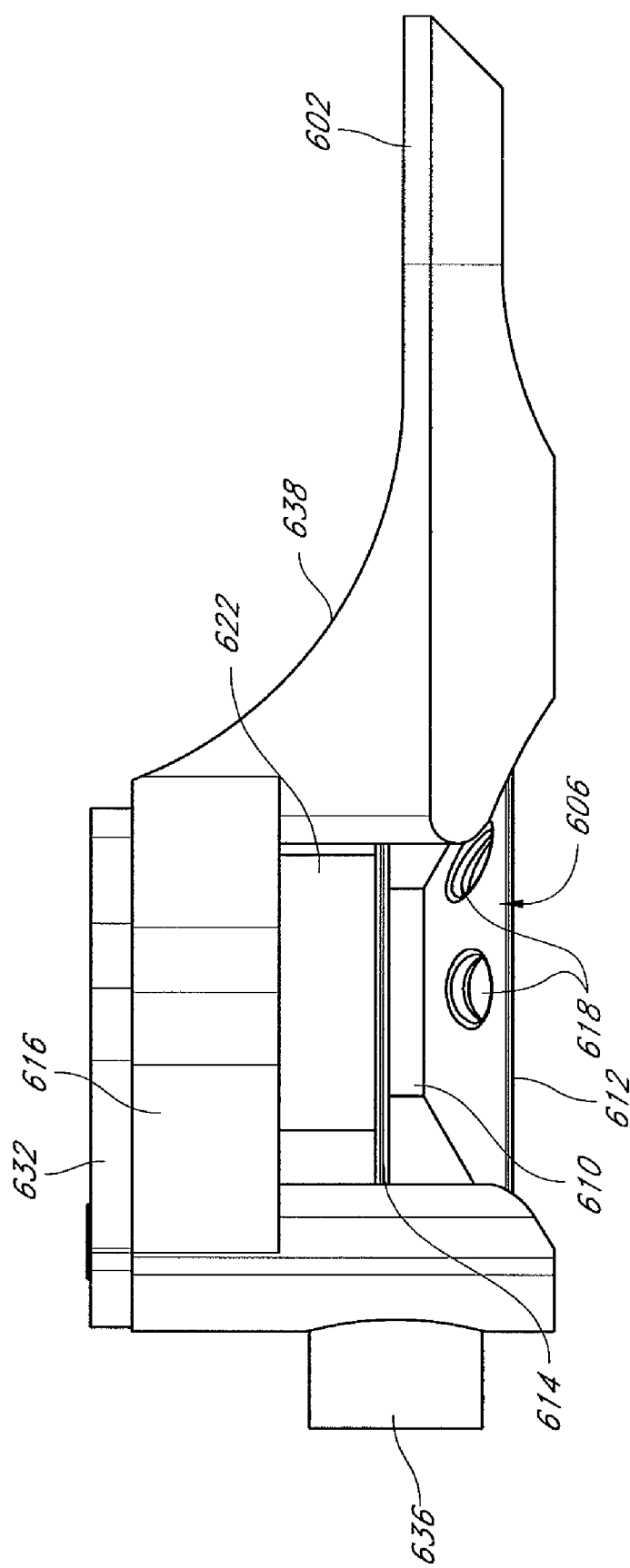
Figure 61G:
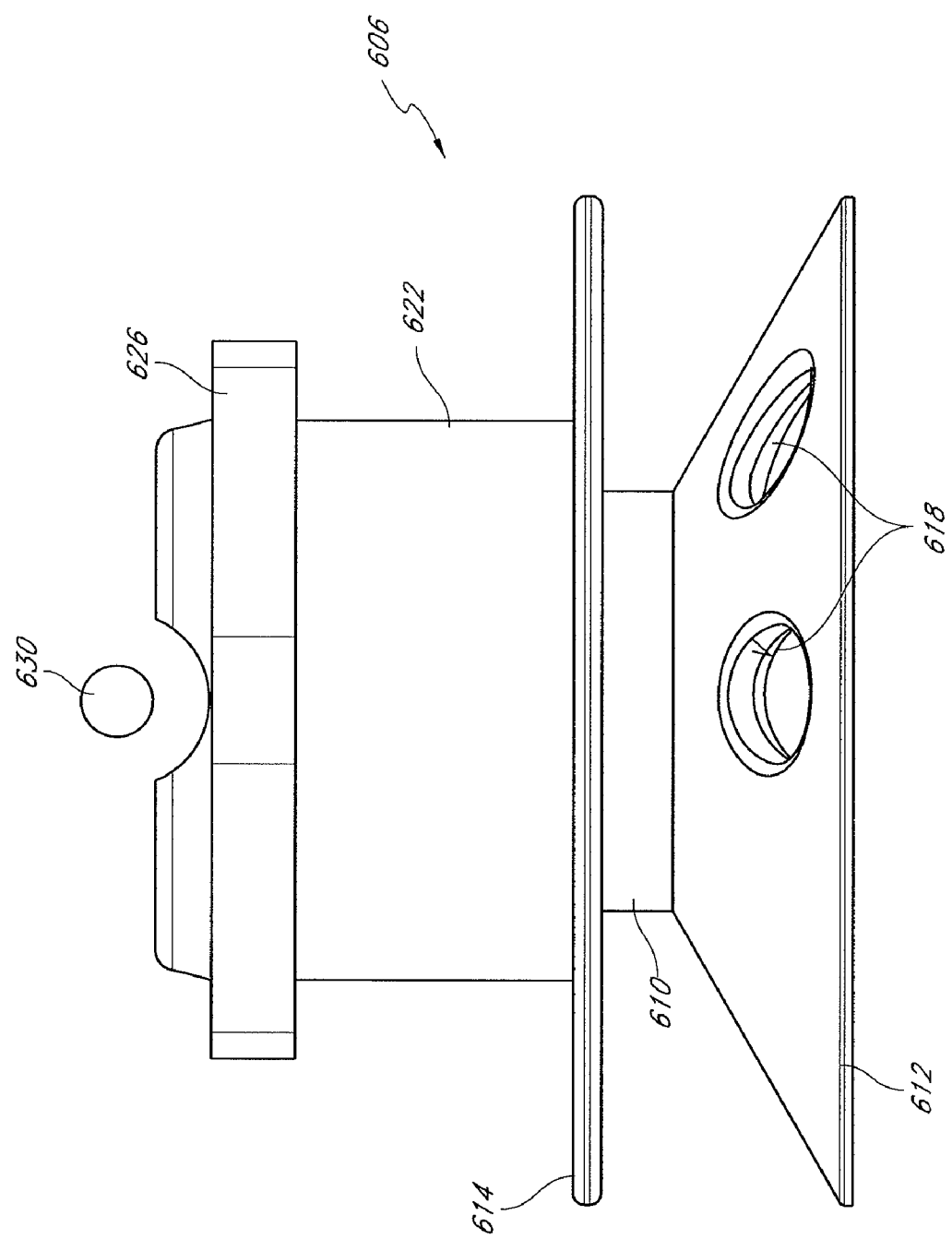
FIG. 61G is a side elevational isolation view of the spool assembly.
Figure 61H:
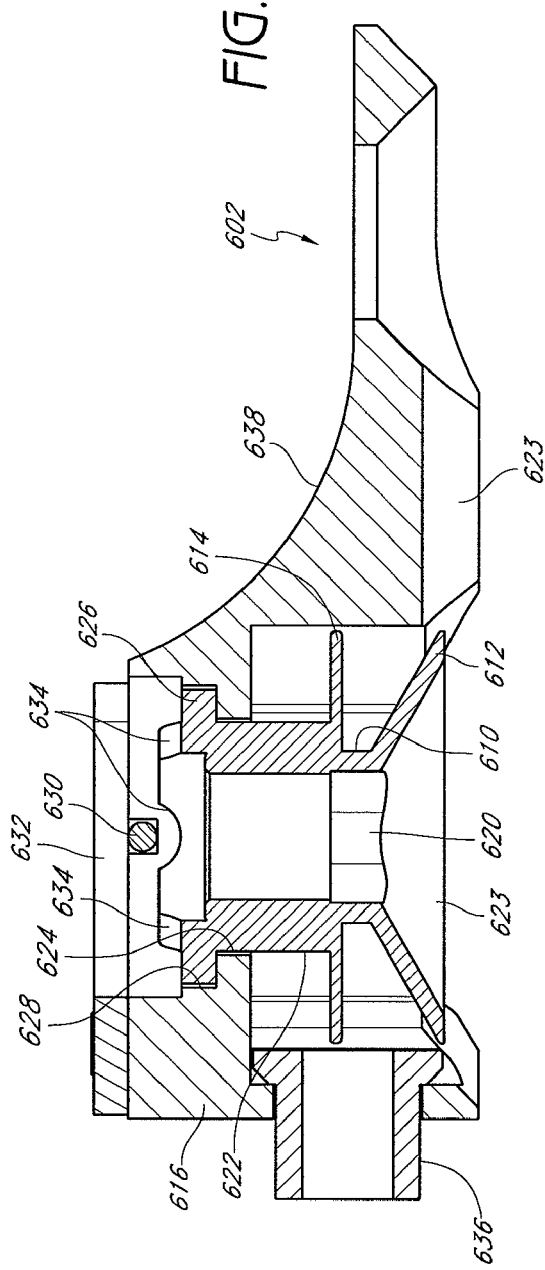
FIGS. 61H and 61I are a longitudinal cross sectional views of the securing assembly in FIG. 61F in the locked and rotation configurations, respectively.
Figure 61I:
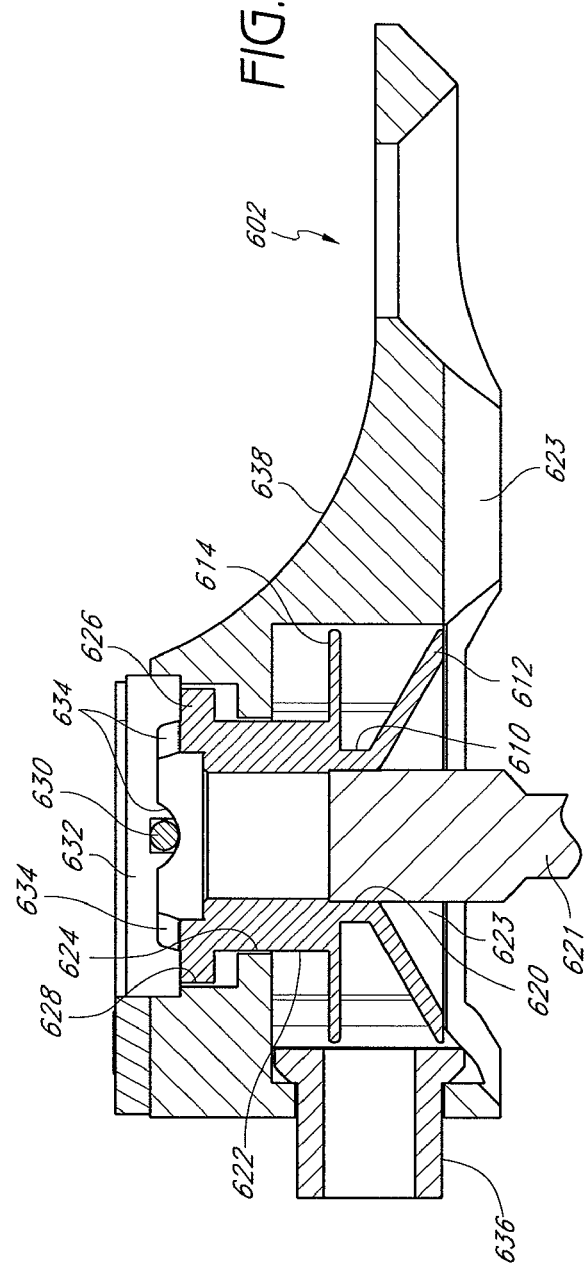

In the specific embodiment of the invention shown in FIG. 61E, the spool 606 may optionally comprise indentations, detents 634, or other surface structures that provide auditory and/or tactile feedback to the user of the adjustment tool 621. As the spool 606 is rotated, the interaction between the bias structure 630 and indentations 634 will cause a clicking that can convey to the user that the adjustment tool 621 is properly inserted into the spool adjustment interface 620 and is properly rotating.

Although one specific embodiment of the invention is depicted in FIGS. 61A to 61I, one of skill in the art will understand that many locking structures or configurations may be used with a spool-based securing assembly. In another embodiment, the bias structure, such as a protruding prong or tab, may be located on the spool itself near the spool adjustment interface and forms a mechanical interfit with a complementary structure about the spool. When the adjustment tool is inserted into the spool adjustment interface, the bias structure is displaced from the complementary structure about the spool. Alternatively, the complementary structure, such as a groove or detent, may be located on the spool about the adjustment interface while the bias structure is located adjacent to the spool and projects into the complementary structure of the spool. In this alternate embodiment, when the adjustment tool is inserted into the spool adjustment interface, the projecting bias structure is displaced form the complementary structure of the spool to allow rotation.

In still another embodiment, the spool is not axially displaceable but comprises an interface with a lock assembly that resists spool rotation in at least one direction using a ratchet element. The ratchet element or mechanical lock may be deactivated independently or as a result of the application of the spool adjustment tool. In another embodiment, the lock assembly may be a resistance lock provided by a rubber resistance pad. The position of the pad may be fixed or mobile.

Although the tether may be taken up or released from the spool directly, in other embodiments the securing assembly may comprise a lumen, ring or bushing to facilitate adjustment of the tether and/or to resist snagging of the tether. FIG. 61B depicts a bushing 636 located on the posterior region of the securing assembly 600. When the curved surface 638 of the securing assembly 600 is attached in a typical fashion to the inferior surface of the mandible, the adjustment interface 620 of the spool 606 will be positioned for access from the inferior chin surface while the bushing 636 will protect the tether as the tether passes in or out of the securing assembly 600.

The use of a spool or rotational assembly for the adjustment of the tether is generally preferred, because it allows a substantial range of tether adjustment in a limited amount of space. Other embodiments of a movable securing assembly that do not use rotational assemblies or are not purely rotational, however, are also contemplated, including those with helical, slide or pivot assemblies for tether manipulation. These alternative mechanisms have a limited movement range compared to a rotational assembly, but can be configured with a broader range of adjustment by incorporating a ratchet and release subassembly with the slide or pivot assembly. One benefit of a movable securing assembly is that it may allow the adjustment of an attached tether without the risks or complications associated with having to detach the tether in order to adjust it. Such risks may occur when using an eyelet or crimping-type securing device. Furthermore, the articulation or joint between the moving and non-moving components of the securing assembly are configured to withstand the stress of repeated adjustment, in comparison to crimp structures, which may fail with repeated crimp/uncrimp adjustment procedures.

Figure 61J:
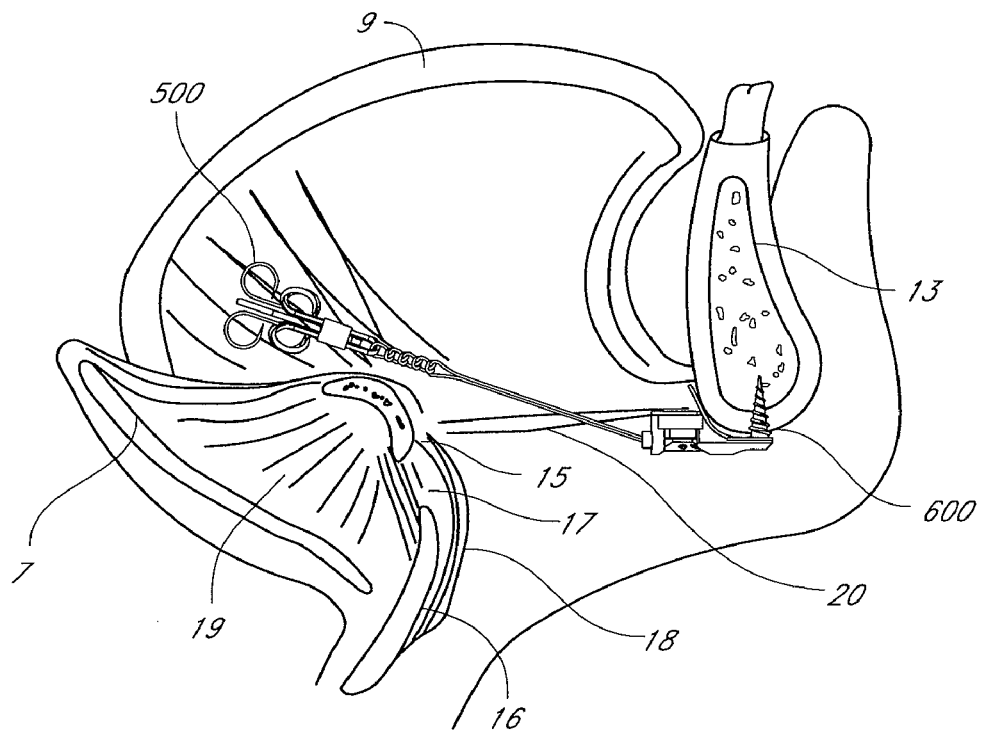
Figure 61K:
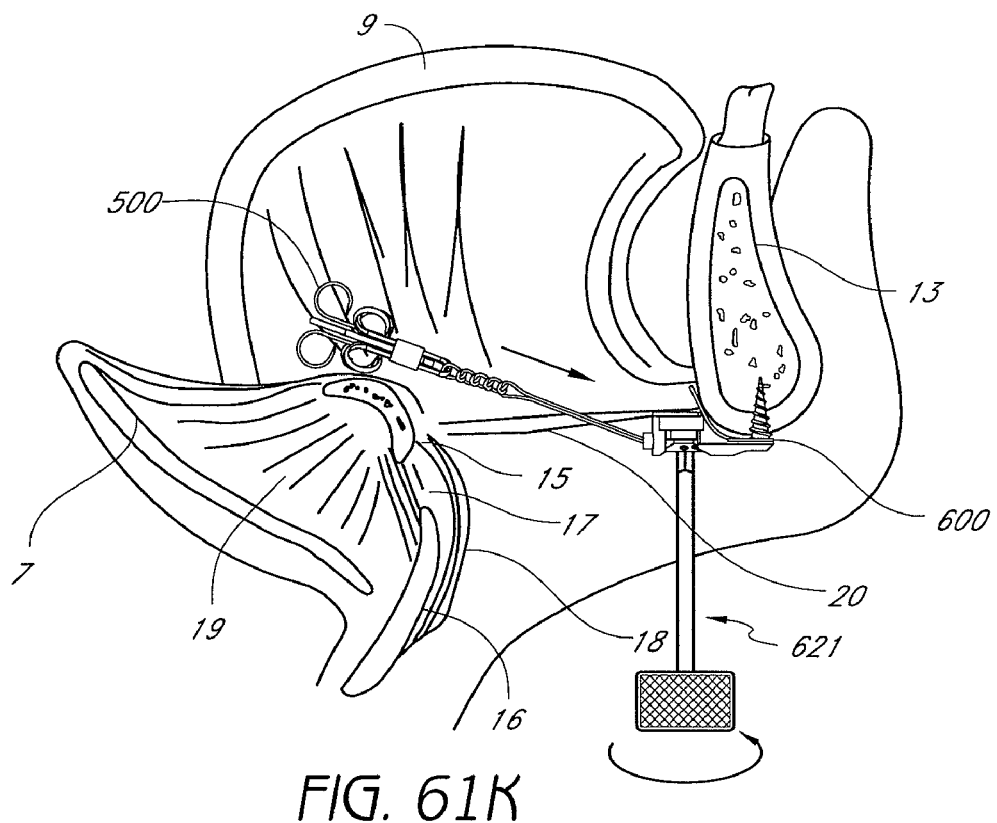

FIGS. 61J and 61K depict one particular embodiment of the invention wherein the distal anchor 500 and tether 28 are implanted into the tongue 9, either the base of the tongue or, preferably the anterior tongue. With the first and second ends (not shown) of the tether 28 protruding from the inferior chin region after implantation, the first and second ends of the tether are attached to the spool of the securing assembly. Excess tether length, if any, may be cut before, during or after the attachment of the tether to the spool. Preferably, the securing assembly 600 is attached to its anchoring site, such as the mandible 13, after the attachment of the tether 28, as this reduces the degree of surgical exposure required to attach the tether 28 after the securing assembly 500 is attached to its anchoring site. In other embodiments of the invention, attachment of the securing assembly to its anchoring site prior to attachment of the tether, or even implantation of the distal anchor, may be desirable.

4. Delivery Systems

Referring to FIGS. 62A to 62D, in a preferred embodiment of the invention, the delivery system 711 for the distal anchor 500 comprises a delivery tool 700 with a tubular body 702, a pushrod 704 within the tubular body 702, a movable handle 708 for altering the relative position between the tubular body 702 and pushrod 704, and an optional retraction assembly 710 for loading the implant into the tubular body. The delivery system 711 may optionally comprise an introducer 712 dimensioned to allow insertion of the delivery tool 700 into its lumen 714. The proximal end 716 of the introducer 712 may be provided with a mechanical fit, such as a male Luer adapter 718, which can be attached to the base 720 of the delivery tool 700 provided with a female Luer adapter 722, to lock the tubular body 702 to the introducer 712 and enhance the accuracy of inserting the distal tip of the delivery tool 700 into the tissue. The delivery system 711 may also comprise a trocar 724 for creating an insertion pathway from the skin insertion site to the desired soft tissue site. The trocar 724 is preferably, but not necessarily, dimensioned to also fit within the lumen 714 of the introducer 712, such that the trocar 724 is insertable into the patient together with the introducer 712 and then removed from the introducer 712 to allow placement of the delivery tool 700. The base 726 of the trocar 724 may also be provided with a female Luer adapter 722 or other complementary interface to engage the introducer. In other embodiments, the locations of the male and female Luer adapters may be reversed, or other mechanical interfit configurations may be used.

In the particular embodiment of the invention illustrated in FIGS. 62B and 62C, the delivery tool 700 comprises a pushrod 702 attached to an actuator handle 708, the pushrod 702 having a distal position and a proximal position which can be manipulated by a user through the actuator handle 708. In an alternate embodiment, rather than moving the pushrod within the tubular body, the actuator handle is attached to a movable tubular to allow withdrawal of the overlying tubular body to expose the distal anchor to the tissue, rather than pushing the distal anchor out of the delivery tube and into the tissue. The alternate embodiment may be advantageous in some instances because it maintains a constant distal anchor position as the distal anchor is deployed, rather than pushing the distal anchor forward during deployment Referring to FIGS. 62B and 62C, the distal anchor and tether may be loaded into the delivery tool by attaching the end(s) of the tether to tether attachment site 727 on a spool 728 located within the delivery tool 700. When the tether is attached to the spool 728 and the dial 730 attached to the spool 728 is rotated, the tether and distal anchor are pulled into the tubular body 702 as the tether is wound around the spool 728. The proximal pulling of the distal anchor into the delivery tube causes the expanded hook elements of the distal anchor to straighten and retract into their delivery profile and into the tubular body 702. In some instances, rotation resistance is provided for the spool 728, for example by using a biased resistance structure 732 with the retraction assembly 710. Rotational resistance may be useful to prevent inadvertent unspooling of a tether during packaging, storage or implantation of the device. FIGS. 62B and 62C depict one embodiment of the biased resistance structure 732 comprising a cantilever 734 biased by a spring 736, the cantilever comprising a rubber grommet 738 or other resistance surface or structure When the actuator handle 708 is moved from the loading position to the deployed position, the actuator handle 708 overcomes the bias of the resistance structure to release the rotation resistance. This allows the spool 728 to freely rotate and to quickly deploy the distal anchor into the tissue. As mentioned previously, the speed with which the distal anchor is deployed may affect the degree of tissue engagement by the distal anchor. In some instances, it is desirable to reduce rotation resistance in the delivery phase compared to the loading phase of the delivery tool usage.

Figure 62D:
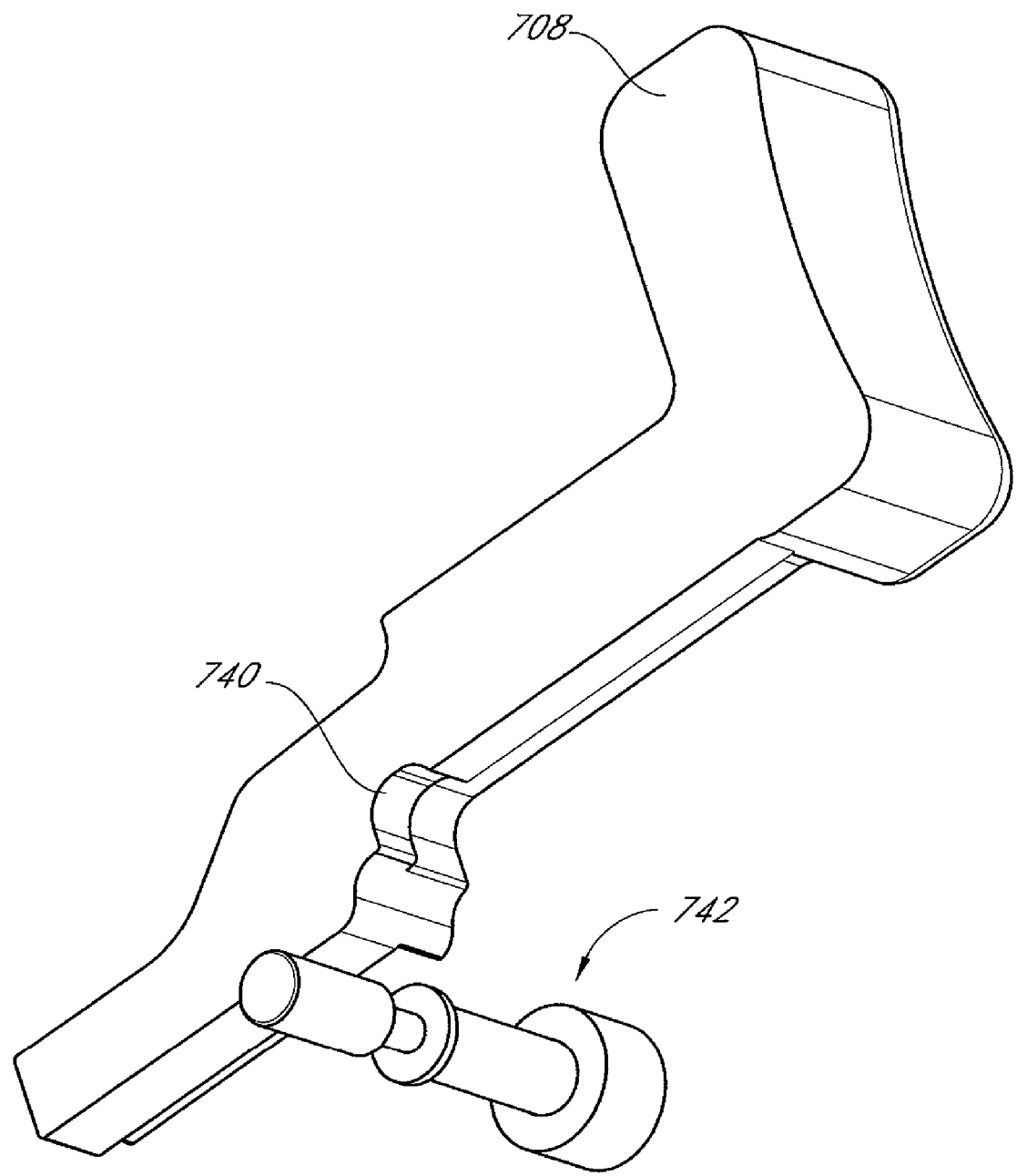
FIG. 62D is an exploded view of the actuator handle and safety lock of the delivery tool.

To avoid inadvertent actuation or deployment of a distal anchor loaded into the delivery tool, the actuator handle 708, spool 728, and/or pushrod 704 may be provided with a safety catch or pin that must first be manipulated before the one or more of these components can be moved. Referring to FIG. 62D, the actuator handle 708 has an indentation 740 or other configuration which can form a mechanical interfit with a movable pin 742 that can resist or prevent movement of the actuator handle 708 when the pin 742. The movable pin 742 can be moved or slid between a safety position wherein a portion of the pin 742 interferes with the movement of the actuator handle 708, and a release position that removes the mechanical interfit and allows movement of the actuator handle 708.

5. Soft Palate

Figure 63A:
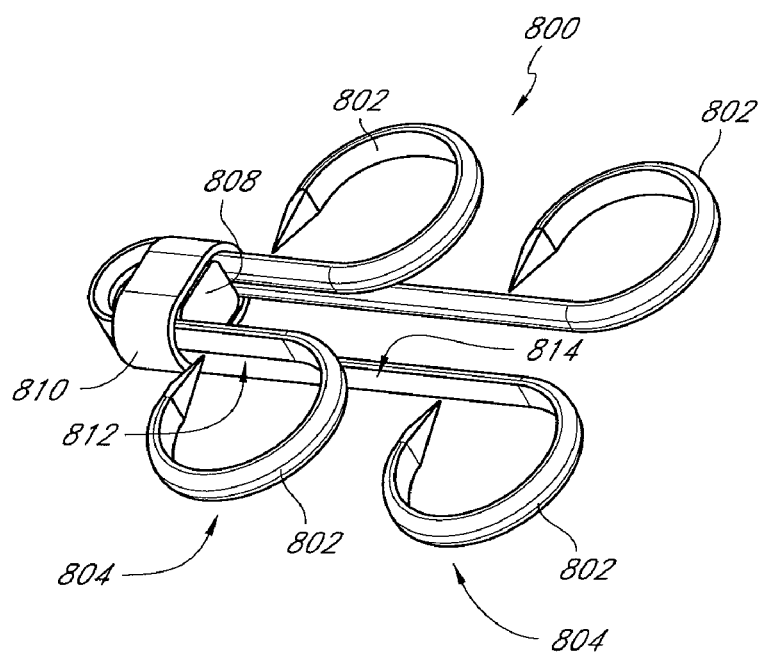
FIGS. 63A and 63B are perspective and exploded views, respectively, of one embodiment of a palate anchor.
Figure 63B:
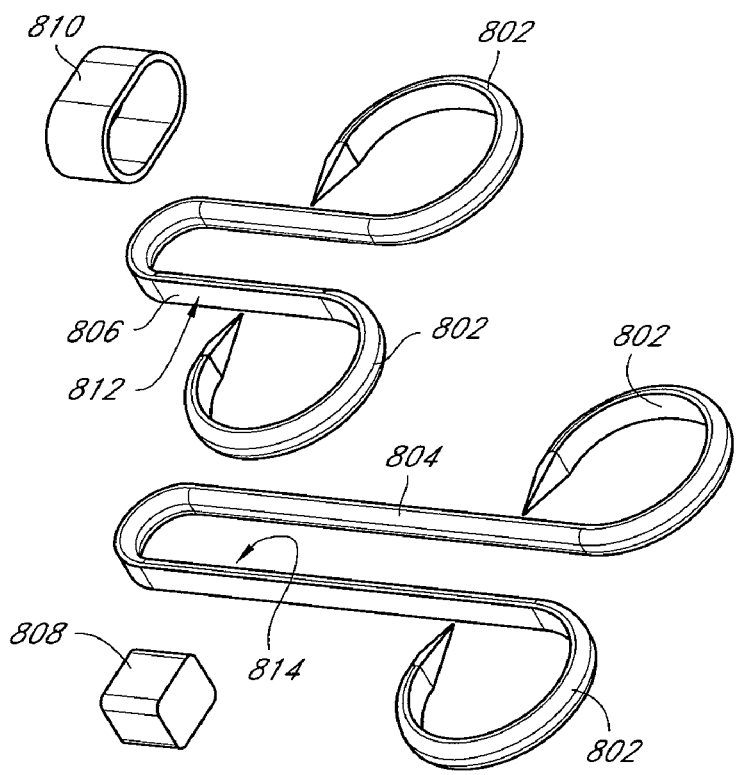

As mentioned previously, the methods and devices described herein may be used to manipulate other body structures besides the tongue. For example, a tissue anchor may be implanted into the soft palate and attached to the hard palate using a tether. Referring to FIG. 63A, in one embodiment, the soft palate anchor 800 comprises one or more expandable hooks 802 that are preferably arranged in a generally planar configuration for insertion into the similarly planar-shaped soft palate tissue. A planar configuration reduces the risk that the tissue anchor 800 forms a palpable nodule or protrudes from the superior or inferior surfaces of the soft palate. However, the expandable hooks 802 need not to lie in the same plane to have a generally planar configuration. A planar configuration may be characterized by an anchor having a maximum dimension as measured perpendicular to the longitudinal axis of the anchor that is greater than its orthogonal dimension also measured perpendicular to the longitudinal axis. For example, FIGS. 63A and 63B illustrate two pairs of hooks 804, 806 that are stacked with the side by side of one pair 806 stacked against the side 814 of the other pair 804 while still having a generally planar configuration. In other embodiments, one pair may be nested within the inside surface of the other pair.

The soft palate anchor 800 may have a unibody design or may comprise a multiple components joined together. As illustrated in FIGS. 63A and 63B, the soft palate anchor 800 may comprise a pair 804 of expandable distal hooks 802 joined with a pair 806 of expandable proximal hooks using a central core 808 and band 810.

Figure 64A:
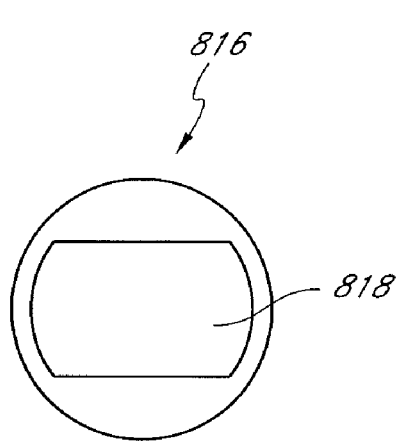
FIGS. 64A to 64D are axial cross sectional views of various embodiments of a delivery tube of the delivery tool for the palate anchor in FIG. 64A.
Figure 64B:
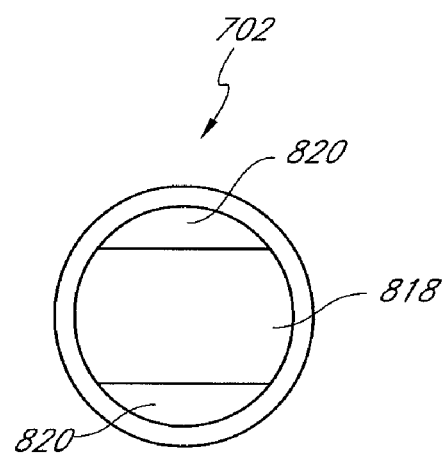
Figure 64C:
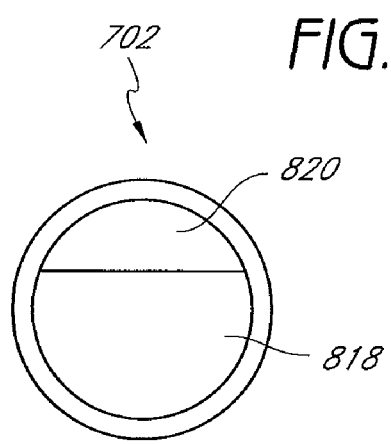
Figure 64D:
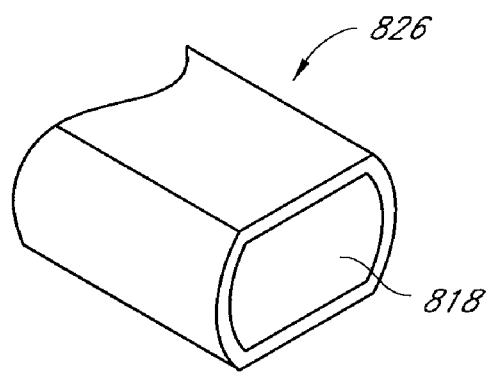

The soft palate anchor 800 may be inserted into the soft palate using a delivery tool similar to that depicted in FIG. 62A. In other embodiments, as shown in FIGS. 64A to 64D, the delivery tube 702, 816 of the delivery tool may be further configured to control the planar orientation of the tissue anchor 800, by a planar-configured delivery lumen 818. The planar-configured delivery lumen 818 may be achieved using a unibody delivery tube 816, as depicted in FIG. 64A, or with one or more additional delivery tube confining structures 820, as depicted in FIGS. 64B and 64C. The planar-configured delivery lumen 818 may be concentrically or eccentrically located along the axis of the delivery tube 702, as illustrated in FIGS. 64B and 64C, respectively. Although the cross-sectional shape of the delivery tube is typically different from the cross-sectional shape of the delivery lumen in order to facilitate rotation of the delivery tool during implantation, in other embodiments, as shown in FIG. 64D, the cross sectional shape of both the delivery lumen 818 and the delivery tube 826 may also has a planar outer shape.

Figure 65:
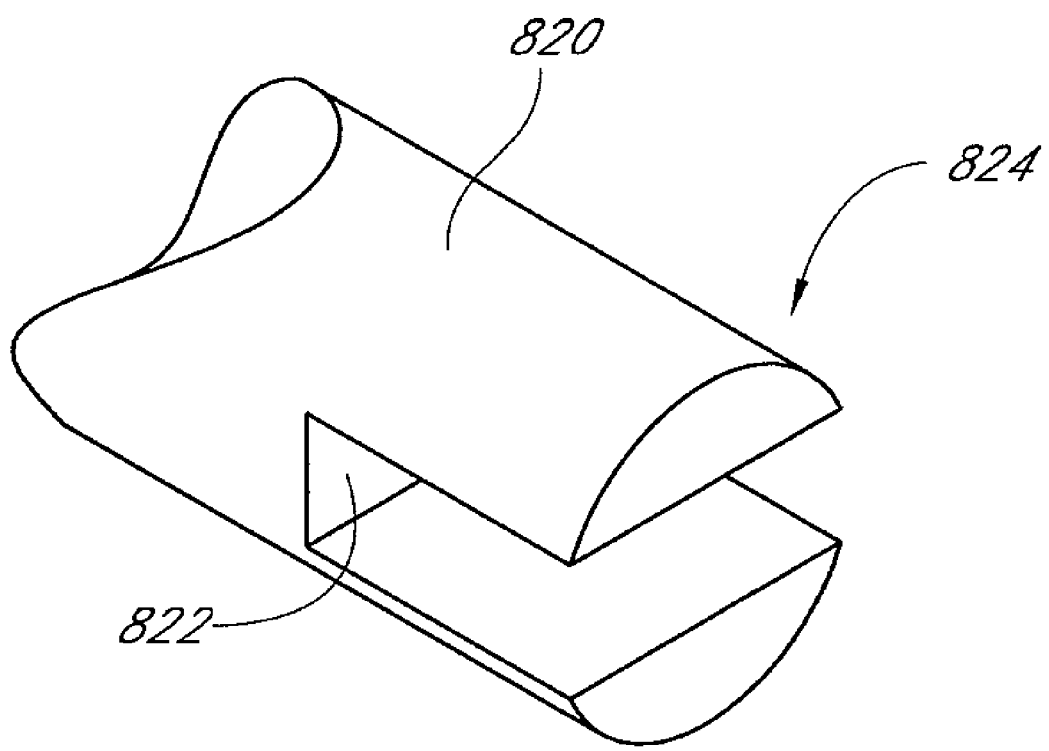
FIG. 65 is a perspective view of a push rod for the palate anchor in FIG. 64A.

As shown in FIG. 65, the rotational position of the planar tissue anchor may also be controlled in the delivery lumen using a push rod 820 with a distal end 824 configured with a slot 822.

Figure 66:
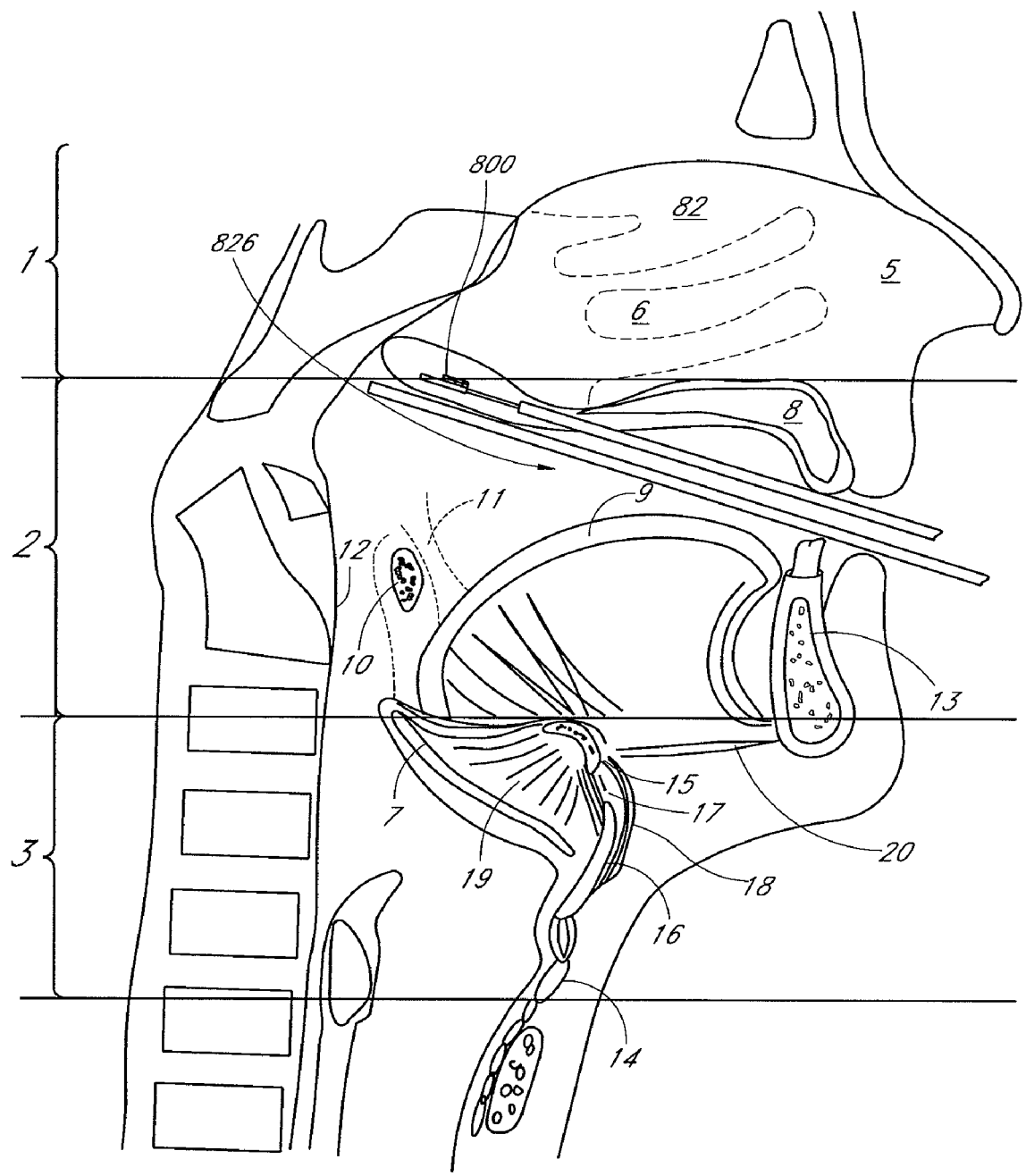
FIG. 66 is a schematic sagittal cross sectional view of the implantation of a palate anchor through the oral cavity.
Figure 67:
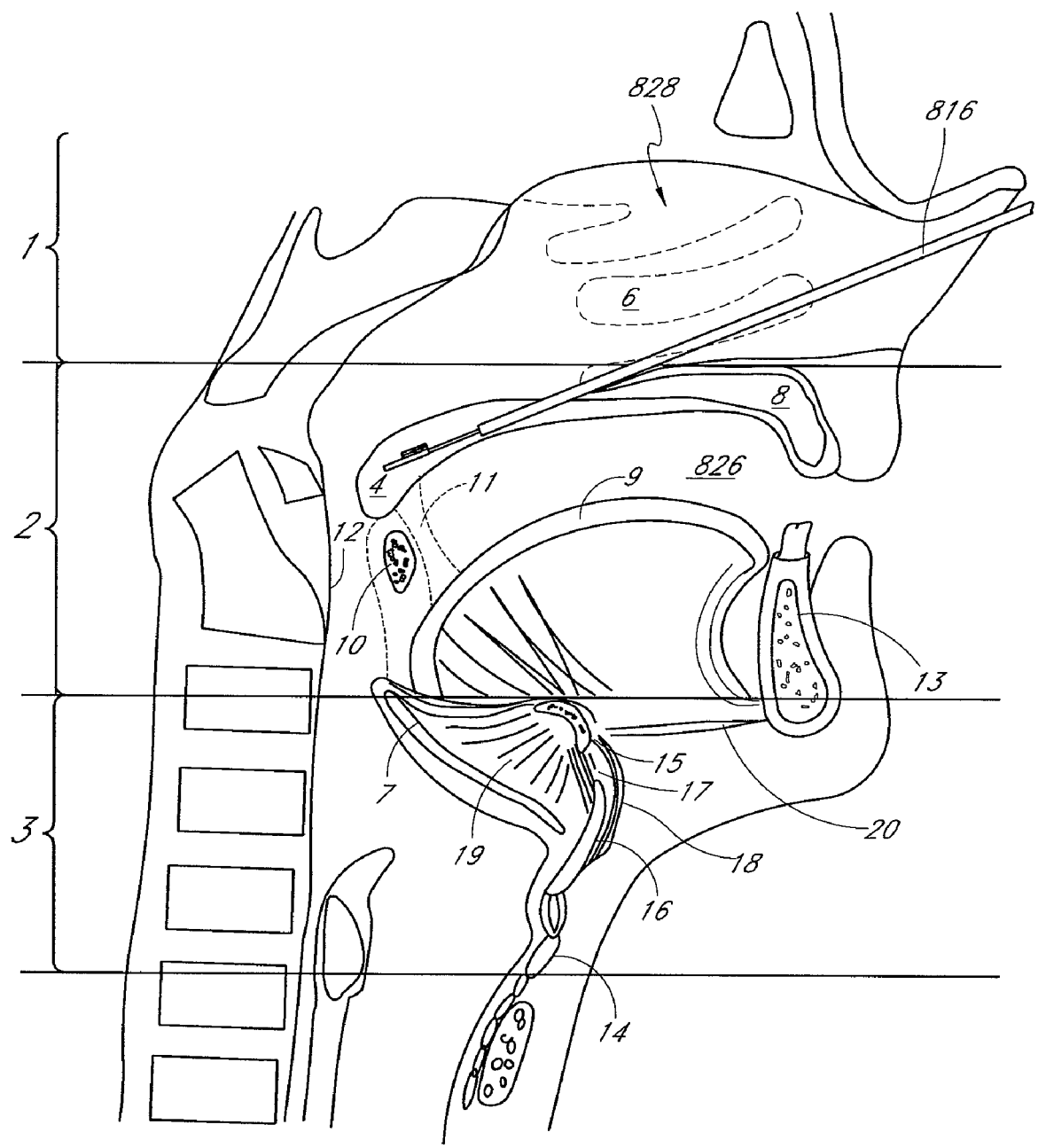
FIG. 67 is a schematic sagittal cross sectional view of the implantation of a palate anchor through the nasal cavity.

The soft palate anchor 800 may be inserted through the oral cavity 826, as shown in FIG. 66, or through the nasal cavity 828, as shown in FIG. 67. Insertion of the soft palate anchor 800 may be facilitated by manipulating the soft palate 4 to align it and the delivery tube 816. One of skill in the art will understand that any of a variety of surgical tools and techniques may be used to manipulate the soft palate 4, including but not limited to forceps manipulation or the use temporary sutures for applying traction to the soft palate 4. In other embodiments, soft palate alignment structures or tools may be integrated into the delivery tube 816. In still other embodiments, the delivery tube 816 may comprise a curved delivery tube to reduce the amount of soft palate manipulation. The curved delivery tube may comprise a curved or flexible push rod with sufficient column strength to resist axial compression when pushed distally.

FIGS. 68 and 69 depict further embodiments of the expandable soft palate anchor 800 system using different insertion and anchoring methods. FIG. 68 depicts the tether 830 of the expandable soft palate anchor 800 attached to the hard palate 8 by a fixation member 832, such as a bone anchor or screw. The tether 830 may also be optionally attached using an adjustment structure 834 that allows adjustment of tether tension or length. These adjustment structures may include those depicted in FIGS. 40A to 51E, and 61A, but are preferably configured with a reduced profile to accommodate the anatomical limitations of the palate. In another embodiment, FIG. 69 depicts the tether 830 with a flat tissue anchor 800 at each end, with one anchor 800 in the soft palate 4 and the other anchor 800 attached to the mucosal tissue 836 overlying the hard palate 8. This mucosal tissue 836 is less mobile than the soft palate tissue and therefore may also be used as an anchoring structure. Alternatively, a loop of suture may also be used to attach the soft palate anchor 800 to the mucosal tissue 836.

6. Recapture Systems

Although FIGS. 7G to 7J depict one embodiment for removing an implanted tongue anchor using a cannula, other embodiments of the invention provide additional features and structures to further facilitate removal of the implanted device.

Referring to FIGS. 70A to 70E, in another embodiment of the invention, a recapture tool 840 is provided when removal of the tissue anchor 800 is desired. The recapture tool 840 comprises a recapture tube 842 with a longitudinal slot 844 at its distal end 846 and a handle housing 848 at its proximal end 850, a movable blocking assembly 852 and a movable tether guide 854 with a longitudinal slot 856. In the preferred embodiment, the blocking assembly 852 and tether guide 854 are concentrically arranged inside the lumen 858 of the recapture tube 842, with the blocking assembly 852 between the tether guide 854 and recapture tube 842. The longitudinal slots 844, 856 of the recapture tube 842 and tether guide 854 are aligned, with the tether guide 854 preferably movable axially, but not rotationally, relative to the recapture tube 842. In one embodiment, axial mobility and rotational alignment of the tether guide 854 is achieved by a longitudinal alignment groove 860 located at the proximal end 861 of the tether guide 854 that interfaces with an alignment pin 862 inserting into the groove 860 and held in place by the handle housing 848. The alignment pin 862 may be further configured to allow locking and unlocking of the tether guide 854 with respect to the recapture tube 842. This may be achieved by any of a variety of locking interfaces known in the art, including but not limited a rotational screw interface or a spring-biased mechanical fit between the alignment pin and the groove.

Figure 70A:
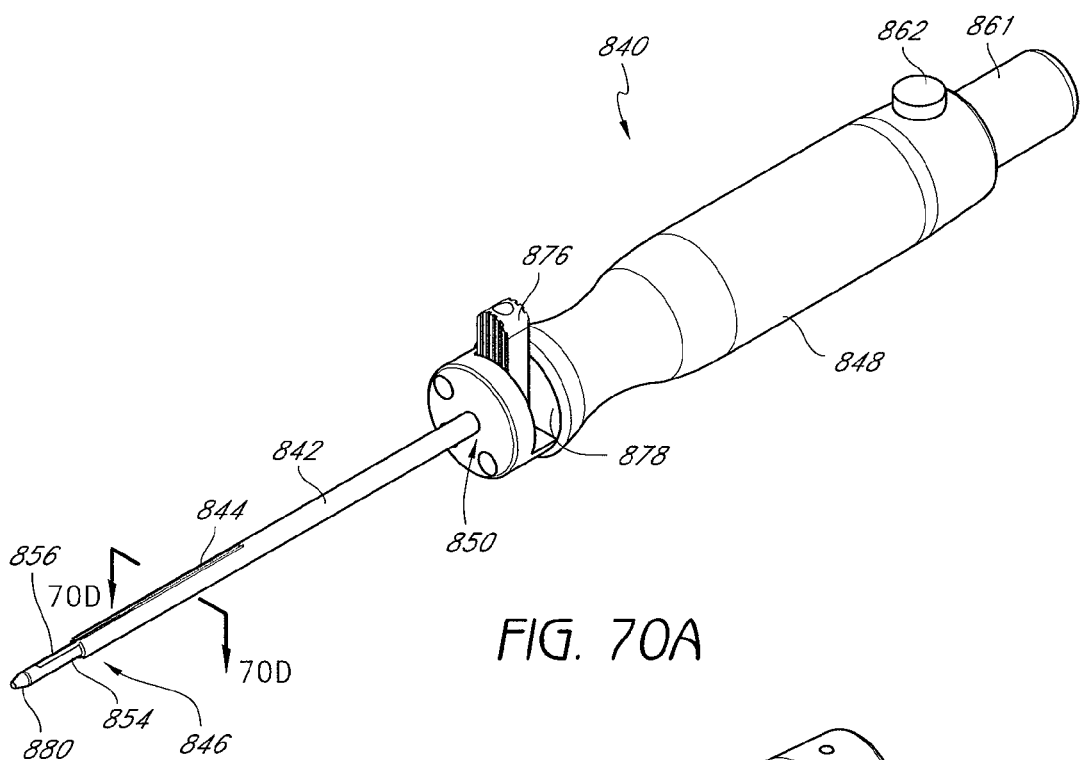
FIG. 70A is a perspective view of one embodiment of a recapture tool.
Figure 70B:
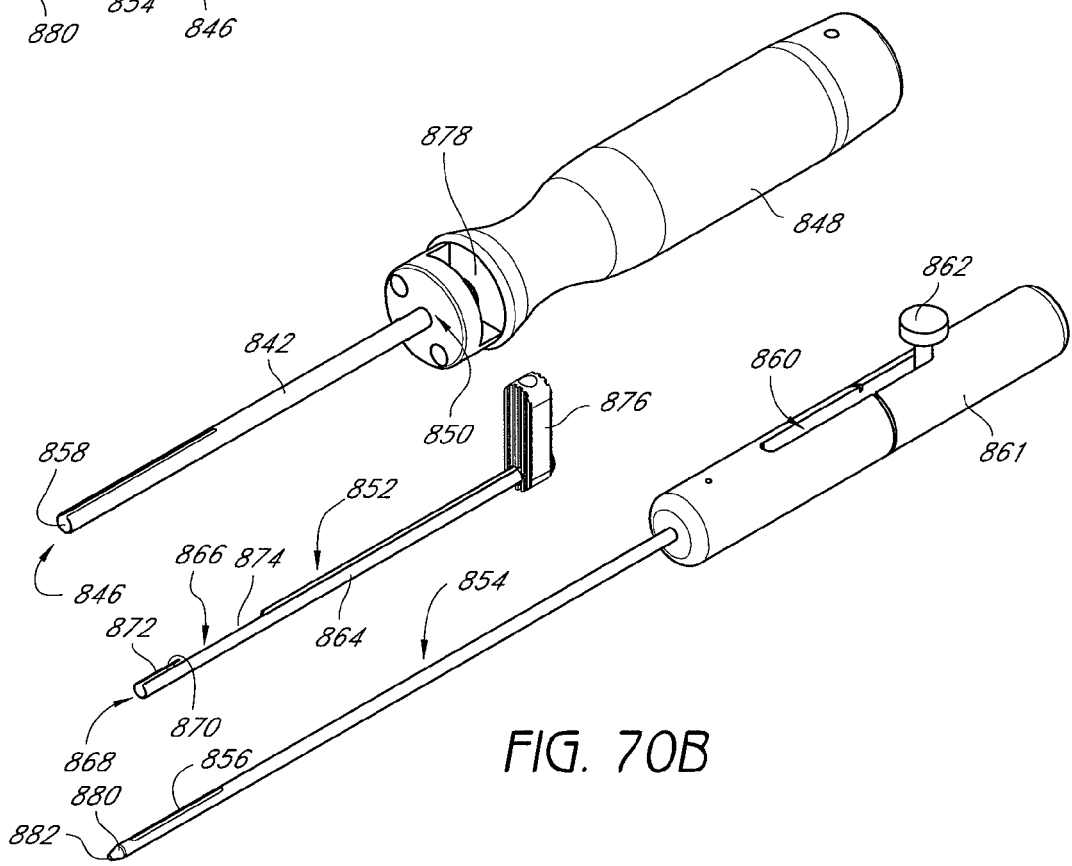
FIG. 70B is an exploded view of the recapture tool in FIG. 70A.
Figure 70C:
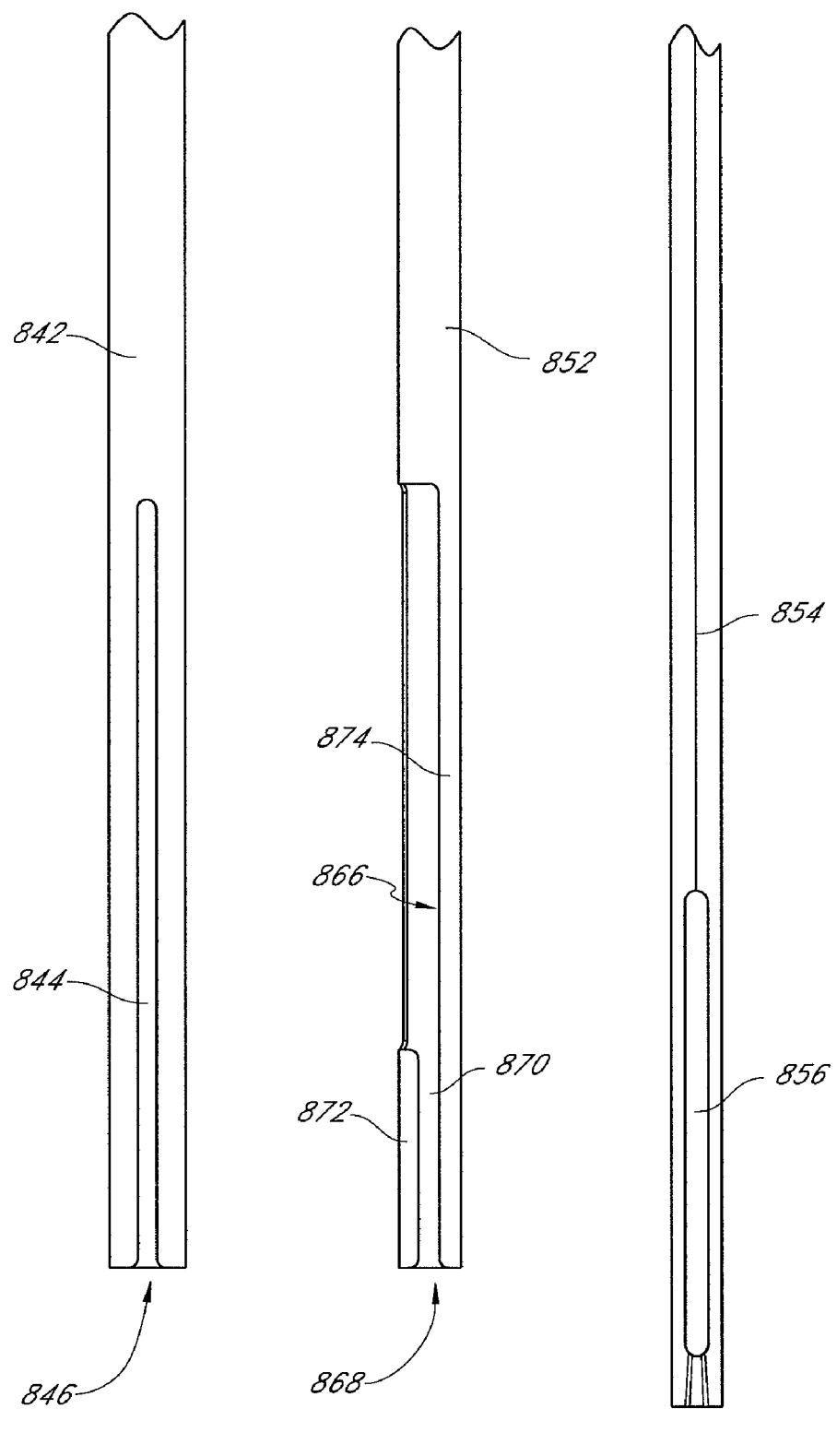
FIG. 70C is a superior exploded view of the distal end of the recapture tool.
Figure 70D:
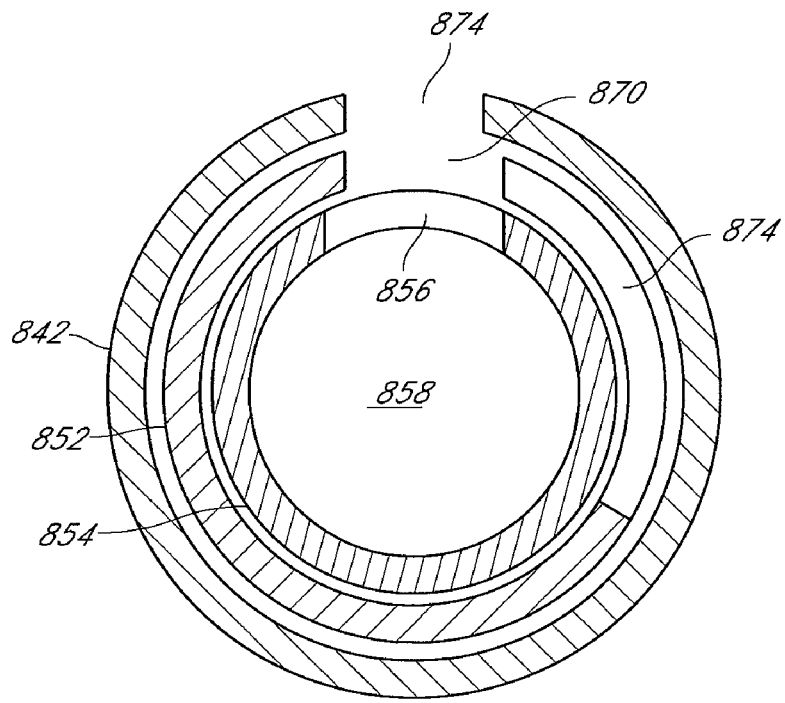
FIG. 70D is an axial cross sectional view of the recapture tool in the open position as identified in FIG. 70A.
Figure 70E:
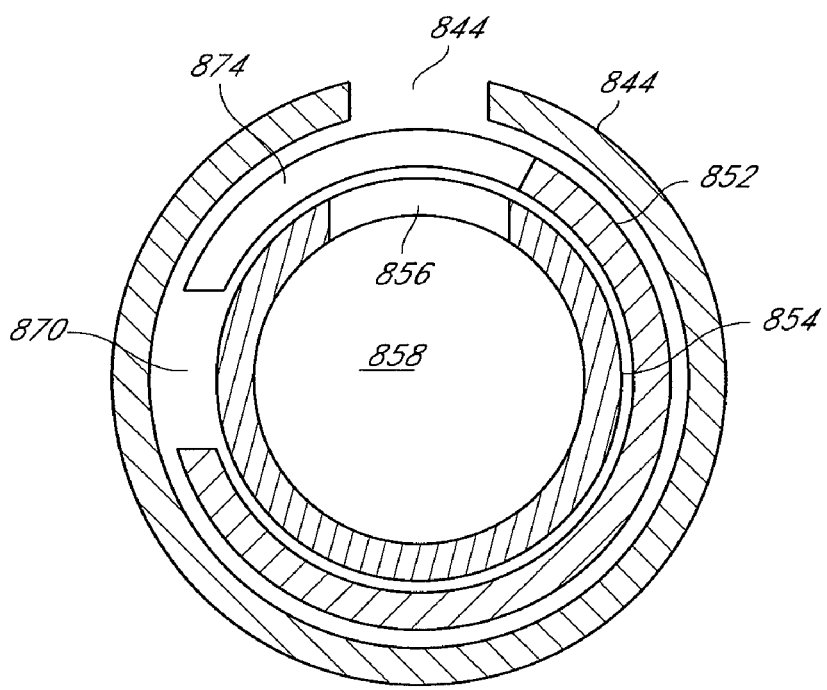
FIG. 70E is an axial cross sectional view of the recapture tool in the closed position

The blocking assembly 852 typically comprises a tubular body 864 with a keyed longitudinal slot 866 at its distal end 868. Referring to FIG. 70C, The keyed longitudinal slot 866 comprises a narrow slot 870 and a blocking surface 872 at its most distal end 868, and a wider slot 874 just proximal to the narrow slot 870 and blocking surface 872. The blocking assembly 852 has a proximal handle 876 to facilitate rotation of the blocking assembly 852 to open and closed positions within the recapture tube 842. The proximal handle 876 projects from an opening 878 in the handle housing 848 of the recapture tube 842. In some embodiments, the opening 878 is configured to limit the range of motion of the proximal handle 876. Referring to FIG. 70D, in the open position, the narrow slot 870 of the blocking assembly 852 is generally aligned with the longitudinal slots 844, 856 of the recapture tube 842 and the tether guide 854. This open position facilitates threading of the proximal end of a tether 830 of an implanted anchor 800 into the recapture tool 840. In the closed position, as shown in FIG. 70E, the blocking surface 872 of the blocking assembly 852 is located at the longitudinal slot 844 of the recapture tube 842, effectively forming a circumferentially closed tube at the distal end 846 of the recapture tube 842. As described in greater detail below and depicted in FIG. 71H, as the implanted anchor 800 is pulled into the recapture tool 840, the circumferentially closed distal end 846 of the recapture tube 842 assures that the expanded members or hooks 802 of the implanted anchor 800 are at least collapsed back to their unexpanded configuration and are not accidentally protruding from the longitudinal slot 844 of the recapture tube 842 in an expanded state as it is pulled into the recapture tube 842 and removed from the body. In the closed position, the wider slot 874 of the blocking assembly 852 remains in general alignment with the proximal portions of the longitudinal slots 844, 856 of the recapture tube 842 and the tether guide 854 so that the captured tether 830 can still slide through the recapture tool 840.

Referring back to FIG. 70A, the tether guide 854 is configured to move longitudinally within the recapture tube 842 and the blocking assembly 852. The tether guide 854 further comprises a conical distal tip 880. In its distal position, the tether guide 854 extends from the distal end 846 of the recapture tube 842 and the conical tip 880 assists with separating the tether 830 from the surrounding ingrown tissue, if any, as the recapture tool 840 is slid over the tether 830 towards the anchor 800. In its distal position, the tether guide also facilitates the threading of the tether 830 into the tether guide 854. Threading is typically accomplished using a needle hole threader that is well known in the art and is inserted through the longitudinal slot 856 of the tether guide 854 and out of the tip lumen 882 of the conical tip 880. Once the tether 830 is engaged to the needle hole threader, it is pulled through the conical tip 880 and out through the longitudinal slot 856 of the tether guide 854.

In the proximal position, the tether guide 854 pulls the tether 830 more proximally into the recapture tube 842 to allow the blocking assembly 852 to rotate into its closed position without snagging the tether 830 with the blocking surface 872. Once the blocking assembly 852 is moved to the closed position, the tether guide 854 may be repositioned back in the distal position in order to allow the conical tip 880 to separate the soft tissue from the tether 830 as the recapture tool 840 is guided toward the implanted anchor 800.

Figure 71A:
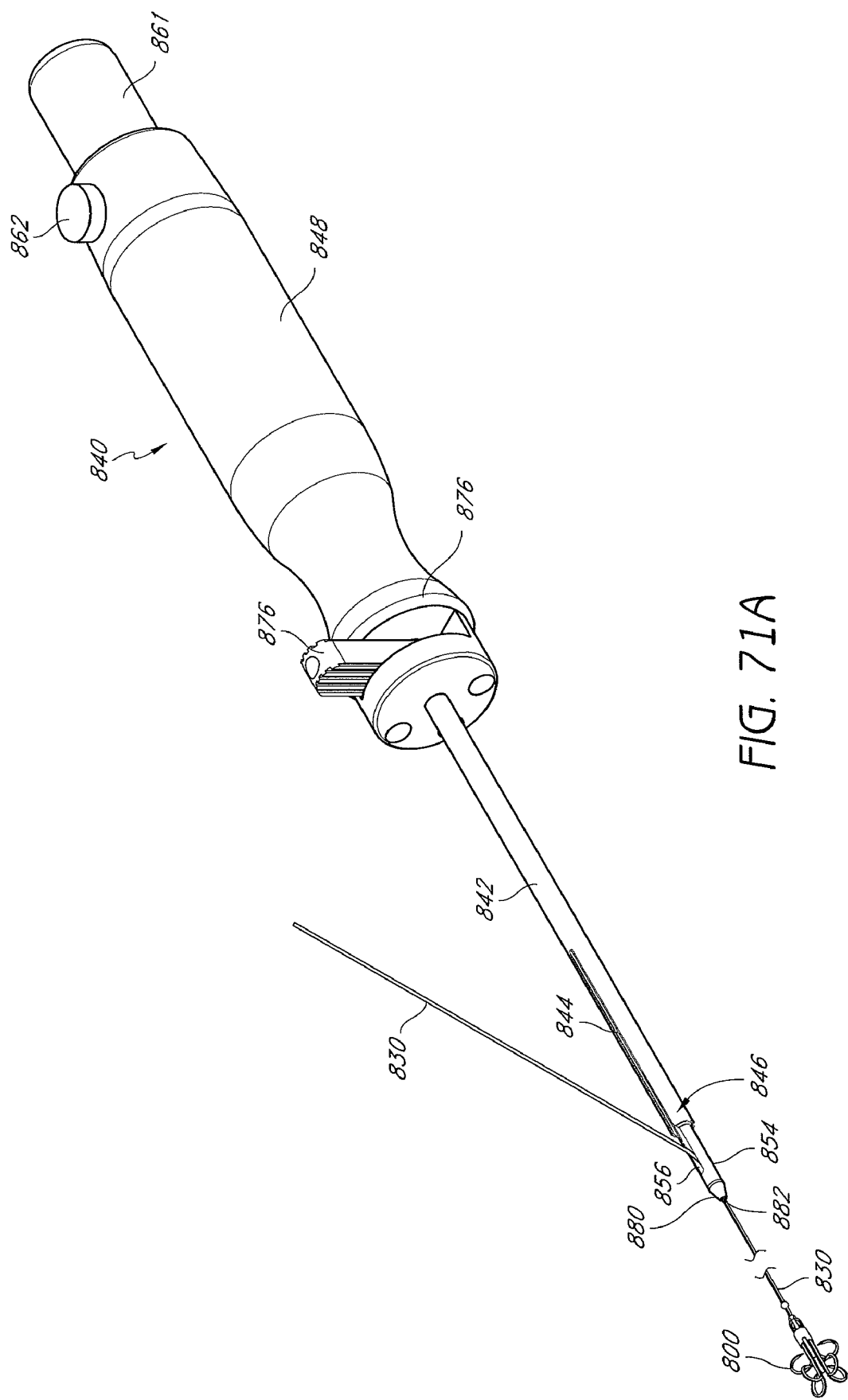
Figure 71B:
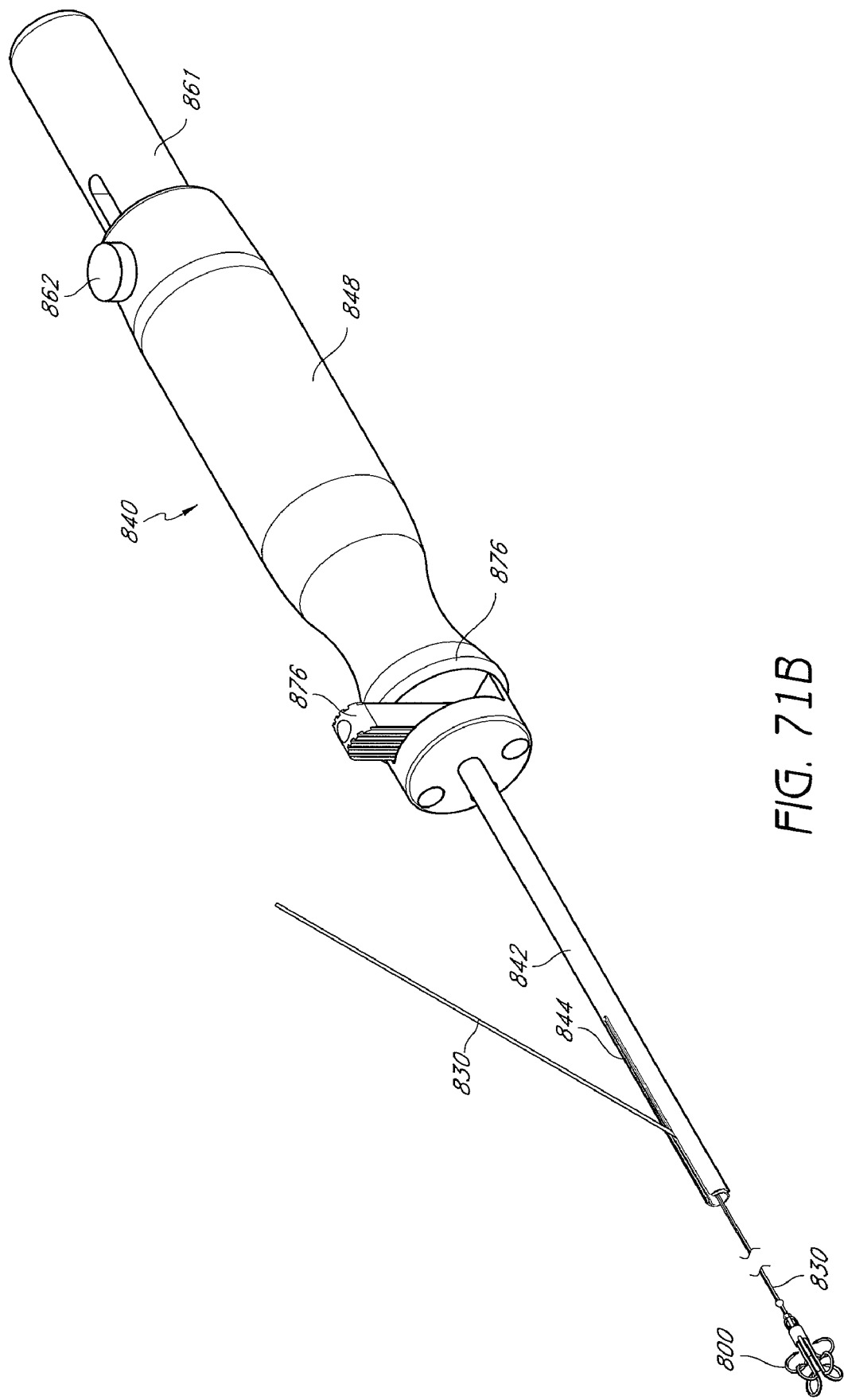
Figure 71C:
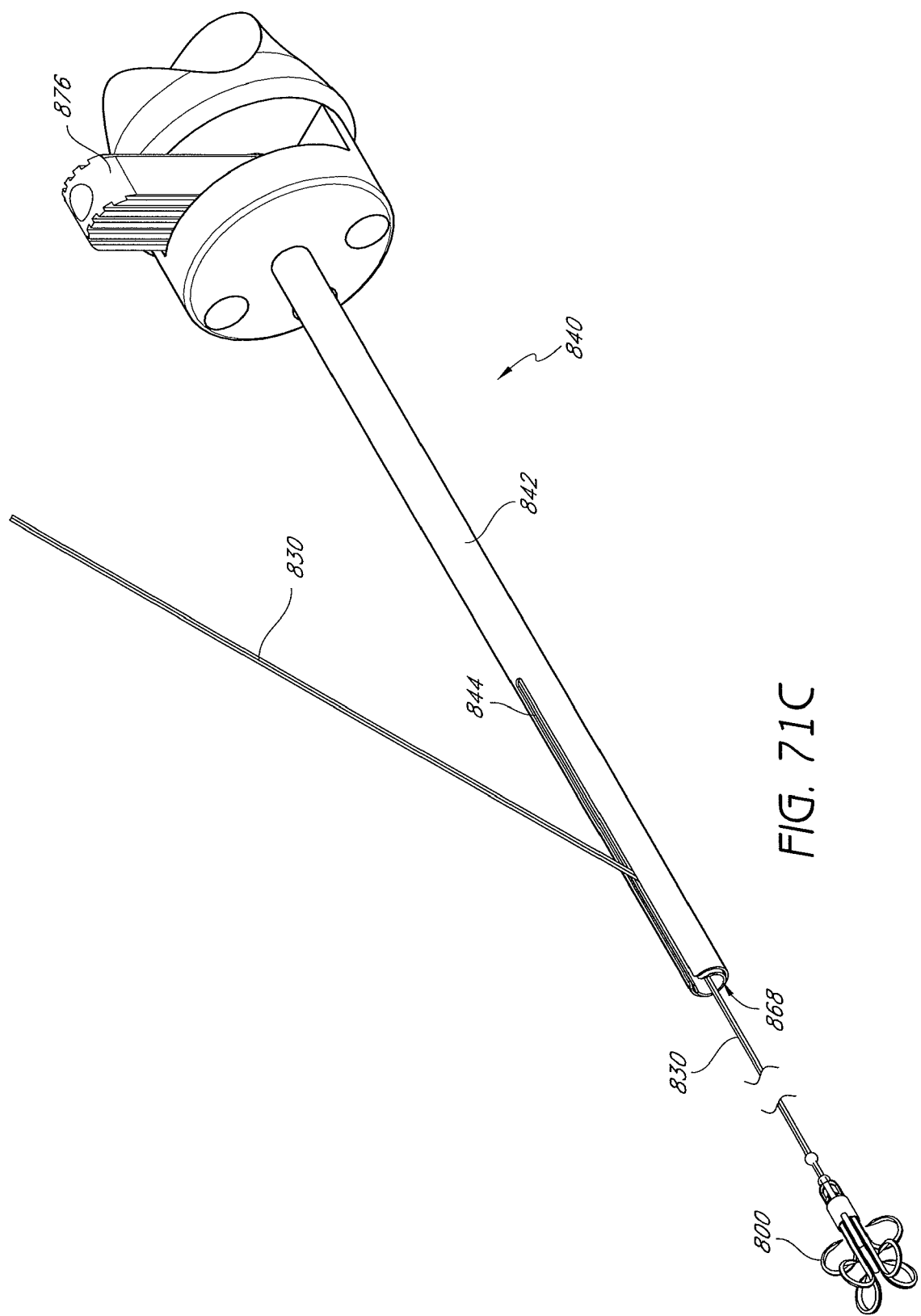
Figure 71D:
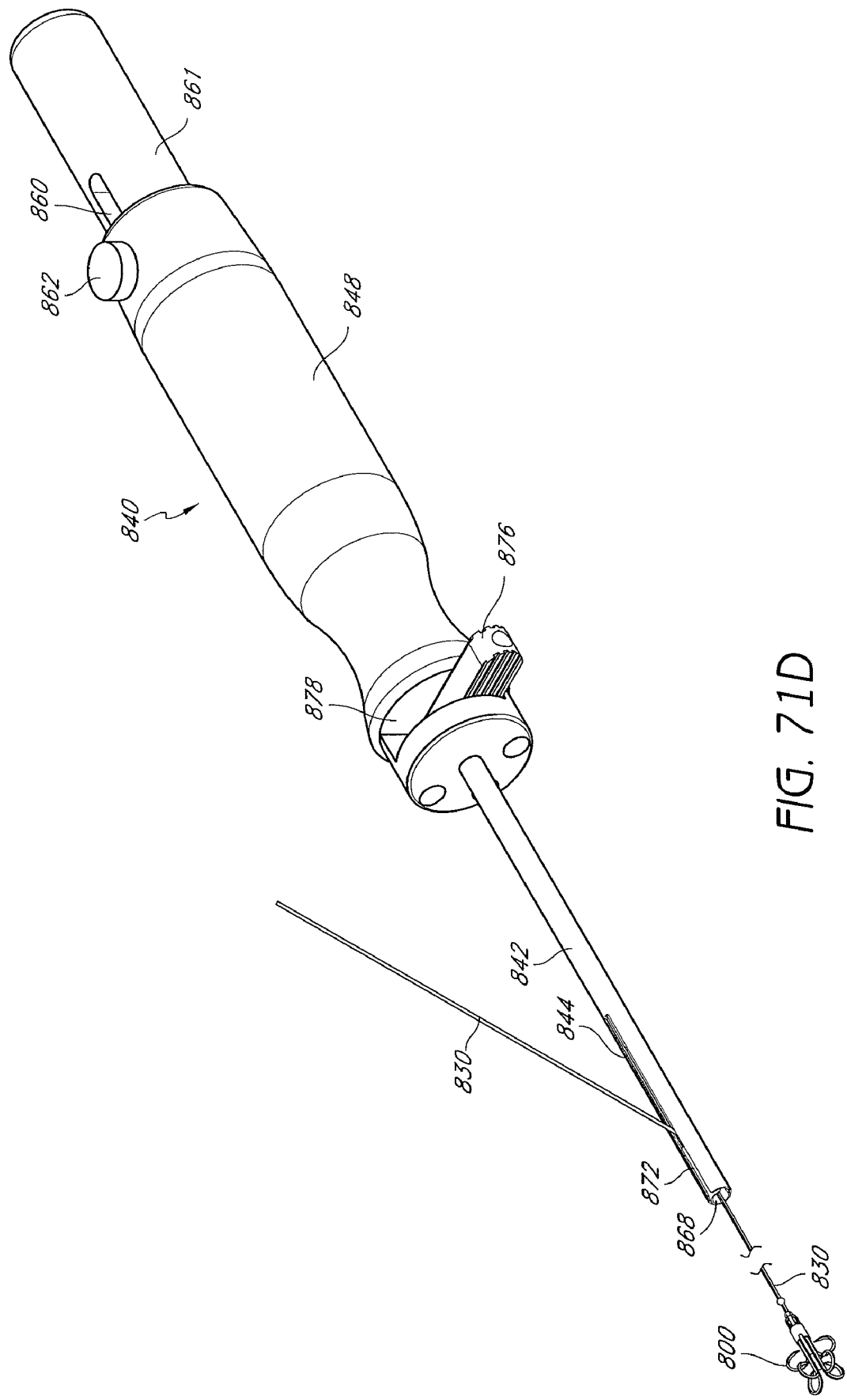
Figure 71E:
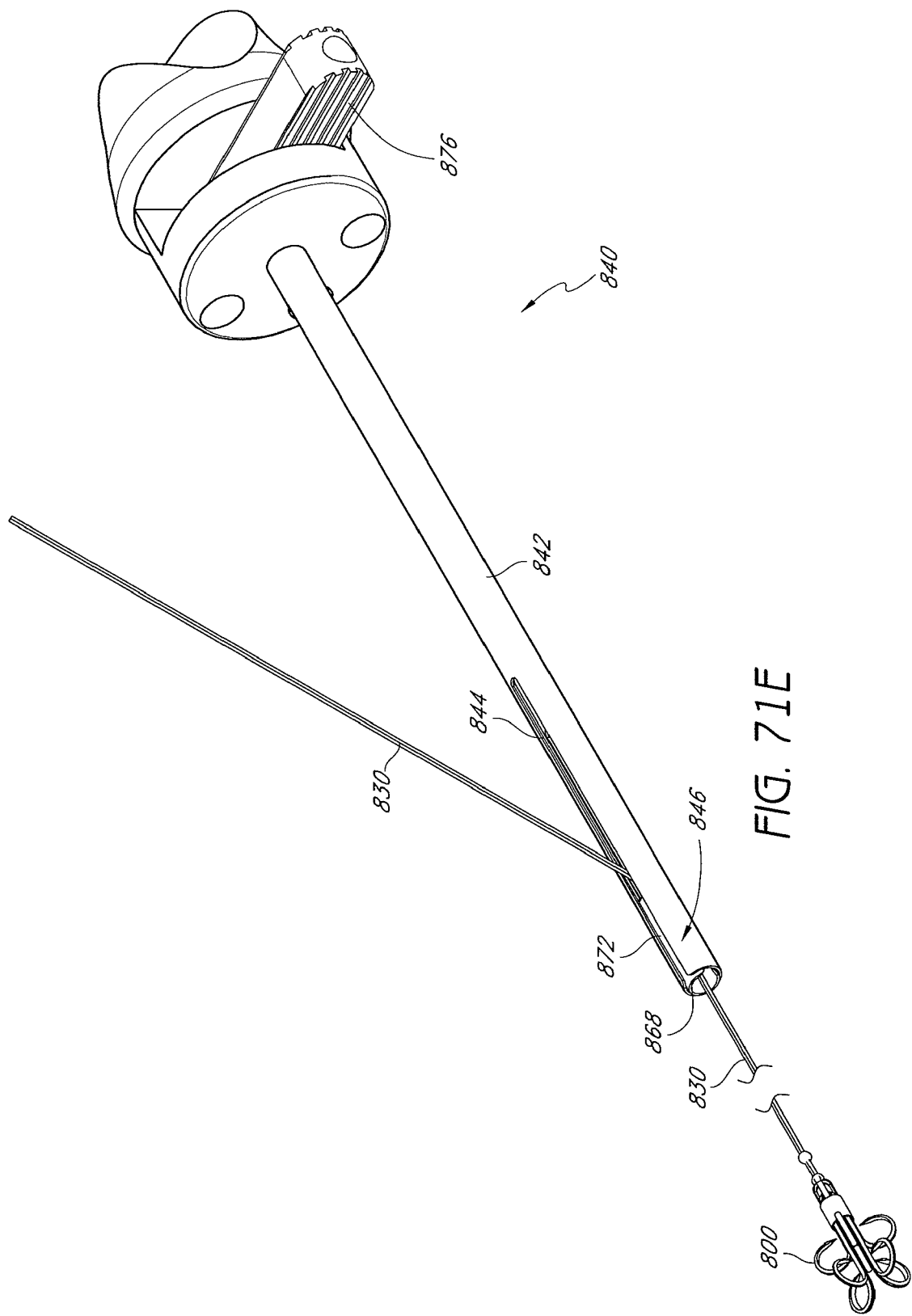
Figure 71F:
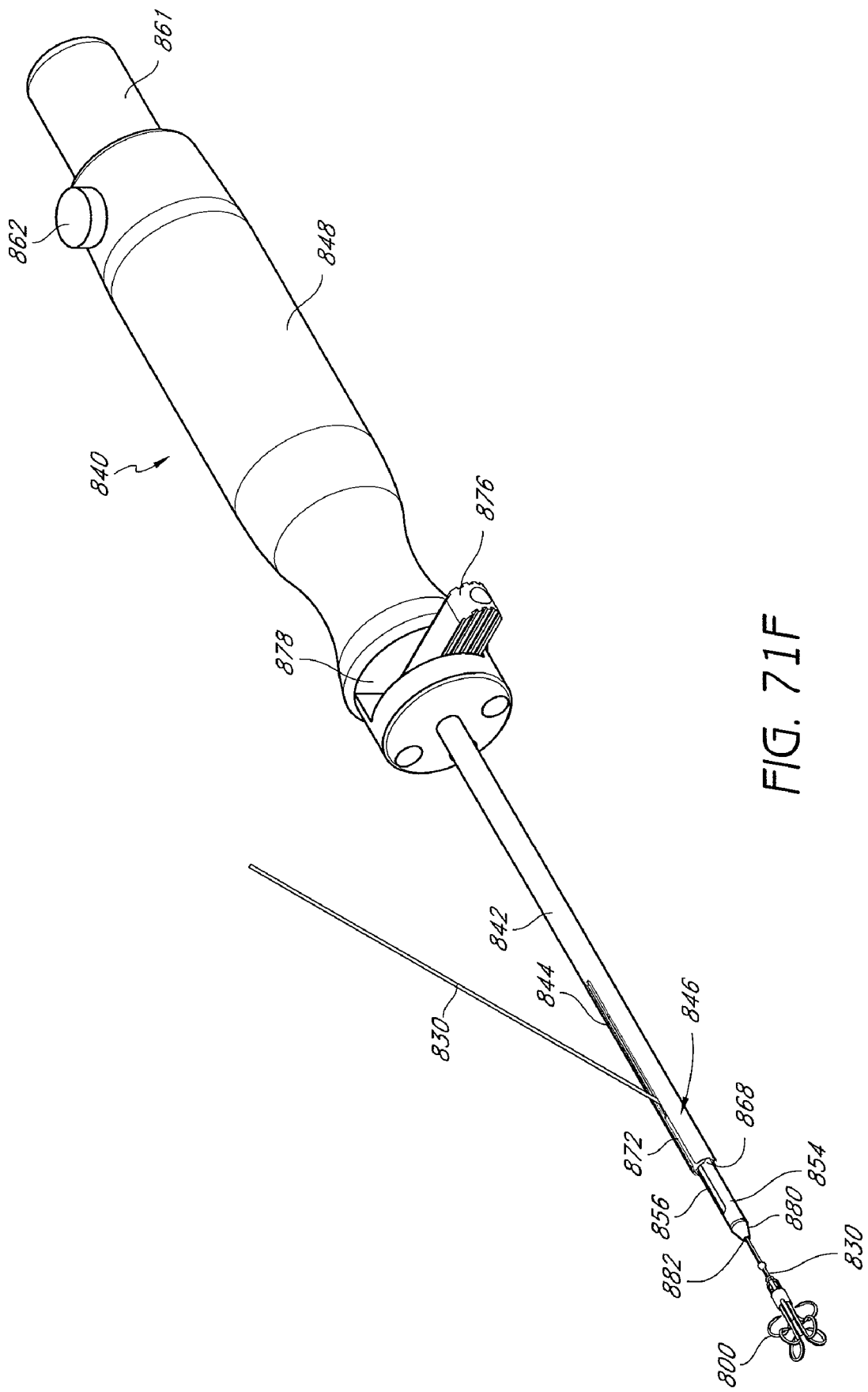
Figure 71G:
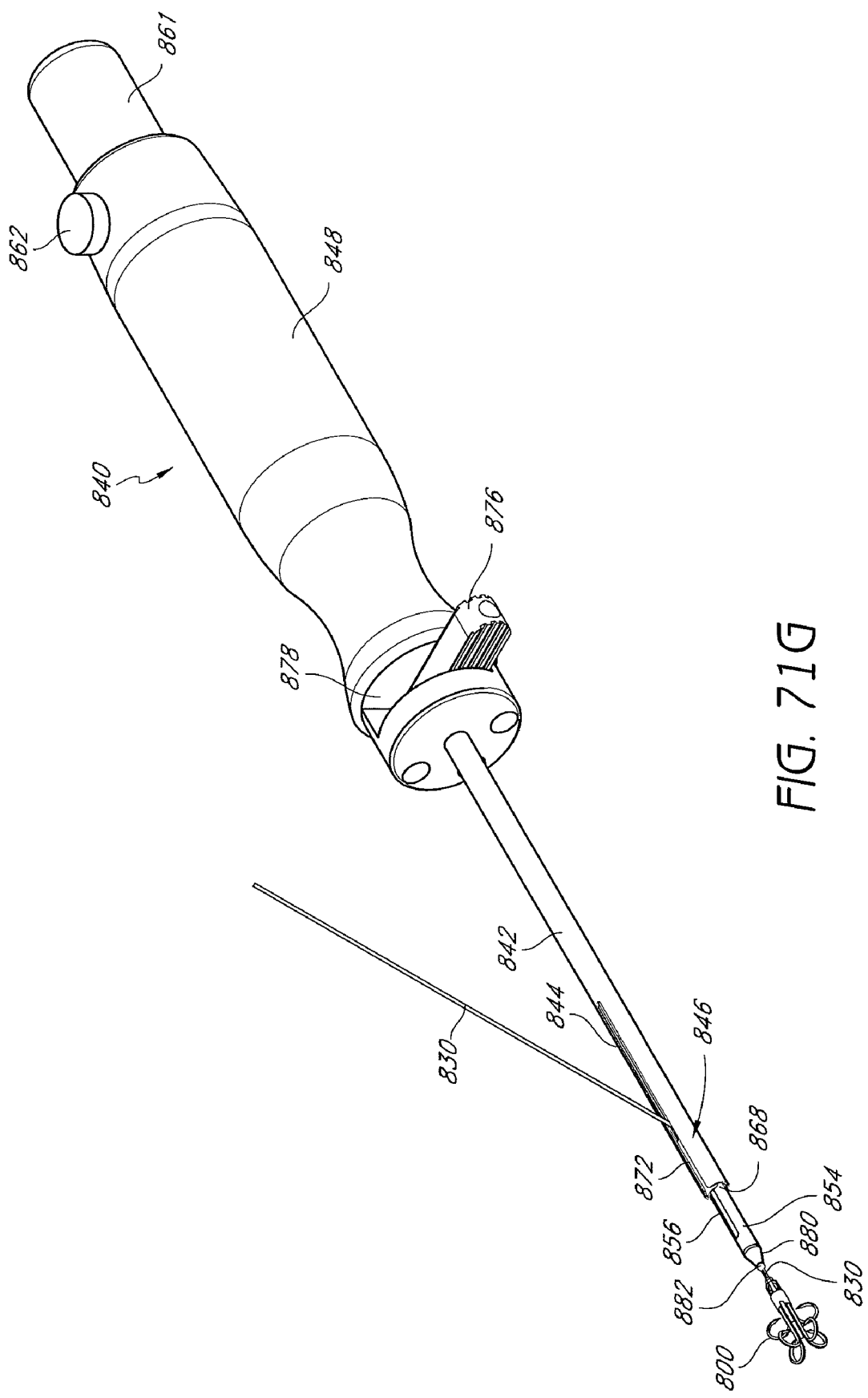
Figure 71H:
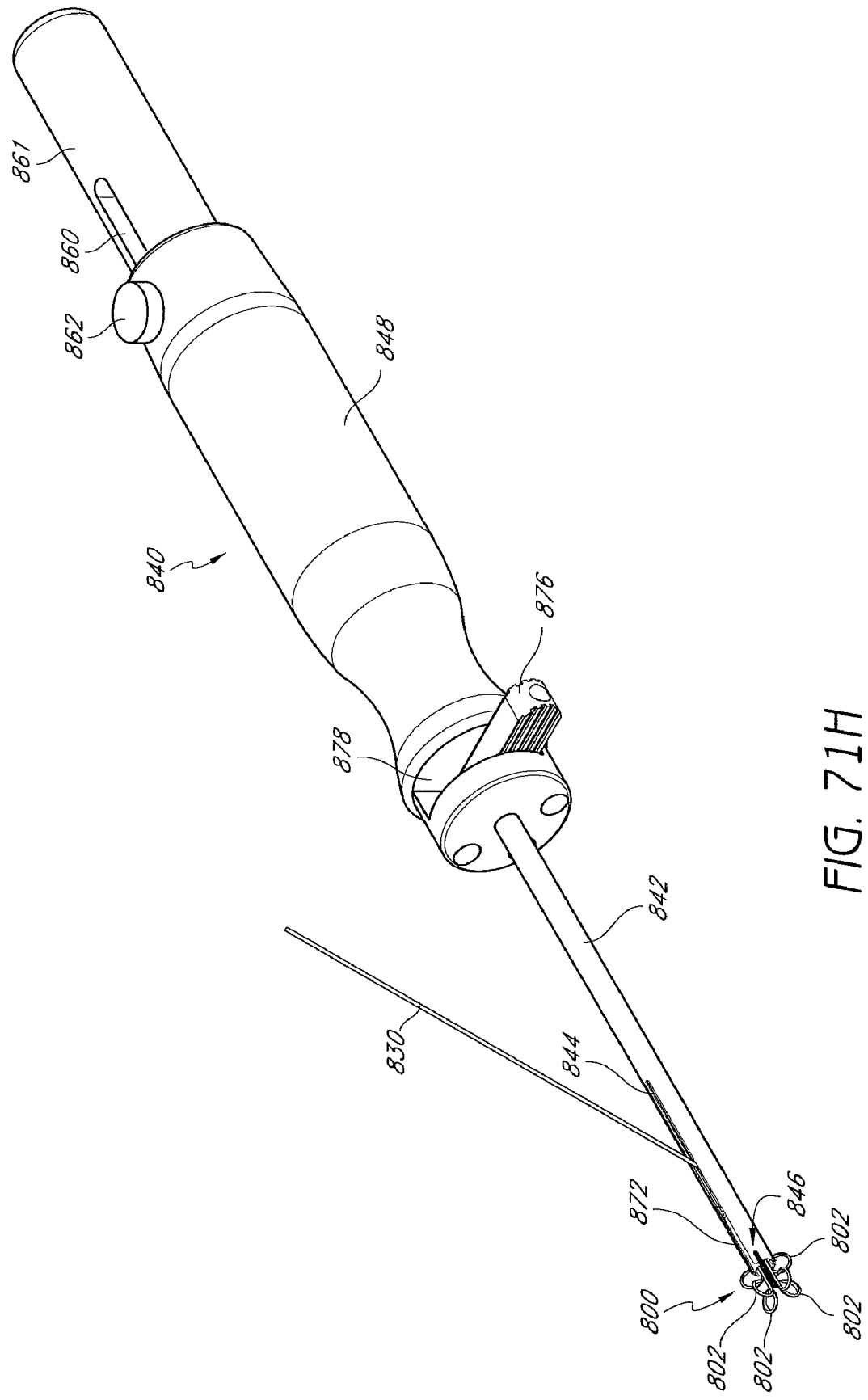
Figure 711:
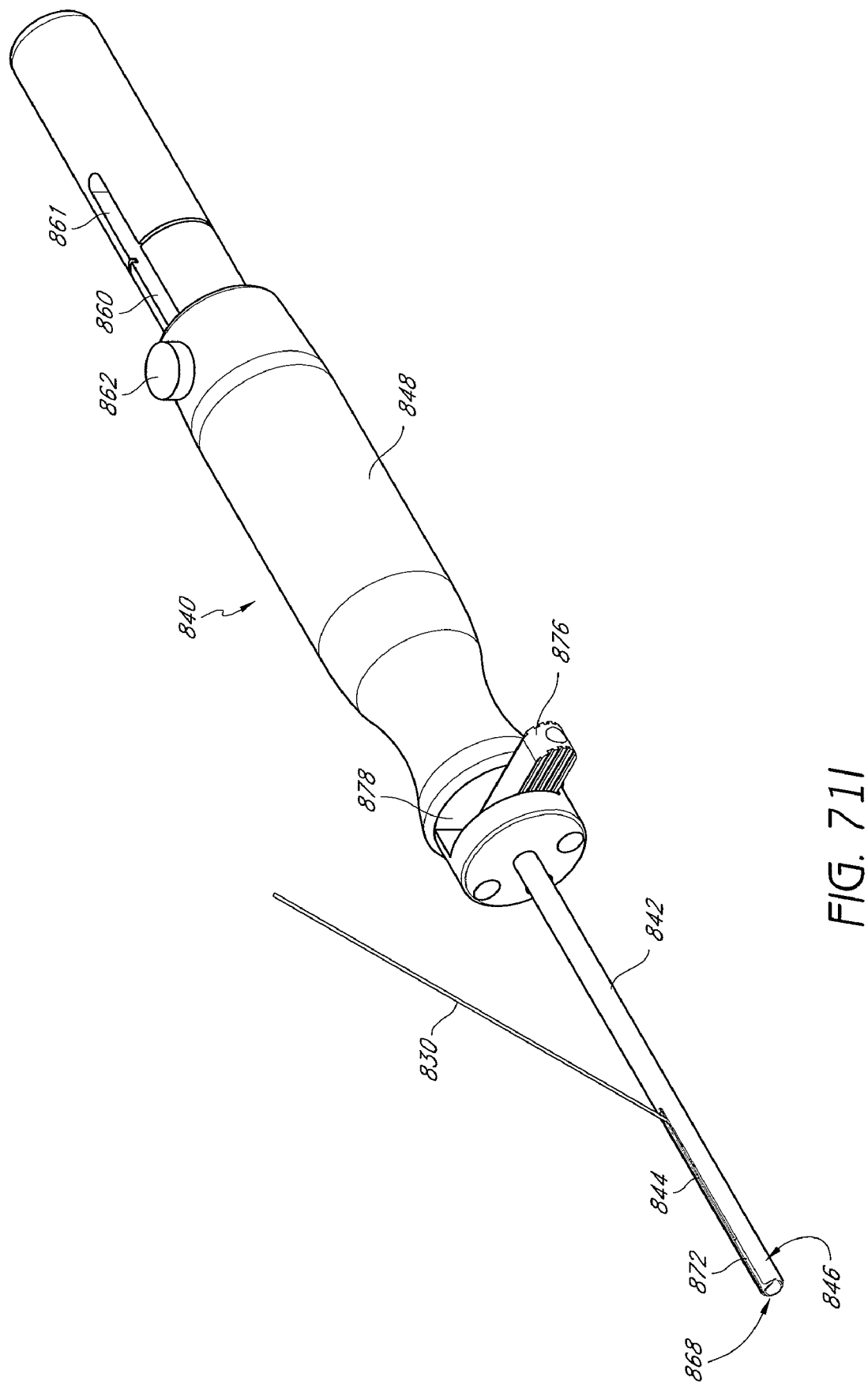

One embodiment for using the above recapture tool 840 comprises achieving anesthesia of the midjaw and anterior tongue and accessing the proximal attachment site of the implanted device. Typically, anesthesia is achieved using local or regional anesthesia, but in other embodiments of the invention, general anesthesia may be used. The proximal end of the tether 830 is released from its attachment site or adjustment assembly and pulled out from the access site. A needle hole threader inserted into the longitudinal slot 856 of the tether guide 854 and out of the lumen 882 of the conical tip 880. The proximal end of the tether 830 can then be pulled into the conical tip 880 and out through the longitudinal slot 856 of the tether guide 854, as depicted in FIG. 71A. In FIGS. 71B and 71C, the tether guide 854 is retracted into the recapture tube 842 to proximally shift the position where the tether 830 exits the longitudinal slot 844 of the recapture tube 842. This allows the blocking assembly 852 to rotate into the closed position without snagging the tether 830, thereby blocking the distal end 846 of the recapture tube's longitudinal slot 844 and forming a circumferentially closed lumen, as shown in FIGS. 71D and 71E. In FIG. 71F, the tether guide 854 is placed back in the extended position so the conical tip 880 may be used to separate the soft tissue from the tether 830 as the recapture tool is passed over the tether 830 toward the implanted anchor 800. Referring to FIG. 71G, the conical tip 880 is pushed distally until it generally abuts the implanted anchor 800. As illustrated in FIG. 71H, tether position is maintained by pulling on the tether 830 as the recapture tube 842 is pushed distally against the implanted anchor 800, causing its expandable members 802 to curl or collapse back into a straighter configuration as it enters the recapture tube 842. Once the anchor 800 is retracted into the recapture tube 842, as illustrated in FIG. 71I, the entire recapture tool 840 may be withdrawn from the patient. The existing bone anchor and/or adjustment assembly may be removed or left in place, depending upon a variety of factors, such as whether replacement anchors will be inserted and the functionality of the existing bone anchor and/or adjustment assembly.

Figure 72:
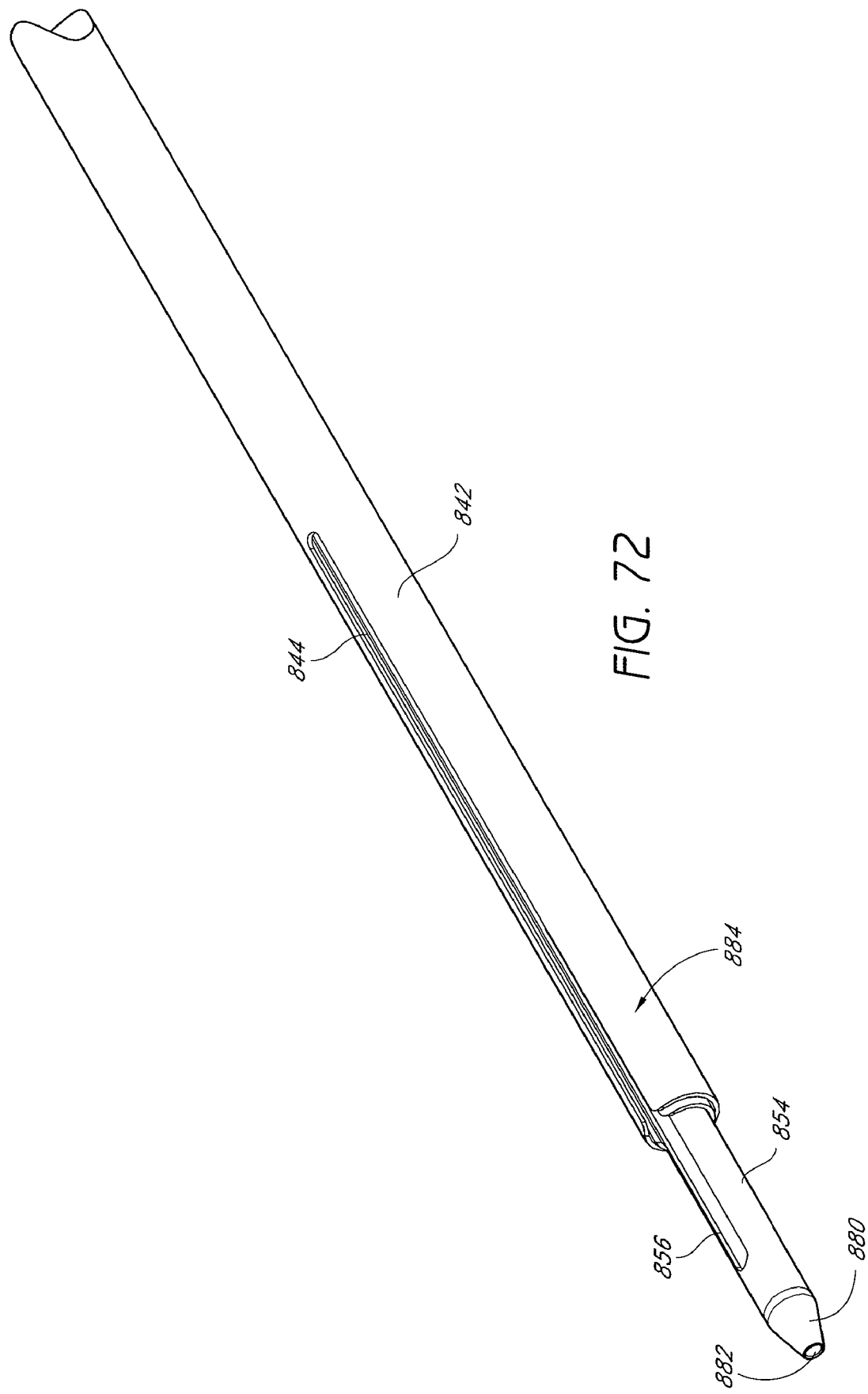
FIG. 72 illustrates another embodiment of a recapture tool with a circumferentially closed distal end.
Figure 73:
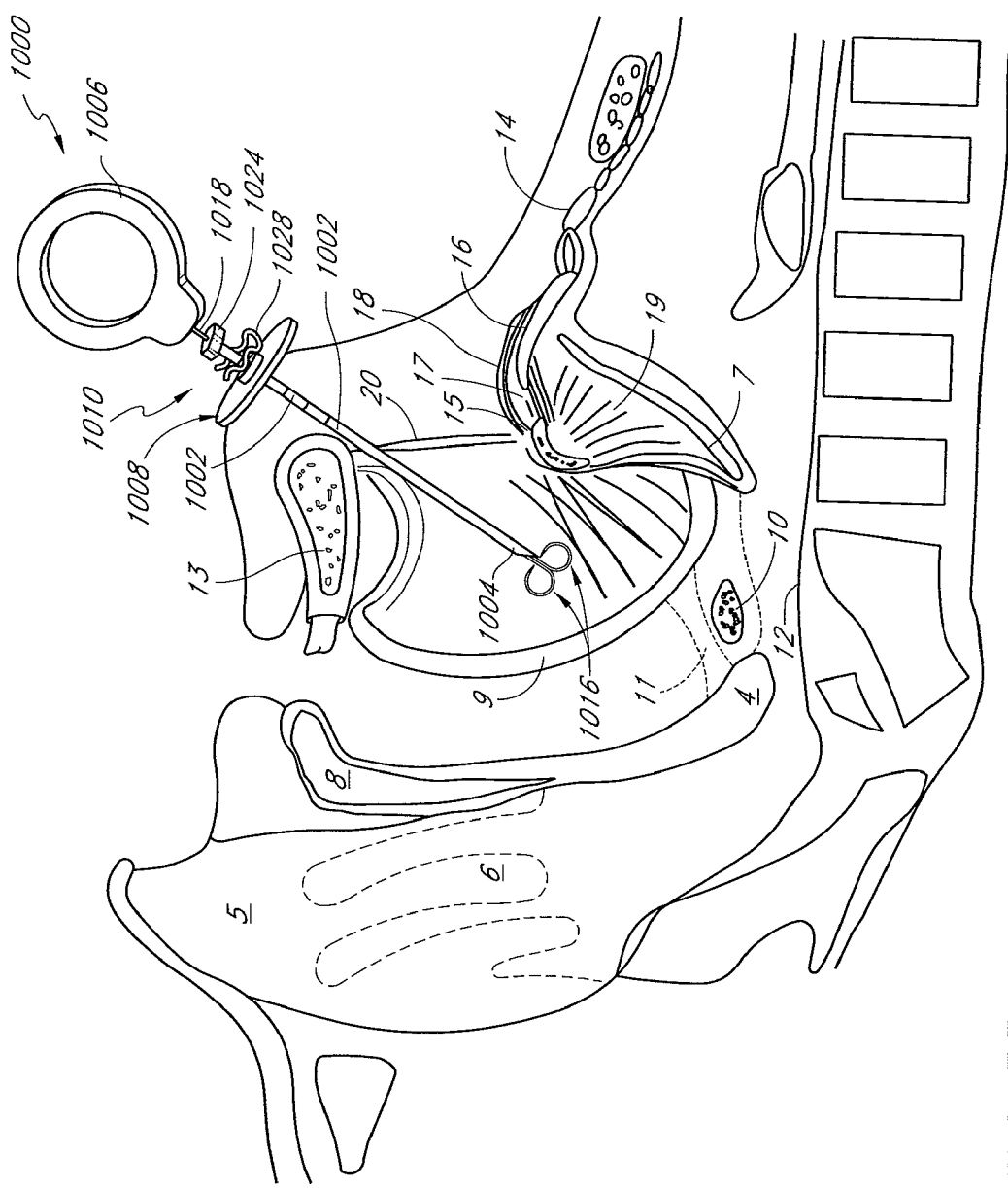
FIG. 73 shows one embodiment of a diagnostic device for temporarily suspending the tongue of a patient.

In another embodiment of the recapture tool, shown in FIG. 72, the longitudinal slot 844 of the recapture tube 842 does not fully extend through the distal end 846 of the recapture tube 842. In this embodiment, the blocking assembly may be omitted and a distal segment 884 of about 0.5 cm to about 2 cm or more of the recapture tube 842 is circumferentially intact. To thread the exposed tether 830 into the recapture device 840, a needle hole threader is inserted through the longitudinal slot 844 of the recapture tube 842 and tether guide 854 until it is visible at the distal end of the recapture tube. The tether guide is optionally retracted into the recapture tube 842 when the needle hole threader is initially inserted and re-extended when the free end of the tether 830 is pulled into the conical tip 880 of the tether guide 854 and out through the slot 844 of the recapture tube 842. The remaining recapturing steps are similar to the prior embodiment of the recapture system. Although this alternate embodiment of the recapture device omits the rotatable blocking assembly, it may be somewhat more difficult to thread the tether into the device than with the other embodiment.

One of skill in art the will also understand that the recapture tool depicted in FIGS. 71A to 71G may be used or adapted to remove expandable anchors implanted elsewhere in the body, including but not limited to the nasopharynx, soft palate, hard palate, pharyngeal wall, GI tract, bronchial tree, biliary tree, and genitourinary tract.

Although the delivery tool for implanting a planar-shaped tissue anchor depicted in FIG. 63A is preferably configured to control for rotation of the anchor during the implantation procedure, rotation control is generally unnecessary for a recapture of a planar anchor, but may be provided in some embodiments.

D. Non-Anchored Tongue Remodeling

In one embodiment of the invention, the glossoplasty device is implanted in the tongue and does not require attachment or anchoring to any bone or other organ. One example of a non-anchored tongue remodeling device is the dual-anchor device described above and depicted in FIGS. 6A and 6B. Other embodiments are described below.

1. Tongue Splinting

In one embodiment of the invention, a tongue splint is provided that is capable of redistributing the mass of the tongue. The tongue splint may be inserted to displace at least a portion of the base of the tongue or posterior tongue away from the posterior pharynx or pharyngopalatine arch to prevent or resist occlusion of the airway during sleep or other activities.

Figure 52A:
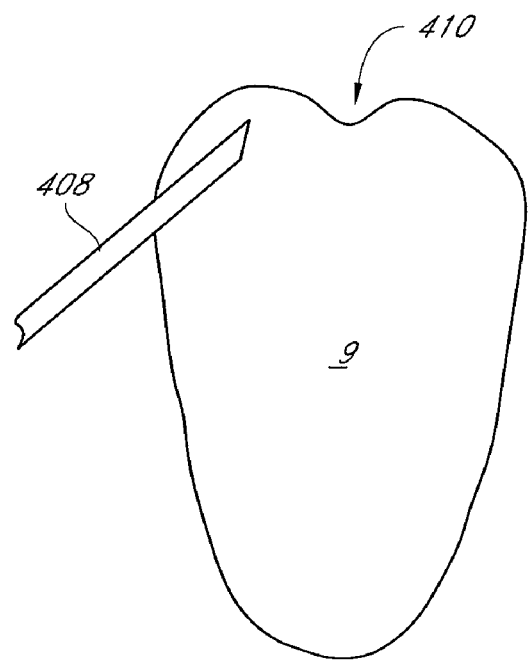
FIGS. 52A through 52F represent one embodiment of the invention comprising a rigid tongue splint.
Figure 52B:
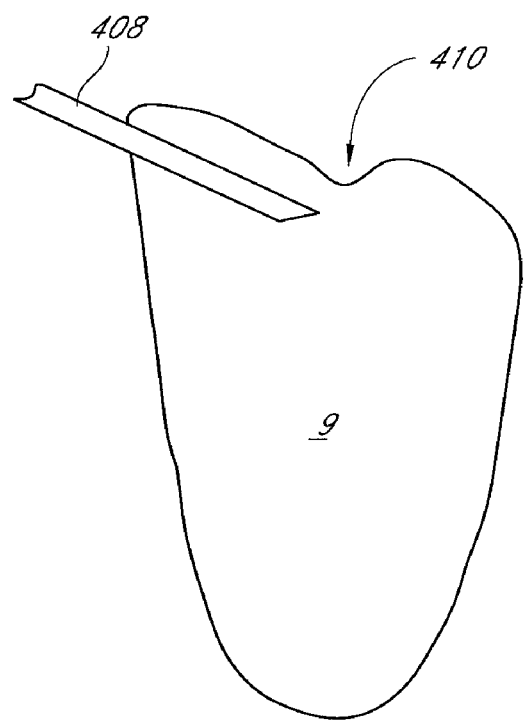
Figure 52C:
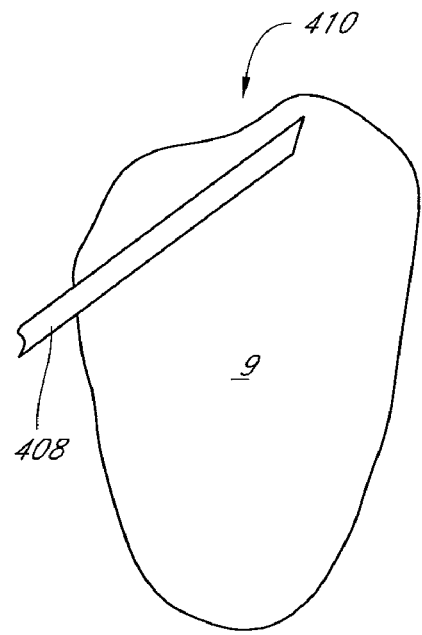
Figure 52D:
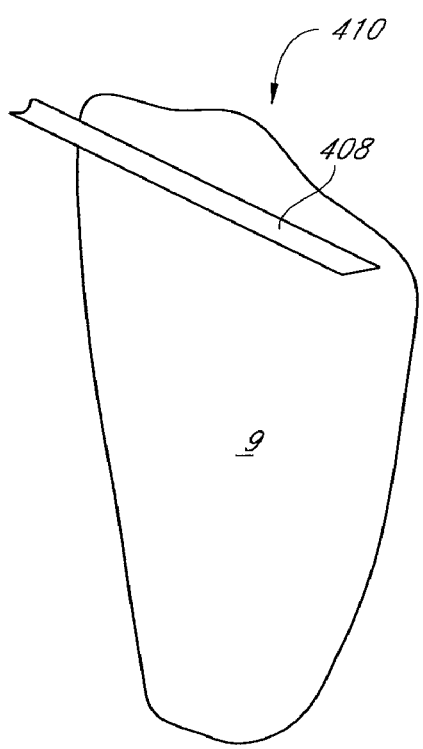
Figure 52E:
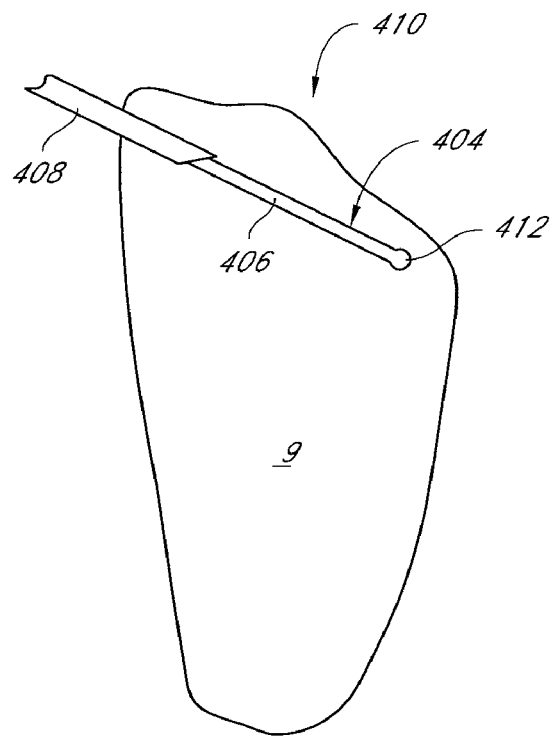
Figure 52F:
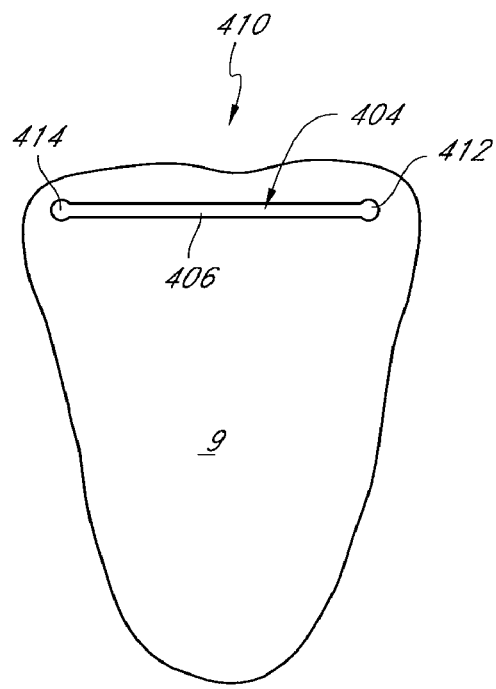

As shown in FIGS. 52E and 52F, in one embodiment of the invention, the tongue splint 404 comprises a rigid linear body 406 that is dimensioned to fit within a hypodermic needle or other piercing delivery tool 408. Referring to FIG. 52A, beginning on one side of the posterior tongue 410, the delivery tool 408 is inserted in a general direction toward the posterior tongue 410 in a postero-medial direction, then, as shown in FIG. 52B, reoriented and advanced in an antero-medial direction until generally the midline is reached. Referring to FIG. 52C, the needle or delivery tool 408 is then reoriented and advanced in a postero-lateral direction toward the opposite side of the tongue 9 before a final reorientation and advancement in an antero-lateral direction. Advancement may be stopped at a submucosal location of the tongue 9, as illustrated in FIG. 52D, or may pierce the opposite side of the tongue 9. One skilled in the art can determine the insertion pathway for the rigid tongue splint 404 based upon the particular tongue 9 and oropharynx anatomy of a particular patient. In FIG. 52E, the needle or delivery tool 408 is withdrawn to deposit the splint 404 along a pathway that redistributes the posterior mass 410 of the tongue 9 to reduce occlusion of the airway, as shown in FIG. 52F. In a further embodiment of the invention comprising the tongue splint 404, one or both ends 412, 414 of the tongue splint 404 may project from the surface of the tongue and may be configured to engage a mouthpiece or appliance inserted into the oral cavity to further displace the tongue mass.

Figure 53A:
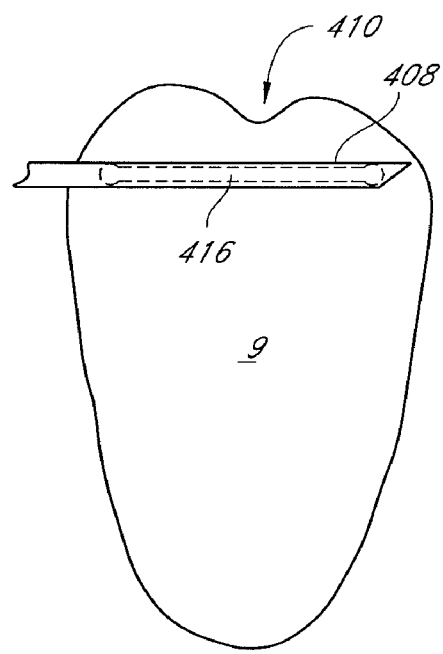
FIGS. 53A and 53B represent another embodiment of the invention comprising a semi-rigid tongue splint.
Figure 53B:
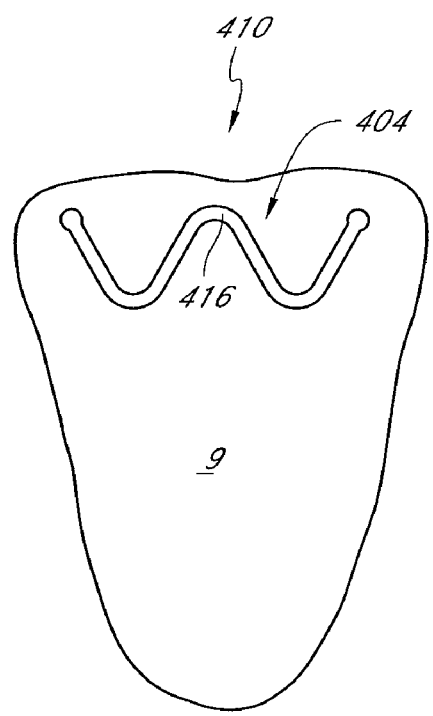

FIGS. 53A and 53B depict another embodiment of the tongue splint 404 comprising a semi-rigid non-linear tongue splint 416. The semi-rigid tongue splint 416 is configured to at least partially straighten within the lumen of a hypodermic needle or delivery tool 408, yet regain at least some of its original configuration upon release from the needle or tool 408 such that the tongue splint 416 is capable of redistributing the tongue mass upon return to its original configuration. The tongue splint 416 may be made of a shape memory or superelastic material. A semi-rigid implant 416 may be advantageous in that it may be implantable into the tongue 9 with a single linear implantation pathway, as shown in FIG. 53A. Referring to FIG. 53B, upon release and regaining of its previous form, the tongue splint 416 will cause a relative redistribution of tongue tissue. To facilitate implantation of a semi-rigid implant 416 into the tongue 9, the delivery tool 408 may have rotational indicators to that allow the physician to properly orient the tongue splint 416 with respect to the tongue anatomy.

2. Tongue Tissue Compression

Figure 54A:
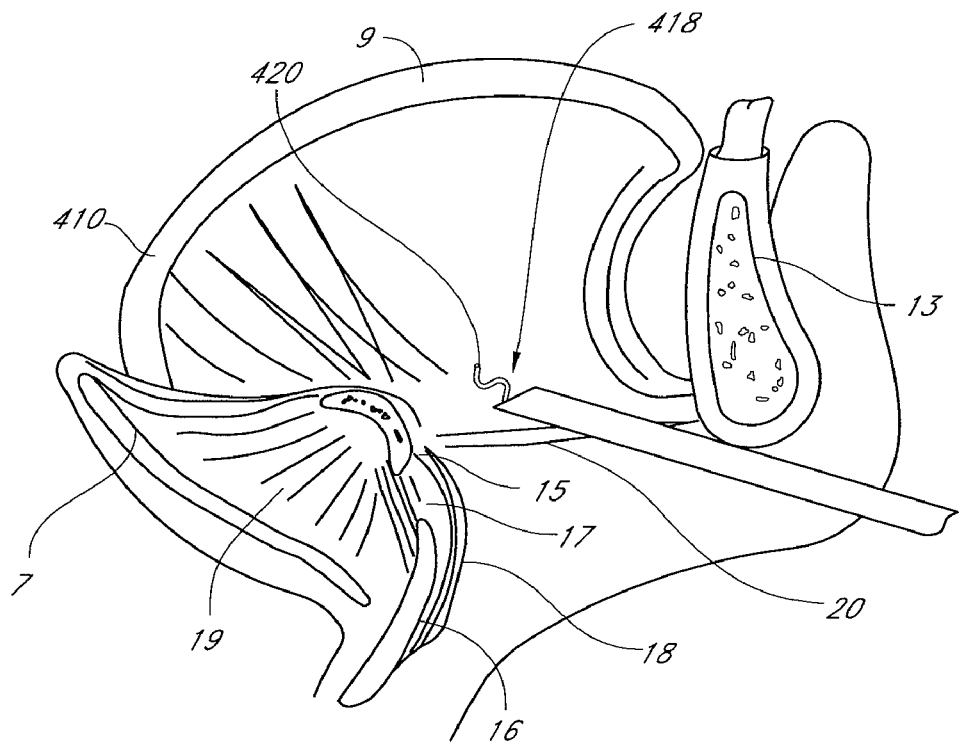
FIGS. 54A and 54B represent one embodiment of the invention comprising a variable pitch tissue compression screw.
Figure 54B:
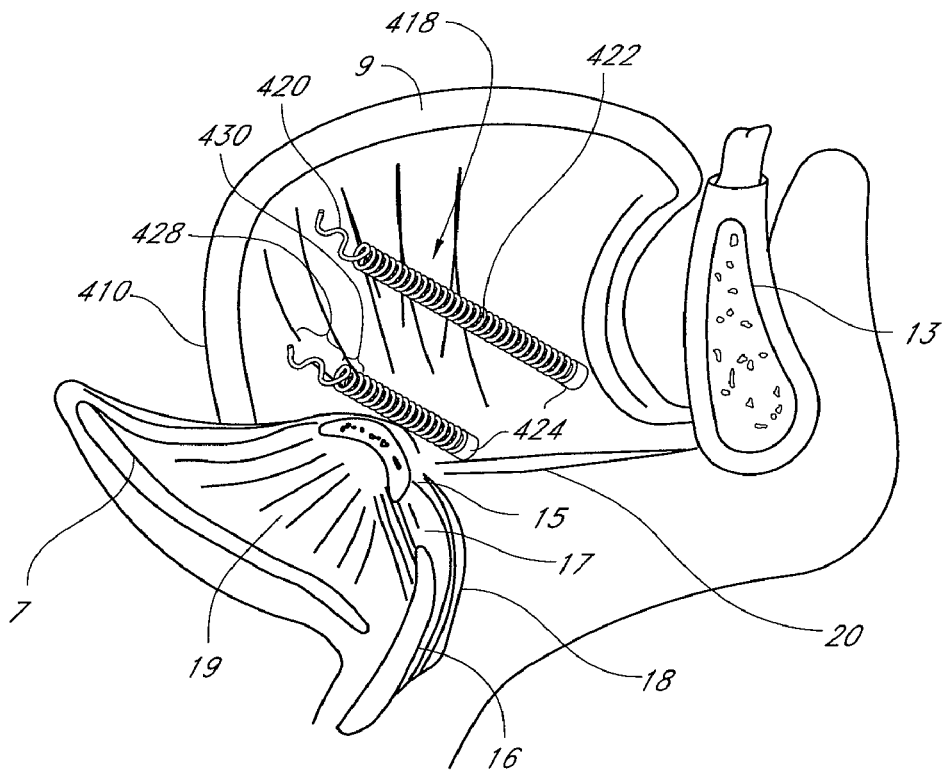

In another embodiment of the invention, a glossoplasty device capable of compressing tongue tissue is provided. In one embodiment, illustrated in FIGS. 54A and 54B, the device comprises a variable pitch tissue screw 418 having a distal end 420 with a long pitch, a middle section 422 with a shorter pitch, and a proximal head 424 configured to engage and disengage a rotational tool 426 for driving the tissue screw 418 into the tongue 9. The tissue screw 418 is configured to pierce and advance through soft tissue. As the tissue screw 418 advances, the distal end 420 with the long pitch defines a spiral pathway through the tissue with a first tissue volume 428 between turns of the spiral pathway. As the shorter pitch portions 422 of the tissue screw 418 are advanced through the pathway defined by the distal end 420, the middle section 422 of the tissue screw 418 will compress the first tissue volume 428 defined by the long pitch distal end 420 into a smaller second volume 430 caused by redefined by the shorter pitched portions 422 of the tissue screw 418. Compression of the tongue tissue along the tissue screw 418 will generally bias or displace the tongue tissue toward the insertion site of the tissue screw 418, and may indirectly bias or displace the base of the tongue 9 or posterior tongue 410 from the posterior pharynx or pharyngopalatine arch. The compression and displacement of tongue tissue by the variable pitch tissue screw 418 may be further augmented by attaching the proximal head 424 or other portion of the tissue screw to a fixed or variable length tether and attaching tether to another structure such as the mandible 13 or hyoid bone 15.

In one embodiment of the invention, shown in FIGS. 55A and 55B, the glossoplasty device comprises a spring or coil 432 that is advanced into the tongue tissue in a first configuration having a long pitch w', and then changed to a second configuration with a shorter pitch w", thereby compressing the tongue tissue about or between the turns of the spring or coil 432. In one embodiment, the coil 432 has a sufficient stiffness to be advanced into the tongue tissue in its first configuration similar to that of the tissue screw previously described. If the spring comprises a shape memory material such as Nitinol, the spring is able to assume the second configuration with a shorter pitch w" upon warming up to body temperature and/or elastic recoil, thereby compressing the tongue tissue. In another embodiment of the invention, the distal tip 434 of the coil 432 is attached to a suture or wire that is first inserted into the tongue 9 along the desired insertion path. Tension is applied to the suture or wire to maintain the coil 432 in its first position as it is advanced into the tongue 9. Once the spring is positioned, the suture tension is released to allow the coil 432 to assume its second configuration to engage and compress the tongue tissue. The suture or wire may be cut to eliminate any exposed foreign body and to reduce the risk of infection tracking down the suture path.

Figure 56:
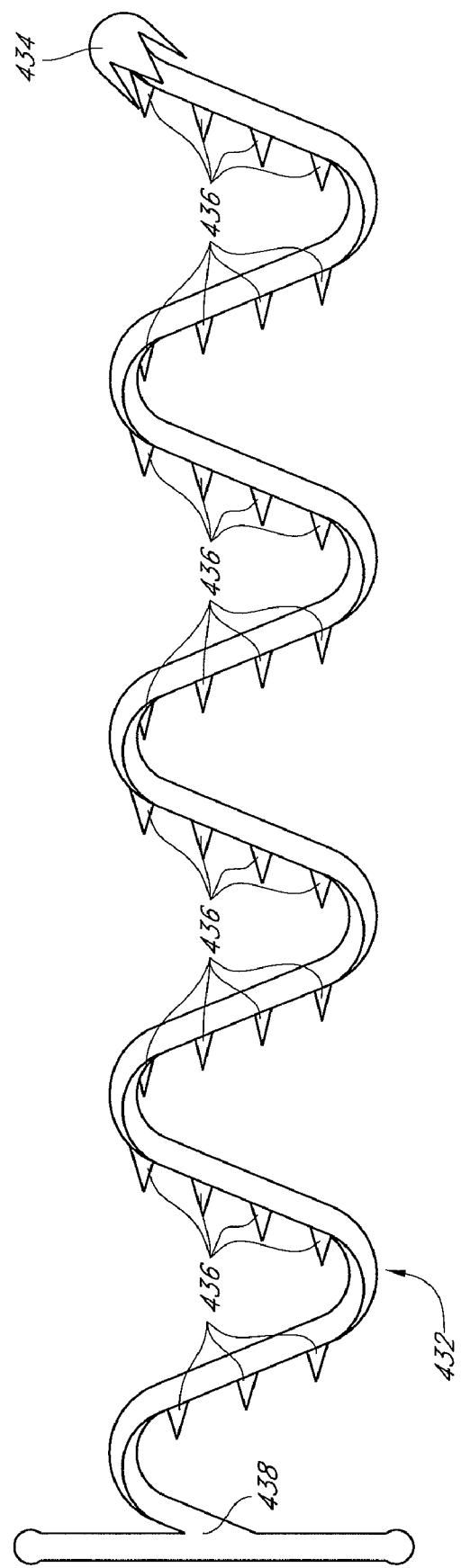
FIG. 56 represents another embodiment of the invention comprising a barbed tissue compression coil.

In some instances, the change in configuration from the first configuration to the second configuration may not cause tissue compression because the coil 432 failed to engage the surrounding tissue. In such situations, the coil 432 may axially contract and radially expand to form a cavity without any tissue between the spirals. As shown in FIG. 56, to reduce the risk of non-engagement of the tongue tissue, the coil 432 may be configured with a series of barbs, hooks, angled pins or other tissue engaging structures 436 to facilitate engagement and compression of the tissue as the coil 432 assumes the second configuration. The location, spacing, orientation and length of the tissue engaging structures 430 may be determined by one skilled in the art with routine experimentation. The characteristics of each tissue engaging structure 436 need not be uniform along the length of the coil 432. For example, the tissue engaging structures at the proximal and distal ends of the coil 432 may be configured differently than the engaging structures 436 in the middle portion of the coil 432 because rather than compress the tongue tissue, the ends 434, 438 of the spring may be configured to attach and pull the surrounding tissue towards the middle section of the coil 432. To facilitate insertion of a spring or coil 432 comprising tissue engagement structures 436, the spring or coil 432 may be covered with a sheath during the insertion process to reduce the risk of engaging tissue prior to final positioning of the device. The sheath can be removed to expose the tissue engaging structures 436 upon final positioning.

Figure 59A:
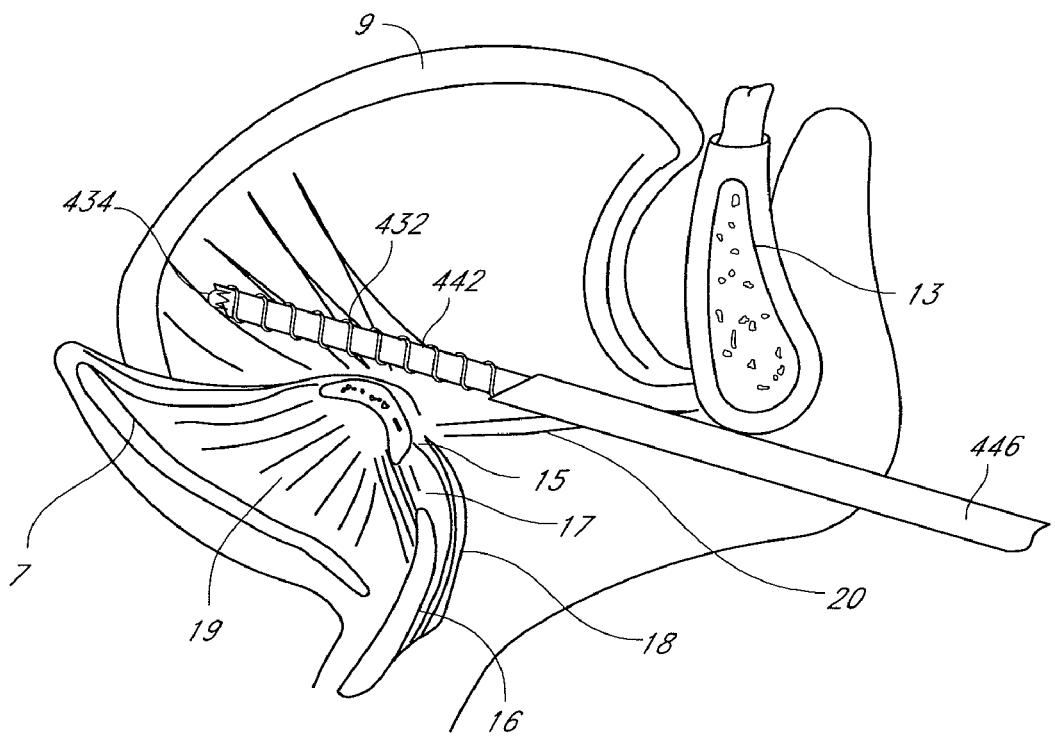
FIGS. 59A and 59B represent one embodiment of the invention for implantation of a tissue compression coil.
Figure 59B:
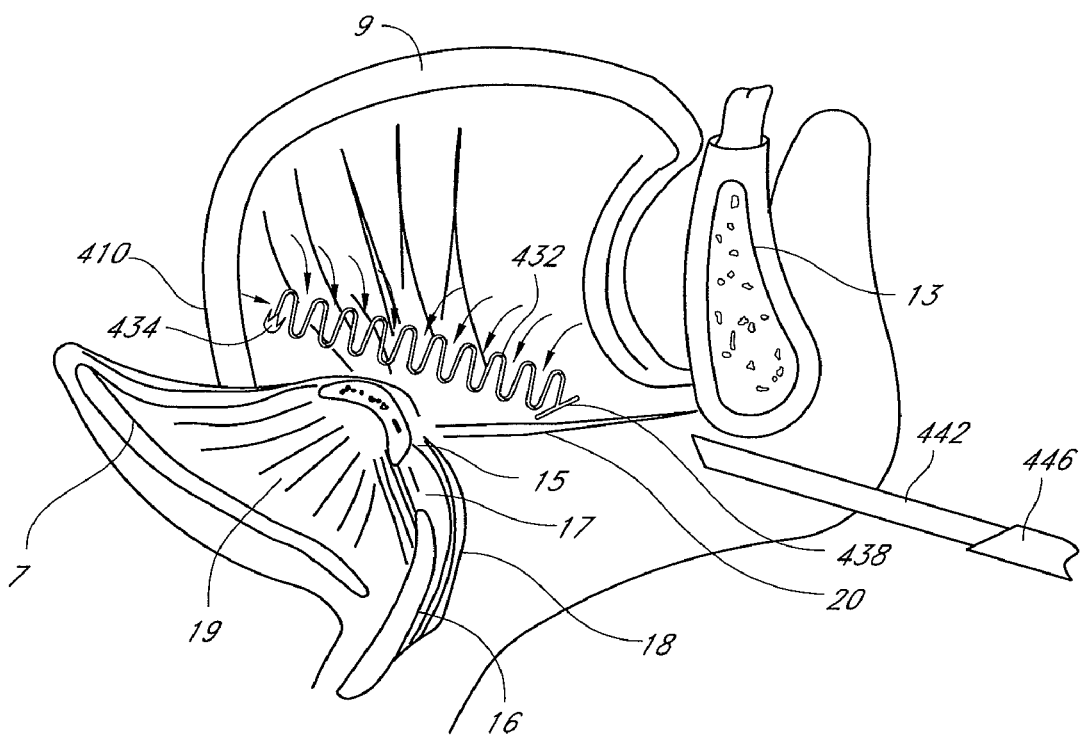

In another embodiment of the invention, the spring or coil 432 may be inserted in its first configuration within the lumen of a needle or other delivery device. In some instances, however, reducing the diameter of the spring or coil 432 sufficiently to fit within a lumen device may cause plastic deformation of the spring or coil 432 such that the spring or coil lack the elastic properties to assume the second configuration. Alternatively, as shown in FIG. 57, the spring or coil 432 may be placed around the outer surface 440 of a needle or other piercing device 442 for insertion into the tongue 9. In a further embodiment, illustrated in FIG. 58, the needle or other piercing device 442 may comprise a fitted spiral groove 444 or tract along the outer surface 440 to reduce or make flush the profile of the spring or coil 432 on the delivery device 442. FIGS. 59A and 59B depict the implantation of the coil-on-needle device 432, 442. FIG. 59A depicts the positioning the distal end 434 of the coil 432 prior to the complete release of the implant from the sheath 446, while FIG. 59B schematically illustrates the resulting tissue compression from the released coil 432.

3. Tongue Tissue Compliance Change

In another embodiment of the invention, the tongue remodeling system changes the compliance of the tongue tissue surrounding the implanted device, but does not require exertion of a continuous force upon the surrounding tongue tissue. In some instances, a change in the tissue compliance without placing the tissue under compression may be sufficient to reduce or eliminate airway occlusion during apnea episodes. The implantation of the device without creating tissue compression may simplify the implantation procedure by eliminating the need to adjust the degree of tissue tension exerted by the device either during or after the initial implantation procedure. Many of the embodiments of the invention mentioned previously may be used without altering the physical characteristics of the tether and/or splint by implanting the device and not exerting tension on the device during the implantation process Thus, although the device exerts reduced or no force while the tongue is in usual or resting position, but when the patient is asleep and the musculature of the oropharynx and/or hypopharynx relaxes, the compliance of the tongue tissue altered by the device such that greater force is required to cause posterior displacement of the tongue. One skilled in the art may also select the materials and/or configurations of the tether and/or splint for the previously disclosed embodiments to modify the degree of change in tissue compliance.

E. Materials

The materials that may be used to construct the tether component of the glossoplasty device were discussed previously. The other components of the invention, such as the distal anchor and/or securing assembly, may be manufactured in accordance with any of a variety of techniques which are well known in the art, using any of a variety of medical-grade construction materials. One or more components can be molded, formed or machined from biocompatible metals such as Nitinol, stainless steel, titanium, and others known in the art. One or more components can also be injection-molded from a variety of medical-grade polymers including high or other density polyethylene, nylon and polypropylene. Portions of the system can be separately formed and secured thereto in a post-molding operation, using any of a variety of securing techniques such as solvent bonding, thermal bonding, adhesives, interference fits, pivotable pin and aperture relationships, and others known in the art.

Reinforcing fibers suitable for use in the components of the present invention include ceramic fibers, like bioabsorbable hydroxyapatite or bioactive glass fibers. Such bioabsorbable, ceramic fiber reinforced materials are described, e.g., in published European Patent Application No. 0146398 and in WO/96/21628, the entire disclosures of which are incorporated herein by way of this reference. The materials may also include a bioabsorbable coating previously described.

As a general feature of the orientation, fiber-reinforcement or self-reinforcement of the tongue remodeling components, many of the reinforcing elements may be oriented in such a way that they can carry effectively the different external loads (such as tensile, bending and shear loads) that are directed to the remodeling system as used.

The components of the invention (or a bioabsorbable polymeric coating layer on part or all of the implant surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In one embodiment, the distal anchor may comprise a bioabsorbable coating and/or structure. As used herein, terms such as bioabsorbable, bioresorbable and biodegradable interchangeably refer to materials which will dissipate in situ, following a sufficient post-operative period of time, leaving acceptable byproducts. A variety of polymers which may be useful for the components of the present invention are identified below. Many of these polymers have been reported to be biodegradable into water-soluble, non-toxic materials which can be eliminated by the body: polycaprolactone, poly (L-lactide), poly (DL-lactide), polyglycolide, poly (L-Lactide-co-D, L-Lactide), 70:30 poly (L-Lactide-co-D, L-Lactide), 95:5 poly (DL-lactide-co-glycolide), 90:10 poly (DL-lactide-co-glycolide), 85:15 poly (DL-lactide-co-glycolide), 75:25 poly (DL-lactide-co-glycolide), 50:50 poly (DL-lactide-co-glycolide), 90:10 Poly (DL-lactide-co-caprolactone), 75:25 poly (DL-lactide-co-caprolactone), 50:50 poly (DL-lactide-co-caprolactone), polydioxanone, polyesteramides, copolyoxalates, polycarbonates, and poly (glutamic-co-leucine). The desirability of any one or a blend of these or other polymers can be determined through routine experimentation by one of skill in the art, taking into account the mechanical requirements, preferred manufacturing techniques, and desired reabsorption time. Optimization can be accomplished through routine experimentation in view of the disclosure herein. Bodily reaction to the bioabsorbable materials or byproducts may furnish at least a portion of the support provided by the device or treatment method. All or portions of any of the devices herein, as may be appropriate for the particular design, may be made from allograft material, or synthetic bone material.

F. Temporary Tongue Suspension

Another embodiment of the invention utilizes a diagnostic device 1000, shown in FIGS. 73 to 75B, for temporarily suspending tongue 9. Temporary suspension of the tongue 9 may be useful during head and neck surgery to expand the airway and increase the visibility and exposure of a surgical site. In one preferred embodiment, however, temporary suspension of the tongue is used diagnostically to determine the clinical desirability of and the optimal parameters for permanent tongue suspension in particular patients. For example, device 1000 can be used to determine optimal anchor placement, advancement and adjustment for the systems described above. In another example, temporary tongue suspension is used during a sleep study to assess whether sleep apnea patients are responders or non-responders to glossopexy procedures.

Figure 74:
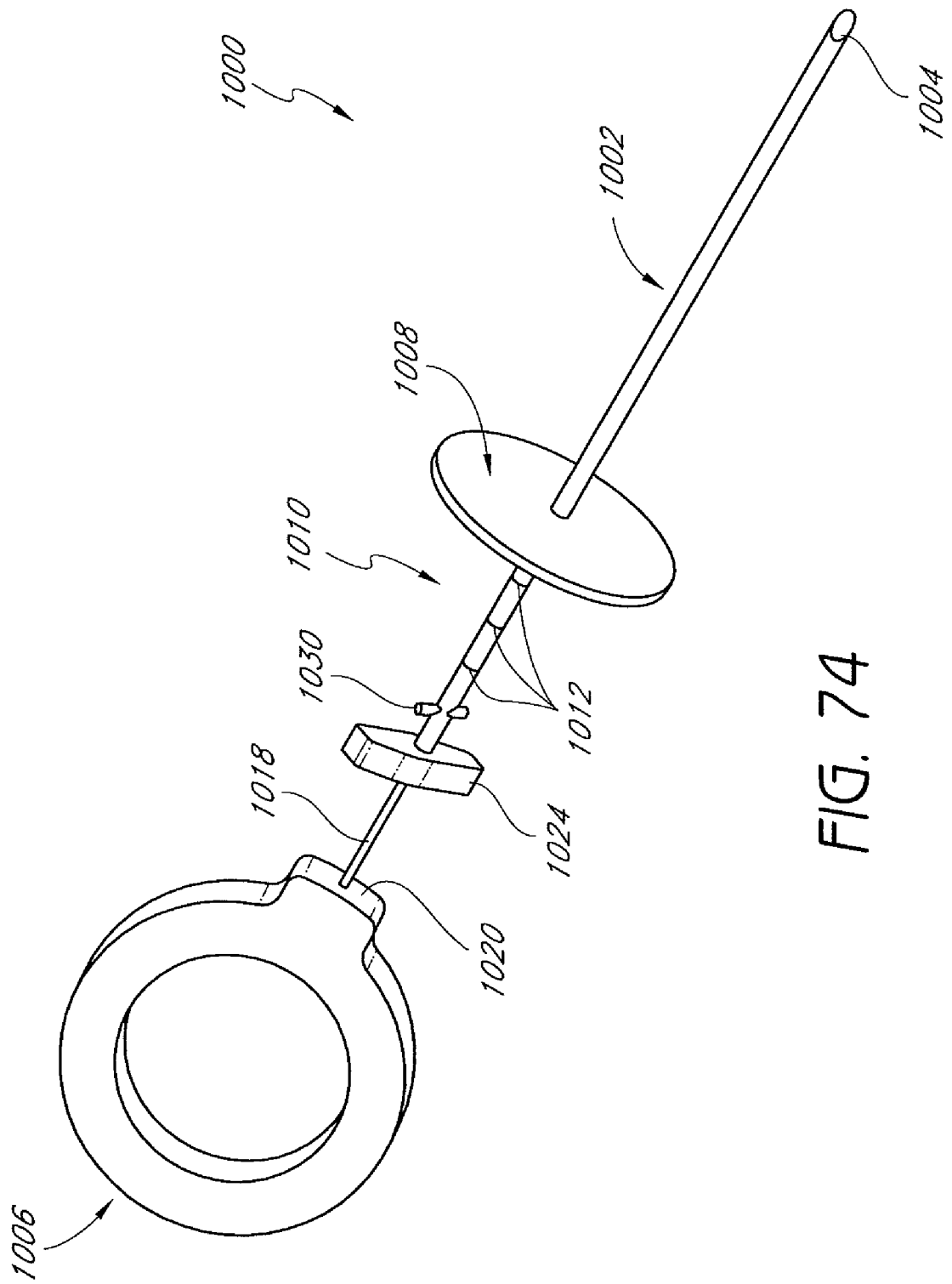
FIG. 74 depicts one embodiment of the temporary tongue suspension system.

Referring to FIG. 74, device 1000 comprises, in some embodiments, a cannula 1002 comprising a needle tip 1004. The needle tip 1004 may be beveled, or circumferentially symmetrical. Device 1000 also comprises a proximal handle, such as a pull ring 1006 and an optional base or pad 1008. In preferred embodiments, cannula 1002 comprises means 1010 for determining the relative position or distance the cannula 1002 has been advanced past a surface. In some embodiments, the reference surface may be the insertion site or the pad 1008. For example, cannula 1002 may comprise grooves 1012 or other markings. In one example, the spacing between each groove 1012 is about 1 mm, but in other embodiments the spacing can range from approximately 2 mm to approximately 10 mm.

Means 1010 can also comprise a threaded portion along at least a portion of the length of cannula 1002 with each thread corresponding to a particular distance. The threaded portion of the cannula 1002 may form a threaded interface with a corresponding threaded lumen of the pad 1008. In one example, cannula 1002 is advanced by turning such that each turn corresponds to a thread and a particular distance advanced. For example, with each turn, corresponding to one thread, cannula 1002 can be advanced 2 mm. Alternatively, in other embodiments, the base or pad 1008 is rotated or manipulated to provide advancement or withdrawal of the cannula 1002. In another embodiment, the means 1010 can comprise a ratchet mechanism between the cannula 1002 and base 1008 that advances with respect to teeth on cannula 1002 and thereby advances the cannula 1002 a particular distance per tooth. For example, for advancement of the ratchet over one tooth, cannula 1002 could be advanced 2 mm. Means 1010 can also comprise any other indicia of distance advanced by cannula 1002 as would be contemplated by those skilled in the art.

As can be seen, the structures used to assess the positioning of the cannula 1002, such as the threaded interface between the cannula 1002 and pad 1008, can also be used to adjustably fix or maintain the relative position of the cannula 1002 and the pad 1008 or chin 1022. One embodiment of the invention therefore comprises an external securing assembly for maintaining the position of the cannula, which may or may not also include an adjustment feature.

Figure 75A:
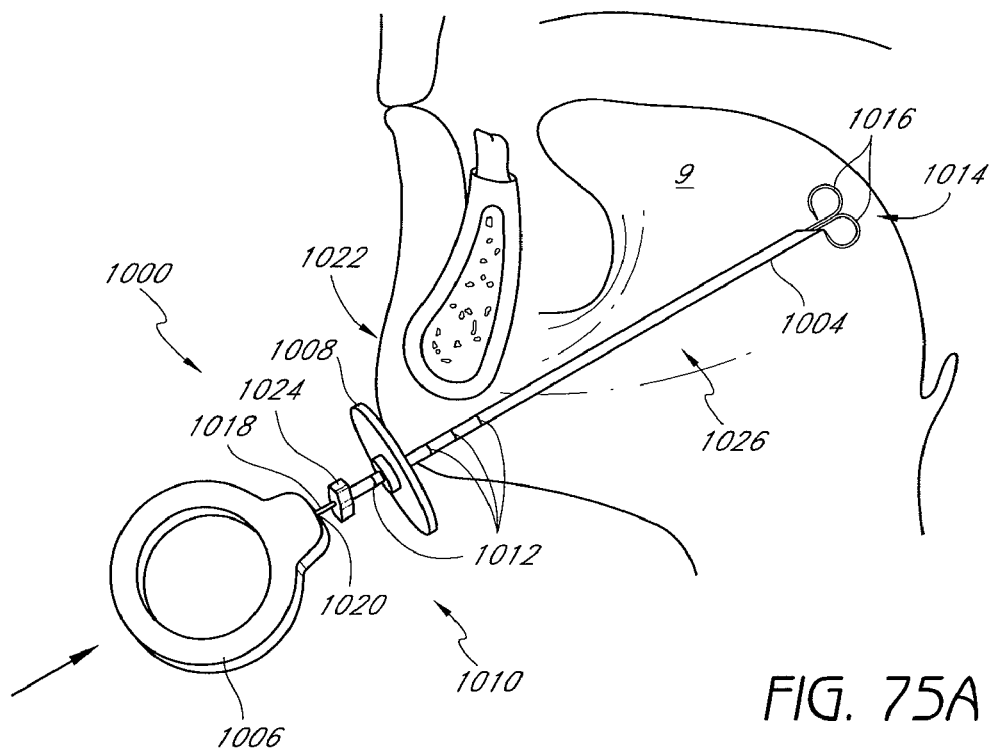
FIGS. 75A-75B show the deployment of one embodiment of a diagnostic device for temporarily suspending the tongue of a patient.
Figure 75B:
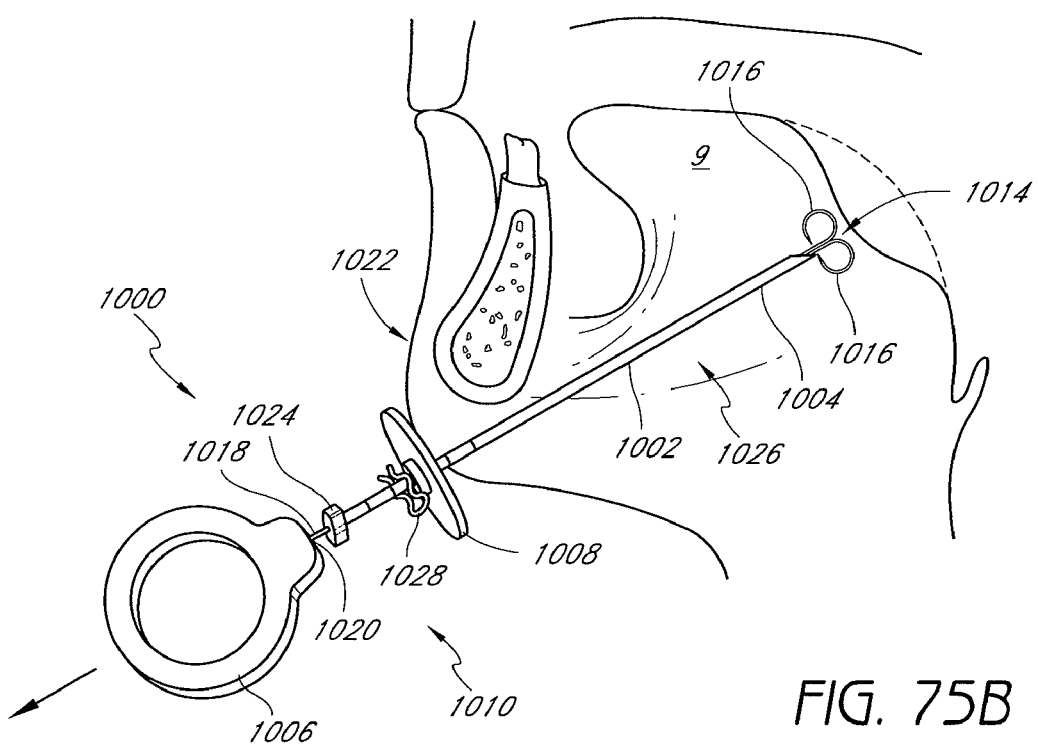

Device 1000 further comprises a barb assembly 1014, shown in FIG. 75B, that movably resides within cannula 1002. Barb assembly 1014 comprises one or more barbs 1016 or other tissue-engaging structures, and a movable elongate member 1018 extending from barbs 1016 through cannula 1002 and attached at its proximal end 1020 to pull ring 1006. In some embodiments, the movable elongate member 1018 comprises a stiff wire having sufficient torqueability and column strength to permit bidirectional control of the distal barbs 1016. The movable elongate member 1018 may also comprise a plurality of barb wires attached together, with each barb wire corresponding to a barb 1016. The barbs 1016 of assembly 1014 have a straightened configuration when contained within cannula 1002 and assume an outwardly curved configuration when they emerge from cannula 1002 as shown in FIGS. 75A and 75B. Barbs 1016 can have an outward bias so that they spring out of needle tip 1004 as they emerge from the cannula tip 1004. The movable elongate member 1018 and barbs 1016 are moved distally and proximally within cannula 1002 by pushing and pulling on an optional pull ring 1006. When advanced outside of cannula 1002, barbs 1016 can engage tongue 9 and provide traction. To disengage tongue 9, barbs 1016 are retracted back into cannula 1002. Barbs 1016 are preferably made of a shape memory material such as Nitinol as described above, but other materials may also be used. Although the barbs 1016 of FIGS. 73 to 75B depict curved barbs, angled barbs or other non-linear barb configurations may also be used.

In other embodiments, the movable elongate member 1018 may comprise a suture or a flexible tether. In such embodiments, while the suture or the tether can be used to retract the barbs 1016 into the cannula 1002, a push rod or tube (not shown) may be needed used to deploy the barbs 1016 from the cannula 1002. In other embodiments, the deployment of the barbs 1016 or tissue-engaging structure is independent of the relationship between the barbs 1016 and cannula 1002, and is controllable by the physician. See, for example, FIGS. 15A to 24B.

Pad 1008 is preferably applied or pressed against a surface, for example chin 1022, such that cannula 1002 is held stable at a particular position. Although a circular configuration is depicted for pad 1044 in FIG. 74, pad 1008 can assume a variety of different configurations as would be understood by those skilled in the art. The cannula 1002 may optionally comprise a flange or handle 1024, as shown in FIGS. 75A-75B, which can be held by an operator to facilitate manipulating or retaining cannula 1012 at a particular position. The cannula may also optionally comprise a stop member 1030 distal to the handle 1024 that limits the degree of cannula extension through the pad 1008 or chin 1022. The stop member 1030 facilitates gripping of the handle 1024 by restricting the handle 1024 from direct contact up against the pad 1008 or chin 1022.

Although the base or pad 1008 may be held against the chin 1022 or body by the tension along the movable elongate member 1018, in other embodiments, pad 1008 may have an adhesive surface to secure the pad location against the body. In still other embodiments, the pad 1008 may further comprises straps with buckles, VELCRO® or an adhesive to secure the pad 1008 to the head of the patient. In still other embodiments, the device 1000 is inserted into the tongue or other airway tissue without using the base or pad 1008. The base or pad 1008 may optionally comprise an antiseptic surface or material to resist infection relating to the diagnostic procedure.

FIG. 74 shows barbs 1016 of barb assembly 1014 retracted within cannula 1002. In this configuration, cannula 1002 can be inserted through the chin 1022 and into the tongue 9. As shown in FIG. 75A, needle tip 1004 is preferably inserted through the skin of chin 1022 just behind the inferior aspect of mandible 13 and then advanced into the genioglossus muscle 1026. Needle tip 1004 can also be advanced, in some embodiments, into other muscles of tongue 9 or floor of the mouth. Then barbs 1016 are advanced or deployed until they emerge from needle tip 1004 and can engage tongue 9. At this stage no tension has been created in tongue 9 or in any of the other surrounding structures.

Then, as shown in FIG. 75B, cannula 1002 and barbs 1016 are retracted such that they pull on tongue 9 and suspend it. Pulling and suspending the tongue 9 then opens the base of the oral airway as shown in FIG. 75B. Referring back to FIG. 73, a clip 1028 or other securing device can then be placed into a groove 1012 or otherwise engaged on the cannula 1002 to hold the assembly 1014 in a suspended position. Circular pad 1008 provides a convenient way to transfer this suspension force, but in other embodiments, the clip 1028 may suspend the airway tissue by providing mechanical interference against the chin 1022 or other body structures about the cannula insertion site.

Device 1000 and the method described above using device 1000 to temporarily suspend tongue 9 can be used to test the clinical desirability of installing a permanent suspension system, to determine optimal anchor positions and degrees of tongue advancement for a particular patient, prior to implantation of a permanent suspension system.

In one embodiment, a patient undergoes temporary tongue suspension to diagnostically assess whether the patient is likely to benefit from glossopexy, and if so, which tongue sites and/or tether tensions would optimize the glossopexy procedure. This procedure may be performed during a sleep study, as well as other inpatient or outpatient settings. The procedure may be performed under local or general anesthesia, and in some instances, may even be performed without anesthesia. To perform the procedure, the patient may either be seated or lying supine on a surface. The chin or other head/neck site is prepped and draped in usual sterile fashion. The cannula in then inserted from the chin to the target site in the tongue tissue. In some instances, a small amount of anesthetic may be delivered to the target site through the cannula. The movable elongate member may be pre-inserted into the cannula or inserted into the cannula after the cannula has been placed into the tongue. Likewise, the cannula may be pre-inserted into the cannula aperture of the optional base or pad, or the base or pad may be placed around the cannula after cannula insertion. Such a pad may have a slit between the cannula aperture and its outer edge to permit placement of the cannula into the cannula aperture without interference from the proximal components of the temporary suspension system.

After cannula insertion, the movable elongate member is advanced out of the cannula to engage the surrounding target tongue tissue. Once the tongue tissue is engaged, the cannula and/or movable elongate member is withdrawn or titrated to achieve the desired tongue suspension and/or patient comfort, which can also involve assessing functional performance relating to swallowing and speech. In other embodiments, insertions of additional cannula and barb assemblies may be used if the initial placement is suboptimal, or to complement the initial placement. When the desired amount of tension is achieved, the position of the cannula and/or movable elongate member is measured and or secured. In some examples, the cannula and/or movable elongate member is removed, while in other instances, the device is left in place to provide an extended diagnostic or testing period which is removed at a later time. The timeframe may be hours, days, weeks or months. In still other examples, the movable elongate member and barb assembly may be converted to permanent implantation by securing an adjustment assembly to an implantable adjustment or fixation mechanism as described elsewhere in this specification.

In some embodiments, the pull ring 1006 is removably attached to the barb assembly 1014 so that the cannula 1002 can be removed while maintaining the barbs 1016 in the tongue. This may be desirable in cases where the presence of cannula 1002 in the genioglossus muscle 1048 interferes with accurate assessment of the clinical desirability of tongue suspension, particular anchor positions and degrees of advancement. This may occur because natural movement of tongue 9 is prevented by the presence of cannula 1002. In other embodiments, the cannula 1002 may be initially inserted using a guidewire, which is then used to replace the cannula 1002 with a pull-away type of introducer or sheath. In one embodiment, the cannula may be removed while the tongue is temporarily suspended. In such an embodiment, a clip or other securing device may be attached to the tissue engaging member and placed against or relative to an external surface of the patient's skin to temporarily suspend the tongue tissue. A friction clip, such as clip 1028, or any of a variety of clamping mechanisms, as would be understood by those skilled in the art, could be used to grasp the movable elongate member or barb wires 1018 when cannula 1002 is removed and wires 1018 could comprise means for determining the distance the wires 1018 have been advanced past a surface, similar to means 1020. In some embodiments of the invention, the securing device or clip 1028 is integrated with the pull ring 1006 such that the pull ring 1006 is movable and securable along the proximal portion of the movable elongate member or barb wires 1018.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method for diagnosing airway obstruction, comprising: percutaneously inserting a tissue-engaging member through the submental region of a patient along a linear access pathway;

engaging a tongue tissue site within the tongue using the tissue-engaging member; forming tension in the tissue-engaging member;

maintaining the tension in the tissue-engaging member using a securing member pressed against the external skin of the patient;

and performing an apnea study on the patient while maintaining tension in the tissue-engaging member.

2. The method for diagnosing airway obstruction as in claim 1, further comprising:

inserting a tubular member from a percutaneous insertion site toward the tongue tissue site, the tubular member comprising a proximal end, a sharpened distal end, and a lumen therebetween.

3. The method for diagnosing airway obstruction as in claim 2, further comprising inserting the tissue-engaging member into the lumen of the tubular member.

4. The method for diagnosing airway obstruction as in claim 3, further comprising removing the tubular member from the patient before securing the repositioned tongue tissue site.

5. The method for diagnosing airway obstruction as in claim 4, wherein the tissue-engaging member comprises a proximal handle.

6. The method for diagnosing airway obstruction as in claim 5, wherein the proximal handle is a detachable proximal handle.

7. The method for diagnosing airway obstruction as in claim 4, wherein the tubular member is a peel-away tubular member.

8. The method for diagnosing airway obstruction as in claim 3, further comprising deploying the tissue-engaging member from the distal end of the tubular member.

9. The method for diagnosing airway obstruction as in claim 2, wherein the tubular member forms a mechanical interfit with the securing member.

10. The method for diagnosing airway obstruction as in claim 9, wherein the mechanical interfit is a threaded interfit.

11. The method for diagnosing airway obstruction as in claim 9, wherein adjusting tension in the tissue-engaging member comprises rotating the tubular member.

12. The method for diagnosing airway obstruction as in claim 9, wherein adjusting tension in the tissue-engaging member comprises rotating the securing member.

13. The method for diagnosing airway obstruction as in claim 2, wherein the securing member comprises a blocking member having a threaded aperture.

14. The method for diagnosing airway obstruction as in claim 13, wherein the blocking member comprises a pad.

15. The method for diagnosing airway obstruction as in claim 2, further comprising checking a plurality of indicia located on an external surface of the tubular member to determine the relative location of the tubular member in the tongue.

16. The method for diagnosing airway obstruction as in claim 2, wherein the securing member is pre-attached to the tissue-engaging member.

17. The method for diagnosing airway obstruction as in claim 2, wherein the securing member comprises a clamp.

18. The method for diagnosing airway obstruction as in claim 2, further comprising adjusting tension in the tissue-engaging member with the tubular member remaining within the patient.

19. The method for diagnosing airway obstruction as in claim 5, wherein the tissue-engaging member forms a mechanical interfit with the securing member.

20. A method for assessing airway obstruction in a patient having a submental region, a tongue, a chin, and a mandible, the method comprising:

providing a glossopexy diagnostic system, the glossopexy diagnostic system comprising:

a cannula having a proximal end, a sharpened distal end, and a lumen therebetween;

an elongate tissue anchor residing in the cannula lumen, the elongate tissue anchor having a proximal handle, at least one distal outwardly biased barb, and an elongate body therebetween;

percutaneously inserting the cannula through the submental region toward the tongue base;

deploying the at least one barb in the tongue;

pulling on the elongate tissue anchor from the chin to assess airway patency;

repositioning the cannula with respect to the chin; and maintaining cannula position with respect to the mandible by securing a clip relative to an external skin surface of the patient.

21. The method for assessing airway obstruction as in claim 20, wherein maintaining the cannula position is carried out during a sleep apnea study.

22. A system for performing tongue suspension, comprising:

a tissue-engaging assembly comprising a proximal handle, at least one distal tissue-engaging element having a sharp or tapered end adapted to be deployed in a tongue, and a body therebetween, the distal tissue engaging element having a linear non-deployed configuration and a non-linear deployed configuration; and an adjustable tensioning member configured to engage to the tissue-engaging assembly and press against an external skin surface of a patient.

23. The system for performing tongue suspension as in claim 22, wherein the proximal handle is a detachable proximal handle.

24. The system for performing tongue suspension as in claim 22, wherein the proximal handle and the adjustable tensioning member are integrally formed.

25. The system for performing tongue suspension as in claim 22, wherein the adjustable tensioning member is configured to threadably engage to the tissue-engaging assembly.

26. The system for performing tongue suspension as in claim 22, further comprising a means for attaching the adjustable tensioning member to the patient's body.

27. The system for performing tongue suspension as in claim 22, wherein the tissue-engaging assembly further comprises a cannula having a proximal handle, a sharpened distal end, and a lumen therebetween in which the body movably resides.

28. The system for performing glossopexy as in claim 27, wherein the cannula comprises indicia on an outer surface of the cannula.

29. The system for performing tongue suspension as in claim 22, wherein the adjustable tensioning member comprises a clamp.

30. The system for performing tongue suspension as in claim 22, wherein the clamp is configured to clamp either the cannula or the body of the tissue-engaging assembly.

31. The system for performing tongue suspension as in claim 22, wherein the body is a rigid body.

* * * * *